United States Patent
Ferrera et al.

(10) Patent No.: US 8,945,143 B2
(45) Date of Patent: Feb. 3, 2015

(54) EXPANDABLE TIP ASSEMBLY FOR THROMBUS MANAGEMENT

(71) Applicant: Covidien LP, Mansfield, MA (US)

(72) Inventors: David A. Ferrera, Redondo Beach, CA (US); Andrew H. Cragg, Edina, MN (US); John Fulkerson, Rancho Santa Margarita, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/924,703

(22) Filed: Jun. 24, 2013

(65) Prior Publication Data

US 2014/0155981 A1 Jun. 5, 2014

Related U.S. Application Data

(63) Continuation of application No. 13/281,363, filed on Oct. 25, 2011, now Pat. No. 8,585,713, which is a continuation-in-part of application No. 12/980,039, filed on Dec. 28, 2010, now Pat. No. 8,066,757, which (Continued)

(51) Int. Cl.
*A61B 17/22* (2006.01)
*A61F 2/91* (2013.01)
(Continued)

(52) U.S. Cl.
CPC ... *A61F 2/91* (2013.01); *A61F 2/01* (2013.01); *A61F 2/95* (2013.01); *A61F 2002/016* (2013.01);
(Continued)

(58) Field of Classification Search
CPC .............. A61B 17/12109; A61B 17/12168; A61F 2/02; A61F 2/06; A61F 2/82; A61F 2/86; A61F 2/90; A61F 2/91
USPC ............ 604/93.01, 96.01, 507; 606/127, 191, 606/192, 194, 200; 623/1.1, 1.12, 1.15, 623/1.16, 1.36, 1.39, 1.4
See application file for complete search history.

(56) References Cited

U.S. PATENT DOCUMENTS

| | | | |
|---|---|---|---|
| 2,709,999 A | 6/1955 | Nagel | |
| 3,174,851 A | 3/1965 | Buehler et al. | |

(Continued)

FOREIGN PATENT DOCUMENTS

| | | |
|---|---|---|
| AU | 2008345624 | 7/2009 |
| AU | 2008352581 | 9/2009 |

(Continued)

OTHER PUBLICATIONS

"Penumbra, Inc. Enrolls First Patients in Pulse Clinical Trial to Evaluate a Fully Retrievable, Dense Mesh Temporary Stent for Immediate Flow Restoration in Interventional Acute Ischemic Stroke Treatment," Business Wire, Nov. 1, 2010, downloaded at http://www.businesswire.com/news/home/20101101006991/en/Penumbra-Enrolls-- Patients-PULSE-Clinical-Trial-Evaluate. WO.

(Continued)

*Primary Examiner* — Ashley Fishback
(74) *Attorney, Agent, or Firm* — Mark J. Kertz, Esq.

(57) ABSTRACT

Systems, methods, and devices for the treatment of acute ischemic stroke that provide immediate blood flow restoration to a vessel occluded by a clot and, after reestablishing blood flow, address the clot itself. Immediate blood flow restoration advantageously can facilitate natural lysis of the clot and also can reduce or obviate the concern for distal embolization due to fragmentation of the clot. Several embodiments of the invention provide for progressive, or modular, treatment based upon the nature of the clot. For example, the progressive treatment can include immediate restoration of blood flow, in-situ clot management, and/or clot removal depending on the particular circumstances of the treatment. The in-situ clot management can include, for example, lysis, maceration, and/or removal.

20 Claims, 70 Drawing Sheets

Related U.S. Application Data is a continuation-in-part of application No. 12/651,353, filed on Dec. 31, 2009, which is a continuation-in-part of application No. 12/123,390, filed on May 19, 2008, said application No. 13/281,363 is a continuation of application No. 13/172,778, and a continuation-in-part of application No. PCT/US2010/062532, filed on Dec. 30, 2010, and a continuation-in-part of application No. 12/136,737, filed on Jun. 10, 2008, and a continuation-in-part of application No. 12/182,370, filed on Jul. 30, 2008, and a continuation-in-part of application No. 12/422,105, filed on Apr. 10, 2009, now Pat. No. 8,545,514, and a continuation-in-part of application No. 12/475,389, filed on May 29, 2009, now Pat. No. 8,088,140, said application No. 13/172,778 is a continuation-in-part of application No. 12/711,100, filed on Feb. 23, 2010, and a continuation-in-part of application No. 12/753,812, filed on Apr. 2, 2010.

(60) Provisional application No. 60/980,736, filed on Oct. 17, 2007, provisional application No. 60/987,384, filed on Nov. 12, 2007, provisional application No. 60/989,422, filed on Nov. 20, 2007, provisional application No. 61/015,154, filed on Dec. 19, 2007, provisional application No. 61/019,506, filed on Jan. 7, 2008, provisional application No. 61/044,392, filed on Apr. 11, 1008, provisional application No. 61/057,613, filed on May 30, 2008, provisional application No. 61/166,725, filed on Apr. 4, 2009.

(51) Int. Cl.
*A61F 2/01* (2006.01)
*A61F 2/95* (2013.01)

(52) U.S. Cl.
CPC ... *A61F 2002/018* (2013.01); *A61F 2230/0006* (2013.01); *A61F 2230/0067* (2013.01); *A61F 2230/0069* (2013.01); *A61F 2230/0091* (2013.01); *A61F 2230/0093* (2013.01); *A61F 2230/0097* (2013.01)
USPC ..................................................... 606/127

(56) References Cited

U.S. PATENT DOCUMENTS

| | | | |
|---|---|---|---|
| 3,351,463 A | 11/1967 | Rozner | |
| 3,506,171 A | 4/1970 | Rupert | |
| 3,753,700 A | 8/1973 | Harrison et al. | |
| 4,650,466 A | 3/1987 | Luther | |
| 4,993,481 A | 2/1991 | Kamimoto | |
| 4,998,539 A | 3/1991 | Delsanti | |
| 5,035,686 A | 7/1991 | Crittenden | |
| 5,057,114 A | 10/1991 | Wittich | |
| 5,222,964 A | 6/1993 | Cooper | |
| 5,222,971 A | 6/1993 | Willard et al. | |
| 5,275,622 A | 1/1994 | Lazarus et al. | |
| 5,327,885 A | 7/1994 | Griffith | |
| 5,344,395 A | 9/1994 | Whalen et al. | |
| 5,370,653 A | 12/1994 | Cragg | |
| 5,425,739 A | 6/1995 | Jessen | |
| 5,449,372 A | 9/1995 | Schmaltz et al. | |
| 5,456,667 A | 10/1995 | Ham et al. | |
| 5,527,282 A | 6/1996 | Segal | |
| 5,643,309 A | 7/1997 | Myler et al. | |
| 5,649,906 A | 7/1997 | Gory et al. | |
| 5,653,743 A | 8/1997 | Martin | |
| 5,681,336 A | 10/1997 | Clement et al. | |
| 5,683,449 A | 11/1997 | Marcade | |
| 5,695,469 A | 12/1997 | Segal | |
| 5,718,724 A | 2/1998 | Goicoechea et al. | |
| 5,792,157 A | 8/1998 | Mische et al. | |
| 5,795,322 A | 8/1998 | Boudewijn | |
| 5,800,457 A | 9/1998 | Gelbfish | |
| 5,800,519 A | 9/1998 | Sandock | |
| 5,827,324 A | 10/1998 | Cassell et al. | |
| 5,853,419 A | 12/1998 | Imran | |
| 5,916,235 A | 6/1999 | Guglielmi | |
| 5,922,019 A | 7/1999 | Hankh et al. | |
| 5,928,260 A | 7/1999 | Chin et al. | |
| 5,938,671 A | 8/1999 | Katoh et al. | |
| 5,938,697 A | 8/1999 | Killion et al. | |
| 5,941,895 A | 8/1999 | Myler et al. | |
| 5,947,995 A | 9/1999 | Samuels | |
| 5,951,599 A | 9/1999 | McCrory | |
| 5,961,547 A | 10/1999 | Razavi | |
| 5,968,013 A | 10/1999 | Smith et al. | |
| 5,972,016 A | 10/1999 | Morales | |
| 5,972,019 A | 10/1999 | Engelson et al. | |
| 5,972,219 A | 10/1999 | Habets et al. | |
| 5,976,120 A | 11/1999 | Chow et al. | |
| 5,980,514 A | 11/1999 | Kupiecki et al. | |
| 6,001,118 A | 12/1999 | Daniel et al. | |
| 6,010,449 A | 1/2000 | Selmon et al. | |
| 6,010,498 A | 1/2000 | Guglielmi | |
| 6,010,521 A | 1/2000 | Lee et al. | |
| 6,039,721 A | 3/2000 | Johnson | |
| 6,051,020 A | 4/2000 | Goicoechea et al. | |
| 6,063,070 A | 5/2000 | Eder | |
| 6,063,104 A | 5/2000 | Villar et al. | |
| 6,063,111 A | 5/2000 | Hieshima et al. | |
| 6,066,149 A | 5/2000 | Samson et al. | |
| 6,066,158 A | 5/2000 | Engelson et al. | |
| 6,093,199 A | 7/2000 | Brown et al. | |
| 6,096,034 A | 8/2000 | Kupiecki et al. | |
| 6,106,548 A | 8/2000 | Roubin et al. | |
| 6,117,167 A | 9/2000 | Goicoechea et al. | |
| 6,123,115 A | 9/2000 | Greenhalgh | |
| 6,136,006 A | 10/2000 | Johnson et al. | |
| 6,146,396 A | 11/2000 | Konya et al. | |
| 6,159,238 A | 12/2000 | Killion et al. | |
| 6,159,239 A | 12/2000 | Greenhalgh | |
| 6,164,339 A | 12/2000 | Greenhalgh | |
| 6,168,592 B1 | 1/2001 | Kupiecki et al. | |
| 6,168,604 B1 | 1/2001 | Cano | |
| 6,190,358 B1 | 2/2001 | Fitzmaurice et al. | |
| 6,192,944 B1 | 2/2001 | Greenhalgh | |
| 6,193,708 B1 | 2/2001 | Ken et al. | |
| 6,210,364 B1 | 4/2001 | Anderson et al. | |
| 6,217,609 B1 | 4/2001 | Haverkost | |
| 6,221,096 B1 | 4/2001 | Aiba et al. | |
| 6,231,598 B1 | 5/2001 | Berry et al. | |
| 6,238,430 B1 | 5/2001 | Klumb et al. | |
| 6,280,413 B1 | 8/2001 | Clark et al. | |
| 6,283,940 B1 | 9/2001 | Mulholland | |
| 6,283,992 B1 | 9/2001 | Hankh et al. | |
| 6,290,720 B1 | 9/2001 | Khosravi et al. | |
| 6,302,906 B1 | 10/2001 | Goicoechea et al. | |
| 6,305,436 B1 | 10/2001 | Andersen et al. | |
| 6,306,141 B1 | 10/2001 | Jervis | |
| 6,322,585 B1 | 11/2001 | Khosravi et al. | |
| 6,325,815 B1 | 12/2001 | Kusleika et al. | |
| 6,325,820 B1 | 12/2001 | Khosravi et al. | |
| 6,325,822 B1 | 12/2001 | Chouinard et al. | |
| 6,344,041 B1 | 2/2002 | Kupiecki et al. | |
| 6,383,205 B1 | 5/2002 | Samson et al. | |
| 6,390,993 B1 | 5/2002 | Cornish et al. | |
| 6,402,771 B1 | 6/2002 | Palmer et al. | |
| 6,454,780 B1 | 9/2002 | Wallace | |
| 6,458,139 B1 | 10/2002 | Palmer et al. | |
| 6,468,301 B1 | 10/2002 | Amplatz et al. | |
| 6,475,236 B1 | 11/2002 | Roubin et al. | |
| 6,475,237 B2 | 11/2002 | Drasler et al. | |
| 6,485,500 B1 | 11/2002 | Kokish et al. | |
| 6,485,509 B2 | 11/2002 | Killion et al. | |
| 6,537,294 B1 | 3/2003 | Boyle et al. | |
| 6,551,341 B2 | 4/2003 | Boylan et al. | |
| 6,551,342 B1 | 4/2003 | Shen et al. | |
| 6,553,810 B2 | 4/2003 | Webb et al. | |

(56) References Cited

U.S. PATENT DOCUMENTS

| | | |
|---|---|---|
| 6,554,856 B1 | 4/2003 | Doorly et al. |
| 6,558,405 B1 | 5/2003 | McInnes |
| 6,562,066 B1 | 5/2003 | Martin |
| 6,569,179 B2 | 5/2003 | Teoh et al. |
| 6,569,193 B1 | 5/2003 | Cox et al. |
| 6,575,997 B1 | 6/2003 | Palmer et al. |
| 6,589,265 B1 | 7/2003 | Palmer et al. |
| 6,592,607 B1 | 7/2003 | Palmer et al. |
| 6,592,615 B1 | 7/2003 | Marcade et al. |
| 6,605,057 B2 | 8/2003 | Fitzmaurice et al. |
| 6,610,077 B1 | 8/2003 | Hancock et al. |
| 6,629,953 B1 | 10/2003 | Boyd |
| 6,632,241 B1 | 10/2003 | Hancock et al. |
| 6,635,081 B2 | 10/2003 | Khosravi et al. |
| 6,638,294 B1 | 10/2003 | Palmer |
| 6,641,590 B1 | 11/2003 | Palmer et al. |
| 6,652,505 B1 | 11/2003 | Tsugita |
| 6,652,576 B1 | 11/2003 | Stalker |
| 6,660,021 B1 | 12/2003 | Palmer et al. |
| 6,663,607 B2 | 12/2003 | Slaikeu et al. |
| 6,666,829 B2 | 12/2003 | Cornish et al. |
| 6,669,723 B2 | 12/2003 | Killion et al. |
| 6,673,025 B1 | 1/2004 | Richardson et al. |
| 6,685,722 B1 | 2/2004 | Rosenbluth et al. |
| 6,685,738 B2 | 2/2004 | Chouinard et al. |
| 6,695,813 B1 | 2/2004 | Boyle et al. |
| 6,702,843 B1 | 3/2004 | Brown et al. |
| 6,709,440 B2 | 3/2004 | Callol et al. |
| 6,716,178 B1 | 4/2004 | Kilpatrick et al. |
| 6,723,112 B2 | 4/2004 | Ho et al. |
| 6,730,104 B1 | 5/2004 | Sepetka et al. |
| 6,733,519 B2 | 5/2004 | Lashinski et al. |
| 6,746,468 B1 | 6/2004 | Sepetka et al. |
| 6,764,506 B2 | 7/2004 | Roubin et al. |
| 6,773,454 B2 | 8/2004 | Wholey et al. |
| 6,790,237 B2 | 9/2004 | Stinson |
| 6,795,979 B2 | 9/2004 | Fournier |
| 6,802,851 B2 | 10/2004 | Jones et al. |
| 6,818,015 B2 | 11/2004 | Hankh et al. |
| 6,821,291 B2 | 11/2004 | Bolea et al. |
| 6,824,558 B2 | 11/2004 | Parodi |
| 6,833,003 B2 | 12/2004 | Jones et al. |
| 6,840,958 B2 | 1/2005 | Nunez et al. |
| 6,881,220 B2 | 4/2005 | Edwin et al. |
| 6,893,413 B2 | 5/2005 | Martin |
| 6,913,612 B2 | 7/2005 | Palmer et al. |
| 6,949,620 B2 | 9/2005 | Aida et al. |
| 6,953,472 B2 | 10/2005 | Palmer et al. |
| 6,955,685 B2 | 10/2005 | Escamilla et al. |
| 6,960,227 B2 | 11/2005 | Jones et al. |
| 6,991,641 B2 | 1/2006 | Diaz et al. |
| 6,994,723 B1 | 2/2006 | McMahon |
| 7,001,422 B2 | 2/2006 | Escamilla et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,018,401 B1 | 3/2006 | Hyodoh et al. |
| 7,029,688 B2 | 4/2006 | Hubbell et al. |
| 7,037,329 B2 | 5/2006 | Martin |
| 7,041,116 B2 | 5/2006 | Goto et al. |
| 7,048,014 B2 | 5/2006 | Hyodoh et al. |
| 7,056,328 B2 | 6/2006 | Arnott |
| 7,056,336 B2 | 6/2006 | Armstrong et al. |
| 7,060,091 B2 | 6/2006 | Killion et al. |
| 7,089,218 B1 | 8/2006 | Visel |
| 7,112,217 B1 | 9/2006 | Kugler et al. |
| 7,118,600 B2 | 10/2006 | Dua et al. |
| 7,125,419 B2 | 10/2006 | Sequin et al. |
| 7,128,736 B1 | 10/2006 | Abrams et al. |
| 7,144,421 B2 | 12/2006 | Carpenter et al. |
| 7,147,655 B2 | 12/2006 | Chermoni |
| 7,147,660 B2 | 12/2006 | Chobotov et al. |
| 7,156,869 B1 | 1/2007 | Pacetti |
| 7,160,317 B2 | 1/2007 | McHale et al. |
| 7,169,165 B2 | 1/2007 | Belef et al. |
| 7,172,575 B2 | 2/2007 | El-Nounou et al. |
| 7,172,617 B2 | 2/2007 | Colgan et al. |
| 7,175,607 B2 | 2/2007 | Lim et al. |
| 7,179,273 B1 | 2/2007 | Palmer et al. |
| 7,179,284 B2 | 2/2007 | Khosravi et al. |
| 7,201,769 B2 | 4/2007 | Jones et al. |
| 7,201,770 B2 | 4/2007 | Johnson et al. |
| 7,223,284 B2 | 5/2007 | Khosravi et al. |
| 7,238,197 B2 | 7/2007 | Sequin et al. |
| 7,240,516 B2 | 7/2007 | Pryor |
| 7,241,301 B2 | 7/2007 | Thramann et al. |
| 7,279,003 B2 | 10/2007 | Berra et al. |
| 7,279,292 B2 | 10/2007 | Imam et al. |
| 7,285,126 B2 | 10/2007 | Sepetka et al. |
| 7,294,147 B2 | 11/2007 | Hartley |
| 7,300,458 B2 | 11/2007 | Henkes et al. |
| 7,306,619 B1 | 12/2007 | Palmer |
| 7,309,345 B2 | 12/2007 | Wallace |
| 7,309,351 B2 | 12/2007 | Escamilla et al. |
| 7,323,000 B2 | 1/2008 | Monstdt et al. |
| 7,323,005 B2 | 1/2008 | Wallace et al. |
| 7,323,006 B2 | 1/2008 | Andreas et al. |
| 7,326,240 B1 | 2/2008 | Caro et al. |
| 7,344,550 B2 | 3/2008 | Carrison et al. |
| 7,344,556 B2 | 3/2008 | Seguin et al. |
| 7,351,255 B2 | 4/2008 | Andreas |
| 7,354,455 B2 | 4/2008 | Stinson |
| 7,402,169 B2 | 7/2008 | Killion et al. |
| 7,407,509 B2 | 8/2008 | Greenberg et al. |
| 7,435,254 B2 | 10/2008 | Chouinard et al. |
| 7,438,720 B2 | 10/2008 | Shaked |
| 7,455,646 B2 | 11/2008 | Richardson et al. |
| 7,473,272 B2 | 1/2009 | Pryor |
| 7,494,474 B2 | 2/2009 | Richardson et al. |
| 7,549,974 B2 | 6/2009 | Nayak |
| 7,691,122 B2 | 4/2010 | Dieck et al. |
| 7,727,242 B2 | 6/2010 | Sepetka et al. |
| 7,727,243 B2 | 6/2010 | Sepetka et al. |
| 7,749,243 B2 | 7/2010 | Phung et al. |
| 7,780,694 B2 | 8/2010 | Palmer et al. |
| 7,833,240 B2 | 11/2010 | Okushi et al. |
| 7,972,342 B2 | 7/2011 | Gandhi et al. |
| 8,052,640 B2 | 11/2011 | Fiorella et al. |
| 8,062,307 B2 | 11/2011 | Sepetka et al. |
| 8,066,757 B2 | 11/2011 | Ferrera |
| 8,070,791 B2 | 12/2011 | Ferrera |
| 8,088,140 B2 | 1/2012 | Ferrera |
| 8,100,918 B2 | 1/2012 | Gandhi et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 8,574,262 B2 | 11/2013 | Ferrera et al. |
| 8,585,713 B2 | 11/2013 | Ferrera et al. |
| 2001/0000797 A1 | 5/2001 | Mazzocchi |
| 2001/0004705 A1 | 6/2001 | Killion et al. |
| 2001/0010013 A1 | 7/2001 | Cox et al. |
| 2001/0031981 A1 | 10/2001 | Evans et al. |
| 2001/0034531 A1 | 10/2001 | Ho et al. |
| 2001/0044633 A1 | 11/2001 | Klint |
| 2001/0044647 A1 | 11/2001 | Pinchuk et al. |
| 2001/0047202 A1 | 11/2001 | Slaikeu et al. |
| 2001/0051823 A1 | 12/2001 | Khosravi et al. |
| 2002/0004681 A1 | 1/2002 | Teoh et al. |
| 2002/0007210 A1 | 1/2002 | Chouinard et al. |
| 2002/0016564 A1 | 2/2002 | Courtney et al. |
| 2002/0016624 A1 | 2/2002 | Patterson et al. |
| 2002/0032479 A1 | 3/2002 | Hankh et al. |
| 2002/0038142 A1 | 3/2002 | Khosravi et al. |
| 2002/0038146 A1 | 3/2002 | Harry |
| 2002/0052643 A1 | 5/2002 | Wholey et al. |
| 2002/0068968 A1 | 6/2002 | Hupp |
| 2002/0072790 A1 | 6/2002 | McGuckin et al. |
| 2002/0087209 A1 | 7/2002 | Edwin et al. |
| 2002/0091355 A1 | 7/2002 | Hayden |
| 2002/0095141 A1 | 7/2002 | Belef et al. |
| 2002/0143387 A1 | 10/2002 | Soetikno et al. |
| 2002/0161377 A1 | 10/2002 | Rabkin |
| 2002/0169458 A1 | 11/2002 | Connors |
| 2002/0183831 A1 | 12/2002 | Rolando et al. |

(56) References Cited

U.S. PATENT DOCUMENTS

| | | |
|---|---|---|
| 2002/0198588 A1 | 12/2002 | Armstrong et al. |
| 2003/0004536 A1 | 1/2003 | Boylan et al. |
| 2003/0023230 A1 | 1/2003 | Lewis et al. |
| 2003/0023299 A1 | 1/2003 | Amplatz et al. |
| 2003/0032941 A1 | 2/2003 | Boyle et al. |
| 2003/0032977 A1 | 2/2003 | Brady |
| 2003/0040771 A1 | 2/2003 | Hyodoh et al. |
| 2003/0040772 A1 | 2/2003 | Hyodoh et al. |
| 2003/0055440 A1 | 3/2003 | Jones et al. |
| 2003/0055451 A1 | 3/2003 | Jones et al. |
| 2003/0074056 A1 | 4/2003 | Killion et al. |
| 2003/0078605 A1 | 4/2003 | Bashiri et al. |
| 2003/0097114 A1 | 5/2003 | Ouriel et al. |
| 2003/0105484 A1 | 6/2003 | Boyle et al. |
| 2003/0125791 A1 | 7/2003 | Sequin et al. |
| 2003/0125798 A1 | 7/2003 | Martin |
| 2003/0130719 A1 | 7/2003 | Martin |
| 2003/0139796 A1 | 7/2003 | Sequin et al. |
| 2003/0139803 A1 | 7/2003 | Sequin et al. |
| 2003/0149475 A1 | 8/2003 | Hyodoh et al. |
| 2003/0153944 A1 | 8/2003 | Phung et al. |
| 2003/0176914 A1 | 9/2003 | Rabkin et al. |
| 2003/0199921 A1 | 10/2003 | Palmer et al. |
| 2003/0204202 A1 | 10/2003 | Palmer et al. |
| 2004/0002752 A1 | 1/2004 | Griffin et al. |
| 2004/0006306 A1 | 1/2004 | Evans et al. |
| 2004/0006381 A1 | 1/2004 | Sequin et al. |
| 2004/0019322 A1 | 1/2004 | Hoffmann |
| 2004/0030378 A1 | 2/2004 | Khosravi et al. |
| 2004/0034386 A1 | 2/2004 | Fulton et al. |
| 2004/0049258 A1 | 3/2004 | Khosravi et al. |
| 2004/0054367 A1 | 3/2004 | Jimenez et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0073300 A1 | 4/2004 | Chouinard et al. |
| 2004/0078071 A1 | 4/2004 | Escamilla et al. |
| 2004/0079429 A1 | 4/2004 | Miller et al. |
| 2004/0088002 A1 | 5/2004 | Boyle et al. |
| 2004/0102838 A1 | 5/2004 | Killion et al. |
| 2004/0106979 A1 | 6/2004 | Goicoechea et al. |
| 2004/0114912 A1 | 6/2004 | Okamoto et al. |
| 2004/0117003 A1 | 6/2004 | Ouriel et al. |
| 2004/0147939 A1 | 7/2004 | Rabkin et al. |
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193246 A1 | 9/2004 | Ferrera |
| 2004/0199201 A1 | 10/2004 | Kellett et al. |
| 2004/0215312 A1 | 10/2004 | Andreas |
| 2004/0215319 A1 | 10/2004 | Berra et al. |
| 2004/0249439 A1 | 12/2004 | Richter et al. |
| 2004/0254628 A1 | 12/2004 | Nazzaro et al. |
| 2004/0260385 A1 | 12/2004 | Jones et al. |
| 2005/0033334 A1 | 2/2005 | Santra et al. |
| 2005/0033349 A1 | 2/2005 | Jones et al. |
| 2005/0033409 A1 | 2/2005 | Burke et al. |
| 2005/0038447 A1 | 2/2005 | Huffmaster |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0060017 A1 | 3/2005 | Fischell et al. |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman et al. |
| 2005/0125023 A1 | 6/2005 | Bates et al. |
| 2005/0126979 A1 | 6/2005 | Lowe et al. |
| 2005/0131515 A1 | 6/2005 | Cully et al. |
| 2005/0131516 A1 | 6/2005 | Greenhalgh |
| 2005/0159774 A1 | 7/2005 | Belef |
| 2005/0177228 A1 | 8/2005 | Solem et al. |
| 2005/0187612 A1 | 8/2005 | Edwin |
| 2005/0192661 A1 | 9/2005 | Griffen et al. |
| 2005/0209673 A1 | 9/2005 | Shaked |
| 2005/0209675 A1 | 9/2005 | Ton et al. |
| 2005/0209678 A1 | 9/2005 | Henkes et al. |
| 2005/0216050 A1 | 9/2005 | Sepetka et al. |
| 2005/0222583 A1 | 10/2005 | Cano et al. |
| 2005/0222607 A1 | 10/2005 | Palmer et al. |
| 2005/0267570 A1 | 12/2005 | Shadduck |
| 2005/0277978 A1 | 12/2005 | Greenhalgh |
| 2006/0020285 A1 | 1/2006 | Niermann |
| 2006/0020321 A1 | 1/2006 | Parker |
| 2006/0025845 A1 | 2/2006 | Escamilla et al. |
| 2006/0025850 A1 | 2/2006 | Feller et al. |
| 2006/0030865 A1 | 2/2006 | Balg |
| 2006/0036281 A1 | 2/2006 | Patterson et al. |
| 2006/0052816 A1 | 3/2006 | Bates et al. |
| 2006/0058833 A1 | 3/2006 | VanCamp et al. |
| 2006/0058836 A1 | 3/2006 | Bose et al. |
| 2006/0058838 A1 | 3/2006 | Bose et al. |
| 2006/0074480 A1 | 4/2006 | Bales et al. |
| 2006/0089703 A1 | 4/2006 | Escamilla et al. |
| 2006/0100663 A1 | 5/2006 | Palmer et al. |
| 2006/0106421 A1 | 5/2006 | Teoh |
| 2006/0106448 A1 | 5/2006 | Shaked |
| 2006/0122685 A1 | 6/2006 | Bonsignore et al. |
| 2006/0135947 A1 | 6/2006 | Soltesz et al. |
| 2006/0142841 A1 | 6/2006 | Khosravi et al. |
| 2006/0142849 A1 | 6/2006 | Killion et al. |
| 2006/0195172 A1 | 8/2006 | Luo et al. |
| 2006/0200048 A1 | 9/2006 | Furst et al. |
| 2006/0200221 A1 | 9/2006 | Malewicz |
| 2006/0224180 A1 | 10/2006 | Anderson et al. |
| 2006/0229645 A1 | 10/2006 | Bonnette et al. |
| 2006/0259119 A1 | 11/2006 | Rucker |
| 2006/0265054 A1 | 11/2006 | Greenhalgh et al. |
| 2006/0271090 A1 | 11/2006 | Shaked et al. |
| 2006/0276883 A1 | 12/2006 | Greenberg et al. |
| 2006/0287701 A1 | 12/2006 | Pal |
| 2006/0287704 A1 | 12/2006 | Hartley et al. |
| 2007/0032852 A1 | 2/2007 | Machek et al. |
| 2007/0043424 A1 | 2/2007 | Pryor |
| 2007/0043425 A1 | 2/2007 | Hartley et al. |
| 2007/0055299 A1 | 3/2007 | Ishimaru et al. |
| 2007/0055358 A1 | 3/2007 | Krolik et al. |
| 2007/0055360 A1 | 3/2007 | Hanson et al. |
| 2007/0055365 A1 | 3/2007 | Greenberg et al. |
| 2007/0067011 A1 | 3/2007 | Krolik et al. |
| 2007/0073376 A1 | 3/2007 | Krolik et al. |
| 2007/0088387 A1 | 4/2007 | Eskridge et al. |
| 2007/0100425 A1 | 5/2007 | Sequin et al. |
| 2007/0118205 A1 | 5/2007 | Davidson et al. |
| 2007/0123972 A1 | 5/2007 | Greenberg et al. |
| 2007/0135888 A1 | 6/2007 | Khosravi et al. |
| 2007/0141036 A1 | 6/2007 | Gorrochategui Barrueta et al. |
| 2007/0142896 A1 | 6/2007 | Anderson et al. |
| 2007/0156170 A1 | 7/2007 | Hancock et al. |
| 2007/0156228 A1 | 7/2007 | Majercak et al. |
| 2007/0162109 A1 | 7/2007 | Davila et al. |
| 2007/0191866 A1 | 8/2007 | Palmer et al. |
| 2007/0191884 A1 | 8/2007 | Eskridge et al. |
| 2007/0191924 A1 | 8/2007 | Rudakov |
| 2007/0198028 A1 | 8/2007 | Miloslavski et al. |
| 2007/0198030 A1 | 8/2007 | Martin et al. |
| 2007/0198075 A1 | 8/2007 | Levy |
| 2007/0203452 A1 | 8/2007 | Mehta |
| 2007/0203559 A1 | 8/2007 | Freudenthal et al. |
| 2007/0208367 A1 | 9/2007 | Fiorella et al. |
| 2007/0208371 A1 | 9/2007 | French et al. |
| 2007/0219621 A1 | 9/2007 | Hartley et al. |
| 2007/0225794 A1 | 9/2007 | Thramann et al. |
| 2007/0233236 A1 | 10/2007 | Pryor |
| 2007/0250040 A1 | 10/2007 | Provost et al. |
| 2007/0266542 A1 | 11/2007 | Melsheimer |
| 2007/0270932 A1 | 11/2007 | Headley et al. |
| 2007/0288034 A1 | 12/2007 | MacCollum et al. |
| 2007/0288037 A1 | 12/2007 | Cheng et al. |
| 2007/0288080 A1 | 12/2007 | Maccollum et al. |
| 2007/0288083 A1 | 12/2007 | Hines |

(56) References Cited

U.S. PATENT DOCUMENTS

| | | |
|---|---|---|
| 2007/0299503 A1 | 12/2007 | Berra et al. |
| 2008/0001333 A1 | 1/2008 | Kleine et al. |
| 2008/0015558 A1 | 1/2008 | Harlan |
| 2008/0015682 A1 | 1/2008 | Majercak et al. |
| 2008/0033528 A1 | 2/2008 | Satasiya et al. |
| 2008/0039926 A1 | 2/2008 | Majercak et al. |
| 2008/0039930 A1 | 2/2008 | Jones et al. |
| 2008/0045995 A1 | 2/2008 | Guterman et al. |
| 2008/0046064 A1 | 2/2008 | Sequin et al. |
| 2008/0046072 A1 | 2/2008 | Laborde et al. |
| 2008/0051803 A1 | 2/2008 | Monjtadt et al. |
| 2008/0058724 A1 | 3/2008 | Wallace |
| 2008/0071178 A1 | 3/2008 | Greenland et al. |
| 2008/0077175 A1 | 3/2008 | Palmer |
| 2008/0082159 A1 | 4/2008 | Tseng et al. |
| 2008/0086196 A1 | 4/2008 | Truckai et al. |
| 2008/0097495 A1 | 4/2008 | Feller, III et al. |
| 2008/0103477 A1 | 5/2008 | Jones |
| 2008/0103585 A1 | 5/2008 | Monstadt et al. |
| 2008/0109063 A1 | 5/2008 | Hancock et al. |
| 2008/0109067 A1 | 5/2008 | Caro et al. |
| 2008/0114445 A1 | 5/2008 | Melsheimer et al. |
| 2008/0125855 A1 | 5/2008 | Henkes et al. |
| 2008/0140107 A1 | 6/2008 | Bei et al. |
| 2008/0140181 A1 | 6/2008 | Reynolds et al. |
| 2008/0147100 A1 | 6/2008 | Wallace |
| 2008/0161903 A1 | 7/2008 | Sequin et al. |
| 2008/0161936 A1 | 7/2008 | Feller et al. |
| 2008/0167708 A1 | 7/2008 | Molland et al. |
| 2008/0195140 A1 | 8/2008 | Myla et al. |
| 2008/0200946 A1 | 8/2008 | Braun et al. |
| 2008/0208319 A1 | 8/2008 | Rabkin et al. |
| 2008/0221554 A1 | 9/2008 | O'Connor et al. |
| 2008/0221600 A1 | 9/2008 | Dieck et al. |
| 2008/0221664 A1 | 9/2008 | Bales et al. |
| 2008/0221671 A1 | 9/2008 | Chouinard et al. |
| 2008/0228216 A1 | 9/2008 | Strauss et al. |
| 2008/0234795 A1 | 9/2008 | Snow et al. |
| 2008/0243229 A1 | 10/2008 | Wallace et al. |
| 2008/0243232 A1 | 10/2008 | Hegg et al. |
| 2008/0247943 A1 | 10/2008 | Lanza et al. |
| 2008/0249598 A1 | 10/2008 | Sherry |
| 2008/0255678 A1 | 10/2008 | Cully et al. |
| 2008/0262506 A1 | 10/2008 | Griffin et al. |
| 2008/0262528 A1 | 10/2008 | Martin |
| 2008/0262532 A1 | 10/2008 | Martin |
| 2008/0262592 A1 | 10/2008 | Jordan et al. |
| 2008/0269774 A1 | 10/2008 | Garcia et al. |
| 2008/0269868 A1 | 10/2008 | Bei et al. |
| 2008/0275497 A1 | 11/2008 | Palmer et al. |
| 2008/0275498 A1 | 11/2008 | Palmer et al. |
| 2008/0275536 A1 | 11/2008 | Zarins et al. |
| 2008/0281302 A1 | 11/2008 | Murphy et al. |
| 2008/0281350 A1 | 11/2008 | Sepetka et al. |
| 2008/0281393 A1 | 11/2008 | Armstrong et al. |
| 2008/0281397 A1 | 11/2008 | Killion et al. |
| 2008/0281403 A1 | 11/2008 | Kavteladze |
| 2008/0306503 A1 | 12/2008 | Que et al. |
| 2008/0306504 A1 | 12/2008 | Win et al. |
| 2008/0312732 A1 | 12/2008 | Hartley et al. |
| 2008/0319525 A1 | 12/2008 | Tieu et al. |
| 2008/0319533 A1 | 12/2008 | Lehe |
| 2009/0018633 A1 | 1/2009 | Lindquist et al. |
| 2009/0018634 A1 | 1/2009 | State |
| 2009/0018640 A1 | 1/2009 | State |
| 2009/0024157 A1 | 1/2009 | Anukhin |
| 2009/0025820 A1 | 1/2009 | Adams |
| 2009/0030502 A1 | 1/2009 | Sun et al. |
| 2009/0036968 A1 | 2/2009 | Hepworth et al. |
| 2009/0036977 A1 | 2/2009 | Rassat et al. |
| 2009/0062726 A1 | 3/2009 | Ford et al. |
| 2009/0062773 A1 | 3/2009 | Cornish et al. |
| 2009/0062834 A1 | 3/2009 | Moftakhar et al. |
| 2009/0068097 A1 | 3/2009 | Sevrain |
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0125053 A1 | 5/2009 | Ferrera et al. |
| 2009/0192455 A1 | 7/2009 | Ferrera et al. |
| 2009/0292297 A1 | 11/2009 | Ferrere |
| 2009/0299393 A1 | 12/2009 | Martin et al. |
| 2010/0022951 A1 | 1/2010 | Ferrera et al. |
| 2010/0100106 A1 | 4/2010 | Ferrera |
| 2010/0114017 A1 | 5/2010 | Lenker et al. |
| 2010/0114135 A1 | 5/2010 | Wilson et al. |
| 2010/0137892 A1 | 6/2010 | Krolik et al. |
| 2010/0152766 A1 | 6/2010 | Dieck et al. |
| 2010/0174309 A1 | 7/2010 | Fulkerson et al. |
| 2010/0217187 A1 | 8/2010 | Fulkerson et al. |
| 2010/0256600 A1 | 10/2010 | Ferrera |
| 2010/0299911 A1 | 12/2010 | Gianotti et al. |
| 2010/0318097 A1 | 12/2010 | Ferrera et al. |
| 2011/0009875 A1 | 1/2011 | Grandfield et al. |
| 2011/0009941 A1 | 1/2011 | Grandfield et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0035648 A1 | 2/2012 | Wilson et al. |
| 2012/0041411 A1 | 2/2012 | Horton et al. |
| 2012/0041449 A1 | 2/2012 | Eckhouse et al. |
| 2012/0041459 A1 | 2/2012 | Fiorella et al. |
| 2012/0041460 A1 | 2/2012 | Ferrera et al. |
| 2012/0041464 A1 | 2/2012 | Monetti et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0089216 A1 | 4/2012 | Rapaport et al. |
| 2012/0116443 A1 | 5/2012 | Ferrera et al. |
| 2014/0121758 A1 | 5/2014 | Ferrera et al. |

FOREIGN PATENT DOCUMENTS

| | | |
|---|---|---|
| AU | 2009234268 | 10/2009 |
| CA | 2709999 | 7/2009 |
| CA | 2717790 | 9/2009 |
| CN | 200980110391 | 4/2009 |
| EP | 0321912 B1 | 2/1995 |
| EP | 1000590 | 5/2000 |
| EP | 1437097 | 7/2004 |
| EP | 2217315 A2 | 8/2010 |
| EP | 2234548 A2 | 10/2010 |
| EP | 2237828 A2 | 10/2010 |
| EP | 2271390 A2 | 1/2011 |
| EP | 2257248 B1 | 10/2011 |
| EP | 2301450 B1 | 11/2011 |
| EP | 2417919 A2 | 2/2012 |
| GB | 2463592 | 11/2008 |

(56) References Cited

FOREIGN PATENT DOCUMENTS

| | | |
|---|---|---|
| JP | 2006-094876 A | 4/2006 |
| JP | 2007-236471 A | 9/2007 |
| JP | 2011-50422 | 1/2011 |
| JP | 2011-502655 | 1/2011 |
| JP | 2011-507633 | 3/2011 |
| WO | WO-94/03127 | 2/1994 |
| WO | WO-98/55173 | 12/1998 |
| WO | WO-00/32265 | 6/2000 |
| WO | WO-00/53120 | 9/2000 |
| WO | WO-01/08743 | 2/2001 |
| WO | WO-01/36034 A2 | 5/2001 |
| WO | WO-01/45569 | 6/2001 |
| WO | WO-03/011188 | 2/2003 |
| WO | WO-03/017823 A2 | 3/2003 |
| WO | WO-2007/121005 | 10/2007 |
| WO | WO-2007/089897 A3 | 11/2007 |
| WO | WO-2008/124728 | 10/2008 |
| WO | WO-2008/117256 A3 | 2/2009 |
| WO | WO-2008/117257 A3 | 2/2009 |
| WO | WO-2009/067629 A2 | 5/2009 |
| WO | WO-2009/086154 A2 | 7/2009 |
| WO | WO-2009/089297 A2 | 7/2009 |
| WO | WO-2009/105710 | 8/2009 |
| WO | WO-2009/114046 A2 | 9/2009 |
| WO | WO-2009/124288 | 10/2009 |
| WO | WO-2009/126747 | 10/2009 |
| WO | WO-2009/126935 A2 | 10/2009 |
| WO | WO-2010/010545 | 1/2010 |
| WO | WO-2010/046897 | 4/2010 |
| WO | WO-2010/023671 A3 | 6/2010 |
| WO | WO-2010/062363 | 6/2010 |
| WO | WO-2010/049121 A3 | 7/2010 |
| WO | WO-2010/102307 | 9/2010 |
| WO | WO-2010/115642 | 10/2010 |
| WO | WO-2010/121037 | 10/2010 |
| WO | WO-2010/121049 A9 | 12/2010 |
| WO | WO-2011/054531 A3 | 7/2011 |
| WO | WO-2011/082319 | 7/2011 |
| WO | WO-2011/095352 | 8/2011 |
| WO | WO-2011/133486 | 10/2011 |
| WO | WO-2011/135556 | 11/2011 |
| WO | WO-2011/144336 | 11/2011 |
| WO | WO-2011/147567 | 12/2011 |
| WO | WO-2012/009675 | 1/2012 |
| WO | WO-2012/025245 | 3/2012 |
| WO | WO-2012/025247 | 3/2012 |

OTHER PUBLICATIONS

David M. Pelz, et al., Advances in Interventional Neuroradiology 2007; American Heart Association Journal, Nov. 2007 edition. WO.

Doerfler, A. et al., "A Novel Flexible, Retrievable Endovascular Stent System for Small-Vessel Anatomy: Preliminary In Vivo," Am. J. Neuroradiol. vol. 26, pp. 862-868 (Apr. 2005). WO.

E.I. Levy et al., Self-Expanding Stents for Recanalization of Acute Cerebrovascular Occulsions; AJNR May 28, 2007. WO.

Eric Sauvegeau, MD et al. Middle Cerebral Artery Stenting for Acute Ischemic Stroke After Unsuccessful Merci Retrieval; Special Technical Report; Neurosurgery 60:701-706, 2007. WO.

Henkes, H. et al., "A Microcatheter-Delivered Highly-Flexible and Fully-Retrievable Stent, Specifically Designed for Intracranial Use," Interventional Neuroradiology, vol. 9, pp. 391-393 (Dec. 2003). WO.

Kathy Robertson, Stroke device startup lands National Science Foundation grant, Sacramento Business Journal, Oct. 23, 2009, Sacramento, California. WO.

Liebig, T. et al., "A novel self-expanding fully retrievable intracranial stent (SOLO): experience in nine procedures of stent-assisted aneurysm coil occlusion," Neuroradiology vol. 48, pp. 471-478 (Jul. 2006). WO.

Michael E. Kelly, MD, et al., Recanalization of an Acute Cerebral Artery Occlusion Using a Self-Expanding, Reconstrainable, Intracranial Microstent as a Temporary Endovascular Bypass; AHA Journal, Jun. 2008 edition. WO.

Micro Therapeutics, Inc., DBA EV3 Neurovascular, Inc., Fully deployable. Completely retrievable, Solitaire AB, Neurovascular Remodeling Device. Mar. 2008. WO.

Micro Therapeutics, Inc., DBA EV3 Neurovascular, Inc., Solitaire FR Revascularization Device, Instructions for Use, Rev. Mar. 2009. WO.

Philippa C. Lavallee, et al., Stent-Assisted Endovascular Thrombolysis Versus Intravenous Thrombolysis in Internal Carotid Artery Dissection with Tandem Internal Carotid and Middle Cerebral Artery Occlusion, AHA 2007. WO.

T.W. Duerig, D.E. Tolomeo, M. Wholey, An Overview of Superelastic Stent Design. Min. Invas Ther & Allied Technol 2000: 9(3/4) 235-246. WO.

Wakhloo, et al., "Retrievable Closed Cell Intracranial Stent for Foreign Body and Clot Removal," Neurosurgery, May 2008. WO.

Yavuz, K. et al., "Immediate and midterm follow-up results of using an electrodetachable, fully retrievable SOLO stent system in the endovascular coil occlusion of wide-necked cerebral aneurysms," J. Neurosurg. vol. 107, pp. 49-55 (Jul. 2007). WO.

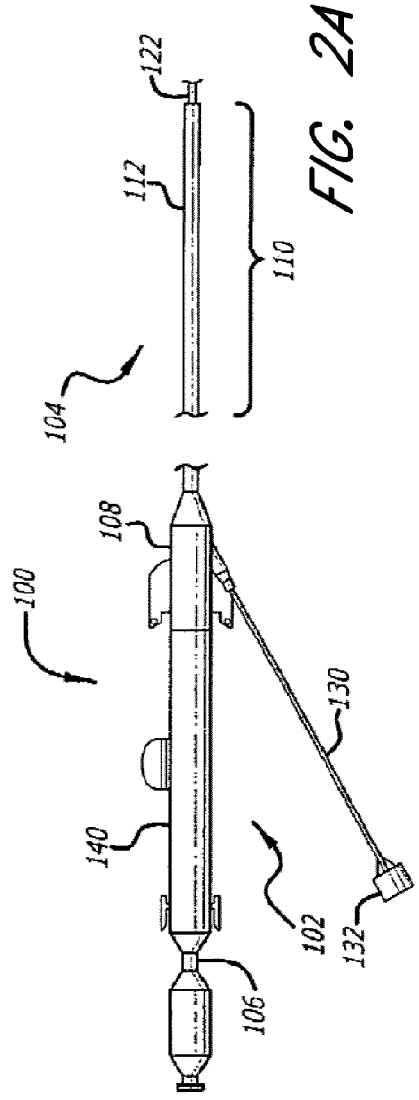
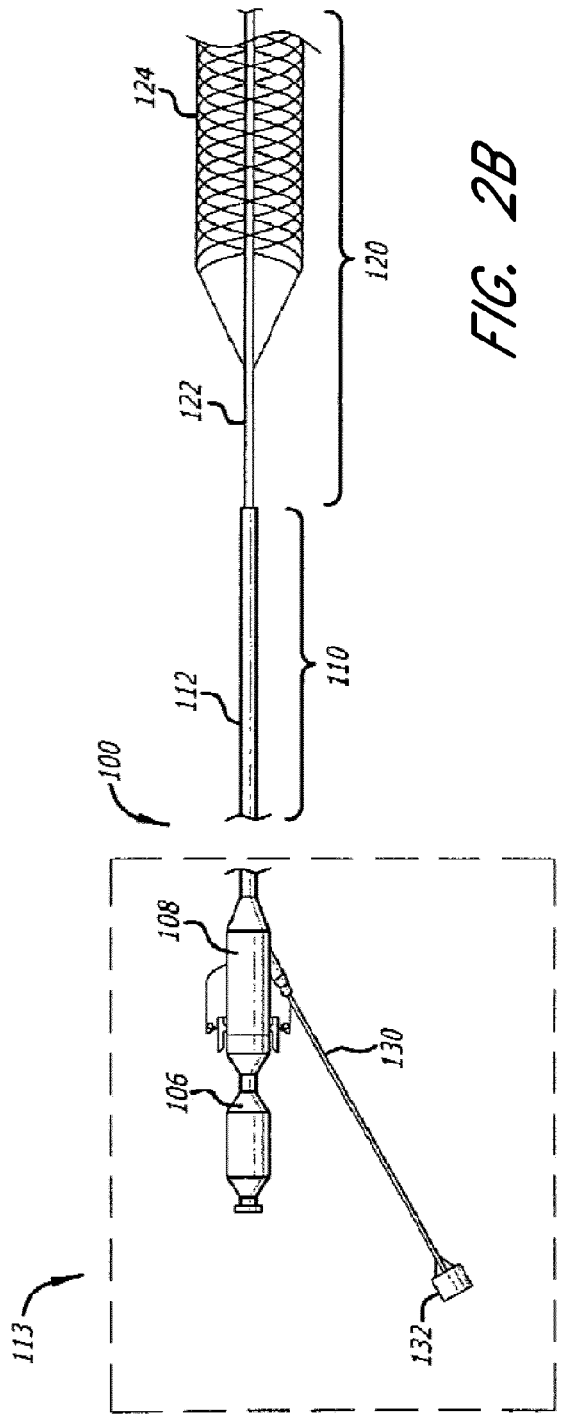

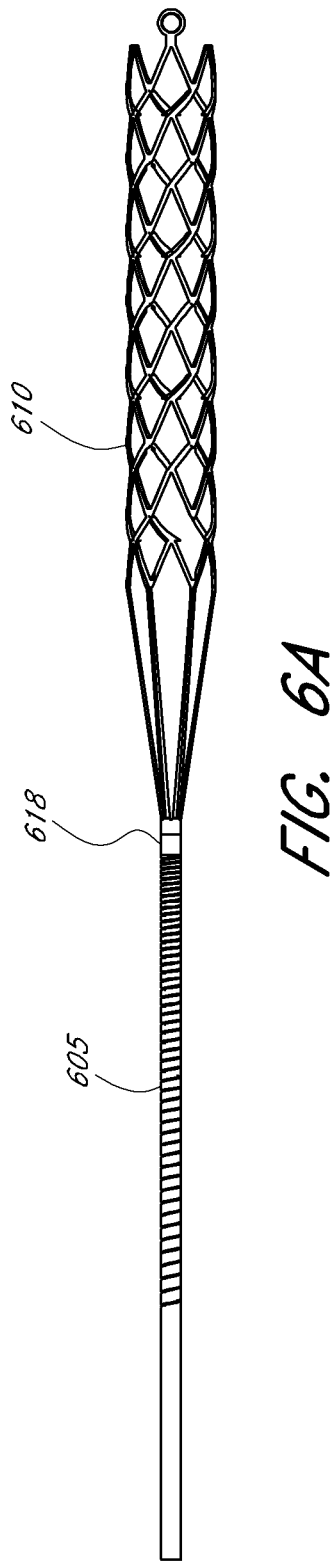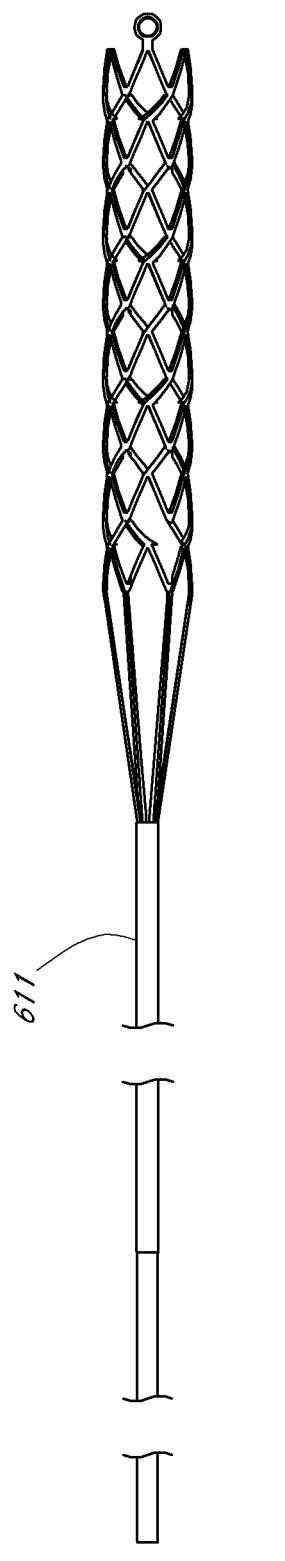
FIG. 6A
FIG. 6B

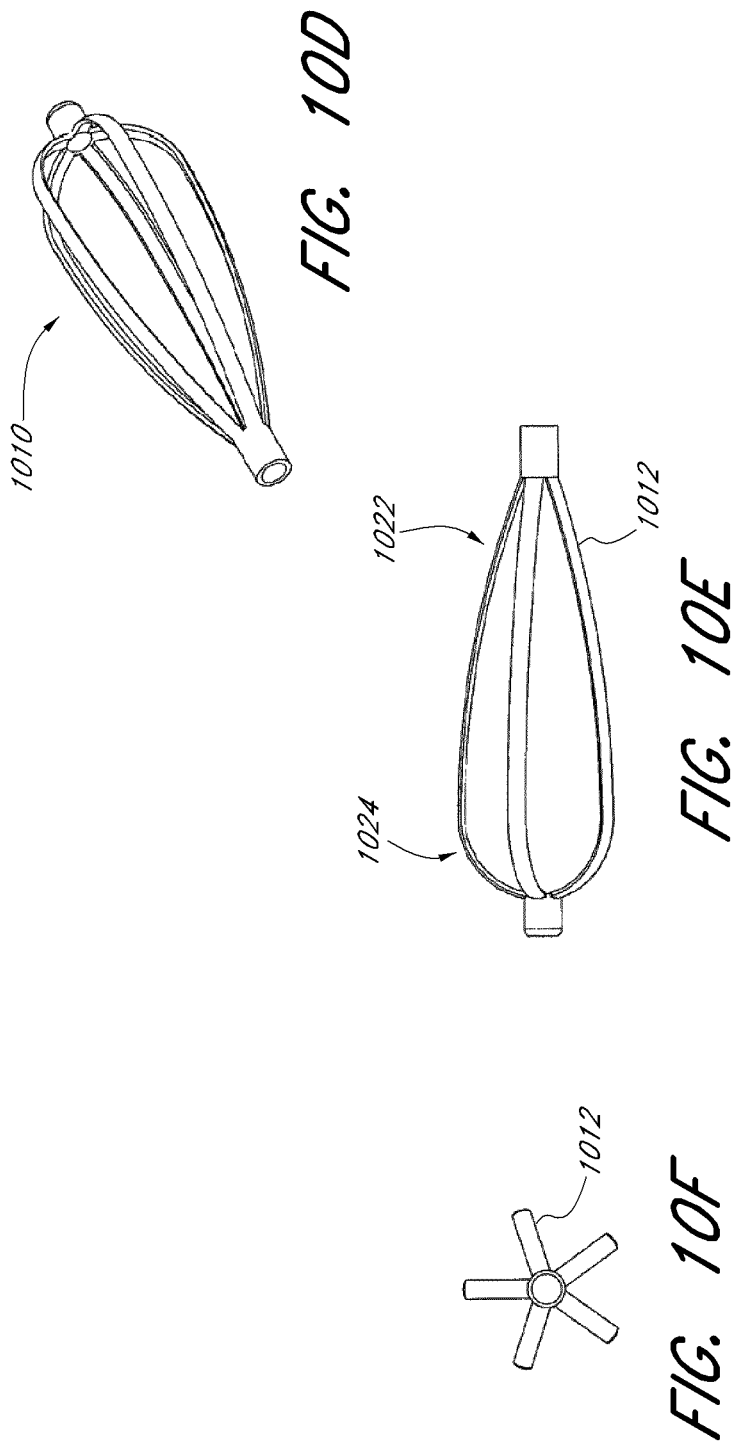

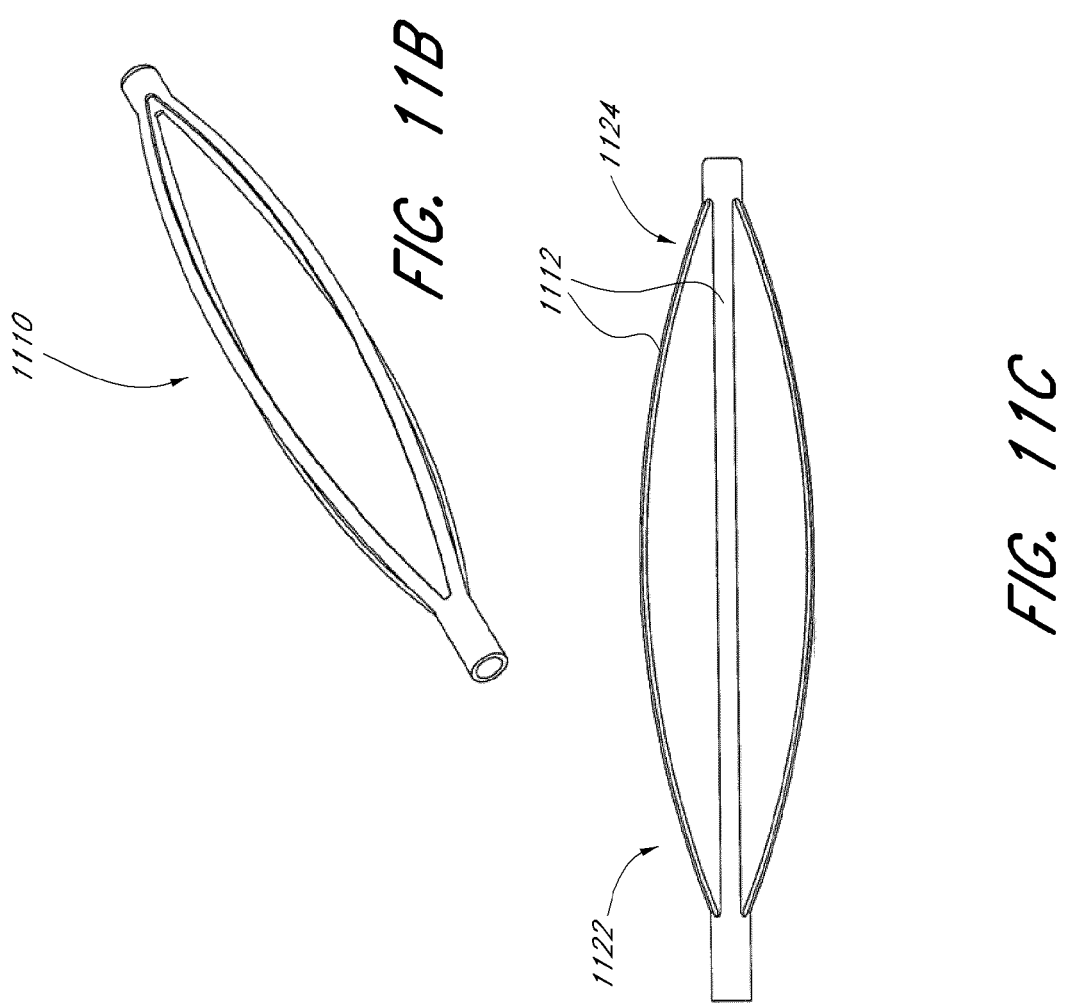

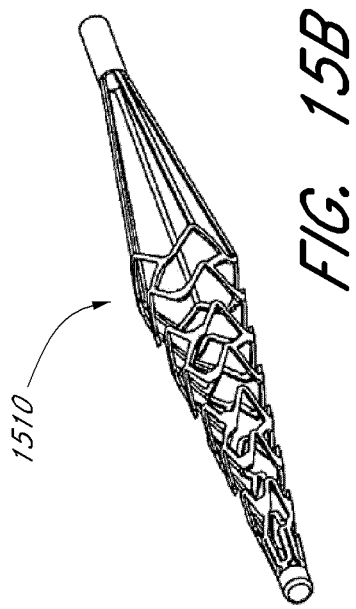
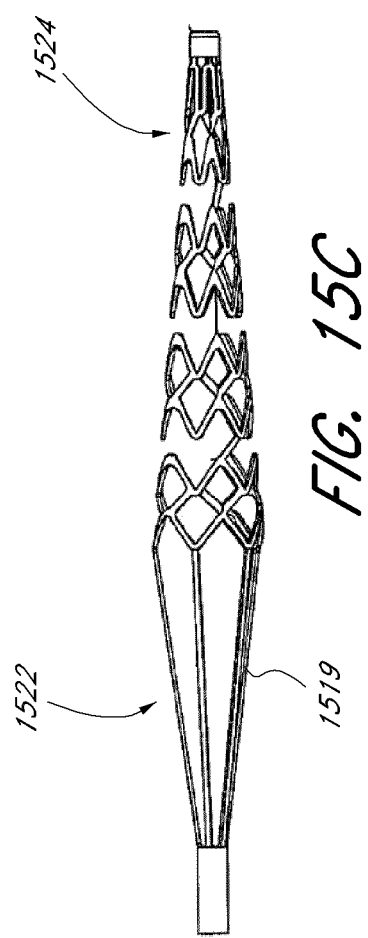

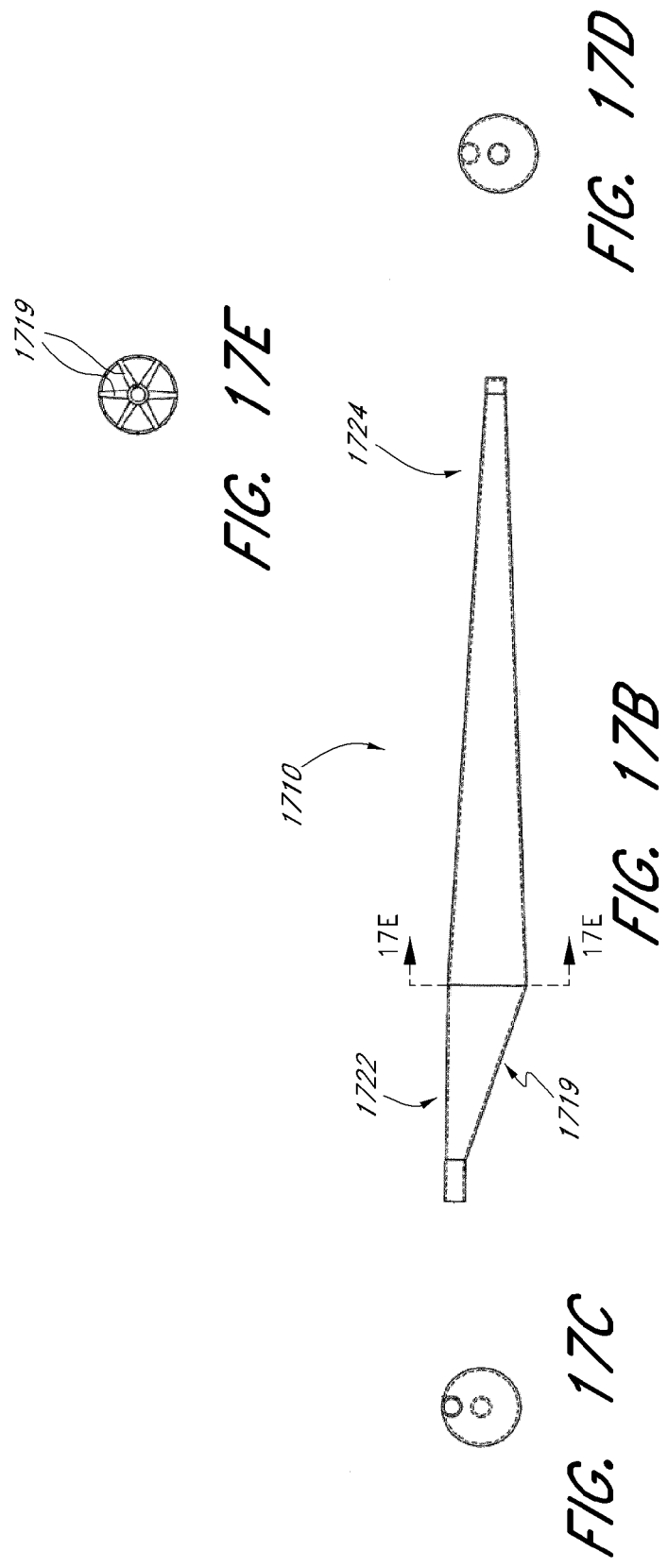

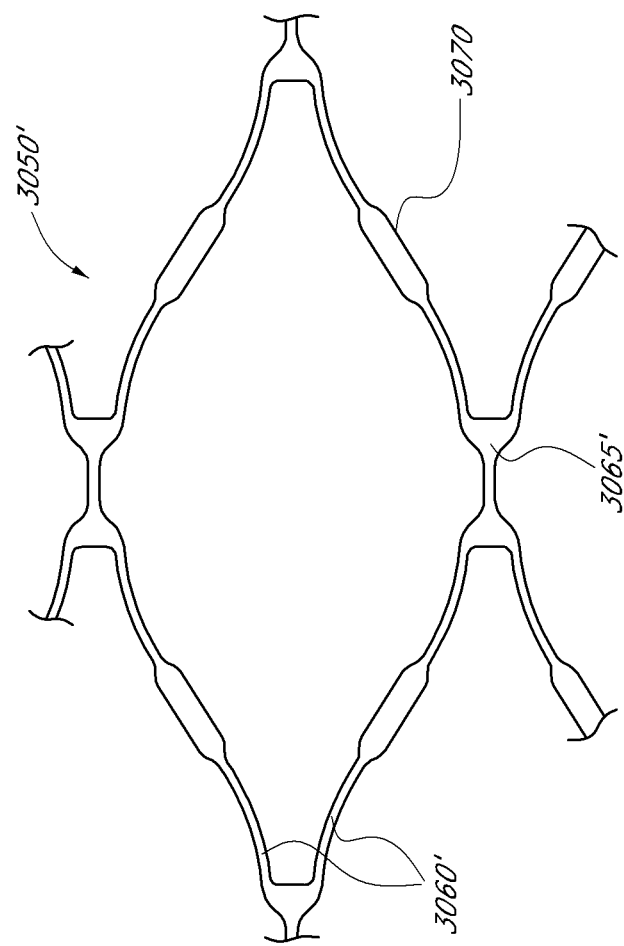

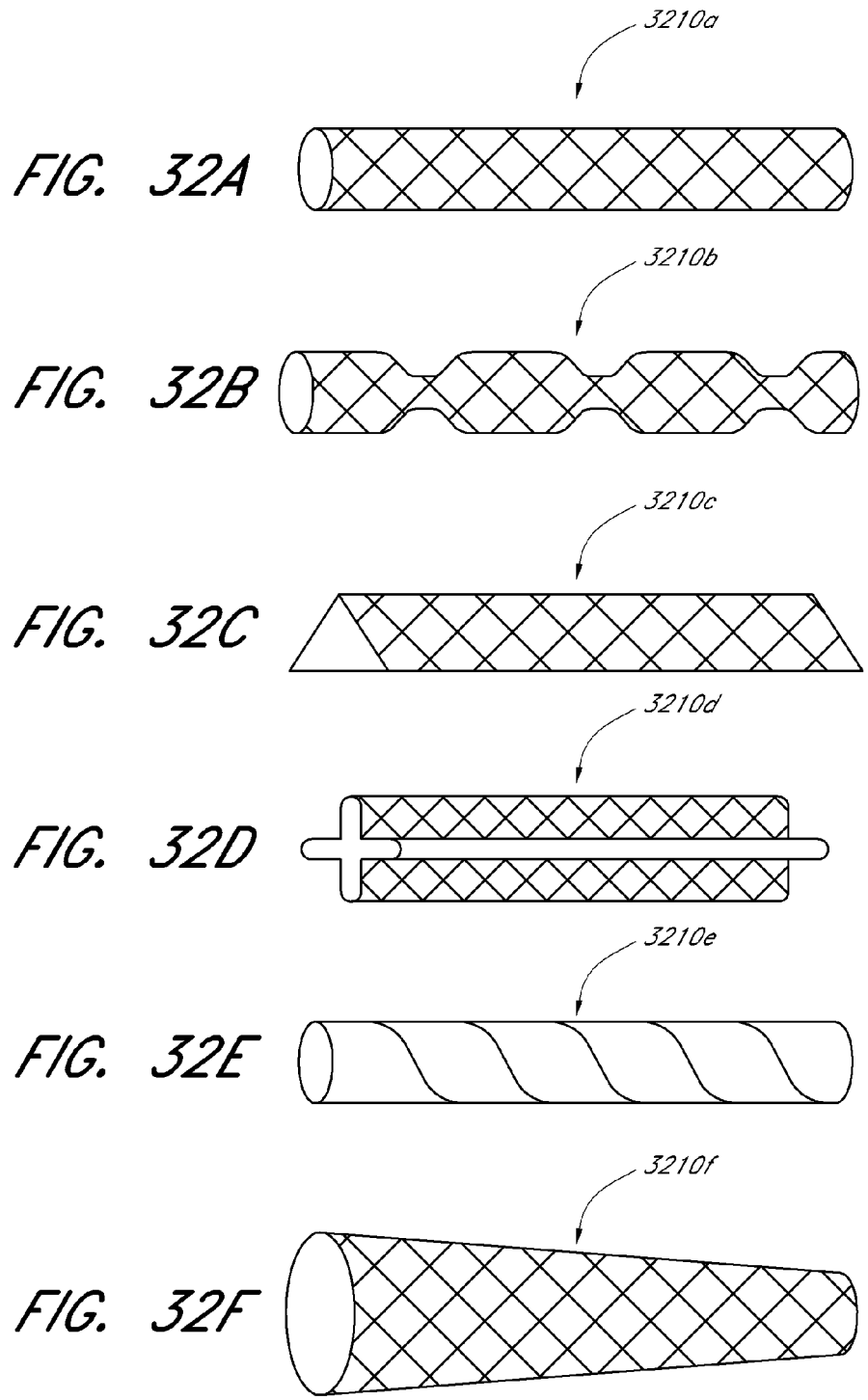

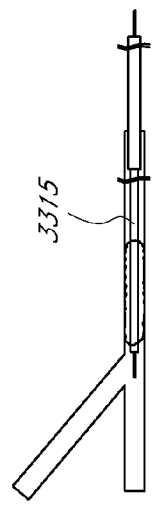
FIG.33B
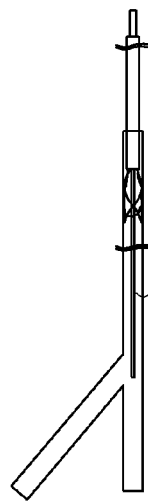
FIG.33C
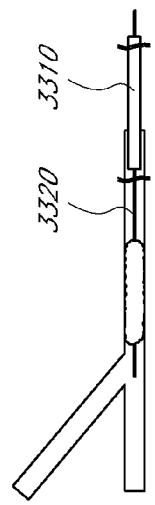
FIG.33A
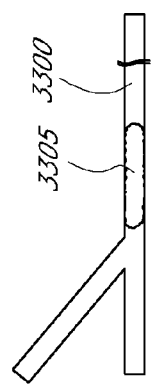
FIG.33D
FIG.33E
FIG.33F

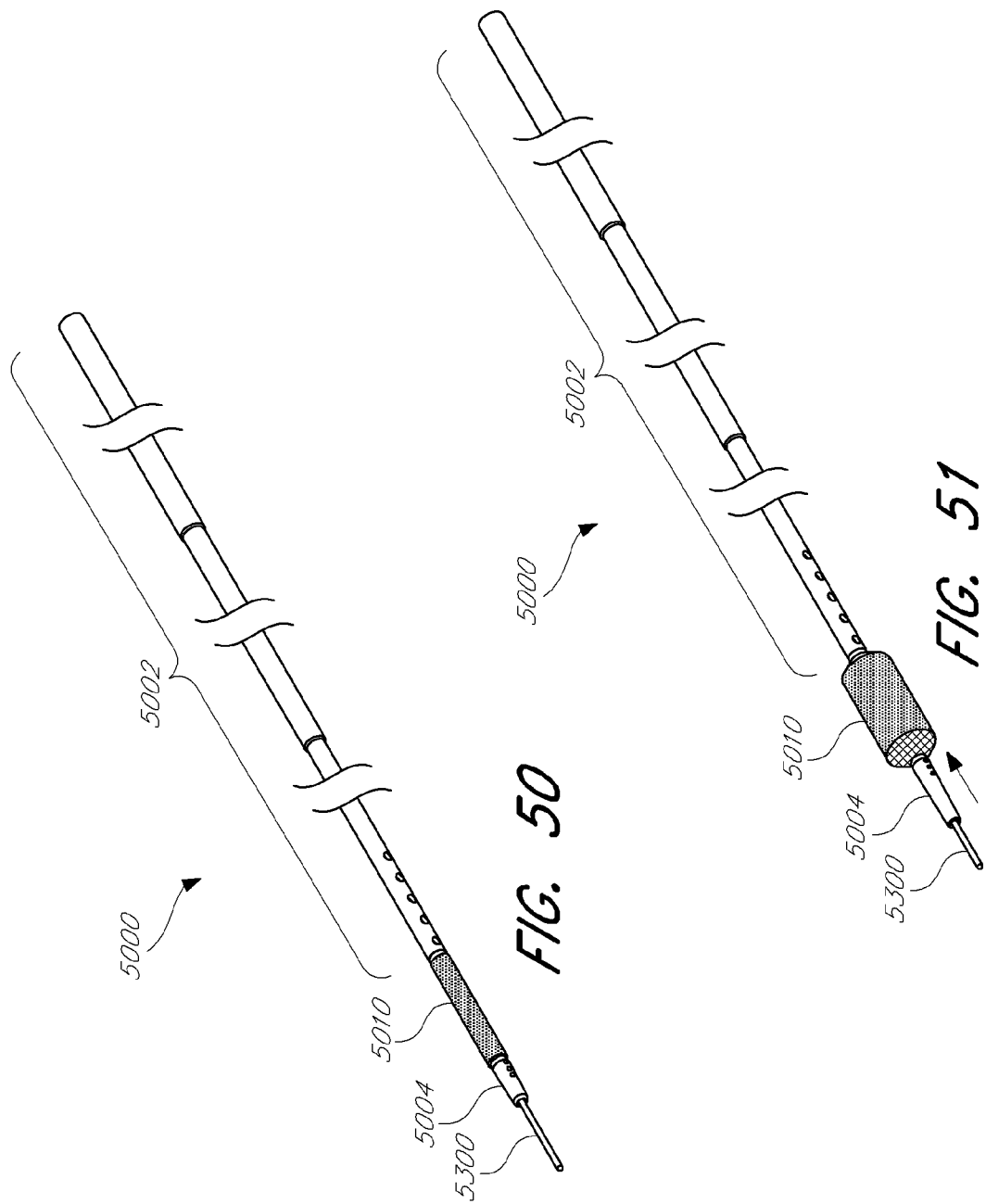

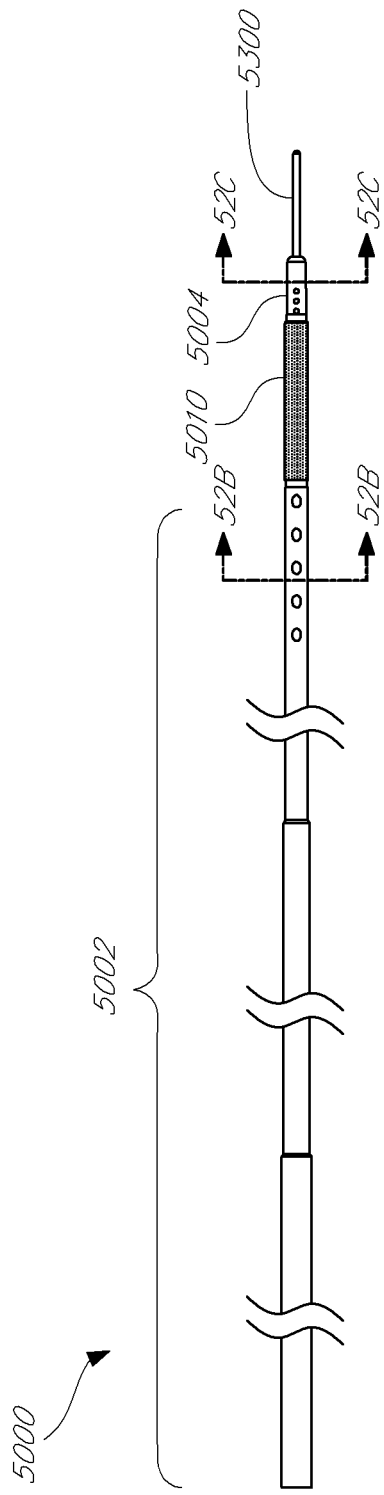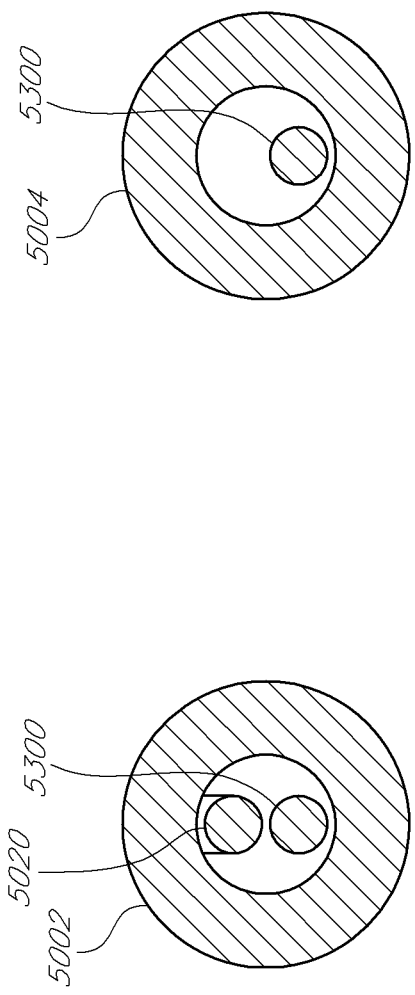

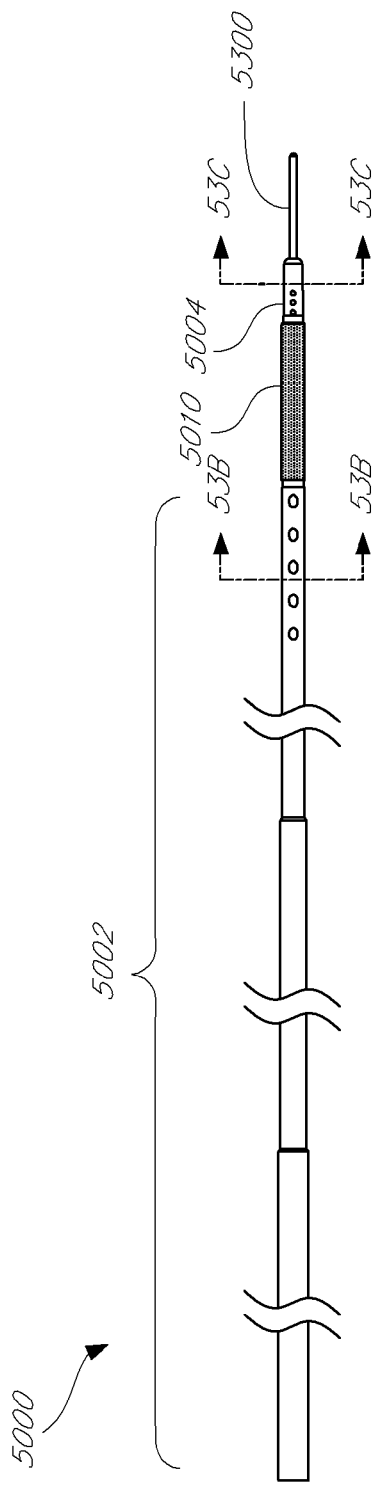
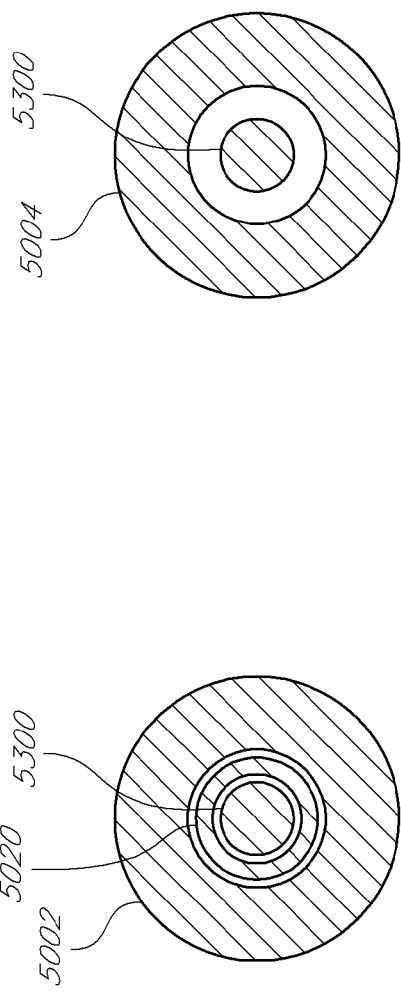
FIG. 53A
FIG. 53C
FIG. 53B

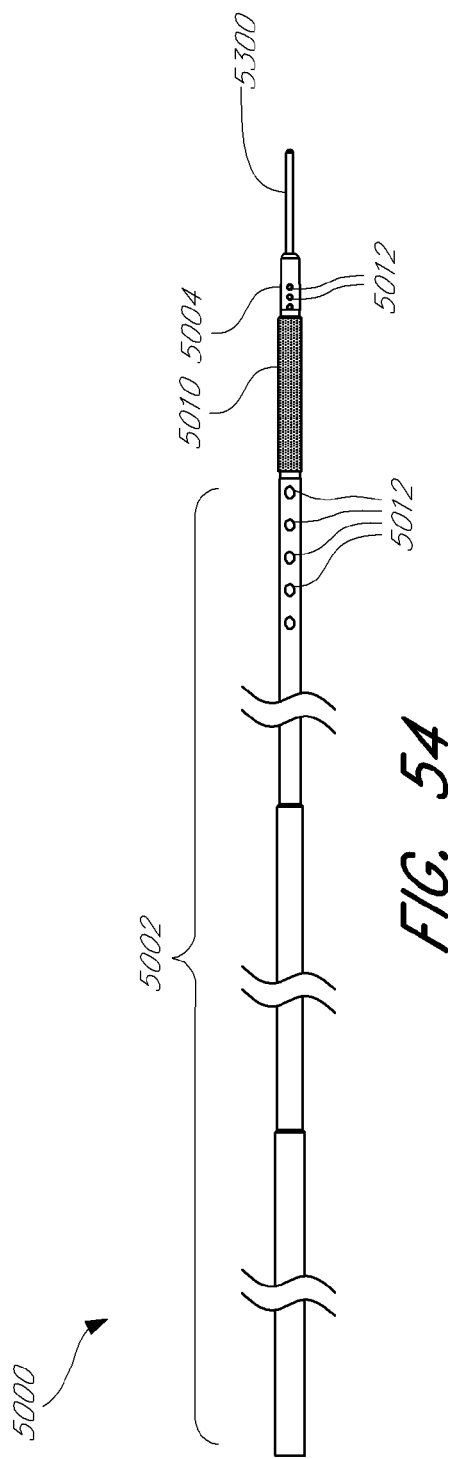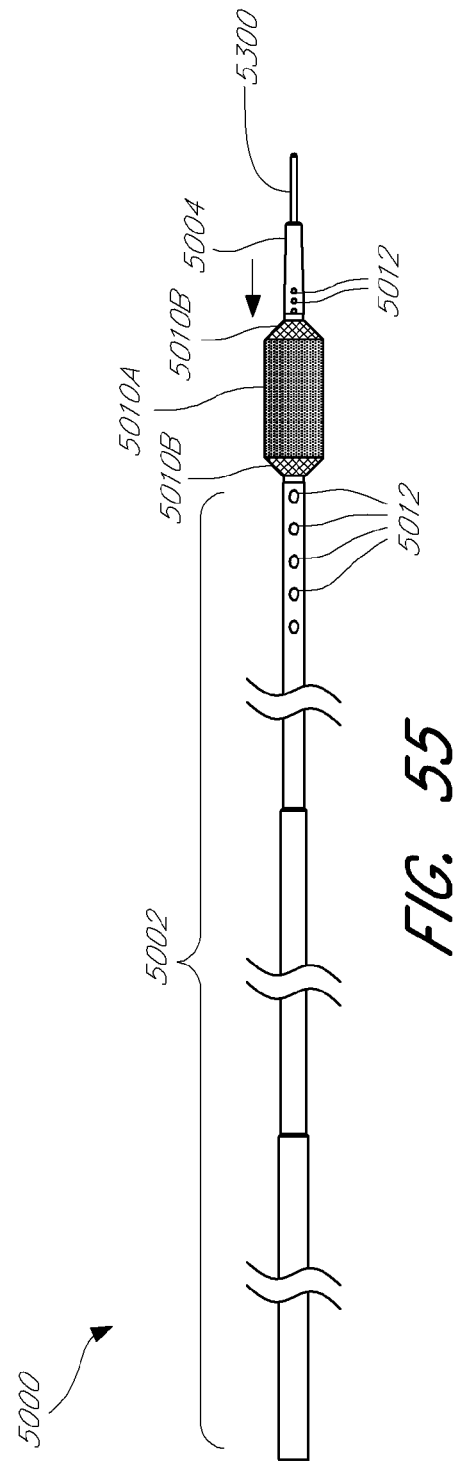

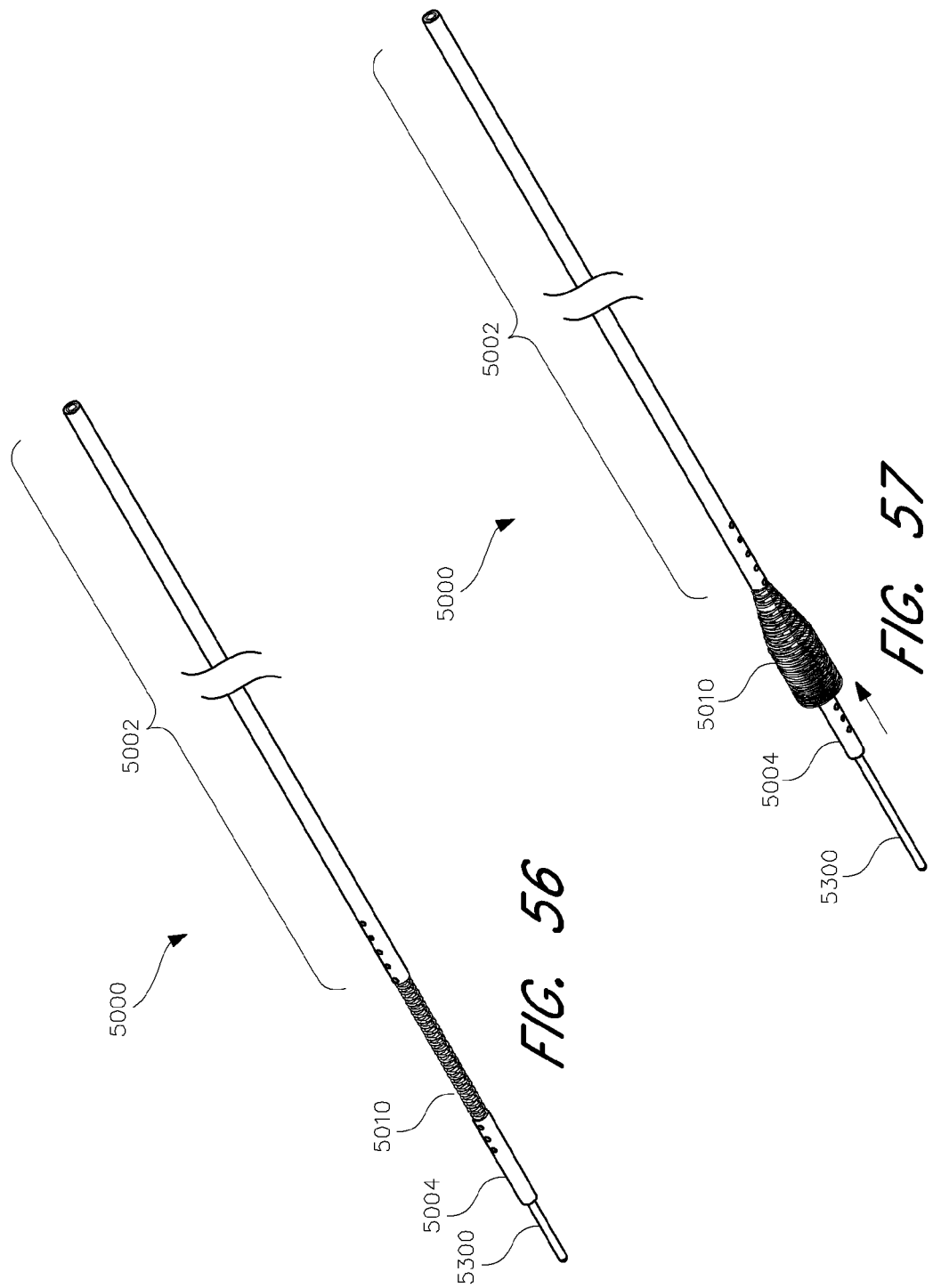

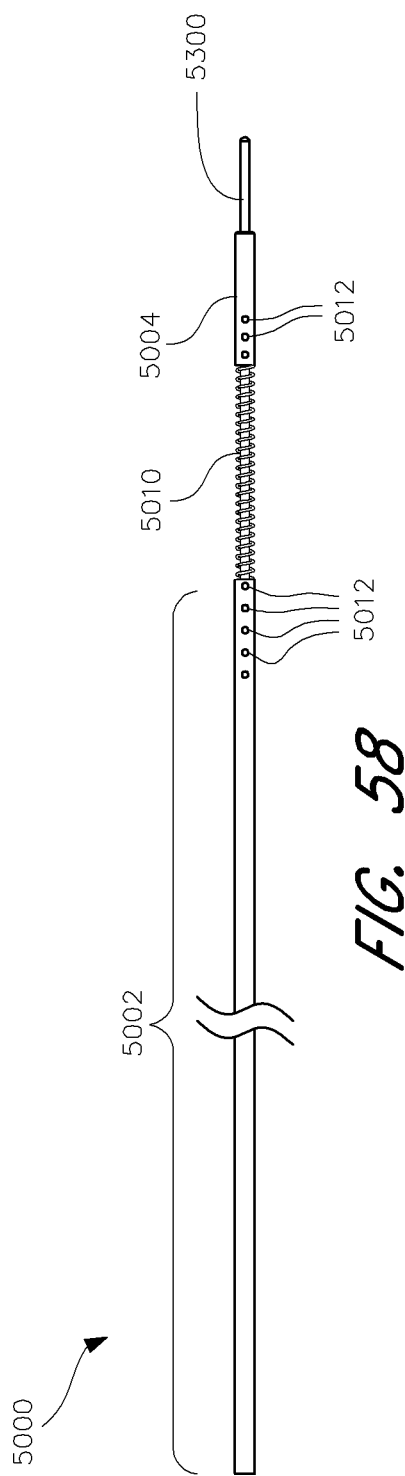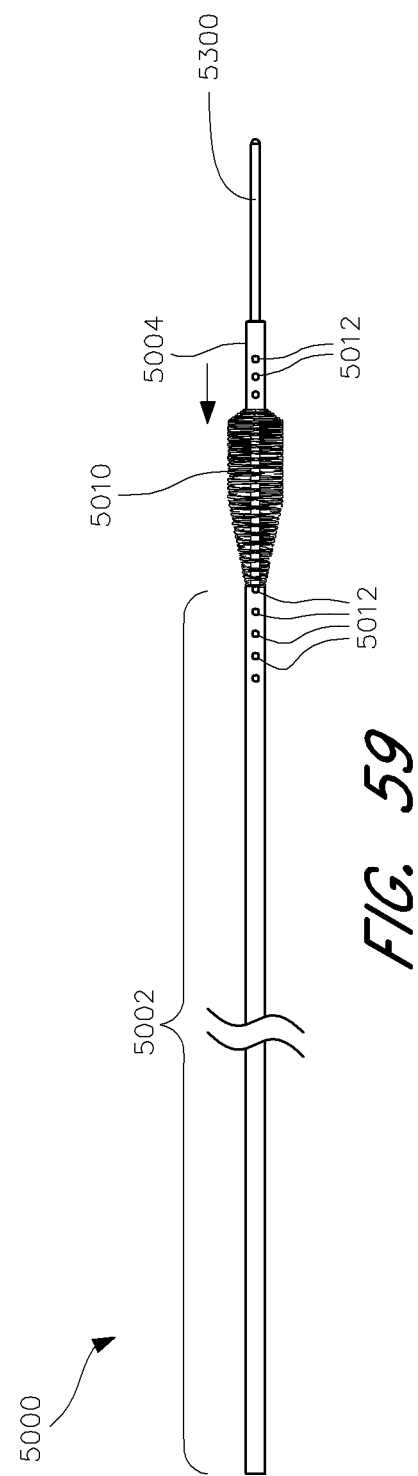

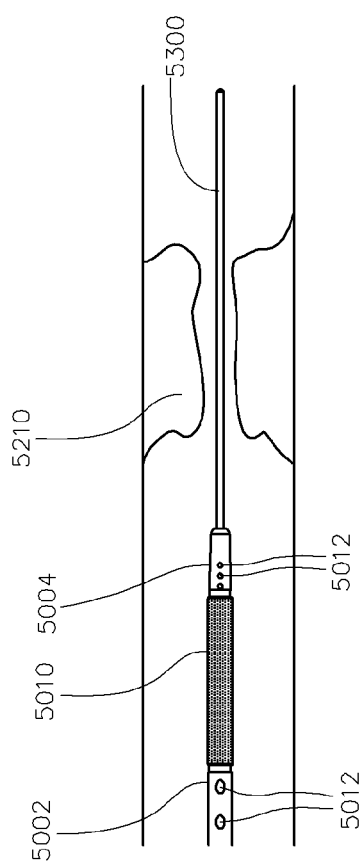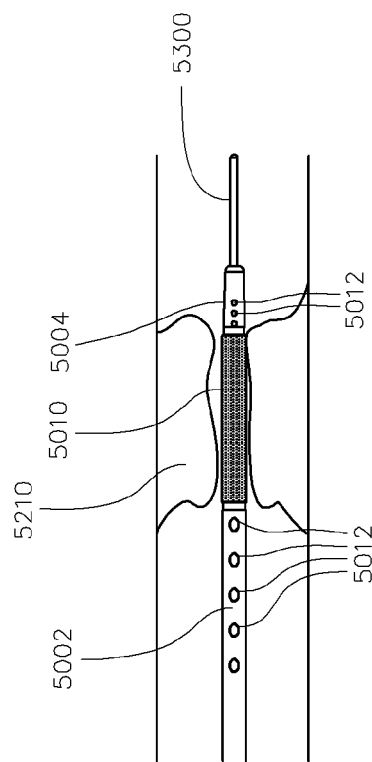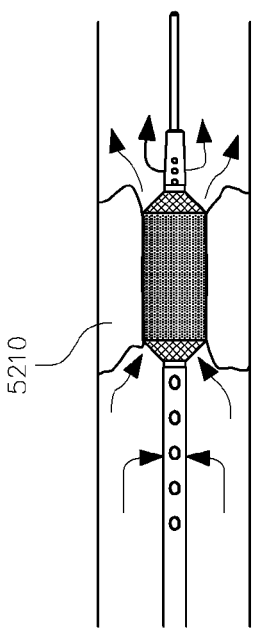
FIG. 60A
FIG. 60B
FIG. 60C

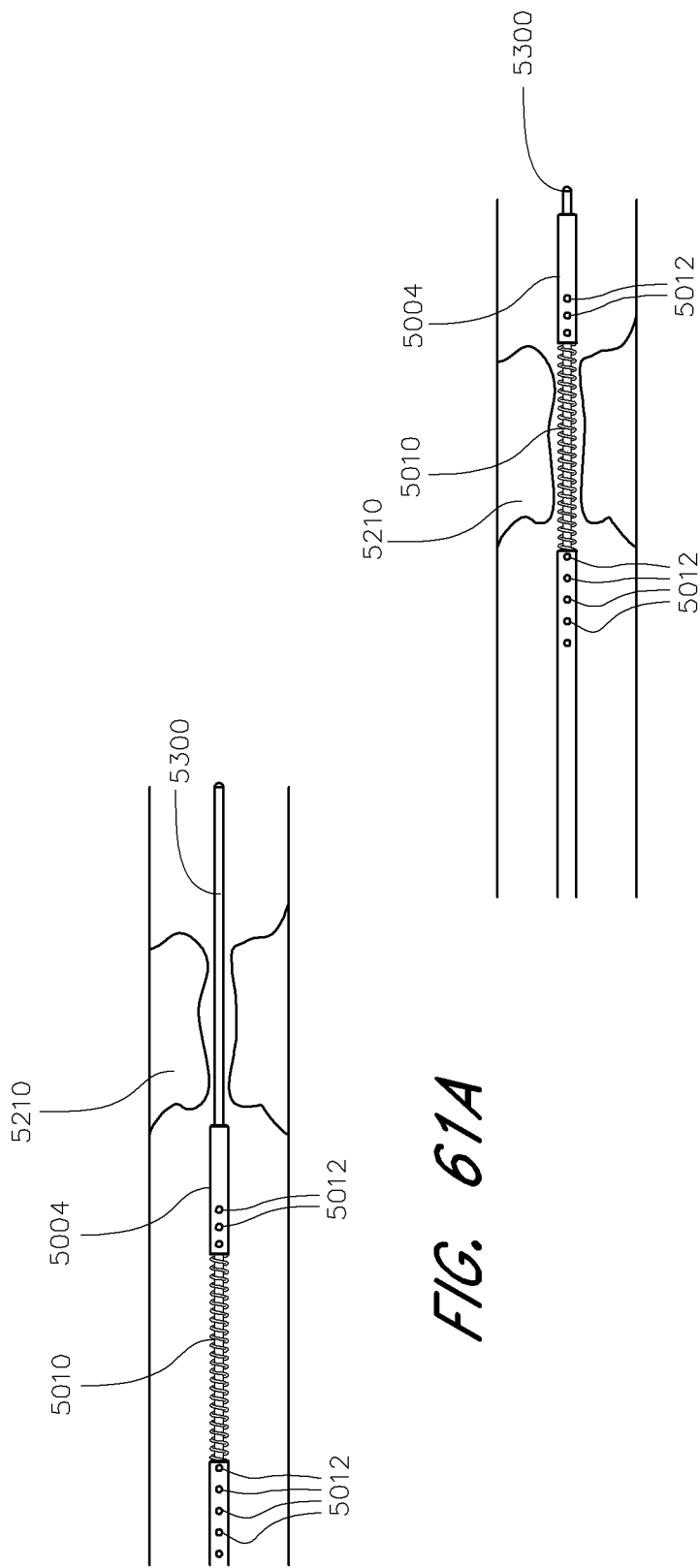
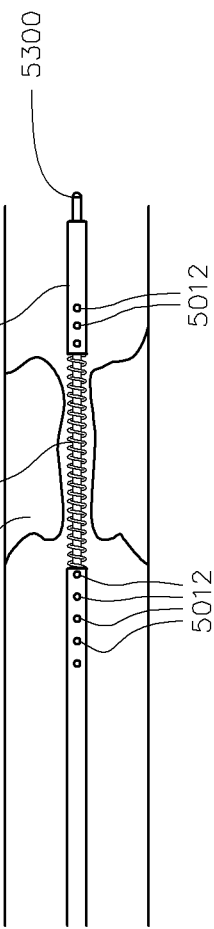
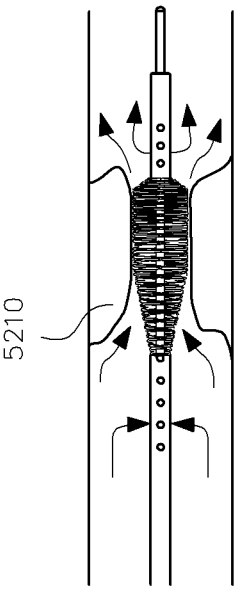
FIG. 61A
FIG. 61B
FIG. 61C

EXPANDABLE TIP ASSEMBLY FOR THROMBUS MANAGEMENT

CROSS-REFERENCE TO RELATED APPLICATIONS

This application is a continuation of U.S. patent application Ser. No. 13/281,363, filed Oct. 25, 2011, which is a continuation-in-part application of U.S. patent application Ser. No. 12/980,039, filed Dec. 28, 2010, and issued as U.S. Pat. No. 8,066,757, which is a continuation-in part application of U.S. patent application Ser. No. 12/651,353 filed Dec. 31, 2009, which is a continuation-in part application of U.S. patent application Ser. No. 12/123,390 filed May 19, 2008, which claims priority to the following provisional applications: U.S. Provisional Application No. 60/980,736, filed Oct. 17, 2007; U.S. Provisional Application No. 60/987,384, filed Nov. 12, 2007; U.S. Provisional Application No. 60/989,422, filed Nov. 20, 2007; U.S. Provisional Application No. 61/015,154, filed Dec. 19, 2007; U.S. Provisional Application No. 61/019,506, filed Jan. 7, 2008; and U.S. Provisional Application No. 61/044,392, filed Apr. 11, 2008.

U.S. patent application Ser. No. 13/281,363 is also a continuation-in-part application of U.S. patent application Ser. No. 12/123,390 filed May 19, 2008, which claims priority to the following provisional applications: U.S. Provisional Application No. 60/980,736, filed Oct. 17, 2007; U.S. Provisional Application No. 60/987,384, filed Nov. 12, 2007; U.S. Provisional Application No. 60/989,422, filed. Nov. 20, 2007; U.S. Provisional Application No. 61/015,154, filed Dec. 19, 2007; U.S. Provisional Application No. 61/019,506, filed Jan. 7, 2008; and U.S. Provisional Application No. 61/044,392, filed Apr. 11, 2008.

U.S. patent application Ser. No. 13/281,363 is a continuation of U.S. patent application Ser. No. 13/172,778, filed Jun. 29, 2011, which is a continuation-in-part application of the following applications: U.S. patent application Ser. No. 12/980,039, filed Dec. 28, 2010, and issued as U.S. Pat. No. 8,066,757; International Application No. PCT/US2010/062532, filed Dec. 30, 2010; U.S. patent application Ser. No. 12/123,390 filed May 19, 2008; U.S. patent application Ser. No. 12/136,737, filed Jun. 10, 2008; U.S. patent application Ser. No. 12/182,370, filed Jul. 30, 2008, U.S. patent application Ser. No. 12/422,105, filed Apr. 10, 2009; U.S. patent application Ser. No. 12/475,389, filed May 29, 2009, and issued as U.S. Pat. No. 8,088,140, which claims priority to U.S. Provisional Application No. 61/057,613, filed May 30, 2008; U.S. patent application Ser. No. 12/711,100, filed Feb. 23, 2010; and U.S. application Ser. No. 12/753,812, filed Apr. 2, 2010, which claims priority to U.S. Provisional Application No. 61/166,725, filed Apr. 4, 2009.

This application is related to the following commonly-owned application: U.S. patent application Ser. No. 12/469,462, filed May 20, 2009.

The entire contents of each of the above-listed applications are hereby expressly incorporated by reference herein.

FIELD

The present disclosure generally relates to devices, systems, and methods for use in the treatment of vascular issues. More particularly, several embodiments relate to systems and methods for providing early blood flow restoration, maceration of an embolus, lysis of the embolus, and retrieval of any non-lysed portions of the embolus.

BACKGROUND

The pathological course of a blood vessel that is blocked is a gradual progression from reversible ischemia to irreversible infarction (cell death). A stroke is often referred to as a "brain attack" and occurs when a blood vessel in the brain becomes blocked or ruptures. An ischemic stroke occurs when a blood vessel in the brain becomes blocked. Occlusions may be partial or complete, and may be attributable to one or more of emboli, thrombi, calcified lesions, atheroma, macrophages, lipoproteins, any other accumulated vascular materials, or stenosis. Ischemic strokes account for about 78% of all strokes. Hemorrhagic strokes, which account for the remaining 22% of strokes, occur when a blood vessel in the brain ruptures. Stroke is the third leading cause of death in the United States, behind heart disease and cancer and is the leading cause of severe, long-term disability. Each year roughly 700,000 Americans experience a new or recurrent stroke. Stroke is the number one cause of inpatient Medicare reimbursement for long-term adult care. Total stroke costs now exceed $45 billion per year in US healthcare dollars. An occlusion in the cerebral vasculature can destroy millions of neurons and synapses of the brain.

SUMMARY

If not addressed quickly, the destruction of neurons and synapses of the brain after a stroke can result in slurred speech, paralysis, loss of memory or brain function, loss of motor skills, and even death. Thus, there remains a need for systems, methods, and devices for the treatment of acute ischemic stroke that provide immediate blood flow restoration to a vessel occluded by a clot and, after reestablishing blood flow, address the clot itself. Immediate blood flow restoration distal to the clot or occlusion reduces the destruction to neurons and neurovasculature. Immediate blood flow restoration facilitates natural lysis of the clot and also can reduce or obviate the concern for distal embolization due to fragmentation of the clot. There also remains a need for systems, methods and devices for the treatment of acute ischemic stroke that provide for progressive treatment based upon the nature of the clot, wherein the treatment involves immediate restoration of blood flow, in-situ clot management, and clot removal depending on the particular circumstances of the treatment. The progressive treatment can be provided by a kit of one or more devices. According to several embodiments of the present disclosure, clot therapy may have one or more of at least three objectives or effects: maceration of a clot, removal of a clot, and lysis of a clot.

In accordance with several embodiments, a thrombus management method for the treatment of ischemic stroke without distal embolic protection is provided. In some embodiments, the thrombus management method comprises identifying a blood vessel (e.g., an artery of the neurovasculature) having a thrombus. In some embodiments, the method comprises inserting a guide catheter (e.g., a balloon guide catheter) into a patient. In some embodiments, the method comprises advancing a distal end of the balloon guide catheter to an arterial location proximal to the thrombus. In some embodiments, the method comprises inserting a guide wire through the guide catheter into the occluded vessel and through the thrombus. In some embodiments, the guidewire is inserted first and then the guide catheter is inserted over the guidewire. In several embodiments, the guidewire follows a path of least resistance through the thrombus. In some embodiments, the guidewire does not travel through the thrombus but travels to the side of the thrombus (for example, if the thrombus is not positioned across the entire diameter, or height, of the vessel). In some embodiments, the method comprises inserting a distal access catheter through the guide catheter and advancing a distal end of the distal access catheter to an origin of the occluded artery. In some embodiments, the occluded artery is a middle cerebral artery and the distal end of the distal access catheter is inserted to a location within the middle cerebral artery or within an internal carotid artery. In some embodiments, the occluded artery is the basilar artery and the distal end of the distal access catheter is inserted to a location within a vertebral artery or to an origin of the basilar artery. In some embodiments, the thrombus management method comprises inserting a microcatheter over the guidewire (which may be through the thrombus or to the side of the thrombus as described above). In some embodiments, the method comprises positioning a distal end of the microcatheter within about a centimeter (e.g., 0.5 to 10 mm) past the thrombus. In some embodiments, the method further comprises positioning a distal end of the expandable tip assembly to substantially align with the distal end of microcatheter.

In some embodiments, the method comprises inserting an expandable tip assembly comprising a scaffold through the microcatheter. In some embodiments, the scaffold comprises a self-expandable scaffold comprising a generally cylindrical body comprised of a plurality of struts and bridges forming a plurality of cells, wherein the cells are sized and shaped to impact, compress and engage thrombus material upon radial expansion of the self-expandable scaffold. In some embodiments, the expandable tip assembly comprising a self-expandable scaffold tethered to a distal end of an elongate delivery member.

In some embodiments, the method comprises retracting the microcatheter proximally, thereby causing the scaffold to expand at the location of the thrombus. The expansion of the scaffold can impact and compress the thrombus against a wall of the blood vessel. The compression of the thrombus can restore blood flow within the blood vessel and the restored blood flow can facilitate natural lysis and/or fragmentation of the thrombus. In some embodiments, the thrombus management method comprises macerating the thrombus by resheathing the scaffold and unsheathing the scaffold (e.g., by advancing and retracting the microcatheter), thereby facilitating mechanical lysis and fragmentation of the thrombus to release embolic particles. The embolic particles can flow in the direction of the blood flow and may not be captured by any distal embolic protection member, but can instead be lysed through the natural lysis process due to the restored blood flow. In some embodiments, resheathing and unsheathing the scaffold comprises movement of the microcatheter with respect to the expandable tip assembly while the expandable tip assembly remains stationary. Macerating the thrombus can comprise resheathing the scaffold and unsheathing the scaffold one time or multiple times (e.g., two times, three times, four times, five times, six times) In some embodiments, blood flow is restored in less than two minutes (e.g., about 90 seconds, 60 seconds, 30 seconds, 15 seconds, etc.) from deployment of the scaffold within the thrombus.

In some embodiments, the thrombus management method comprises capturing one or more non-lysed portions of the thrombus on the exterior surface of the scaffold (e.g., open cell structure of the self-expandable scaffold sized and shaped to engage, grab, or otherwise capture thrombus material). In some embodiments, the thrombus management method comprises removing the expandable tip assembly from the subject, thereby removing the captured non-lysed portions of the thrombus engaged by the scaffold from the occluded artery. In some embodiments, the one or more non-lysed portions comprises an inner core of the thrombus.

In some embodiments, the thrombus management method comprises providing local aspiration at a location proximal to the thrombus within the occluded artery through the distal access catheter. In some embodiments, the method comprises providing proximal aspiration at a location proximal to and remote from the location of thrombus through the balloon guide catheter.

In some embodiments, the thrombus management method comprises engaging a remaining portion of the thrombus after said maceration and extracting or removing said remaining portion of the thrombus from the blood vessel. The engaging and extracting of the remaining portion of the thrombus can be performed by the expandable tip assembly that performed the blood flow restoration and/or maceration (e.g., the first expandable tip assembly) or by a second expandable tip assembly configured or adapted for thrombus removal. If a second expandable tip assembly is used, the second expandable tip assembly can be inserted into the microcatheter after removing the first expandable tip assembly from the microcatheter after macerating the thrombus. The first expandable tip assembly can comprise a self-expanding scaffold with open cells having a cell size configured or adapted to facilitate blood flow restoration and natural lysis of the thrombus. The second expandable tip assembly can comprise a self-expanding scaffold with open cells having a cell size configured to increase penetration, or protrusion, of the remaining thrombus material into the cells to facilitate capture of the remaining thrombus material.

In some embodiments, the thrombus management method comprises delivering one or more agents configured to promote thrombus adhesion or platelet activation or one or more lytic agents to a location of the thrombus through or over the expandable tip assembly. For example, the agents can be infused through a lumen of the expandable tip assembly or around the expandable tip assembly through a lumen of the microcatheter.

In accordance with several embodiments of the invention, a thrombus management method comprises identifying a blood vessel having an occlusive thrombus and selecting an expandable tip assembly based, at least in part, on a diameter of the identified occluded blood vessel. The expandable tip assembly can comprise a proximal elongate member and a distal self-expanding scaffold. In some embodiments, the method comprises inserting the selected expandable tip assembly within the occluded vessel through a microcatheter such that the self-expanding scaffold is positioned at a location of (e.g., to coincide with the position of) the thrombus in a non-expanded configuration. Positioning the self-expanding scaffold at a location of the thrombus can refer to a location that spans (partially or completely) the thrombus. For example, if a thrombus in a vessel has a height and a length, wherein the length is substantially parallel with the longitudinal axis of the vessel, spanning the thrombus includes, but is not limited to, positioning a device to extend partially across the length of the thrombus, to extend from one end of the thrombus to the other end of the thrombus, or to extend past (e.g., just past, such as 0.5 to 5 mm past, 1 mm to 10 mm past, or overlapping ranges thereof)) one or both ends of the thrombus. Depending on whether the height of the thrombus extends along the entire height, or diameter, of the vessel, the non-expanded device may be in contact with a portion of the thrombus or may not be in contact with the thrombus. The self-expanding scaffold can be positioned either within the thrombus or outside the thrombus (e.g., depending on the location of the microcatheter and the size of the thrombus). The microcatheter can then be retracted, thereby causing the scaffold to expand to an expanded configuration. The expansion can compress the thrombus against a wall of the blood vessel, thereby restoring blood flow within the blood vessel by creating a bypass channel through or past the thrombus. The restored blood flow facilitates natural lysis of the thrombus. In some embodiments, the proximal elongate member of the expandable tip assembly comprises a flexible, distal portion configured to navigate curved portions of the cerebral vasculature.

In accordance with several embodiments of the invention, a method for providing multiple layer embolus removal from a cerebral artery is provided. In some embodiments, the method comprises identifying an embolus within a cerebral artery and inserting an expandable reperfusion device within the cerebral artery to the location of the embolus (e.g., positioned to coincide with a position of the embolus). The embolus, or thrombus, can comprise one or more soft outer layers and a firm fibrin core. In some embodiments, the method comprises expanding the reperfusion device within the embolus, thereby establishing one or more blood flow channels through or past the embolus. The one or more blood flow channels facilitate natural lysis of the embolus to remove one or more outer layers of the embolus. The one or more outer layers of the embolus can comprise platelets and red blood cells.

In some embodiments, the method comprises removing the reperfusion device and inserting an expandable embolus removal device within the cerebral artery to the location of the embolus. In some embodiments, the method comprises expanding the embolus removal device within a remaining portion of the embolus, thereby engaging the remaining portion of the embolus. In some embodiments, the method comprises extracting the remaining portion of the embolus with the embolus removal device from the cerebral artery by removing the embolus removal device.

In some embodiments, the reperfusion device comprises an expandable tip assembly including a proximal elongate member and a distal self-expanding scaffold. The scaffold of the reperfusion device can comprise open cells having a cell size that is configured to decrease, hinder, prevent, deter, discourage, inhibit, or reduce penetration, or protrusion, of the embolus within the scaffold, thereby increasing blood flow through the scaffold because the flow channel through the scaffold is larger. In some embodiments, the embolus removal device comprises an expandable tip assembly including a proximal elongate member and a distal self-expanding scaffold. The scaffold of the embolus removal device can comprise open cells having a cell size that is configured to increase, promote, facilitate, enhance, allow, or enable penetration, or protrusion, of the remaining portion of the embolus material within the scaffold to facilitate capture of the remaining portion of the embolus. The cell size of the embolus removal device can be larger than the cell size of the reperfusion device.

In accordance with some embodiments, a method for providing multiple layer embolus removal comprises identifying an embolus having an outer layer and an inner core. In some embodiments, the method comprises establishing one or more blood flow channels through the embolus to restore blood flow. In one embodiment, establishing one or more blood flow channels comprises inserting an expandable reperfusion scaffold within or adjacent the thrombus and expanding it. In some embodiments, the method comprises disturbing the embolus by mechanical maceration of the embolus to release embolic particles from the outer layer, thereby allowing the embolic particles to freely flow in the direction of the blood flow without capturing said embolic particles. Free flow can refer to downstream flow without obstruction or capture, such as a distal embolic protection device (e.g., a basket, a net, a filter). The disturbance may be caused by maceration of the embolus with an expandable scaffold, thereby enhancing lysis of the embolic particles. In some embodiments, restored blood flow causes further release of embolic particles from the outer layer of the embolus. In some embodiments, the method comprises extracting the inner core of the embolus. The one or more outer layers of the embolus can comprise softer layers than the inner core of the embolus. The inner core can comprise a fibrin core that has a hardness that exceeds the one or more outer layers of the embolus.

In accordance with several embodiments of the invention, a method for providing progressive therapy for thrombus management in blood vessels is provided. In some embodiments, the method comprises identifying a thrombus within a blood vessel. In some embodiments, the method comprises inserting an expandable reperfusion device within the blood vessel to the location of the thrombus. The expandable reperfusion device can comprise an expandable reperfusion scaffold having a plurality of interconnected struts that form cells having a cell size that is sized and configured to reduce, prevent, hinder, or deter penetration, or protrusion, of the thrombus into the reperfusion scaffold, thereby increasing a diameter of a flow path established by the reperfusion scaffold. In some embodiments, the method comprises deploying the reperfusion device within the thrombus, thereby compressing the thrombus against the inner vessel wall and establishing one or more blood flow channels through the thrombus. The one or more blood flow channels can facilitate natural lysis of the thrombus. In some embodiments, the method comprises removing the reperfusion device.

In some embodiments, the method for providing progressive therapy for thrombus management of blood vessels comprises inserting an expandable thrombus removal device within the blood vessel to the location of the thrombus. The expandable thrombus removal device can comprise an expandable removal scaffold having a plurality of interconnected struts that form cells having a cell size that is sized and configured to allow thrombus penetration, or protrusion, within the cells, thereby facilitating engagement of the thrombus by the removal scaffold. In some embodiments, the method comprises deploying the thrombus removal device within a remaining portion of the thrombus, thereby engaging the remaining portion of the thrombus. In some embodiments, the method comprises extracting the remaining portion of the thrombus engaged by the thrombus removal device from the blood vessel. In some embodiments, the method comprises removing the thrombus removal device.

In some embodiments, the expandable reperfusion device and/or the expandable thrombus removal device comprise self-expanding devices. In some embodiments, the expandable reperfusion device and the expandable thrombus removal device are inserted into the blood vessel within a microcatheter. In some embodiments, deploying the reperfusion device comprises retracting the microcatheter, thereby allowing the reperfusion device to expand within the thrombus. In some embodiments, deploying the thrombus removal device comprises retracting the microcatheter, thereby allowing the thrombus removal device to expand within the thrombus. In some embodiments, removing the reperfusion device comprises resheathing the reperfusion device by advancing the microcatheter over the reperfusion device while keeping the reperfusion device stationary and then removing the microcatheter with the reperfusion device together. In some embodiments, the method comprises resheathing the reperfusion device within the microcatheter by advancing the microcatheter and then unsheathing the reperfusion device by retracting the microcatheter to provide maceration of the thrombus.

In some embodiments, an expansion diameter of the reperfusion device is configured to provide increased cell deformation of the reperfusion scaffold, thereby reducing thrombus penetration or protrusion, within the reperfusion scaffold. In some embodiments, an expansion diameter of the thrombus removal device is configured to provide reduced cell deformation of the removal scaffold, thereby increasing thrombus penetration, or protrusion, within the removal scaffold. In some embodiments, the cells of the reperfusion scaffold in an expanded configuration have a cell length of between 2 mm and 4 mm and a cell height between 1 mm and 3 mm and wherein the cells of the removal scaffold in an expanded configuration have a have a cell length of between 4 mm and 6 mm and a cell height between 2 mm and 4 mm.

In accordance with several embodiments of the invention, a method for providing progressive therapy for thrombus management is provided. In some embodiments, the method comprises inserting an expandable reperfusion device within an occluded blood vessel having a thrombus. In some embodiments, the method comprises positioning the expandable reperfusion device to span at least a portion of a length of the thrombus. The expandable reperfusion device can comprise a self-expanding reperfusion scaffold having a plurality of interconnected struts that form cells sized and configured to inhibit penetration, or protrusion, of the thrombus into the reperfusion scaffold, thereby increasing a diameter of a flow path established by the reperfusion scaffold. In some embodiments, the method comprises deploying the reperfusion device within the thrombus, thereby compressing the thrombus against the inner vessel wall and establishing blood flow through the occluded blood vessel. The established blood flow facilitates natural lysis of the thrombus. In some embodiments, the method comprises macerating the thrombus (for example, by resheathing and unsheathing the reperfusion scaffold). At least one of the natural lysis and the maceration can fragment the thrombus until only a portion of the thrombus remains. In some embodiments, the method comprises removing the reperfusion device.

In some embodiments, the method for providing progressive therapy for thrombus management comprises inserting a thrombus removal device within the blood vessel to span at least a portion of a length of the remaining thrombus. The thrombus removal device can comprise a self-expanding removal scaffold having a plurality of interconnected struts that form cells having a cell size that is sized and configured to allow or facilitate thrombus penetration, or protrusion, within the cells, thereby facilitating engagement of the remaining thrombus by the removal scaffold. In some embodiments, the method comprises deploying the thrombus removal device within the remaining thrombus to engage the remaining thrombus. In some embodiments, the method comprises removing the thrombus removal device, thereby extracting the remaining thrombus.

In accordance with several embodiments of the invention, a system for providing progressive therapy for clot management is provided. In some embodiments, the system comprises a microcatheter. In some embodiments, the clot management system comprises a first expandable tip assembly comprising a first elongate member and a first self-expanding scaffold. In some embodiments, the first self-expanding scaffold comprises open cells formed by a pattern of struts and bridges. The cells can have a cell size configured to hinder, inhibit, or reduce penetration, or protrusion, of clot material within the scaffold, thereby increasing an amount of blood flow through the scaffold. In some embodiments, the system comprises a second expandable tip assembly comprising a second elongate member and a second self-expanding scaffold. In some embodiments, the second self-expanding scaffold comprises open cells formed by a pattern of struts and bridges. The cells of the self-expanding scaffold can have a cell size larger than the cell size of the first self-expanding scaffold. The larger cell size can be configured to enhance penetration, or protrusion, of clot material within scaffold to facilitate capture of the thrombus.

In some embodiments, the first elongate member and the second elongate member comprise a variable-stiffness hypotube having a lumen. The variable stiffness can be created by intermittently-spaced spiral laser cuts. The cuts can be spaced so as to provide increased flexibility toward the distal end of the hypotube. In some embodiments, the cuts are spaced closer together toward the distal end of the hypotube. In some embodiments, the laser spiral cut pattern allows the distal section to bend to navigate through tortuous, curved portions of the cerebral vasculature (e.g., the carotid siphon). In some embodiments, the laser spiral cut pattern spans a length of at least about 35 cm from the distal end of the hypotube. In some embodiments, the system comprises a guidewire configured to be received by the first elongate member and the second elongate member. The first and second expandable tip assemblies can be delivered over the guidewire. The guidewire can provide maintained access to the treatment site during removal of the first expandable tip assembly and insertion of the second expandable tip assembly.

In some embodiments, the first elongate member and/or the second elongate member comprise a wire without a lumen. In some embodiments, the first self-expanding scaffold and the second self-expanding scaffold have an average chronic outward force across a diameter of 1.5 mm to 4.5 mm that does not decrease by more than 10% to 90%, by more than 50% to 75%, by more than 25% to 60%, by more than 40% to 85%, or overlapping ranges thereof. In some embodiments, the average chronic outward force is non-zero across an expansion diameter of 1 mm to 4.5 mm.

In accordance with several embodiments of the invention, a thrombus management system for providing progressive therapy is provided. In some embodiments, the system comprises a microcatheter configured to be inserted within a blood vessel (e.g., cerebral artery) having an occlusive thrombus. In some embodiments, the system comprises a temporary expandable reperfusion device configured to be inserted through the microcatheter to treat the thrombus. The expandable reperfusion device can comprise a self-expanding scaffold having a plurality of interconnected struts that form cells having a cell size that is sized and configured to hinder penetration of the thrombus into the self-expanding scaffold, thereby increasing a diameter of a flow path established by the expandable scaffold. In some embodiments, the system comprises a temporary expandable thrombus removal device configured to be inserted through the microcatheter to treat the thrombus. The expandable thrombus removal device can comprise a self-expanding scaffold having a plurality of interconnected struts that form cells having a cell size that is sized and configured to facilitate thrombus penetration within the cells, thereby increasing engagement of the thrombus by the self-expanding scaffold.

In some embodiments, the cells of the scaffold of the expandable reperfusion device have a cell length of between 2 mm and 4 mm (e.g., 2, 2.5, 3, 3.5, 4 mm) and a cell height between 1 mm and 3 mm (e.g., 1, 1.5, 2, 2.5, 3 mm) in an expanded configuration. In some embodiments, the ratio of the length and the height is about 4:1, 3:1, 2:1, 1:1, 1:2, 1:3 or 1:4. The cells may have the same dimensions or different dimensions in a single scaffold. Layers of cells or multiple scaffolds can be used to, for example, provide different cell sizes. In some embodiments, the scaffold of the expandable reperfusion device has a chronic outward force across an expansion diameter of 1.5 mm to 4.5 mm (e.g., 1.5 mm, 2.0 mm, 2.5 mm, 3.0 mm, 3.5 mm, 4.0 mm of between 0.0040 N and 0.0120 N (e.g., between 0.0040 N and 0.0100 N, between 0.0060 N and 0.0120 N, about 0.0040N, about 0.0050 N, about 0.0060 N, about 0.0070 N, about 0.0080 N, about 0.0090 N, about 0.0100 N, about 0.0110 N, about 0.0120 N). In some embodiments, the chronic outward force is an average chronic outward force. In some embodiments, the cells of the scaffold of the expandable thrombus removal device in an expanded configuration have a cell length of between 4 mm and 6 mm and a cell height between 2 mm and 4 mm. In some embodiments, the expandable thrombus removal device has an average chronic outward force across a diameter of 1.5 mm to 4.5 mm of between 0.0020 N and 0.0090 N. In some embodiments, a central portion of each strut of the expandable thrombus removal device has a greater thickness than adjacent portions of the strut. In several embodiments, the central portion of the strut comprises the middle 10%, 20%, 25%, 30%, 35%, 40% or 50% of the strut. In some embodiments, the central portion of the strut is about 5%, 10%, 15%, or 20% thicker than the adjacent portions and/or the end portions. In one embodiment, the central portion is thicker than the adjacent portions, which in turn are thicker (or thinner) than the end portions. In another embodiment, the central portion is thicker than the adjacent portions, wherein the adjacent portions have the same thickness as the end portions.

In accordance with several embodiments of the invention, a system for providing progressive therapy for clot management is provided. In some embodiments, the clot management system comprises a microcatheter (e.g., a neuro microcatheter). In some embodiments, the system comprises a variable-stiffness, laser-cut hypotube having a lumen sized and adapted to receive a guidewire. The distal end of the hypotube can have a greater flexibility than the proximal end to facilitate introduction within tortuous cerebral vasculature (e.g., the carotid siphon).

In some embodiments, the system comprises an expandable and reconstrainable scaffold coupled to a distal end of the hypotube. The scaffold can be adapted to radially self-expand from a non-expanded configuration to an expanded configuration upon unsheathing of the scaffold and adapted to transition from the expanded configuration to the non-expanded configuration upon sheathing of the scaffold. In some embodiments, the scaffold comprises a generally cylindrical configuration. In some embodiments, the scaffold comprises an undulating configuration, a tapered or conical configuration, a triangular configuration, an elliptical configuration, a spiral configuration, or other configuration. In some embodiments, the scaffold comprises a plurality of open cells defined by struts and connected by bridges. In some embodiments, each strut of the scaffold has a strut width and a strut thickness providing effective pinching stiffness and hoop stiffness for compressing a vascular clot to promote at least one of lysis, maceration, and removal of the clot without compromising trackability of the stroke device. In some embodiments, the struts have a squared-off configuration, a rounded configuration, a pointed configuration (e.g., tapered, wedge-shaped, triangular), and/or a grooved configuration. In some embodiments, struts having a pointed configuration are adapted to facilitate penetration into a thrombus or clot, thereby facilitating protrusion of thrombus material within an interior of the scaffold through the cells of the scaffold, and thereby facilitating engagement of the thrombus material by the scaffold. The enhanced engagement of the thrombus material increases the likelihood of complete removal of the thrombus material in a single pass. In some embodiments, the exterior contact surfaces of the struts are textured or include surface features designed to facilitate engagement or adhesion of thrombus material (e.g., ridges, bumps, grooves, cut-outs, recesses, serrations, etc.). In some embodiments, the struts are coated with one or more materials adapted to promote platelet activation or adhesion of thrombus material.

In some embodiments, the system for providing progressive therapy for clot management comprises a guidewire configured to be received by the lumen of the hypotube. In some embodiments, the scaffold has a chronic outward force (COF) per unit length that does not decrease by more than 75% from a diameter of 1.5 mm to a diameter of 4.5 mm. In some embodiments, the scaffold has a chronic outward force (COF) per unit length that does not decrease by more than 95%, 90%, 85%, 80%, 75%, 70%, 65%, 60%, 55%, 50%, 45%, 40%, 35%, 30%, 25%, 20%, 15%, or 10%. In some embodiments, each bridge of the scaffold is connected by three or four struts. In some embodiments, the scaffold comprises a closed-cell scaffold to facilitate resheathing. In some embodiments, a distal end of the elongate member is soldered to a proximal end of the scaffold using a radiopaque band comprising a different material than the elongate member and the scaffold.

In accordance with several embodiments of the invention, an expandable tip assembly is provided. In some embodiments, the expandable tip assembly comprises an elongate member. The elongate member can include a hypotube having a lumen or a wire (e.g., guidewire or delivery wire) without a lumen. In some embodiments, the hypotube can comprise a variable-stiffness hypotube having a proximal portion, a distal portion and a lumen sized and adapted to receive a guidewire. In some embodiments, the distal portion of the hypotube has a greater flexibility than the proximal portion to facilitate introduction within tortuous cerebral vasculature. In some embodiments, the greater flexibility is provided by spiral laser cuts spaced along the distal portion of the hypotube. The spacing between the spiral cuts can decrease from a proximal end of the distal portion to a distal end of the distal portion. In some embodiments, the expandable tip assembly comprises a self-expanding scaffold coupled to a distal end of the elongate member. The self-expanding scaffold can be detachably coupled or permanently coupled (e.g., non-detachably, non-releasably) to the distal end of the elongate member. In some embodiments, the scaffold is coupled to the distal end of the elongate member by a plurality of tether lines. The tether lines can extend concentrically or eccentrically from (e.g., from one side, from one half, from below center, from above center) of the distal end of the elongate member. In some embodiments, the scaffold is adapted to radially expand from a non-expanded configuration to an expanded configuration upon unsheathing of the scaffold and is adapted to transition from the expanded configuration to the non-expanded configuration upon unsheathing and resheathing of the scaffold. In some embodiments, the scaffold comprises a generally cylindrical configuration. In some embodiments, the scaffold comprises an open distal end without a distal embolic protection member or device. In some embodiments, a proximal end of the scaffold comprises a cut-out portion configured to facilitate re-sheathing of the scaffold. In some embodiments, the scaffold comprises a plurality of open cells defined by struts and connected by bridges. In some embodiments, each strut has two ends, with each end connected to one of the bridges. In some embodiments, each bridge is connected to four struts. In some embodiments, the struts and the bridges have varying thickness to impart flexibility to the scaffold. For example, a central portion of each strut can have a greater thickness than adjacent portions of the strut. As another example, a central portion of each strut can have a greater width than adjacent portions of the strut.

In some embodiments, the scaffold has a chronic outward force per unit length that does not decrease by more than 75% from a diameter of 1.5 mm to a diameter of 4.5 mm. In some embodiments, the scaffold has a chronic outward force per unit length that does not decrease by more than 50% from a diameter of 1.5 mm to a diameter of 4.5 mm. In some embodiments, the open cells have a cell size of about 5 mm by about 3 mm. In some embodiments, the scaffold comprises nitinol, stainless steel, nickel titanium alloy, and/or other shape memory materials.

In accordance with several embodiments of the invention, an expandable tip assembly comprises a self-expanding scaffold having an average COF per unit length across a diameter of 2.0 mm to 4.5 mm of between at least about 0.0025 N/mm and at least about 0.007 N/mm, between at least about 0.0030 N/mm and at least about 0.0059 N/mm, between at least about 0.00165 N/mm and at least about 0.0090 N/mm, or overlapping ranges thereof. In some embodiments, the scaffold has a radial resistive force (RRF) range per unit length across a diameter of 2.0 mm to 4.5 mm of between at least about 0.005 N/mm and at least about 0.016 N/mm. In some embodiments, the ratio of strut thickness to strut width is less than at least about 1:4 (e.g., 1:4, 1:4.5, 1:5, 1.5:5, 1:6). In some embodiments, the strut thickness is substantially equal to the strut width or greater than the strut width. The struts can be substantially linear across their length or at least a portion of the struts can have a curve. In some embodiments, the open cells of the scaffold are substantially diamond-shaped or parallelogram-shaped, and the bridges are substantially "C"-shaped, substantially "U"-shaped, substantially "S"-shaped, or substantially "X"-shaped. In some embodiments, each open cell is defined by six struts. In some embodiments, the cells of the scaffold have an area that varies between about 0.010 sq. inches and about 0.020 sq. inches. In some embodiments, each of the cells has the same area. In some embodiments the open cells have a length from about 0.120 inches to about 0.250 inches and a height from about 0.050 inches to about 0.100 inches when the scaffold is in an expanded configuration. In some embodiments, the ratio between the length of the cells and the height of the cells is 1:1, 2:1, 2.5:1, 3:1, 3.5:1, 4:1, 4.5:1, 5:1, 3:2, 4:3, 5:3, 1:2, 1:3, or 1:4. In some embodiments the scaffold has a length of about 30 mm. In some embodiments, the scaffold has a length from about 5 mm to about 50 mm, from about 10 mm to about 40 mm, from about 15 mm to about 35 mm, from about 20 mm to about 40 mm, or overlapping ranges thereof.

In accordance with several embodiments of the invention, a kit is provided for providing progressive therapy to address an occlusive thrombus. In some embodiments, the kit comprises a plurality of expandable tip assemblies, such as those described herein. For example, the kit can comprise a first expandable tip assembly, or reperfusion device, that is adapted to facilitate reperfusion of a blood vessel occluded by a thrombus, and therefore, facilitate lysis of the thrombus. The first expandable tip assembly, or reperfusion device, can comprise a proximal elongate member and a self-expanding scaffold coupled to a distal end of the proximal elongate member. The elongate member can comprise a wire without a lumen or a tube with a lumen. The self-expanding scaffold can comprise cells having a cell size adapted to hinder, inhibit, or reduce the likelihood of penetration within an interior of the scaffold upon expansion of the scaffold adjacent to, across, or within, the thrombus. In some embodiments, the kit comprises a second expandable tip assembly, or thrombus removal device, that is adapted to facilitate engagement with, capture, and/or extraction of thrombus material. In some embodiments, the second expandable tip assembly can be used after the first expandable tip assembly to remove any thrombus material remaining after use of the first expandable tip assembly. In some embodiments, the second expandable tip assembly, or thrombus removal device, comprises a proximal elongate member and a self-expanding scaffold coupled to a distal end of the proximal elongate member. The elongate member can comprise a wire without a lumen or a tube with a lumen. The self-expanding scaffold of the second expandable tip assembly can comprise cells having a cell size adapted to facilitate, promote, or increase the likelihood of penetration within an interior of the scaffold upon expansion of the scaffold adjacent to, across, or within, the thrombus, thereby facilitating engagement with, and capture of, the thrombus.

In some embodiments, the kit comprises a microcatheter, such as a neuro-microcatheter. The microcatheter can be adapted to deliver the expandable tip assemblies within blood vessels. The microcatheter can be sized so as to be inserted within cerebral vasculature of a human patient (e.g., an outer diameter of less than 0.040 inches, less than 0.030 inches, less than 0.025 inches). In some embodiments, the microcatheter provides a sheathing function as described in more detail herein. In some embodiments, the kit comprises a guidewire. In some embodiments, the microcatheter and the expandable tip assemblies can be delivered over the guidewire, thereby providing maintained access to the occlusive thrombus during removal of a first expandable tip assembly and insertion of a second expandable tip assembly or during repositioning of an expandable tip assembly. In some embodiments, the kit comprises a guide catheter adapted to access vasculature of a patient (e.g., a femoral artery) and adapted to be inserted within the vasculature to a region near the cerebral vasculature. The guide catheter can be sized to receive the microcatheter. The kit can be provided with instructions for use.

In some embodiments, a kit is provided that includes a plurality of expandable tip assemblies having varying maximum expansion diameters to be inserted within vessels having varying diameters. The kit of differently-sized expandable tip assemblies can provide adjustable targeted treatment options depending on a location of a clot. The expandable tip assemblies can be selected based on the location of the clot. An appropriately-sized expandable tip assembly can be selected to reduce or increase cell deformation and/or wall apposition. For example, an expandable tip assembly having a maximum expansion diameter of 3 mm can be adapted for use in the M1 or M2 segment of the middle cerebral artery and an expandable tip assembly having a maximum expansion diameter of 5 mm can be adapted for use in the internal carotid artery. The kit can be provided with instructions for use.

In some embodiments, the expandable scaffolds or self-expanding scaffolds described herein include cells having variable cell size at different portions of the scaffold. For example, the scaffolds can have relatively smaller cells at one or both distal end portions of the scaffold and relatively larger cells at a middle portion of the scaffold. Portions of the scaffold having relatively small cell sizes (e.g., reperfusion portions) can be configured to provide or facilitate effective blood flow restoration or reperfusion and the portions of the scaffold having relatively large cell sizes (e.g., removal portions) can be configured to provide or facilitate effective clot removal. In some embodiments, the cell size can be configured to provide or facilitate effective blood flow restoration or reperfusion and effective clot removal.

For purposes of summarizing the disclosure, certain aspects, advantages and novel features of various embodiments have been described herein. It is to be understood that not necessarily all such advantages may be achieved in accordance with any particular embodiment disclosed herein. Thus, embodiments disclosed herein may be embodied or carried out in a manner that achieves or selects one advantage or group of advantages as taught herein without necessarily achieving other advantages as may be taught or suggested herein.

BRIEF DESCRIPTION OF THE DRAWINGS

The features of embodiments of the inventions disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIGS. 2A and 2B illustrate an embodiment of an acute stroke recanalization system tailored for use in the neurovasculature of FIG. 1, further illustrating modular aspects of the system as used with tethered or reconstrainable self-expanding neurological medical devices.

FIGS. 6A-6C illustrate an embodiment of an expandable tip assembly.

FIGS. 10D-10F illustrate a perspective view, a side view and a front view of the expandable scaffold in an expanded configuration.

FIG. 11A illustrates a side view of an embodiment of an expandable scaffold in a compressed configuration and FIGS. 11B and 11C illustrate a perspective view and a side view of the expandable scaffold of FIG. 11A in an expanded configuration.

FIG. 15A illustrates a laser cut profile of an embodiment of an expandable scaffold and FIGS. 15B and 15C illustrate a perspective view and a side view of the expandable scaffold formed from the laser cut profile of FIG. 15A in its expanded configuration.

FIG. 17A illustrates a laser cut profile of an embodiment of an offset expandable scaffold and FIGS. 17B-17E illustrate a side view, a front view, a back view, and a section view of the expandable scaffold formed from the laser cut profile of FIG. 17A.

FIG. 30B shows a detailed schematic representation of a cell of one embodiment of an expandable scaffold.

FIGS. 32A-32F illustrate various embodiments of expandable scaffold profiles or shape configurations.

FIGS. 33A-33F illustrate an embodiment of a revascularization process.

FIG. 50 shows a perspective view of an embodiment of a rapid reperfusion device in an unexpanded state.

FIG. 51 shows a perspective view of an embodiment of a rapid reperfusion device in an expanded state.

FIG. 52A shows a side view of an embodiment of a rapid reperfusion device.

FIG. 52B shows a sectional view of an embodiment of a rapid reperfusion device.

FIG. 52C shows a sectional view of an embodiment of a rapid reperfusion device.

FIG. 53A shows a side view of an embodiment of a rapid reperfusion device.

FIG. 53B shows a sectional view of an embodiment of a rapid reperfusion device.

FIG. 53C shows a sectional view of an embodiment of a rapid reperfusion device.

FIG. 54 shows a side view of an embodiment of a rapid reperfusion device in an unexpanded state.

FIG. 55 shows a side view of an embodiment of a rapid reperfusion device in an expanded state.

FIG. 56 shows a perspective view of an embodiment of a rapid reperfusion device in an unexpanded state.

FIG. 57 shows a perspective view of an embodiment of a rapid reperfusion device in an expanded state.

FIG. 58 shows a side view of an embodiment of a rapid reperfusion device in an unexpanded state.

FIG. 59 shows a side view of an embodiment of a rapid reperfusion device according to one embodiment in an expanded state.

FIG. 60A shows a view of a rapid reperfusion device according to one embodiment near a target embolus.

FIG. 60B shows a view of a rapid reperfusion device according to one embodiment deployed across a target embolus.

FIG. 60C shows a view of a rapid reperfusion device according to one embodiment deployed against a target embolus.

FIG. 61A shows a view of a rapid reperfusion device according to one embodiment near a target embolus.

FIG. 61B shows a view of a rapid reperfusion device according to one embodiment deployed across a target embolus.

FIG. 61C shows a view of a rapid reperfusion device according to one embodiment deployed against a target embolus.

DETAILED DESCRIPTION

I. General

Figure 1:
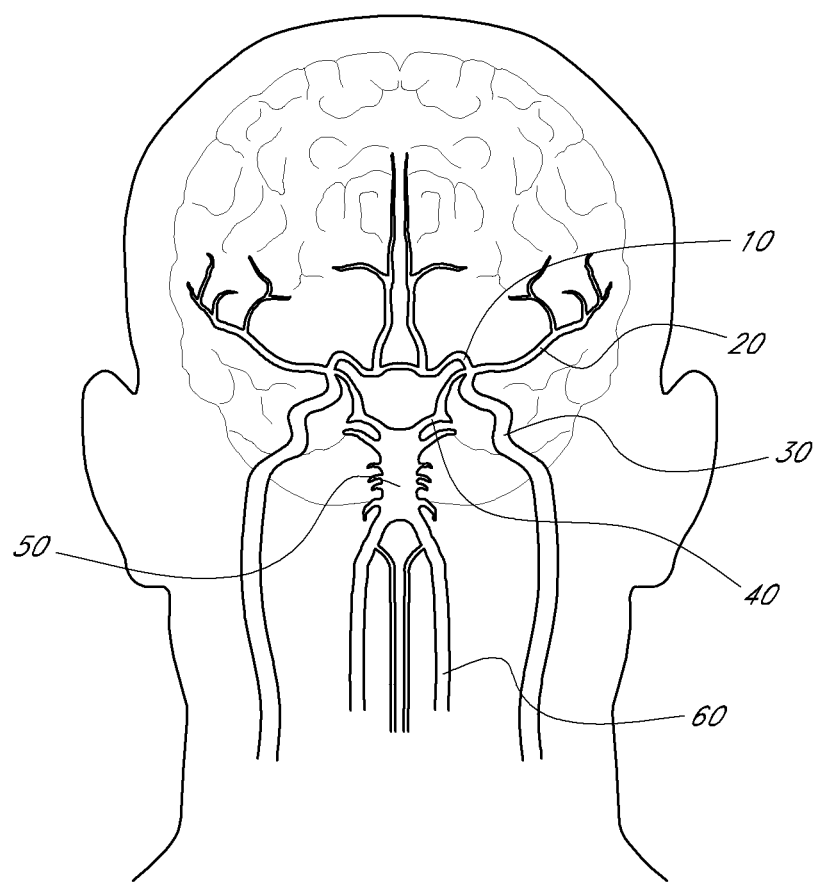
FIG. 1 is an illustration of the anatomy of the human cerebral vasculature or neurovasculature.

Several embodiments of the invention disclosed herein provide systems, methods, and devices for the treatment of acute ischemic stroke that provide immediate blood flow restoration to a vessel occluded by a clot and, after reestablishing blood flow, address the clot itself. Immediate blood flow restoration to the neurovasculature distal to the clot can reduce the destruction of neurons and synapses of the brain that may otherwise occur if the clot is attempted to be removed without first restoring blood flow. Immediate blood flow restoration advantageously can facilitate natural lysis of the clot and also can reduce or obviate the concern for distal embolization due to fragmentation of the clot. In accordance with some embodiments, the clot can be addressed in-situ to reperfuse a blood vessel without occluding or blocking blood flow and without requiring the use of additional structures to address distal embolization.

Prior to Applicant's discoveries, accepted wisdom generally dictated that the thrombus should be carefully preserved so as not to disrupt or disturb the thrombus during retrieval (to avoid embolic particles from flowing distally and causing morbidity or mortality) and/or to employ distal embolic protection to capture any such embolic particles. Several embodiments of the present invention are particularly unexpected because lysis of the embolus to generate particles is enhanced, and moreover, embolic particles are allowed to be released (e.g., through maceration and/or lysis) without the need for distal embolic protection. According to several embodiments of the invention, the release of embolic particles is, surprisingly, facilitated because blood flow (which has previously been advantageously restored) causes lysis (e.g., enzymatic digestion) of those particles such that the particles no longer pose issues distally.

Several embodiments of the invention provide for progressive, or modular, treatment based upon the nature of the clot. For example, the progressive treatment can comprise a three-step progressive treatment process that includes immediate restoration of blood flow, in-situ clot management, and/or clot removal depending on the particular circumstances of the treatment (e.g., using a single expandable tip assembly or multiple expandable tip assemblies). The in-situ clot management can include, for example, lysis, maceration, or both. The progressive, or modular, treatment can be provided by one or more treatment devices. In some embodiments, clot removal may not be necessary due to the natural lytic destruction provided by the restoration of blood flow. In some embodiments, the progressive treatment of flow restoration, in-situ clot management, and clot removal or capture can be performed in a matter of minutes instead of hours (e.g., less than 5 minutes, less than 10 minutes, less than 15 minutes, less than 20 minutes, less than 25 minutes, less than 30 minutes, less than 45 minutes). In some embodiments, a clot management system provides treating physicians with a synergistic, two-device system optimized for both rapid reperfusion and versatile clot removal. By equipping the physician to achieve rapid perfusion, the system can help to alleviate the stress associated with racing against the clock to retrieve the clot.

In several embodiments, the outer layer of an embolus is removed via maceration and/or lysis, and the inner core of the thrombus is captured and removed. This is particularly beneficial in some embodiments because the outer layer particles are lysed by natural (or artificial) lytics or mechanical disruption and the inner core, which may be more adhesive, can be removed with minimal risk that any particles will slough off. Moreover, any small particles that are released can also be lysed by the lytic process. In some embodiments, about 30-80% of the thrombus is lysed and about 20-70% is captured and removed.

According to some embodiments of the invention, a self-expanding device, which is microcatheter-based, can be deployed across a thrombus, thereby restoring blood flow distal to the thrombus upon unsheathing. The device can then be resheathed and unsheathed one or more times to break up, or macerate, at least a portion of the clot. The device can then remain unsheathed for a period of time in order for the device to maintain restored flow, thereby facilitating natural lysis of the clot and allowing for incubation of the device within the clot to increase engagement of the clot into the interior of the device (e.g., from the exterior surface). The increased engagement can facilitate removal of the clot (if removal is necessary). In some embodiments, clot removal is performed while maintaining flow through or perfusion of the blood vessel.

Various embodiments according to the present disclosure relate to revascularization systems and devices used to treat, among other things, ischemic stroke. Naturally, therefore, the revascularization systems and devices of several embodiments of the present disclosure are designed to be used in neuro-type applications, wherein the specifications of the present catheters and revascularization devices may be deployed in the blood vessels of the cerebral vascular system. For example, the systems and devices disclosed herein can be configured to be deployed in the cerebral arteries, including but not limited to: the anterior cerebral arteries (ACA), the anterior communicating artery, the middle cerebral arteries (MCA) (including the M1 and M2 segments), the posterior communicating arteries, the internal carotid arteries (ICA), the vertebral arteries, the basilar artery, and the posterior cerebral arteries (PCA). In some embodiments, the systems and devices are configured to be deployed in the region above the subclavian and common carotid arteries.

Other embodiments of the invention are not limited to the neurovasculature and may be used in other regions, including but not limited to vessels (e.g., veins or arteries) in, to or from the heart, lungs, extremities (e.g., legs), and pelvis. Moreover, some embodiments of the invention are not limited to vascular thrombi, but instead can be directed to treatment (e.g., maceration, lysis, capture or combinations thereof) of undesired targets (e.g., gallstones, kidney stones, calcifications, cysts, fibroids, tumors, etc.). Embolic debris caused by interventions involving carotid artery stent placement and treating saphenous vein aortocoronary bypass grafts stenosis are treated according to several embodiments described herein.

In several embodiments, a method of treating a thrombus is provided. In one embodiment, the method first includes restoring blood flow within an occluded vessel. To restore flow, a reperfusion device having a self-expanding scaffold at a distal end of a long pusher tube or wire can be temporarily inserted into the occluded vessel and advanced to the location of the thrombus. In one embodiment, the location of the thrombus refers to a location wherein the scaffold effectively spans the thrombus (completely or substantially). Advancing the reperfusion device to the location of the thrombus can mean advancing the reperfusion device through the thrombus or to the side of the thrombus (e.g., within a microcatheter) depending on the path of least resistance and the location and morphology of the clot. In some embodiments, the reperfusion device is delivered through a microcatheter so that the self-expanding scaffold remains in a non-expanded configuration until a desired location is reached. The microcatheter can be pre-inserted or inserted together with the reperfusion device. The microcatheter can be advanced to a position wherein a distal tip of the microcatheter is located just beyond a distal end of the thrombus (e.g., within 2 cm past the thrombus, within 1 cm past the thrombus, within 5 mm past the thrombus, within 2 mm past the thrombus, aligned with the distal end of the thrombus). The reperfusion device can then be advanced within the microcatheter until the distal end of the self-expanding scaffold is aligned with, or slightly distal to, the distal end of the microcatheter.

The microcatheter can then be retracted proximally, thereby unsheathing the self-expanding scaffold and allowing the self-expanding scaffold to deploy to its expanded configuration within the thrombus. The microcatheter and the reperfusion device can be positioned such that when the self-expanding scaffold is fully deployed, it spans or substantially spans the thrombus. The self-expanding scaffold can compress (e.g., impact or press against or exert radial force from within) the thrombus against the vessel wall, thereby creating channels within or past the clot for blood to flow and facilitate clot lysis. The self-expanding scaffold can comprise cells having a relatively small cell size designed to minimize, hinder, prevent, deter, or reduce penetration of the thrombus, thereby maximizing the blood flow through the self-expanding scaffold. If the scaffold is not positioned as effectively as desired, the microcatheter can be advanced distally to resheath the scaffold and the microcatheter and the reperfusion device can then be moved to a new position and redeployed.

In several embodiments, after a period of time after initial expansion of the self-expanding scaffold, the microcatheter can be advanced proximally to reconstrain and resheath the self-expanding scaffold and then the microcatheter can be advanced distally again to redeploy the scaffold in the same position in an effort to macerate the thrombus. The resheathing and unsheathing can be repeated one or more times. The reperfusion device can then be removed by advancing the microcatheter distally to resheath the scaffold and then withdrawing the reperfusion device from the body (with or without the microcatheter).

After a period of waiting time in which lysis is allowed to occur due to the restored blood flow and maceration, an angiographic or other type of flow assessment can be performed. Angiographic or other flow assessments can be performed at any time during the treatment method (e.g., before or after the reperfusion device is removed). If the thrombus has completely lysed or lysed to a sufficient degree, the treatment may be complete and no further steps may be necessary.

If the thrombus has not sufficiently lysed after a predetermined amount of wait time and after repeated maceration attempts, a thrombus removal device can be inserted into a microcatheter (which may be the same microcatheter as above) and advanced to the location of the remaining thrombus material within the cerebral vasculature. The thrombus removal device can be deployed in a similar manner as described above with respect to the reperfusion device. The thrombus removal device can include a self-expanding scaffold at a distal end of a long pusher tube or wire similar to the reperfusion device. In one embodiment, the self-expanding scaffold of the thrombus removal device can include cells having a relatively large cell size compared to the reperfusion device designed to maximize, increase, facilitate, aid, encourage, enhance, promote, or allow penetration of the remaining thrombus material, thereby increasing the likelihood of engagement with and capture of the remaining thrombus material.

In some embodiments, the thrombus removal device can be resheathed and redeployed one or more times to increase the likelihood of engagement with and capture of the remaining thrombus material. The thrombus removal device (along with the captured thrombus material) can then be withdrawn from the blood vessel. In some embodiments, the microcatheter is advanced distally to resheath the self-expanding scaffold of the thrombus removal device before being withdrawn. In other embodiments, the self-expanding scaffold remains in its deployed configuration and the microcatheter and the thrombus removal device are withdrawn proximally into a larger guide catheter.

FIG. 1 illustrates a representation of the anatomy of the cerebral vasculature of a human from an anterior view. With reference to one hemisphere of the brain, the cerebral vasculature includes an anterior cerebral artery 10, a middle cerebral artery 20, an internal carotid artery 30 and a posterior cerebral artery 40. FIG. 1 also illustrates a basilar artery 50 and a vertebral artery 60. Occlusions or blockage within these arteries can prevent blood flow to the brain, thereby resulting in ischemic stroke.

In accordance with some embodiments, the systems, methods, and devices disclosed herein are used in a patient's neurovasculature in order to treat intracranial atherosclerotic disease (WAD) or to treat aneurysms by providing an aneurysm neck bridge. Treatment of aneurysms is described in more detail herein and is also described in U.S. Publication No. 2009/0125053 filed on Jun. 10, 2008, the entire content of which is hereby expressly incorporated by reference herein. Similarly contemplated for the revascularization systems and devices of the present disclosure is deployment in other parts of the body wherein the specifications of the present disclosure may be used in other vessels or lumens of the body in a minimally invasive or non-invasive manner.

In accordance with some embodiments, the systems, methods and devices disclosed herein provide ease of use, increased effectiveness, and enhanced safety over existing systems, methods and devices. For example, in embodiments incorporating deployment over a guidewire, the systems can provide enhanced trackability and maintained access to the treatment site during the treatment procedures. If multiple treatment devices are to be used, the guidewire can remain in place to maintain access, thereby decreasing the complexity and time of the overall clot therapy treatment. In some embodiments, multiple passes are not required to remove the clot; instead the clot can be removed in a single pass.

In accordance with some embodiments, large distal embolic fragments are not created, thereby preventing a need for distal embolic protection. In some embodiments, blood flow is not occluded, restricted, or obstructed during reperfusion, in-situ clot management, and/or clot removal.

In some embodiments, relatively small embolic fragments are produced as a result of maceration without concern for distal embolization based in part on the new and surprising discovery that distal embolization is not a concern when a blood vessel is first reperfused and blood flow is restored. Early blood flow restoration can provide new blood to the stunned ischemic region that is distal to the occlusive thrombus. The new blood can transport plasminogen activators and plasminogen to the thrombus surface. In accordance with some embodiments, after new blood has penetrated distal to the thrombus, if emboli is created as a result of thrombectomy, the emboli will lyse via enzymatic digestion rather than becoming a new occlusive thrombus requiring additional lysis.

In accordance with some embodiments, the systems and devices do not require an actuator that requires mechanical actuation or manipulation to effect deployment and retraction. For example, the systems and devices disclosed herein can be configured to provide automatic expansion without mechanical actuation using self-expanding devices that allow the devices to self-conform, self-adjust, or self-regulate to any size lumen or vessel. The self-conforming feature prevents or reduces the likelihood of overexpansion, thereby improving safety, and reduces complexity of the structure and operation of the systems and devices.

The systems, methods and devices described herein can provide increased effectiveness. Some embodiments of the invention advantageously provide for immediate restoration of blood flow. The immediate restoration of blood flow advantageously can facilitate natural lysis of the clot and, even if complete lysis does not occur, results in the clot being altered to be more manageable, thereby facilitating effective removal. As used herein, the term "immediate" as used herein shall be given its ordinary meaning and shall also include a designated action or result that occurs in less than about 10 seconds, less than about 30 seconds, less than about one or two minutes, less than about five minutes, less than about ten minutes, less than about twenty minutes, or less than about thirty minutes. In some embodiments, the term immediate can mean that a designated action occurs in a matter of seconds or minutes rather than in a matter of hours. In one embodiment, blood flow is restored immediately (e.g., within about 1 to 2 minutes) upon placement of the device in the neurovasculature. In one embodiment, blood flow is restored immediately (e.g., within about 5-30 minutes) upon initial insertion of the device into a patient (e.g., into the femoral artery). In several embodiments, blood flow is restored according to several embodiments of the invention in less than about half the time it would take for other devices to restore flow. In other embodiments, blood flow is restored according to several embodiments of the invention in less than about $\frac{1}{4}$, $\frac{1}{5}$, or $\frac{1}{10}$ time it would take for other devices to restore flow.

In some embodiments, the systems, methods, and devices disclosed herein reduce the time required to restore blood flow through an occluded vessel. In accordance with some embodiments, the systems, methods and devices provide restored blood flow in an amount of time that is at least thirty seconds less than existing systems, methods and devices. In some embodiments, the time from initial puncture of the skin to begin the delivery procedure to initial restoration of normal flow is between thirty seconds and thirty minutes (e.g., between thirty seconds and five minutes, between one minute and three minutes, between five minutes and ten minutes, between five minutes and fifteen minutes, between ten minutes and twenty minutes, between fifteen minutes and thirty minutes, or overlapping ranges thereof).

According to scientific estimates based on studies of large vessel, supratentorial ischemic strokes, every minute of occluded flow results in the loss of approximately 1.9 million neurons and 14 billion synapses and every second of occluded flow results in the loss of approximately 32,000 neurons and 230 million synapses. See Jeffrey Saver, "Time is Brain—Quantified," *Stroke*, volume 37, pages 233-236 (2006). Accordingly, even a thirty-second reduction in the time required for blood flow restoration is significant. Several embodiments of the systems, methods and devices described herein provide increased flow rates (e.g., Thrombolysis in Myocardial Infarction or TIMI scores) in shorter time than current systems and improved modified Rankin scores more frequently and in shorter time than current systems.

The systems, methods and devices described herein can provide enhanced safety. For example, according to several embodiments, the invention provides one or more of the following advantages: reduced vessel perforation or dissection, lower hemorrhage rate, less distal embolization, and lower death rates. In some embodiments, the invention comprises an expandable scaffold to be deployed, resheathed, and re-deployed in-situ without significant risk of damage to the vessel because the expandable scaffold is not moved laterally within the vessel while in its expanded configuration. In some embodiments, the expandable scaffolds described herein include a tapered (e.g., angled) proximal end having an everted or scooped-out (e.g., open) portal or mouth that reduces the likelihood of vessel damage (e.g., vessel perforation, vessel dissection, endothelial disruption) when the expandable scaffold is being recaptured or resheathed within a microcatheter.

II. Terminology

As used herein, the terms "treat," "treatment" and "treating" shall be given their ordinary meaning and shall refer to therapy, management, preventive care, repair, assessment, removal, and/or the like. With particular reference to stroke treatment, the terms can refer to the reduction or amelioration of the progression, severity, and/or duration of a stroke or a symptom thereof. Treatment as used herein with reference to stroke treatment includes, but is not limited to, decreasing the size or firmness of a clot, removing a clot, increasing blood flow, increasing cerebral perfusion, facilitating natural lysis of a clot, macerating a clot, repairing aneurysms, reducing destruction of brain synapses, improving modified Rankin scores, and improving brain function.

The term "scaffold" as used herein shall be given its ordinary meaning and shall include, without limitation, support members, collapsible members, expandable members, distensible members, reconstrainable members, solid structures, mesh structures, braided structures, woven structures, porous structures, open-cell structures, closed-cell structures, struts, stents, baskets, polymeric structures, membranes, bladders, umbrella-type devices, ribs, spokes, frames, and the like, and combinations thereof. Scaffolds may be fully or partially covered or may be uncovered. Covered scaffolds may comprise skeletons that are partially or fully covered by membranes, fabrics, films, multiple layers, and/or coated. Scaffolds may be mechanically actuated, self-actuated, inflated, and/or combinations thereof.

As used herein, the terms "reperfusion," "recanalization," "revascularization", and their derivatives shall be given their ordinary meanings and can refer to restoration of blood flow or blood supply. The terms reperfusion, recanalization, and revascularization can refer to the creation of a bypass from the patent vessel to beyond the occlusive thrombus. The terms are used interchangeably throughout the disclosure.

The terms "clot," "thrombus," or embolus" as used herein can be used interchangeably and shall be given their ordinary meanings and can refer to any occlusion or obstruction of a blood vessel. The terms can refer to a body of biological material or a foreign, non-biological material.

The terms "lysis," "lytic" and their derivatives as used herein shall be given their ordinary meanings and can refer to natural lysis (e.g., due to restored blood flow), mechanical lysis (e.g., due to contact or pressure), or chemical lysis (e.g., thrombolysis due to lytic agents and/or enzymatic digestion). Natural lysis due to restored blood flow can occur due to natural lytic compounds found in the blood (e.g., enzymes) and/or to the shear force of the flow. In some embodiments, lysis refers to any biological or other cellular or sub-cellular process or result of altering the structure of a clot. Lysis may refer to fibrinolysis—degradation of fibrin—within a fibrin clot by application of enzymes. For example, lysis may occur in the presence of plasmin, heparin, etc.; precursors or activation peptides thereof; or inhibitors of fibrin development. Lysis includes partially or fully dissolving or shrinking a thrombus (or embolic particles released from a thrombus). Lysis can be considered sufficient if the thrombus is lysed (e.g., dissolved, broken up into pieces, or shrunk) such that the thrombus no longer presents a risk of further occlusion or blockage of blood flow.

The term "maceration" and its derivatives as used herein shall be given their ordinary meanings and can refer to the process or result of softening of the clot or breaking the same into pieces mechanically or by using vascular fluids. Macerating can refer to pressing, compressing, diffusing, dissolving, disrupting, fragmenting, obliterating, destroying, breaking up, imploding, and/or softening. For example, pressing or compressing the clot with a mechanical member can cause the clot to soften, break up or fragment, whereby, exposure of the clot (or portions thereof) to vascular flow may cause the clot (or portions thereof) to fragment, soften, or diffuse.

The term "removal" and its derivates as used herein shall be given their ordinary meaning and can refer to capture and extraction from a patient's body or engagement and relocation of material or portions of the material, to a different region of the body. In some embodiments, "removal" can refer to destruction or reduction in size or content and not extraction in toto, or as a whole.

III. Clot Management Systems

A. General Systems

According to several embodiments, disclosed herein are catheter-based revascularization systems (e.g., clot management systems, stroke treatment systems). In accordance with some embodiments, the revascularization systems described herein comprise one or more expandable tip microcatheter assemblies that are configured to be temporarily inserted into cerebral vasculature of patients experiencing an acute ischemic stroke.

A catheter-based revascularization system effective for delivering a neurological medical device into a desired location in the cerebral vascular system is provided according to several embodiments. The revascularization system (e.g., stroke treatment system, clot management system) can function in at least three respective modes for addressing a clot: a reperfusion/blood restoration mode, a clot management mode, and a clot removal mode. The clot management mode can include maceration and/or lysis of the clot.

The revascularization systems (e.g., stroke treatment systems, clot management systems) can comprise two-part systems wherein blood flow is first restored and then an occlusion is removed, rather than just removing the occlusion without first reperfusing the vessel. In accordance with some embodiments, the revascularization systems provide lysis and maceration in situ before removal of the clot. In some embodiments, the in situ lysis and maceration can result in more effective removal of the clot. For example, the clot morphology can be improved by the lysis and maceration (e.g., reduced clot size or removal of soft, rubbery portions that make the clot difficult to grasp and remove). In some embodiments, the revascularization systems, or at least components of the systems, are configured for single use only and are disposable.

According to some embodiments, deployment of the systems disclosed herein increases the diameter of the flow channel and/or the flow rate through the blocked vessel by at least about 25%, 50%, 75% or more. In some embodiments, the systems have an adequately small profile with flexibility to promote improved access for in-site treatment is known which may be used as a temporary (e.g., not implanted) solution.

Figure 2C:
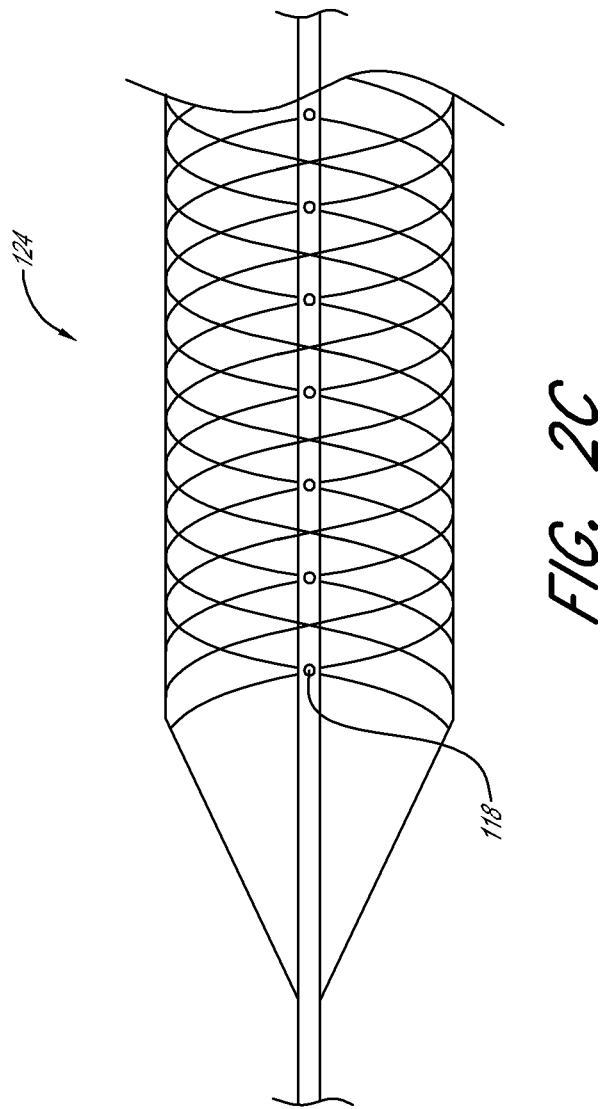
FIG. 2C illustrates a close-up view of the inner catheter of FIG. 2B.

According to several embodiments and as illustrated in FIG. 2A, a catheter-based revascularization system 100 provides a platform for lysing emboli in occluded blood vessels. Accordingly, the catheter-based revascularization system 100 generally comprises a control end 102 and a deployment end 104. In one embodiment, control end 102 is a portion of the device that allows a user, such as a surgeon, to control deployment of the device through the blood vessels of a patient. Included as part of the control end 102 is a delivery handle 106 and a winged apparatus 108, in some embodiments. Control end 102 can include a Tuohy Borst adapter and one or more rotating hemostasis valves. In some embodiments, module 113 (see FIG. 2B) is detachable.

According to some embodiments of systems, during shipping of the catheter-revascularization system 100, shipping lock (not shown) is installed between the delivery handle 106 and the winged apparatus 108 to prevent deployment and premature extension of a revascularization device 124 (see FIG. 2B) while not in use. Furthermore, by preventing the delivery handle 106 from being advanced towards the winged apparatus 108, coatings applied to the revascularization device 124 are stored in a configuration whereby they will not rub off or be otherwise damaged while the catheter-based revascularization system 100 is not in use.

According to several embodiments, an agent delivery device 130 provides a conduit in fluid communication with the lumen of the catheter-based revascularization system 100 enabling users of the system to deliver agents (e.g., lytic agents, clot adhesion agents) through catheter-based revascularization system 100 directly to the location of the embolus. The revascularization system delivery device (e.g., distal segment 120 of FIG. 1B) may be made from materials known to artisans, including stainless steel hypotube, stainless steel coil, polymer jackets (e.g., polymeric liners), and/or radiopaque jackets (e.g., markers or bands).

A luer connector 132 or a functional equivalent can provide sterile access to the lumen of the catheter-based revascularization system 100 to effect delivery of a chosen agent. The agent can include, but is not limited to, lytic agents, blood-thinning agents, and compounds or adherents formulated to promote clot adhesion or platelet activation. An example of an embodiment of a luer connector that can be used with the systems described herein is described in U.S. Patent Publication No. 2010/022951 filed May 20, 2009, the entirety of which is incorporated by reference herein.

Deployment end 104 of the catheter-based revascularization system 100 comprises a proximal segment 110 and a distal segment 120. The proximal segment 110, according to several embodiments, houses the distal segment 120 and comprises an outer catheter 112 (e.g., a microcatheter) that is of a suitable length and diameter for deployment into the blood vessel of the neck, head, and cerebral vasculature.

Referring also to FIG. 2B, distal segment 120 (e.g., an expandable tip assembly or expandable stroke treatment device) comprises an inner catheter 122 (e.g., an elongate member having a lumen) and a revascularization device 124 (e.g., an expandable scaffold)—as shown here in one embodiment having uniform cells, variable cells likewise being within other embodiments—which is connected to the inner catheter 122. The inner catheter 122, according to several embodiments, is made from coil, wire, or ribbon or laser cut hypotube and is of a suitable length and diameter to move through the outer catheter 112 during deployment. In some embodiments, the inner catheter 122 comprises stainless steel or any other metallic, alloy-based, or polymeric material.

In accordance with some embodiments, the revascularization systems (e.g., stroke treatment systems) include a guide catheter, an outer catheter (e.g., a microcatheter), one or more guidewires and/or one or more stroke treatment devices (e.g., recanalization devices, revascularization devices, reperfusion devices, expandable tip assemblies). In some embodiments, one or more stroke treatment devices (e.g., expandable tip assemblies) can be provided in a kit and appropriately-sized off-the-shelf or conventional guide catheters, microcatheters and guidewires can be used at the discretion of a clinician to effect delivery of a selected one or more of the stroke treatment devices (e.g., expandable tip assemblies) to target treatment locations. The kit of stroke treatment devices can include reperfusion devices designed and configured to provide immediate blood flow restoration and removal devices designed and configured to facilitate effective clot removal.

Figure 3:
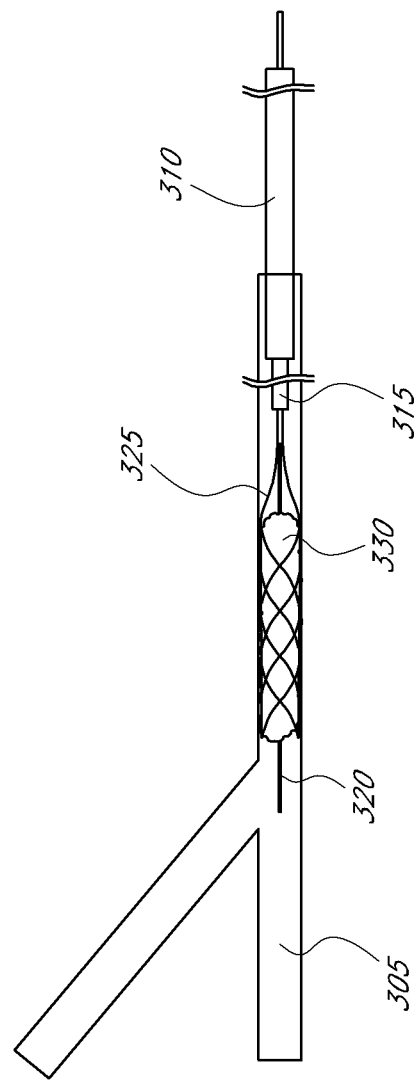
FIGS. 3 and 3A illustrate schematic representations of embodiments of a revascularization system being used to address a clot in an occluded vessel.
Figure 3A:
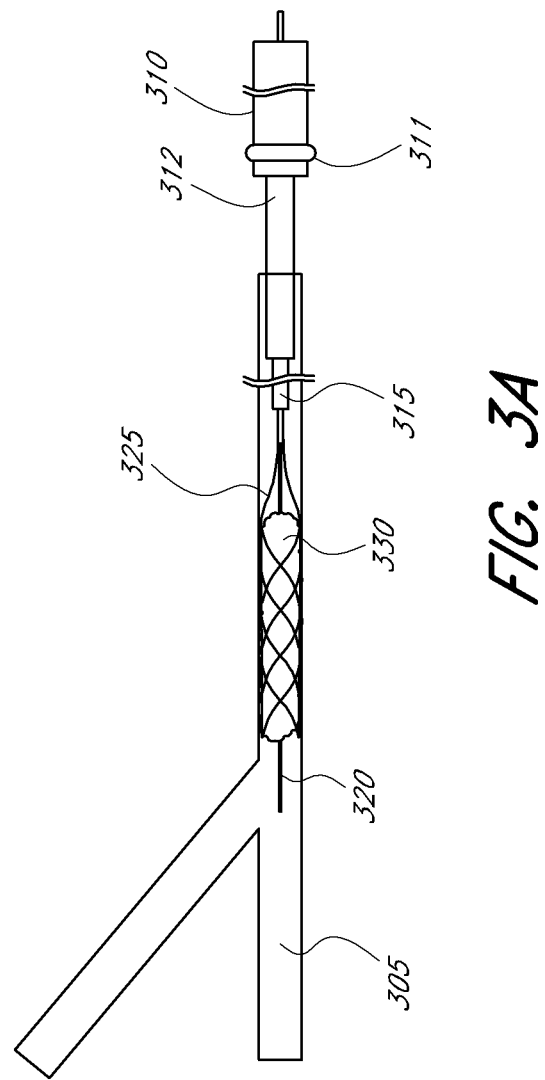

With reference to FIG. 3, an embodiment of a revascularization system 300 (e.g., clot management system, stroke treatment system) is illustrated within an occluded vessel 305. The revascularization system 300 includes a guide catheter 310, a microcatheter 315, a guidewire 320, and an expandable tip assembly 325. The expandable tip assembly 325 (e.g., stroke treatment device) is shown in its deployed configuration within an occlusion 330 during an embodiment of a revascularization process (e.g., clot management process illustrated in FIGS. 33A-33F). In some embodiments, the revascularization system 300 does not include one or more of the above-recited components. With reference to FIG. 3A, in some embodiments, the revascularization system 300 includes a neuro distal access catheter 312.

1. Guide Catheter

In some embodiments, the guide catheter 310 accesses a blood vessel under standard interventional procedures (e.g., using an endovascular or percutaneous approach via an incision in a femoral artery and/or using the Seldinger technique). The guide catheter 310 can have an inner diameter large enough to receive a microcatheter and still allow for contrast injection while the microcatheter is in place, thereby advantageously allowing for fluoroscopic road mapping during the procedures. In some embodiments, the guide catheter 310 has an inner diameter of at least 0.056 inches; however, inner diameters between 0.030 inches and 0.090 inches, between 0.040 inches and 0.085 inches, between 0.050 inches and 0.080 inches, less than 0.020 inches, greater than 0.090 inches, or overlapping ranges thereof can be used. In some embodiments, the guide catheter 310 comprises a balloon guide catheter having a balloon 311 configured to temporarily obstruct flow (partially or completely) during removal of an occlusion (e.g., clot or foreign body). In some embodiments, the guide catheter 310 is aspirated (e.g., with a syringe) during removal of an occlusion. The guide catheter 310 can comprise a 6 French (F) or larger guide catheter; however guide catheters of larger or smaller diameters can be used as desired and/or required. In some embodiments, the inner diameter of the guide catheter is 7 F (0.059 inches), 8 F (0.078 inches) or 9 F (0.085 inches). The guide catheter can comprise a neuro guide catheter having a length of 90 cm, 100 cm, less than 90 cm, or greater than 100 cm.

2. Distal Access Catheter

With reference to FIG. 3A, in some embodiments, the revascularization system, or stroke treatment system, 300 comprises a neuro distal access catheter 312 configured to be inserted within a guide catheter (e.g., guide catheter 310) and a microcatheter (e.g., microcatheter 315) is configured to be inserted within the distal access catheter 312. The term "distal access catheter" as used herein shall be given its ordinary meaning and shall also include distal support catheters and/or aspiration catheters. In some embodiments, the guide catheter 310 is configured to provide proximal aspiration (e.g., aspiration within an upstream artery proximal to an occluded downstream artery and remote from the thrombus or clot) and the distal access catheter 312 (e.g., distal aspiration and/or aspiration catheter) is configured to provide local aspiration (e.g., aspiration at a location proximal to and in close proximity to the thrombus or clot but within the occluded artery). For example, the distal access catheter 312 can be a thrombus-aspiration catheter and a syringe, needle, vacuum, or other aspiration device can be connected, attached or otherwise coupled to, or inserted within, a proximal end (e.g., end outside the body) of the distal access catheter 312. The aspiration can be provided by manual aspiration or automatic aspiration devices and/or methods.

In some embodiments, local aspiration at or in close proximity to the location of the thrombus provided by the distal access catheter 312 (e.g., distal support and/or aspiration catheter) advantageously increases the likelihood of, or facilitates, capture or removal of portions of the thrombus as the expandable tip assembly. In some embodiments, the local aspiration increases the likelihood of, or facilitates, capture or removal of a core of the thrombus. In some embodiments, the distal access catheter 312 is a distal support catheter that provides increased arterial and/or microcatheter support and facilitates access to the occluded vessel (e.g., cerebral arteries) over the microcatheter 315 alone. In some embodiments, the distal access catheter 312 (e.g., distal support and/or aspiration catheter) provides arterial and/or microcatheter support distal to the distal end of the guide catheter 310. In some embodiments, the distal access catheter 312 adjusts a direction of the force on the thrombus during removal to substantially align with a longitudinal axis of the blood vessel, thereby increasing the likelihood of successful removal of the thrombus.

In some embodiments, the distal access catheter 312 has an outer diameter that is less than the inner diameter of the guide catheter 310 and an inner diameter that is greater than the outer diameter of the microcatheter 315. In some embodiments the outer diameter is between 4 F and 8 F (e.g., between 4 F and 7 F, between 5 F and 8 F, between 5 F and 7 F and overlapping ranges thereof) and the inner diameter is between 0.030 inches and 0.070 inches (e.g., between 0.030 inches and 0.050 inches, between 0.040 inches and 0.070 inches, between 0.050 inches and 0.060 inches, or overlapping ranges thereof). In one embodiment, the distal access catheter 312 is a 6 F catheter having an inner diameter of 0.057 inches. In some embodiments, the inner diameter of the distal access catheter 312 is greater than the outer diameter of the guide catheter 310. In some embodiments, the distal access catheter 312 is used instead of the guide catheter 310. In some embodiments, the distal access catheter 312 is used instead of the microcatheter 315. In some embodiments, the larger diameter of the distal access catheter 312 allows for more effective aspiration than if aspiration were performed through the microcatheter 315 alone.

In some embodiments, the distal access catheter 312 can slow down blood flow but not totally occlude flow (e.g., through aspiration). In some embodiments, the distal access catheter 312 comprises a balloon. In some embodiments, the distal access catheter 312 comprises one or more lumens. In one embodiment, the distal access catheter 312 comprises a single central lumen. In some embodiments, the distal access catheter 312 comprises multiple holes at its distal or proximal ends to facilitate increased aspiration and to reduce the likelihood of blockage.

In one embodiment of a method of managing blood clots in neurovasculature, the balloon guide catheter 310 is inserted into the body and a distal end of the guide catheter 310 is advanced to the cerebral vasculature proximal or downstream of an occluded artery (e.g., to the common carotid artery or proximal segment of the ICA for MCA occlusions or to an origin of one of the vertebral arteries for basilar artery occlusions). The distal access catheter 312 can then be inserted within a lumen of the guide catheter 310 and a distal end of the distal access catheter 312 can be advanced to a location adjacent an occlusion (e.g., clot, thrombus, embolus) within an occluded artery (e.g., within an MCA or at the bifurcation between the ICA and the MCA for MCA occlusions or within the basilar artery or a proximal segment of a vertebral artery for basilar occlusions). In some embodiments, a distal end of the distal access catheter 312 can be positioned at an origin of an occluded artery or other blood vessel. The microcatheter 315 can then be inserted through a lumen of the distal access catheter 312 and a distal end of the microcatheter 315 can be positioned at a location that coincides with the occlusion (e.g., clot, thrombus, embolus). The expandable tip assembly 325 can then be inserted through a lumen of the microcatheter 315 and advanced to the distal end of the microcatheter 315. The microcatheter 315 can then be retracted proximally as described in more detail in connection with FIGS. 33A-33F to cause the expandable tip assembly 325 to be deployed in a manner that at least partially spans the occlusion (e.g., clot, thrombus, embolus).

In some embodiments, the distal access catheter 312 can provide local aspiration (e.g., aspiration in close proximity to a thrombus or other occlusion). The distal end of the distal access catheter 312 can be positioned between 10 mm and 10 cm of the thrombus or a proximal end of the expandable tip assembly 325 (e.g., between 10 mm and 30 mm, between 20 mm and 50 mm, between 30 mm and 80 mm, between 40 mm and 100 mm, or overlapping ranges thereto). In some embodiments, the distal end of the distal access catheter 312 is positioned less than 10 mm from the thrombus or a proximal end of the expandable tip assembly 325 or greater than 10 cm from the thrombus or a proximal end of the expandable tip assembly 325.

As described in more detail herein, the expandable tip assembly 325 can restore blood flow through an occluded vessel and the natural lytic action of the restored blood flow can lyse thrombus or embolus material within the neurovasculature. The expandable tip assembly 325 can also be configured to engage and capture at least a portion of a thrombus or other occlusive object within the occluded artery and remove the occlusive object upon removal of the expandable tip assembly 325.

In several embodiments, the expandable tip assembly 325, the microcatheter 315, the guide catheter 310 and the distal access catheter 312 are removed from the patient after the thrombus or other occlusive object has been treated, managed, or otherwise addressed and blood flow has been restored. In some embodiments, the distal access catheter 312 is removed from the patient simultaneously with the expandable tip assembly 325, microcatheter 315 and the guide catheter 310. In other embodiments, the distal access catheter 312 is removed from the patient before or after the expandable tip assembly 325, microcatheter 315 and/or the guide catheter 310.

3. Microcatheter

In some embodiments, the microcatheter 315 is configured to receive, house, deliver, and remove the expandable tip assembly 325. The microcatheter 315 can be configured to provide a sheathing function for the expandable tip assembly 325. In some embodiments, the expandable tip assembly 325 can be inserted within the microcatheter 315 in a compressed, or non-expanded, configuration and advanced to a distal end of the microcatheter 315. The microcatheter 315 can then be retracted proximally with respect to the expandable tip assembly 325 to allow the expandable tip assembly 325 to transition to a deployed, or expanded, configuration at least a portion thereof having a diameter greater than in the unexpanded configuration. The microcatheter 315 can comprise a conventional microcatheter selected by a particular medical professional or clinician (e.g., due to familiarity, ease of use, or cost) or a proprietary microcatheter that is provided in a kit together with one or more expandable tip assemblies.

According to several embodiments, the microcatheter length and diameter are suitable for inserting into a human patient and capable of reaching a target embolus in the region above the subclavian and common carotid arteries while still being accessible to a clinician from outside a patient's body. For example, according to several embodiments, the microcatheter 315 is between about 135 cm and about 175 cm long, between about 135 cm and about 150 cm, between about 140 cm and about 150 cm, shorter than 135 cm, longer than 175 cm, or overlapping ranges thereof. In various alternative embodiments, the microcatheter 315 has a length of 90 cm, 100 cm, 115 cm, 125 cm, 130 cm, 135 cm, 136 cm, 140 cm, or 150 cm. The microcatheter 315 can comprise a neuro microcatheter.

The microcatheter 315 includes a proximal segment (at a control end of the microcatheter) and a distal segment (at a deployment end of the microcatheter). In some embodiments, the proximal segment is about 115 cm long with an outer diameter of between about 2.0 F and 3.5 F (e.g., 2.5 F, 2.8 F, 3.5 F) and the distal segment is about 35 cm with an outer diameter of between about 1.5 F and 3.0 F (e.g., 1.7 F, 1.9 F, 2.3 F 2.5 F, 2.8 F); however the proximal segment can be from 75 cm to 150 cm long, from 100 cm to 130 cm long, from 90 cm to 120 cm long, shorter than 75 cm, longer than 150 cm, or overlapping ranges thereof and have an outer diameter between about 1.5 F and 3.7 F, between about 3.0 F and 4.0 F, between about 2.5 F and 3.5 F, less than 1.5 F, greater than 4.0 F, or overlapping ranges thereof. The distal segment can be between about 20 cm and 40 cm long, between about 25 cm and 50 cm long, between about 30 cm and 40 cm long, shorter than 20 cm, longer than 50 cm, or overlapping ranges thereof and have an outer diameter between about 1.0 F and 3.0 F, between about 1.5 F and 3.5 F, between about 1.5 F and 2.5 F, less than 1.0 F, greater than 3.5 F, or overlapping ranges thereof.

According to some embodiments, a gradual decrease or stepwise in the outer diameter dimension of the microcatheter 315 as a function of the distal distance from the proximal segment. For example, the proximal segment can be 3.5 F at the most proximal end and the distal segment can be 2.7 F at the most distal end. As another example, the proximal segment can be 2.7 F at the most proximal end and 1.7 F at the most distal end. Disposed between is an intermediate segment having one or more intermediate outer diameters between the maximum and minimum diameters. For example, for a microcatheter with a maximum diameter at the proximal end of 3.5 F and a minimum diameter at the distal end of 2.7 F, the intermediate outer diameters can comprise 3.4 F, 3.3 F, 3.2 F, 3.1 F, 3.0 F, 2.9 F, and 2.8 F. For a microcatheter with a maximum diameter at the proximal end of 2.7 F and a minimum diameter at the distal end of 1.7 F, the intermediate outer diameters can comprise 2.5 F, 2.4 F, 2.3 F, 2.2 F, 2.1 F, 2.0 F, 1.9 F, and 1.8 F.

The inner diameter of microcatheter 315 can range from 0.010 inches to 0.020 inches, from 0.015 inches to 0.030 inches (e.g., 0.0165 inches, 0.017, inches, 0.021 inches, 0.025 inches, 0.027 inches), less than 0.010 inches, greater than 0.030 inches, or overlapping ranges thereof, which can allow the microcatheter 315 to be inserted along a preinserted guidewire or used to infuse therapeutic agents. The inner diameter can be reduced to a size that still allows for infusion when an expandable tip assembly or other device is in place within the microcatheter. In some embodiments, infusion capabilities can be sacrificed and the inner diameter can be reduced to a size as small as material properties (e.g., Young's modulus) will allow. According to several embodiments, the performance of the microcatheter 315 is comparable to standard microcatheters and is designed to track over a guidewire through the neurovasculature.

4. Expandable Tip Assembly

In some embodiments, the revascularization systems, or stroke treatment systems, comprise an acute stroke recanalization device, an acute stroke revascularization device, a reperfusion device, or a clot removal device. The acute stroke recanalization devices, the acute stroke revascularization devices, the reperfusion devices, and the clot removal devices shall generally be referred to herein as expandable tip assemblies. The expandable tip assembly 325 can comprise an elongate member and an active segment (e.g., an expandable scaffold). In some embodiments, the elongate member comprises a generally tubular member having a lumen. The expandable scaffold can be coupled to a distal end of the elongate member. In some embodiments, the expandable scaffold is permanently or detachably tethered (e.g., coupled, attached, connected) to a distal end of the elongate member via tether wires or one or more other tethering members. In some embodiments, the expandable scaffold is a temporary device that is tethered or coupled to the elongate member during the entire procedure (e.g., not releasably or detachably tethered and not designed to be, configured to be, or capable of being, detached, released or implanted). In other embodiments, the expandable scaffold can be detached and left in place within a vessel on a long-term or permanent basis.

The expandable scaffold can comprise a self-expanding scaffold, a mechanically expandable scaffold, or a balloon inflatable scaffold. The expandable scaffold can be configured to transition between a compressed, or non-expanded, configuration or state and a deployed, or expanded, configuration or state. At least a portion of the scaffold has a greater diameter in the expanded configuration than in the non-expanded configuration. In some embodiments, the expandable scaffold is reconstrainable. In accordance with some embodiments, an expandable tip assembly can be sized and configured to be inserted within and longitudinally movable within the microcatheter, which can act as a sheath to maintain the expandable scaffold in its compressed configuration. Upon retraction of the microcatheter, the expandable scaffold can be deployed to its expanded configuration within a blood vessel. Embodiments of expandable tip assemblies will be described in more detail below.

5. Guidewire

The revascularization systems (e.g., stroke treatment systems) described herein, or components thereof, can be configured to be deployed over one or more guidewires. In some embodiments, a guidewire (e.g., guidewire 320) is inserted into a vessel via a guide catheter and advanced through a clot. In some embodiments, a microcatheter and an expandable tip assembly are advanced over the one or more guidewires to the location of the clot; however, in other embodiments, only the expandable tip assembly is advanced over a guidewire. In some embodiments, the elongate members of the expandable tip assemblies comprise a guidewire lumen configured to receive the guidewire. In some embodiments, leaving the guidewire in place after deployment of an expandable tip assembly in curved vessels might be an option to stabilize the expandable tip assembly and thus prevent displacement. The guidewire advantageously can be left in place to maintain access to a target location when multiple devices are inserted and removed in succession during a treatment procedure.

In some embodiments, at least a portion of the guidewire advantageously can comprise soft, flexible material that can flex to traverse tortuous or curved vessels. In some embodiments, the guidewire comprises a coating to facilitate insertion and removal (e.g., to reduce friction) through lumens of a microcatheter and/or expandable tip assemblies.

In some embodiments, the guidewire comprises a standard off-the-shelf neuro guidewire having a maximum diameter of between 0.005 inches and 0.015 inches (e.g., 0.010 inches, 0.011 inches, 0.012 inches, 0.013 inches, 0.014 inches, 0.015 inches, 0.009 inches, 0.008 inches, 0.007 inches, 0.006 inches, 0.005 inches). The guidewire can have a useable length that is at least greater than the length of the expandable tip assembly. In some embodiments, the guidewire has a useable length of between 165 cm and 350 cm, between 175 cm and 215 cm, between 200 cm and 310 cm, 180 cm, 205 cm, 300 cm, less than 165 cm, greater than 350 cm, or overlapping ranges thereof. In some embodiments, the revascularization system (e.g., stroke treatment system) does not include a separate guidewire configured to be received by a lumen of an elongate member of an expandable tip assembly.

B. Multiple Device Modular System

In some embodiments, the revascularization systems (e.g., stroke treatment systems, clot management systems) comprise a kit of expandable tip assemblies (e.g., stroke treatment devices, reperfusion devices, clot removal devices) configured to provide a poly-modic, or modular, system of separate individual devices that can be selected by a clinician depending on the circumstances of the situation, thereby providing progressive therapy or treatment. The modular system provided by the kit of individual devices increases the number of options available to the medical professional during treatment and facilitates access to vessels of different sizes, thereby allowing the medical professional to adapt the stroke treatment in real time based on particular patient or clot characteristics. In some embodiments, the modular system can be iterated to impact, address and/or cross an embolus, radially filter, and/or remove the offending embolus or be optionally emplaced to address the same.

For example, multiple expandable tip assemblies (e.g., stroke treatment devices) having varying characteristics and properties to accommodate differing vessel sizes and to address variable clot morphology can be included as a kit. The kit of multiple treatment devices advantageously can allow a clinician to select the device or sequence of devices that have the best chance of restoring flow the fastest and/or removing the obstruction most effectively. The kit of multiple treatment devices allow for access to all treatable vessels of the cerebral vasculature. In some embodiments, the clinician can select the best device depending on anatomic location and blood clot morphology. In accordance with some embodiments, the clinician can adjust the treatment to address particular circumstances (e.g., patient characteristics, clot characteristics, time restrictions, vessel diameters, success of prior treatment steps, etc.) in a progressive, modular fashion. In some embodiments, all of the treatment devices can be delivered over the same guidewire and within the same microcatheter.

In some embodiments, the multiple treatment devices comprise expandable tip assemblies. The expandable tip assemblies can be sized and configured for specific vessel diameters. In some embodiments, the expandable tip assemblies can include mechanical properties and design features configured to address or enhance particular treatment options (e.g., different cell sizes, hoop strengths, strut thicknesses or widths, radial resistive forces, chronic outward forces, exterior surface finishes). For example, one or more expandable tip assemblies (e.g., reperfusion devices) can be configured to provide therapeutically effective reperfusion and/or maceration of a clot (e.g., relatively small cell size, increased radial strength, and a polished exterior surface). Other expandable tip assemblies (e.g., clot removal or clot capture devices) can be configured to provide effective engagement and removal of a clot (e.g., relatively large cells that resist deformation and a rough exterior surface). In accordance with some embodiments, some of the expandable tip assemblies can be configured to treat soft clots and some of the expandable tip assemblies can be configured to treat firm clots. For example, the expandable tip assemblies configured to treat soft clots can be configured to gently massage the clot and the expandable tip assemblies configured to treat firm clots can comprise a relatively stiff structure that resists cell deformation. Cell deformation can refer to the decrease in the area of the cell opening.

C. Single Device Systems

Figure 4:
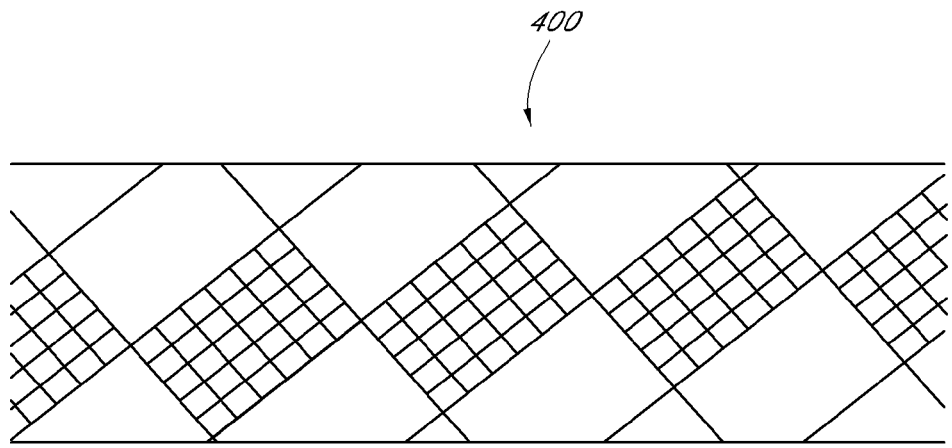
FIGS. 4 and 5 illustrate expandable scaffolds having variable cell sizes and patterns.

In some embodiments, the revascularization systems (e.g., stroke treatment systems, clot managements systems) comprise a single device configured to address variable clot morphologies and/or provide various treatment effects. For example, a single device can comprise variable mechanical structural features or designs (e.g., cell size, chronic outward force, strut thickness, and/or other scaffold parameters or characteristics described herein), that allow a single device to provide effective blood flow restoration, in-situ clot management (e.g., maceration), and/or effective clot removal. In some embodiments, a single device can be configured to address and/or treat both hard and soft clots. In some embodiments, as shown in FIG. 4, an expandable scaffold 400 comprises variable cell sizes at different portions of the expandable scaffold 400. The portions of the expandable scaffold 400 having relatively small cell sizes can be configured to provide or facilitate effective blood flow restoration or reperfusion and the portions of the expandable scaffold 400 having relatively large cell sizes can be configured to provide or facilitate effective clot removal.

Figure 5:
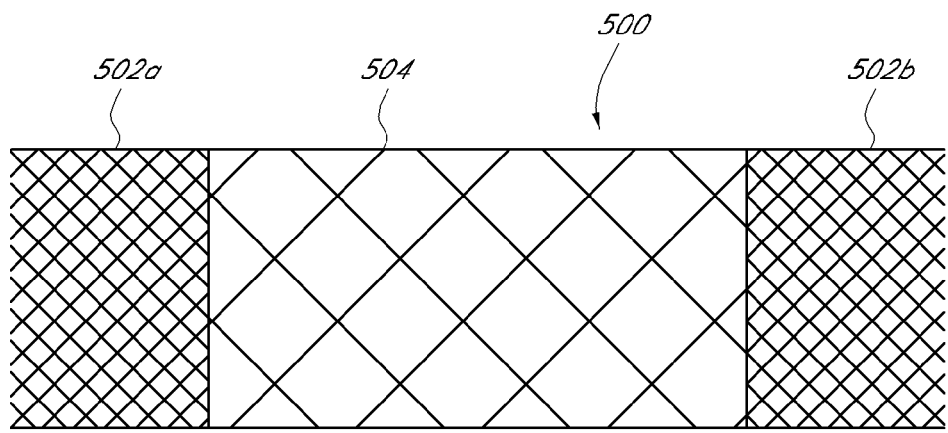

With reference to FIG. 5, an expandable scaffold 500 can comprise a reperfusion portion 502 configured to provide effective reperfusion of a blood vessel and a removal portion 504 configured to provide effective clot removal. The reperfusion portion 502 can comprise an intertwined tight lattice structure (e.g., mesh, struts, wires) having a very small cell size and the removal portion 504 can comprise large, open cells configured to facilitate penetration, or protrusion, into, and adhesion of the clot to, the expandable scaffold 500 (e.g., exterior surfaces of the scaffold 500).

In some embodiments, the expandable scaffold 500 is configured to be deployed in multiple steps in order to provide a progressive, or modular, treatment. For example, the reperfusion portion 502 having small cell sizes advantageously can comprise at least a distal end of the expandable scaffold 500 such that only the reperfusion portion 502 is deployed initially, thereby providing effective reperfusion of the occluded vessel and facilitating natural lysis of a clot. After a period of time (e.g., matter of minutes), the expandable scaffold 500 can be fully deployed such that the removal portion 504 having larger cell sizes (e.g., an open cell structure configured to engage and grab or capture the clot), which comprises a main central portion of the expandable scaffold 500 in the illustrated embodiment, can be used to effect removal of the clot. In some embodiments, the reperfusion portion 502 comprises the proximal and/or distal end portion(s) of the expandable scaffold 500.

IV. Expandable Tip Assemblies

As briefly described above, the expandable tip assemblies can include a proximal elongate member and a distal expandable scaffold. The elongate member can comprise the majority of the expandable tip assembly with the expandable scaffold comprising the expandable tip portion at a distal end of the expandable tip assembly. The expandable scaffold can be coupled to a distal end of the elongate member by any suitable mechanical attachment methods or devices (including, but not limited to, welding, soldering, adhesive, press-fitting, sheathing, molding, heat shrink tubing, curing, and/or combinations of the same). In some embodiments, the expandable scaffold is permanently coupled (e.g., directly or indirectly) to the elongate member (e.g., is designed or configured not to be uncoupled from the elongate member or is integral with the elongate member). The expandable scaffold can include a collar (e.g., a radiopaque marker) at its proximal end to facilitate coupling (e.g., welding, soldering, press-fitting) to the elongate member.

According to some embodiments, the expandable scaffold may optionally be detachable from the elongate member if it is determined that the expandable scaffold should remain in the patient. Detachment methods comprise mechanical, electrical, hydraulic, chemical, thermal, and/or electrolytic methods.

As described above, progressive, or modular, stroke therapy can be facilitated by the use of multiple expandable tip assemblies that are designed to perform different clot treatment functions (e.g., reperfusion, maceration, removal). The expandable tip assemblies can include reperfusion (e.g., revascularization or recanalization) devices that provide therapeutically effective reperfusion and maceration of emboli and embolus removal or capture devices that facilitate the capture and extraction of emboli.

A. Elongate Member

Figure 6C:
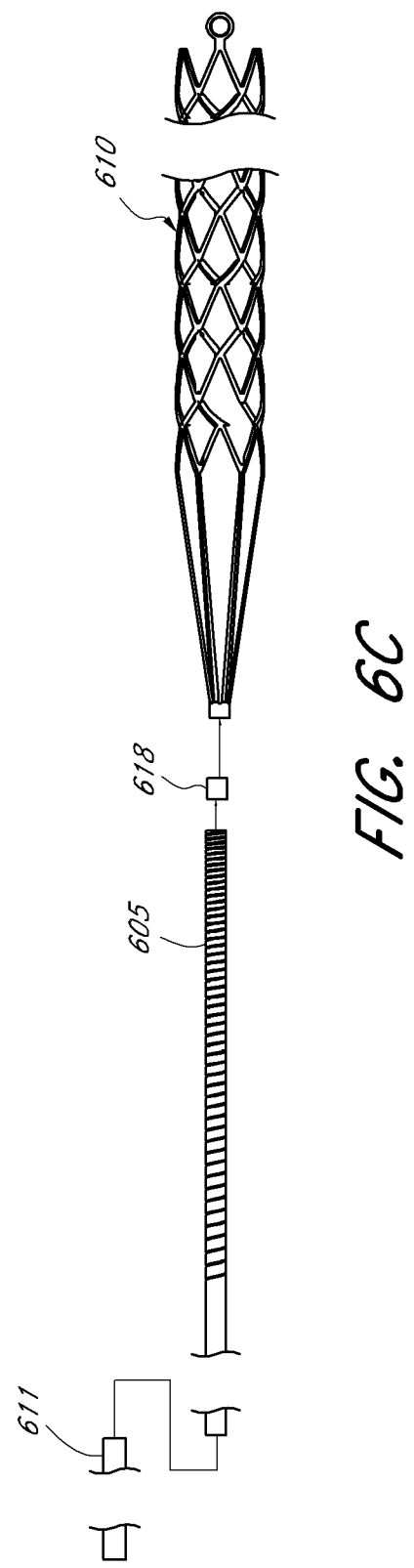

FIGS. 6A-6C illustrate a side view, a top view, and exploded view of an embodiment of an expandable tip assembly 600. The expandable tip assembly includes an elongate member 605 and an expandable scaffold 610. In some embodiments, the elongate member 605 comprises a pusher tube having a lumen. In some embodiments, the lumen is sized and shaped to receive a guidewire and/or allow for infusion of agents, fluids, compounds, or other materials to an occlusion site or target treatment site.

With reference to FIG. 6A, the elongate member 605 can comprise a hypotube. In some embodiments, the hypotube comprises a variable pitch and/or variable stiffness hypotube, which will be described in more detail below in connection with FIGS. 7A and 7B. In some embodiments, the elongate member 605 comprises an intermittently cut hypotube. For example, the elongate member 605 can be intermittently cut by a laser to form a laser spiral-cut hypotube.

In some embodiments, the elongate member 605 comprises an outer diameter that is less than the inner diameter of the microcatheter within which it is to be inserted. In some embodiments, an outer diameter of the elongate member 605 can be between 0.005 inches and 0.030 inches, between 0.010 inches and 0.020 inches (e.g., 0.010 inches, 0.011 inches, 0.012 inches, 0.013 inches, 0.014 inches, 0.015 inches, 0.016 inches, 0.017 inches, 0.018 inches, 0.019 inches, 0.020 inches), between 0.015 inches and 0.025 inches (e.g., 0.021 inches, 0.022 inches), or overlapping ranges thereof. In some embodiments wherein the elongate member 605 comprises a lumen, the inner diameter of the elongate member 605 can be sufficiently large so as to allow infusion through the elongate member 605 to provide thrombolytic therapy with or without a guidewire being inserted therein. For example, the inner diameter of the elongate member 605 can be between 0.005 and 0.025 inches, between 0.005 inches and 0.015 inches, between 0.010 inches and 0.015 inches, between 0.015 and 0.020 inches (e.g., 0.163 inches), or overlapping ranges thereof. In some embodiments, the elongate member 605 extends beyond a proximal end of the expandable scaffold. The elongate member 605 can include a plurality of apertures allowing infusible lytic agents or other materials to be delivered to a subject embolus or to a treatment location.

In some embodiments, the elongate member 605 is a guidewire (e.g., delivery wire) without a lumen, thereby enabling the elongate member 605 to have a smaller diameter to access smaller vessels. Infusion fluids or other materials can be delivered along the outsides of the elongate member through the microcatheter.

The elongate member 605 can comprise stainless steel, titanium, one or more polymers, polyimide, fluoropolymers, nitinol or other shape memory alloys, vectran, kevlar, or other biocompatible materials. In one embodiment, a stainless steel elongate member comprises spring tempered stainless steel. In some embodiments, the elongate member comprises a coil (e.g., a stainless steel coil). In some embodiments, the elongate member 605 includes a spring element to facilitate clot removal.

With continued reference to FIG. 6A, the expandable tip assembly 600 can include radiopaque markers as described in more detail herein. The radiopaque markers can include one or more distal markers 616 and one or more proximal markers 618. The proximal radiopaque marker 918 can comprise platinum and/or iridium; however, other radiopaque materials can be used such as, but not limited to, gold, tantalum, palladium, tungsten, silver, lead, and/or radiopaque polymers, or combinations thereof.

In some embodiments (for example, where the elongate member 605 comprises stainless steel and the expandable scaffold 610 comprises nitinol) it may not be possible to solder or otherwise couple the elongate member 605 to the expandable scaffold 610 due to their material properties. Accordingly, an element having a different material (e.g., the radiopaque marker 618, which may comprise platinum) can be positioned at the junction between the proximal end of the expandable scaffold 610 and the distal end of the elongate member 605 to facilitate the coupling of the expandable scaffold 610 to the elongate member 605.

With reference to FIG. 6B, in some embodiments, a sleeve 611 covers the junction between the distal end of the elongate member 605 and the proximal end of the expandable scaffold 610 and serves as a strain relief for the junction. The sleeve 611 can comprise a heat-shrink tube or clamp formed of polyethylene terephthalate (PET) or other heat-shrink tubing material, such as Pebax, nylon, polytetrafluoroethylene (PTFE), polyurethane, polyester, or other polymeric or elastomeric material. In some embodiments, the sleeve 611 is positioned such that the distal end of the sleeve 611 stops at the expansion transition of the expandable scaffold 610. The length of the sleeve 611 can be between 10 cm and 20 cm, between 15 cm and 25 cm, between 20 cm and 30 cm, between 30 cm and 40 cm, between 35 cm and 45 cm (e.g., 40 cm), or overlapping ranges thereof. In embodiments wherein the elongate member 605 comprises a laser-cut hypotube, the sleeve 611 can have a length to cover the laser-cut portion of the elongate member 605 (as shown in FIG. 6B). The expandable scaffold 610 can be attached or coupled to the elongate member 605 by any suitable attachment method or device, such as, for example, heat shrink tubing, adhesive, wound wire, suture, epoxy, interference fits, other low-profile mechanical attachment methods and/or the like. In some embodiments, the tensile strength of the coupling between the expandable scaffold 610 and the elongate member 605 is between 0.5 lbs to 2 lbs (e.g., 0.75 lbs., 0.85 lbs., 1 lb., 1.25 lbs, 1.5 lbs), which is well above the tensile strength required for manipulation within the cerebral vasculature.

Figure 6D:
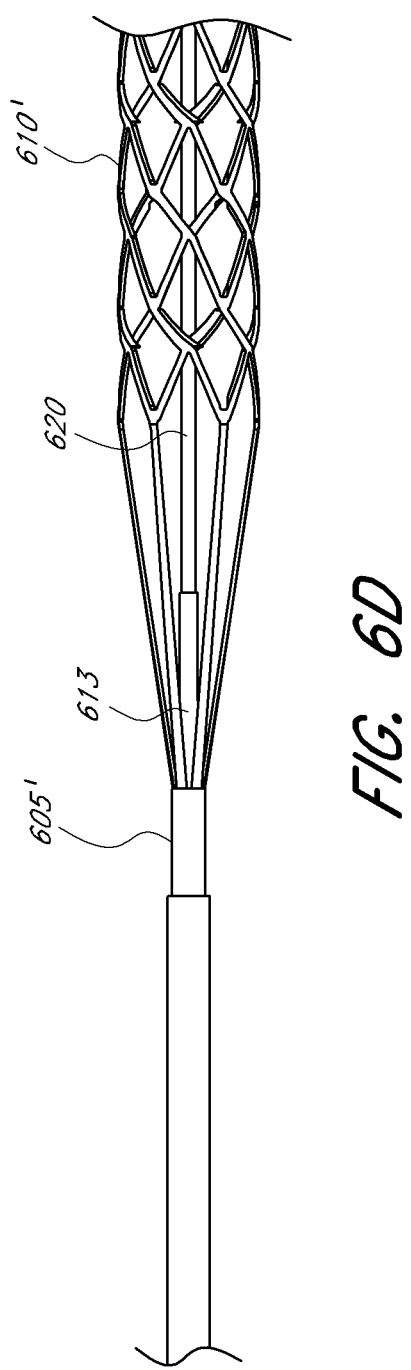
FIG. 6D illustrates another embodiment of an expandable tip assembly.

FIG. 6D illustrates a side view of a portion of an embodiment of an expandable tip assembly 600'. With reference to FIG. 6D, a polymeric liner or jacket 613 can be incorporated within the elongate member 605' to improve trackability of a guidewire 620. In some embodiments, the polymeric liner 613 extends beyond the distal tip of the elongate member 605' for guiding the guidewire 620 and preventing entanglement in the expandable scaffold 610'. In one embodiment, the polymeric liner 613 extends beyond the distal tip of the elongate member 605' to a length greater than the length of the expandable scaffold 610' to direct the guidewire 620 and prevent it from entanglement in the expandable scaffold 610'.

Figures 7A, 7B:
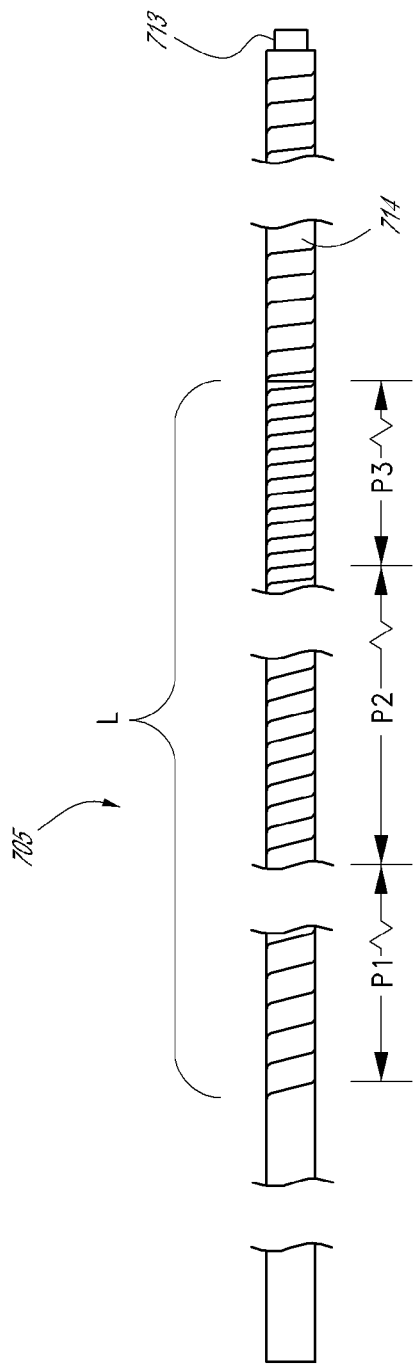
FIGS. 7A and 7B illustrate a side view and a front view of an embodiment of an elongate member of an expandable tip assembly.

FIGS. 7A and 7B illustrate a side view and a front view of an embodiment of an elongate member 705 comprising a variable pitch, laser spiral-cut hypotube. The elongate member 705 may be of variable stiffness that is able to track to and through the tortuous anatomy of the cerebral vasculature (e.g., internal carotid arteries, middle cerebral arteries, anterior cerebral arteries, vertebral arteries, basilar artery). The elongate member 705 may be one or two pieces and may have greater proximal pushability (stiffness) and greater distal flexibility (softness) to allow tracking to distal cerebral arteries.

Figure 35:
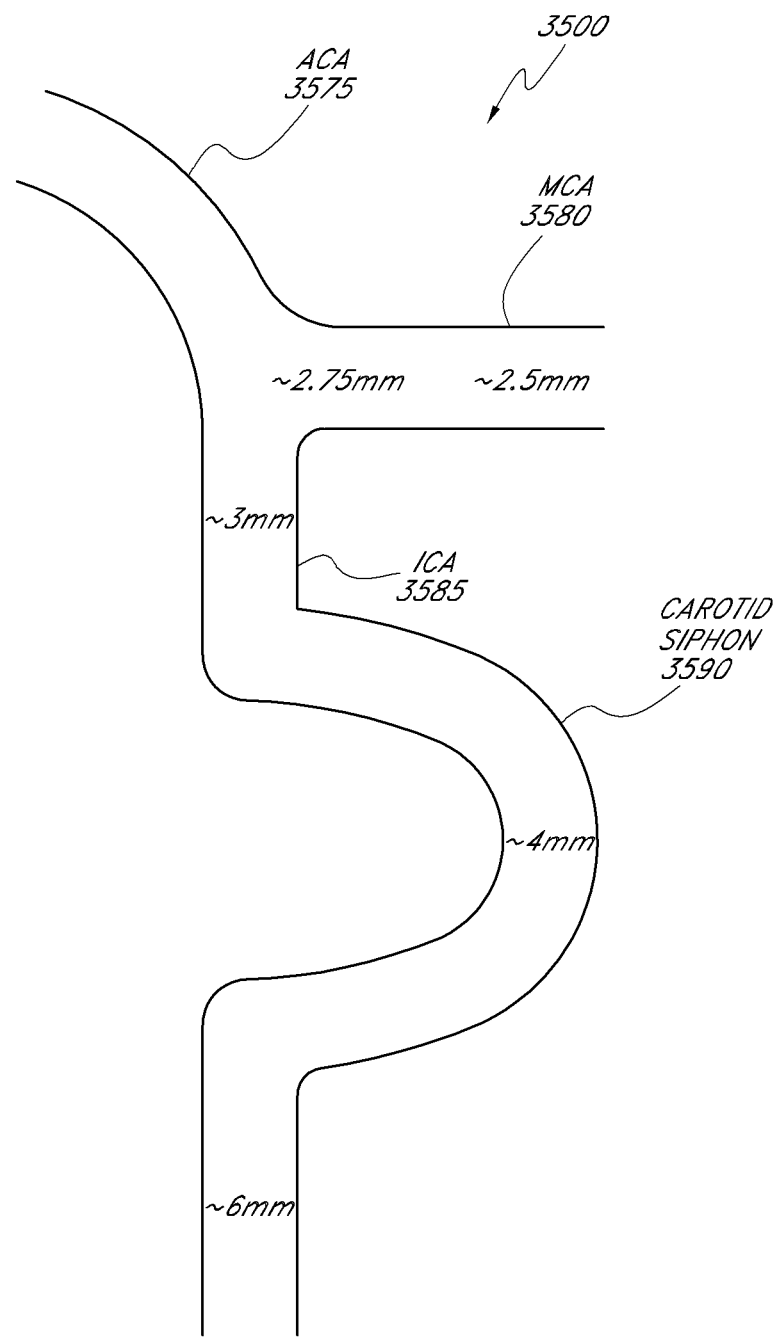
FIG. 35 illustrates a schematic representation of a portion of the cerebral vasculature.

For example, a distal portion (e.g., at least approximately the distal 35 cm) of the variable stiffness hypotube can be more flexible to allow for access through the tortuous vessels of the cerebral vasculature (e.g., to get above the carotid siphon (as shown in FIG. 35) and/or past the C1/C2 vertebral arteries). The elongate member 505 can gradually decrease in stiffness from the proximal end to the distal end or can decrease in step-wise fashion. With reference to FIG. 7A, region L illustrates a laser cut transition region of the variable-pitch hypotube. Regions P1, P2 and P3 comprise three regions of the variable-pitch hypotube having variable pitch. In one embodiment, the pitch decreases from region P1 to region P2 and from region P2 to region P3.

In some embodiments, a distalmost portion 714 of the elongate member 705 comprises a ribbon coil portion. In other embodiments, the laser cut transition region L can extend all the way to the distal end of the elongate member 705. FIGS. 7A and 7B also illustrate a polymeric liner 713 extending outward from the distal end of the elongate member 705, as described above in connection with FIG. 6D.

Figure 7C:
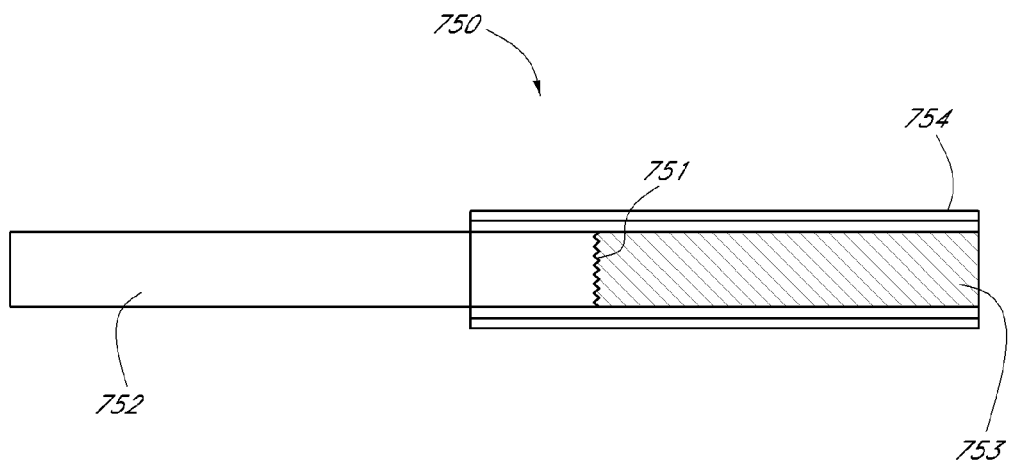
FIGS. 7C and 7D illustrate embodiments of delivery device assemblies.

FIG. 7C illustrates embodiments of a distal end of a hypotube assembly 750 that includes a solder joint 751 between a hypotube 752 and a ribbon coil 753 and a PET heat shrink 754. FIG. 7C illustrates example outer diameter and length dimensions of the hypotube or delivery system assembly.

Figure 7D:
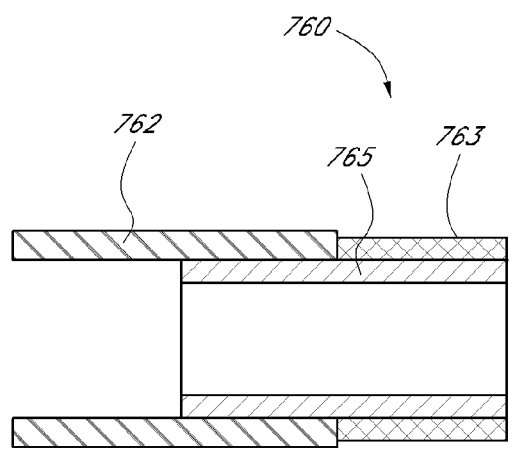

FIG. 7D illustrates an embodiment of a distal end of a delivery system assembly 760. In one embodiment, the delivery system assembly 760 includes a proximal hypotube 762, a distal braid 763 and a polyimide liner 765. In one embodiment, the polyimide liner 765 may be a braid. In one embodiment, the polyimide liner 765 improves trackability of the elongate member 705 over a guidewire.

B. Expandable Scaffold

FIGS. 8A-8C, 9A-9C, 10A-10F, 11A-11C, 12A-12D, 13A, 13B, 14, 15A-15C, 16, 17A-17E, 18A-18F, 19, 20, 21A and 21B generally illustrate various embodiments of expandable scaffolds. The features, designs, and/or elements described in connection with particular embodiments of expandable scaffolds herein can be used in any of the other embodiments of expandable scaffolds described herein.

Figure 8A:
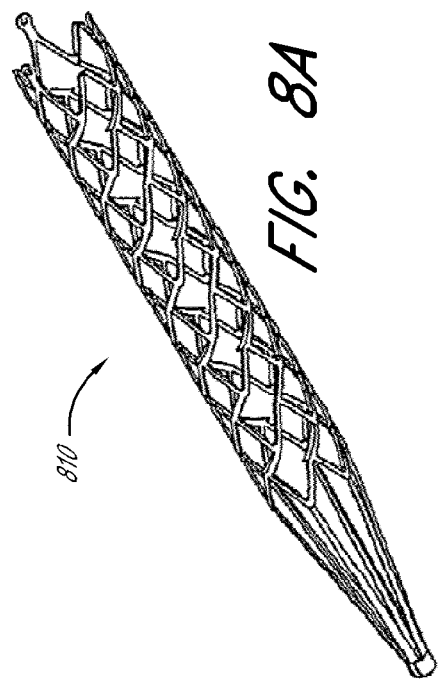
FIGS. 8A-8C illustrate a perspective view, a side view, and a front view, respectively, of an embodiment of an expandable scaffold.
Figure 8B:
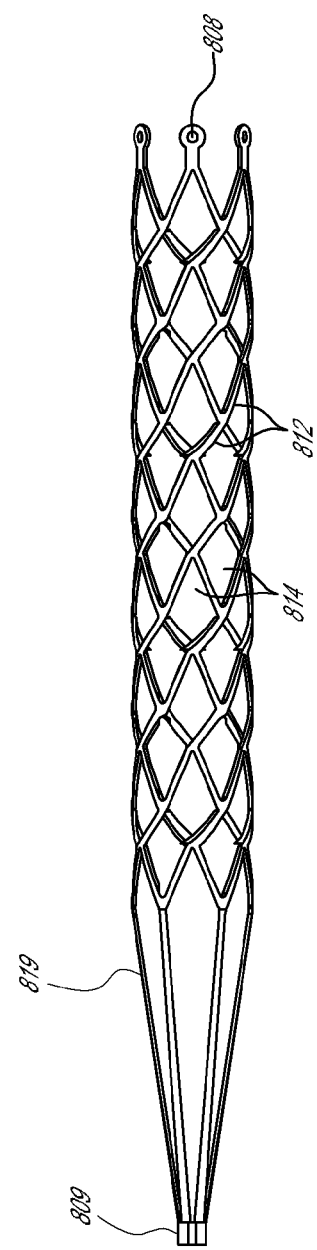
Figure 8C:
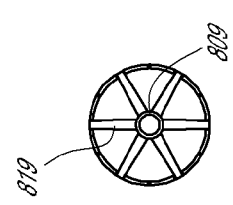

FIGS. 8A-8C illustrate a perspective view, a side view, and a top view of an embodiment of an expandable scaffold 810. In accordance with some embodiments, the expandable scaffold 810 comprises a self-expanding scaffold without the need for mechanical actuation; however, the expandable scaffold 810 can be mechanically expanded or inflated in other embodiments. For example, the expandable scaffold 810 can comprise shape memory material, such as a nickel titanium alloy. In one embodiment, the expandable scaffold 810 comprises a nitinol device or member. In some embodiments, the expandable scaffold 810 comprises a closed cell design (for example, as shown in FIGS. 8A-8C); however, in other embodiments, an expandable scaffold can comprise an open cell design. The closed cell design advantageously can facilitate recapturability and resheathability of the expandable scaffold 810. The expandable scaffold 810 can be configured to transition between a compressed, or non-expanded, configuration or state and a deployed, or expanded, configuration or state.

The expandable scaffold 810 can comprise a stent-like member comprised of a pattern of struts 812 and cells 814. In one embodiment, the expandable scaffold 810 comprises a self-expanding microstent. The struts 812 can permit flexion and extension of the expandable scaffold 810 to navigate through curved vessels. The expandable scaffold 810 can be formed by laser cutting a tube. For example, the expandable scaffold 810 can comprise a nitinol laser-cut tube. The cut tube scaffold advantageously facilitates inclusion of a tapered proximal end. In some embodiments, an expandable scaffold can comprise a rolled woven mesh or braided scaffold. A rolled mesh scaffold advantageously can improve vessel apposition and adjust to varying vessel diameters; however, the rolled mesh scaffold may be configured so as to not collapse under a load but to curl up instead, thereby making it difficult to resheath the rolled mesh scaffold in situ. In some embodiments, the expandable scaffold 810 does not comprise a rolled mesh scaffold. In some embodiments, the expandable scaffold 810 does not have a backbone extending along its length, which may be configured to distribute a load along the entire length or a portion of the scaffold.

In some embodiments, the expandable scaffold 810 (e.g., for intracranial use) can be flexible, precisely delivered, retrievable, able to be repositioned, atraumatic, available in various lengths and diameters, thin-walled and radiopaque. The expandable scaffold 810 can be delivered through a microcatheter, allowing standard microcatheter/wire techniques to reach locations inaccessible to standard over-the-wire stents. In accordance with some embodiments, the expandable scaffold 810 advantageously can be retrieved and repositioned after complete delivery, if its position is felt to be suboptimal. In some embodiments, the expandable scaffold 810 conforms completely to the normal vessel geometry and is not prone to strut opening on convexities. In some embodiments, the expandable scaffold 810 is adapted so as to provide a continuous radial pressure when in the expanded state. In some embodiments, the expandable scaffold 810 is MR compatible.

With reference to FIG. 8B, the expandable scaffold 810 includes one or more laser-cut apertures or eyelets 808 that can receive radiopaque markers. The radiopaque markers can comprise pegs that can be press-fit and/or adhered within the laser-cut apertures 808. With reference to FIG. 8C, the expandable scaffold 810 can include tether lines or tangs 819 that are arranged in an equally spaced or substantially equally spaced fashion around the entire circumference of a proximal collar 809 of the expandable scaffold. The tether lines or tangs 819 can extend concentrically from the proximal collar 809. Although not illustrated in all of the figures, each of the embodiments of the expandable scaffolds described herein can include one or more radiopaque markers.

Figures 9A, 9B:
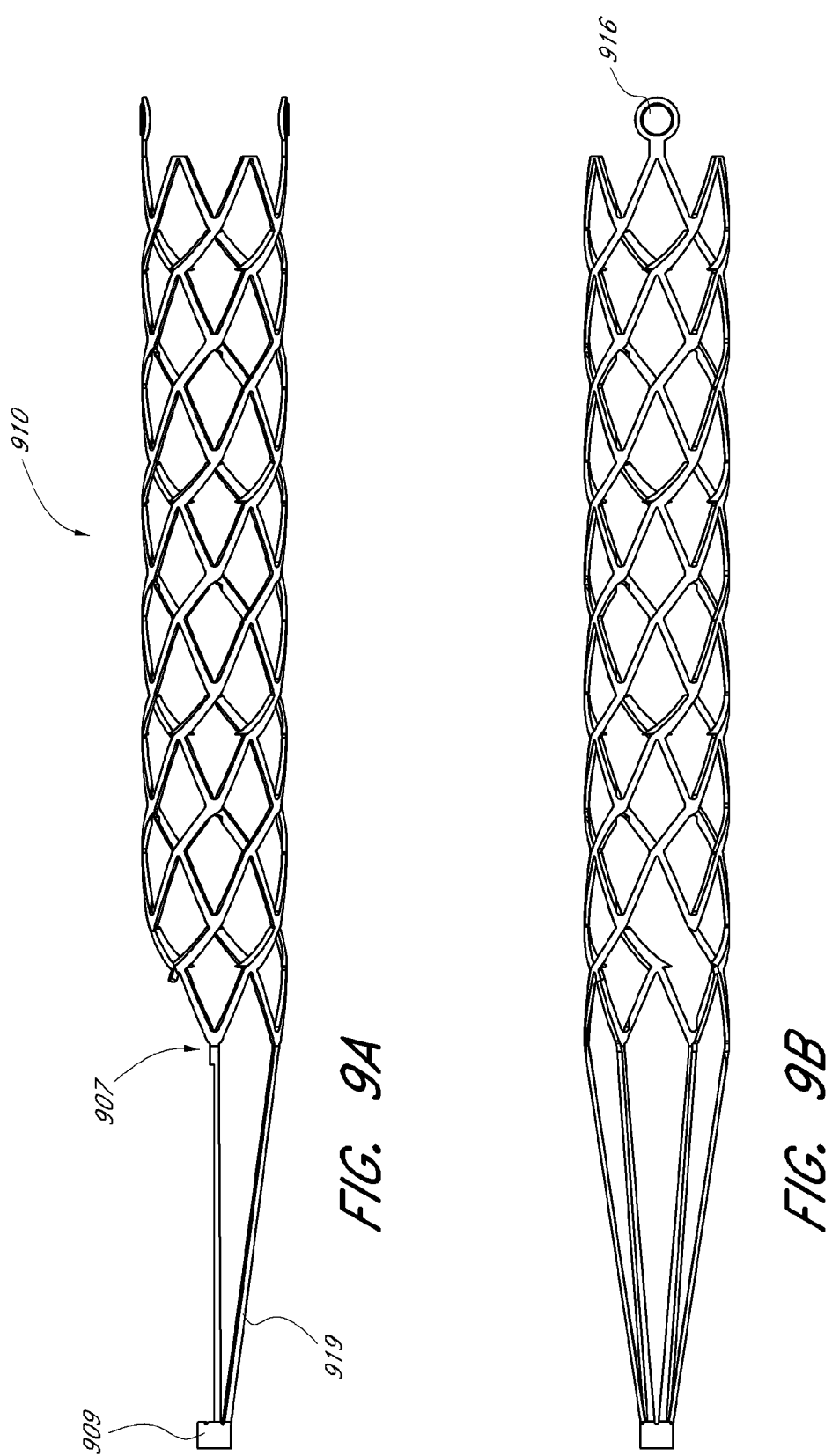
FIGS. 9A-9C illustrate a side view, a top view, and a front view of an embodiment of an expandable scaffold.
Figure 9C:
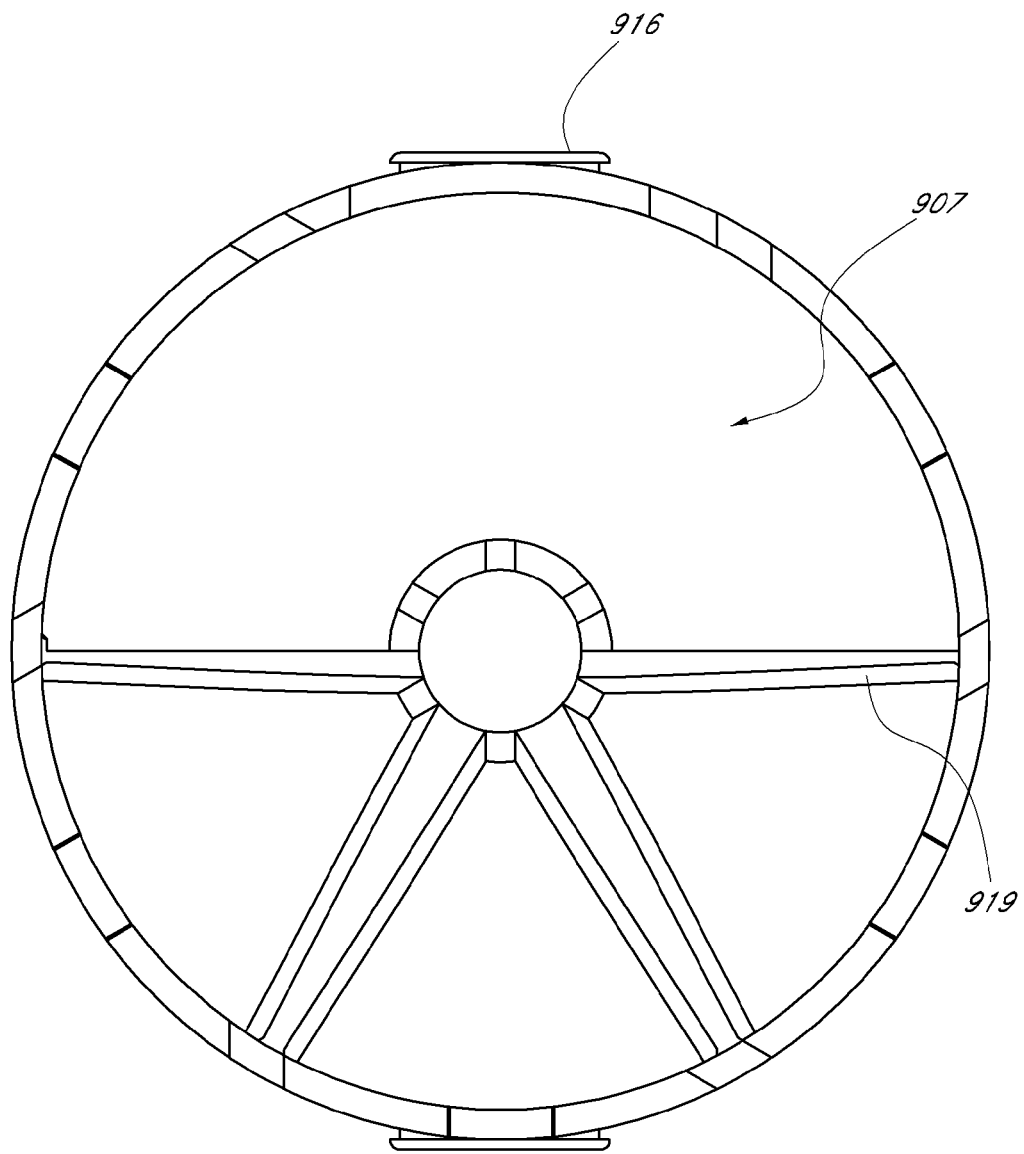

FIGS. 9A-9C illustrate side, top, and front views of an expandable scaffold 910. With reference to FIGS. 9A-9C, the expandable scaffold 910 can include tether lines or tangs 919 that extend eccentrically, or off-center, from a collar of 909 the expandable scaffold 910. For example, as best shown in FIGS. 9A and 9C, the tether lines 919 can extend only from one side (e.g., from one half, below center, above center) of the proximal end of the expandable scaffold 910. The eccentricity advantageously can improve blood flow by reducing the profile or amount of space of the vessel occupied by the proximal end of the expandable scaffold 910.

As best shown in FIGS. 9A and 9C, the expandable scaffold 910 may provide an everted or scooped out geometry (e.g., an everted or open, tapered or angled section) to facilitate recapture of the expandable scaffold 910 into the microcatheter. For example, the everted, scalloped, scooped-out or cut-out geometry can comprise an open mouth or port 907 at a proximal end of the expandable scaffold 910 to facilitate resheathing. The open mouth or port 907 can also enhance blood flow through the expandable scaffold 910. In some embodiments, an everted or open tapered or angled section, such as an open mouth or port, can facilitate clot capture and extraction (e.g., can allow passage of a clot from the exterior of the scaffold 910 to the interior of the scaffold 910). Using everted scaffolds, emboli can be removed without compromising access, as the emboli become enmeshed with the scaffolds and can be removed without vessel damage. For example, a clot can enter the scaffold 910 via the mouth or port 907. In some embodiments, a portion of the clot can be caught or captured within the mouth or port 907 and a portion of the clot can be caught or captured on an external surface of the scaffold 910. The everted section (e.g., mouth or port 907) can be located at a distal or proximal end of the scaffold 910 or anywhere along the length of the scaffold 910. In some embodiments, the mouth or port 907 can be positioned to surround a clot and capture the clot within the scaffold 910.

With reference to FIGS. 9B and 9C, the expandable scaffold 910 can comprise radiopacity for imaging purposes. The expandable scaffold 910 can include one or more radiopaque markers 916 at a distal end of the scaffold 910. The radiopaque markers 916 at the distal end of the scaffold 910 can be pressed into pre-laser cut apertures or eyelets designed to receive them. In some embodiments, the radiopaque markers 916 comprise platinum or gold; however, other radiopaque materials can be used such as, but not limited to, tantalum, palladium, tungsten, silver, lead, and/or radiopaque polymers, or combinations thereof. The distal radiopaque markers 916 can be ground flush to provide a smooth, low profile (as best shown in FIG. 9C). The expandable scaffold 910 can include a radiopaque marker 918 at a proximal end of the scaffold 910. As described above, one or more proximal radiopaque markers can be positioned at the junction between an expandable scaffold and the distal end of an elongate member to facilitate tracking and to facilitate coupling of the expandable scaffold to the elongate member.

The design of the expandable scaffold 910, according to several embodiments, includes a pattern whereby when the expandable scaffold 910 is retracted, it is able to fully retract into the microcatheter. The expandable scaffold 910 advantageously can comprise features that facilitate single-step resheathing within the microcatheter. With reference to FIGS. 9A-9C, the expandable scaffold 910 can comprise a tapered proximal end having a plurality of tether lines or tangs 919. In some embodiments, the tether lines 919 can be relatively long to facilitate retraction. An expandable scaffold comprising a laser cut tube can provide enhanced resheathing ability over a rolled mesh or a scaffold having a backbone along its length. In some embodiments, the tether lines 919 comprise between one-tenth and one-third (e.g., about one-tenth, about one-ninth, about one-eighth, about one-seventh, about one-sixth, about one-fifth, about one-fourth, about one-third) of the total length of the expandable scaffold 910.

In some embodiments, the expandable scaffolds can be open at their distal, or downstream, end because distal embolization is not a concern when blood flow is first restored. Although the embodiments of the scaffolds described above have open distal ends, in some embodiments, a capturing device (e.g., scaffold) may include a distal portion that is resistant to the passage of a clot or large portion of a clot from the interior of the capturing device to the exterior of the capturing device. FIGS. 12A-12D, 15A-15C, 17A, 17B, 18A-18F, 19, and 20 illustrate expandable scaffolds with closed or substantially closed distal ends. A closed distal end may prohibit the escape of a clot out of the distal end while the capturing device is retracted. For example, the distal end of the capturing device may be closed, such that the open-cell structure at the distal end is more confined than the open-cell structure at the middle section of the capturing device or other section configured to accept a clot.

Figure 10A:
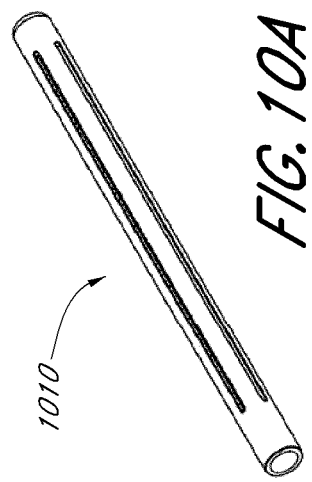
FIGS. 10A-10C illustrate a perspective view, a side view and a front view of one embodiment of an expandable scaffold in a compressed configuration
Figure 10B:
Figure 10C:

FIGS. 10A-10C illustrate a perspective view, a side view and a front view of an expandable scaffold 1010 in a compressed configuration and FIGS. 10D-10F illustrate a perspective view, a side view and a back view of the expandable scaffold 1010 in an expanded configuration. The expandable scaffold 1010 comprises a laser-cut tube. The cut pattern includes five straight or substantially straight cuts equally spaced around the circumference of the expandable scaffold 1010. The struts 1012 formed by the laser cuts are not interconnected. The expandable scaffold 1010 has a tapered proximal end 1022 and is substantially closed at its proximal end 1022 and distal end 1024. The relatively large open spaces between the struts 1012 can provide sufficient blood flow through the expandable scaffold 1010. The maximum diameter of the expandable scaffold 1010 in the expanded configuration is located near the distal end 1024. The expandable scaffold 1010 has a variable diameter along its length.

Figure 11A:
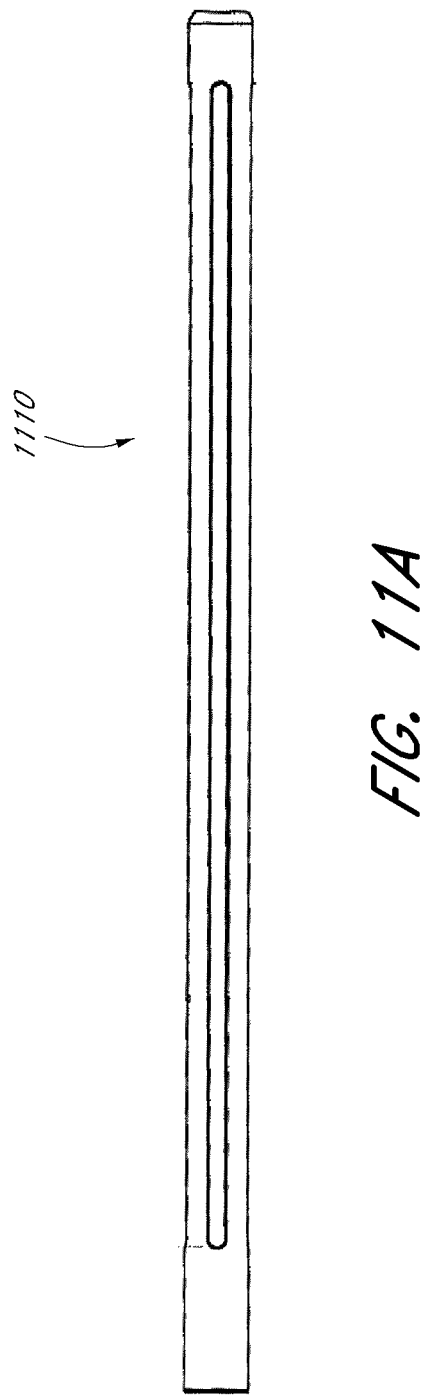

FIG. 11A illustrates a side view of an embodiment of an expandable scaffold 1110 in a compressed configuration and FIGS. 11B and 11C illustrate a perspective view and a side view of the expandable scaffold of FIG. 11A in an expanded configuration. The expandable scaffold 1110 comprises a laser-cut tube having a cut pattern that includes four straight or substantially straight cuts equally spaced around the circumference of the expandable scaffold 1110. The struts 1112 formed by the laser cuts are not interconnected. The expandable scaffold 1110 has a closed proximal end 1122 and a closed distal end 1124. The proximal end 1122 and the distal end 1124 are substantially evenly tapered in the expanded configuration, with the maximum diameter occurring in the middle of the expandable scaffold 1110.

Figure 12A:
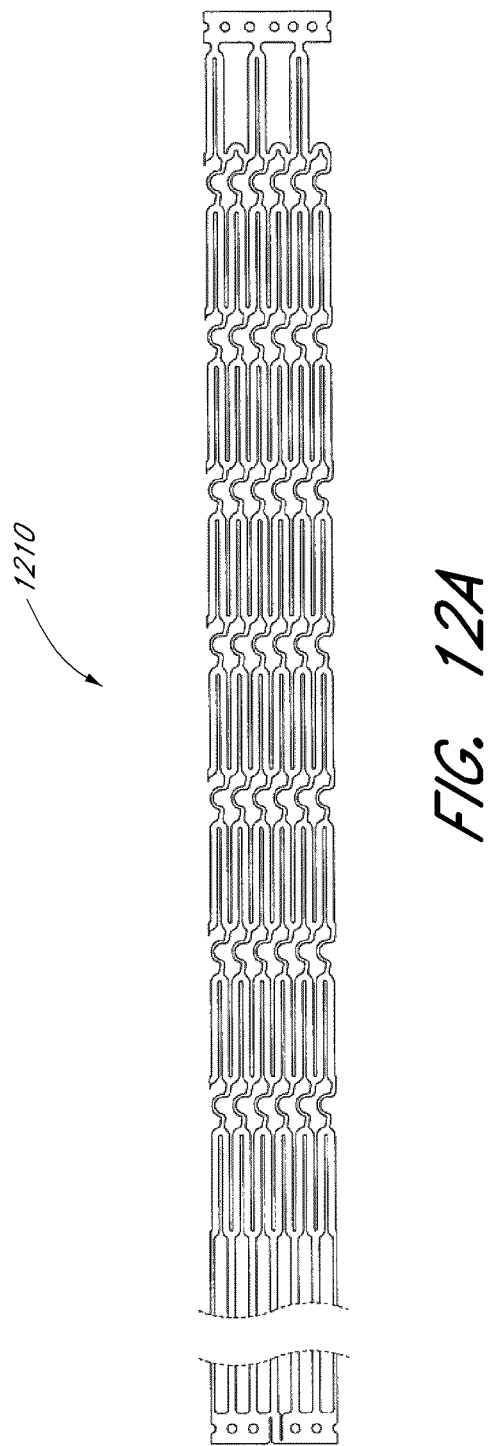
FIG. 12A illustrates a laser cut profile of an embodiment of an expandable scaffold.
Figure 12B:
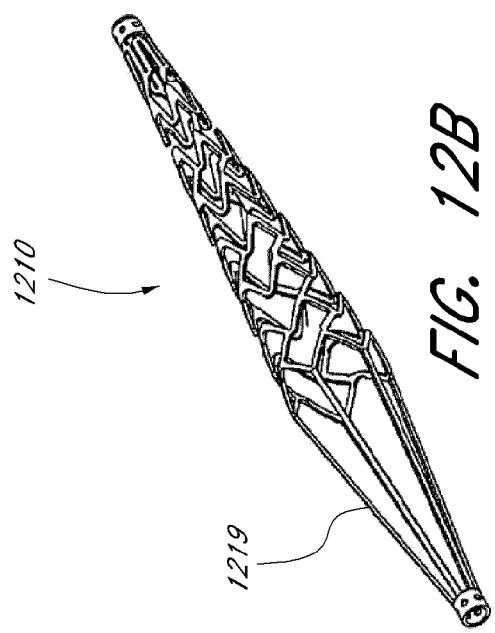
FIGS. 12B and 12C illustrate a perspective view and a side view of the expandable scaffold formed from the cut profile of FIG. 12A in its expanded configuration.
Figure 12C:
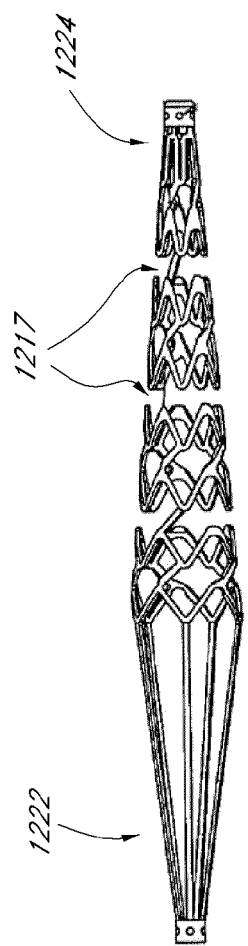
Figure 12D:
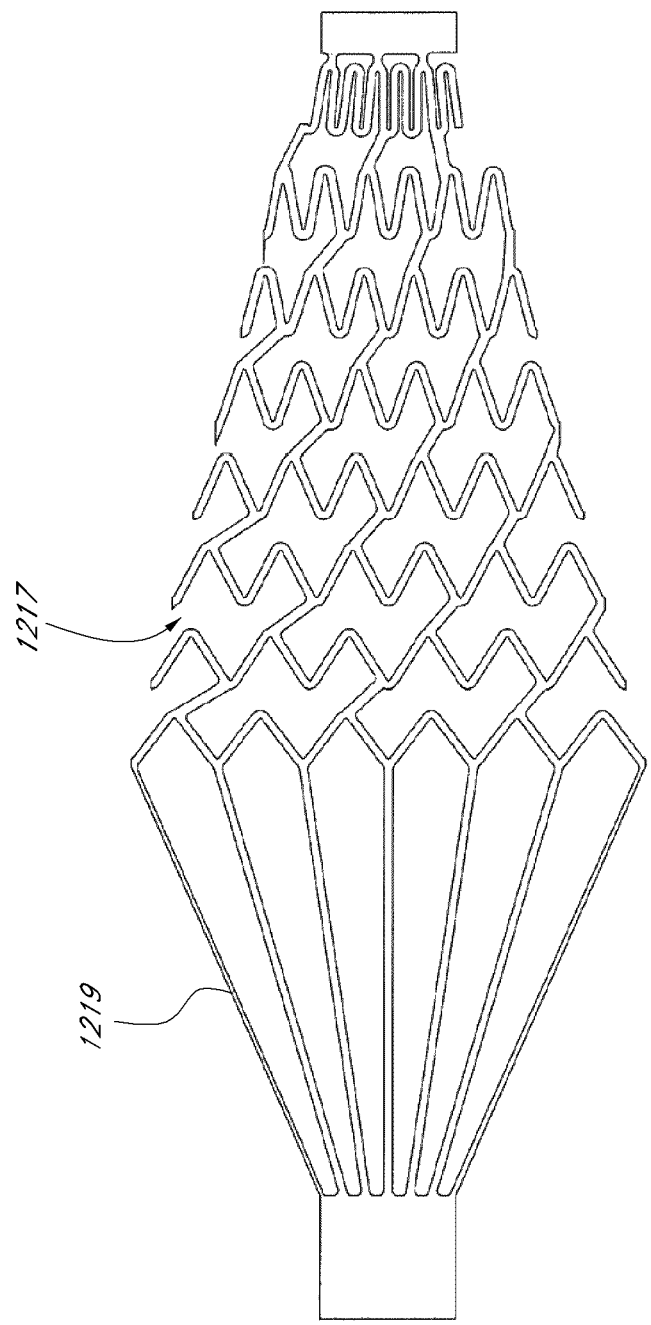
FIG. 12D illustrates a two-dimensional view of the cut profile of FIG. 12A in its expanded configuration.

FIG. 12A illustrates a cut file of an embodiment of an expandable scaffold 1210 formed of a laser-cut tube. FIGS. 12B and 12C illustrate a perspective view and a side view of the expandable scaffold formed from the cut profile of FIG. 12A in its expanded configuration. As best shown in FIG. 12C, the expandable scaffold 1210 can include an open-celled configuration. FIG. 12C illustrates that the expandable scaffold has open gaps 1217 between segments of the expandable scaffold 1210. FIG. 12D illustrates a two-dimensional view of the cut profile of FIG. 12A in its expanded configuration. The expandable scaffold 1210 includes relatively long tether lines or tangs 1219 at a proximal end 1222 of the scaffold 1210. The expandable scaffold 1210 is tapered at its proximal end 122 and its distal end 1224. The expandable scaffold 1210 includes a series of interconnected struts and bridges.

Figure 13A:
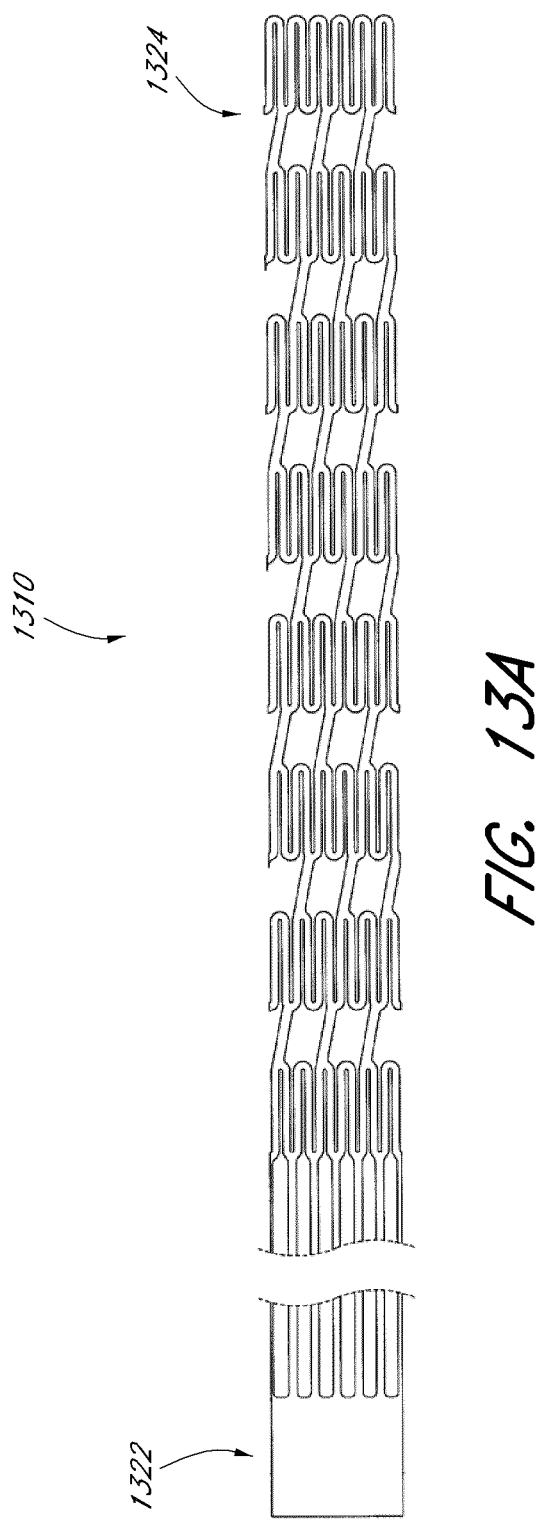
FIGS. 13A and 13B illustrate two-dimensional cut profiles of an embodiment of an expandable scaffold in its compressed and expanded configurations, respectively.
Figure 13B:
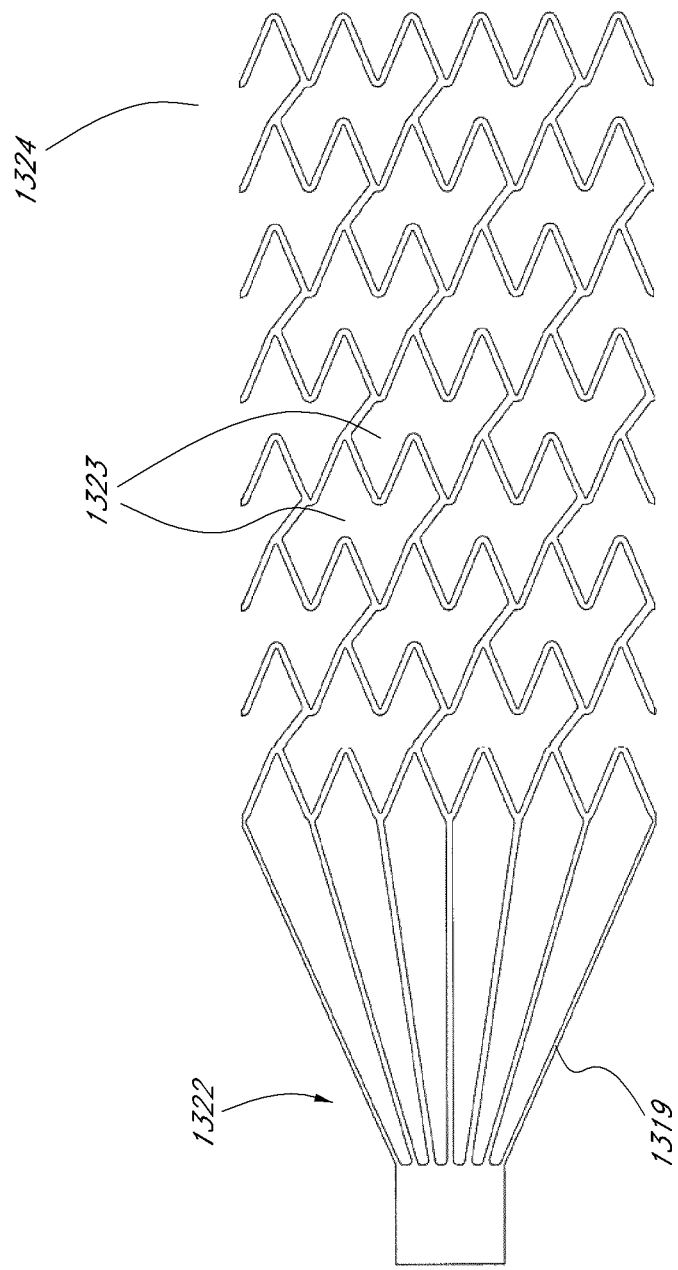

FIGS. 13A and 13B illustrate cut profiles of an embodiment of an expandable scaffold 1310 in its compressed and expanded configurations, respectively. The expandable scaffold 1310 includes an open-cell design. As shown in FIG. 13B, the expandable scaffold 1310 has an open distal end 1324 and a plurality of tether lines or tangs 1319 at its substantially closed proximal end 1322. The expandable scaffold 1210 comprises a pattern of interconnected struts arranged in a zig-zag-like manner to form substantially Z-shaped cells 1323.

Figure 14:
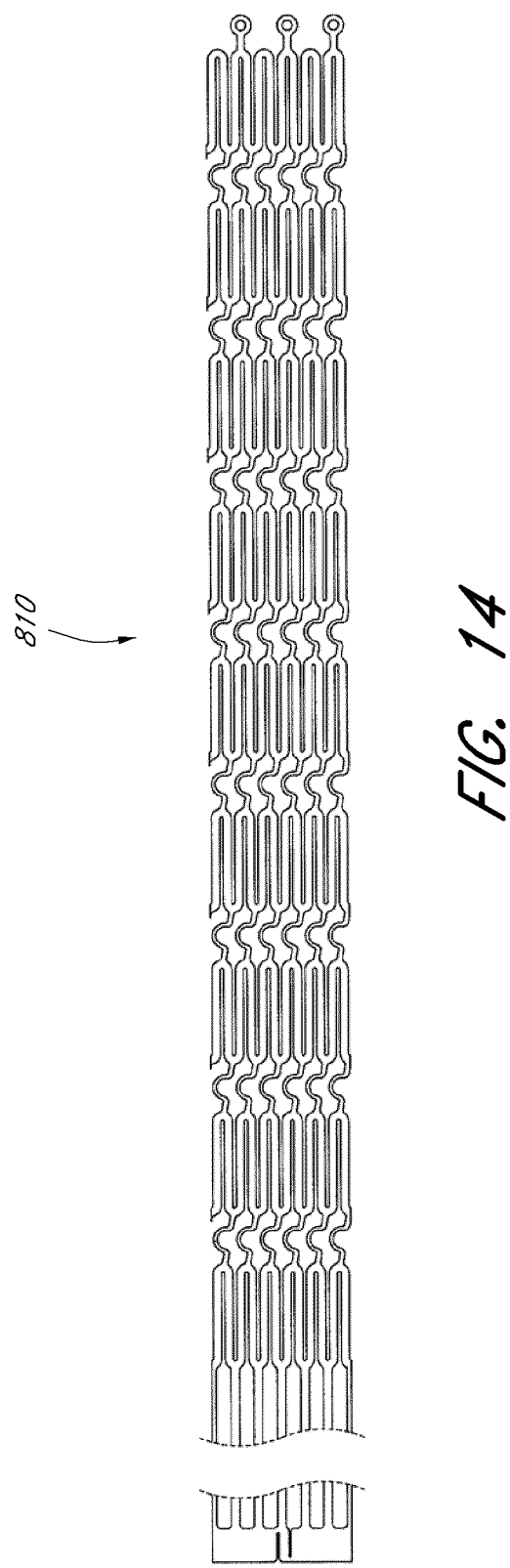
FIG. 14 illustrates a laser cut profile of the expandable scaffold of FIGS. 8A-8C.

FIG. 14 illustrates a laser cut profile of the expandable scaffold 810 of FIGS. 8A-8C and FIG. 16 illustrates a laser cut profile of the expandable scaffold 910 of FIGS. 9A-9C.

Figure 15A:
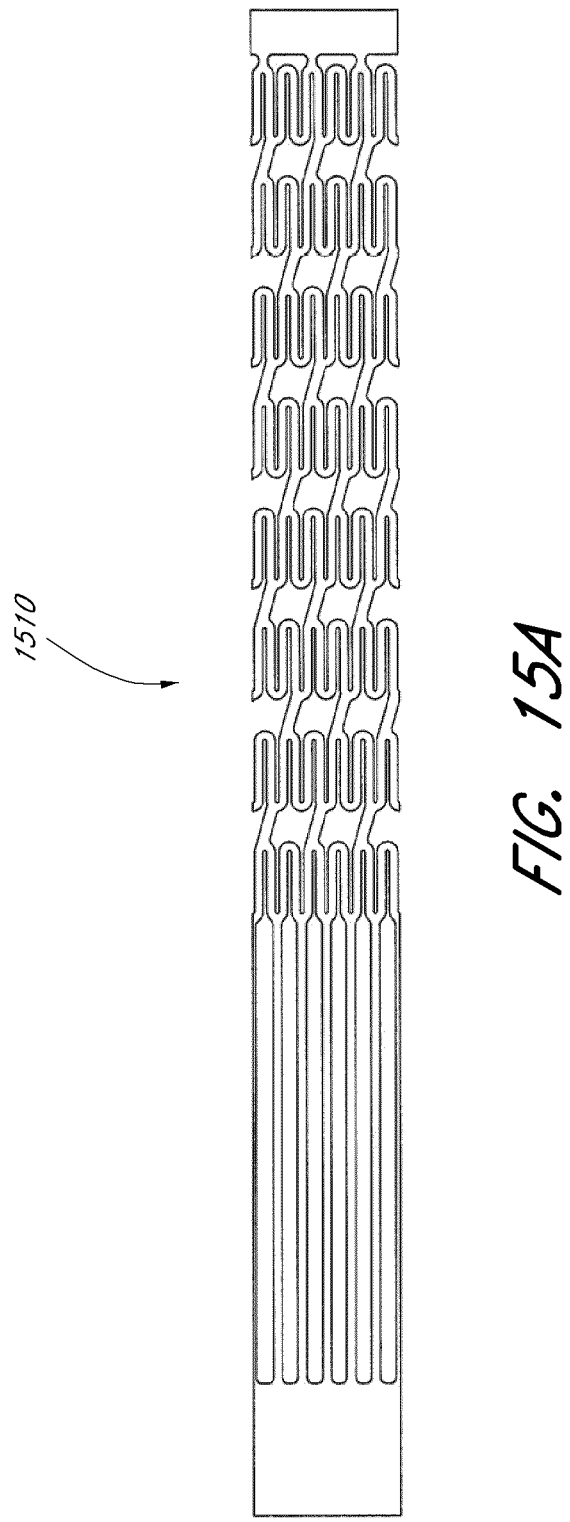
Figure 16:
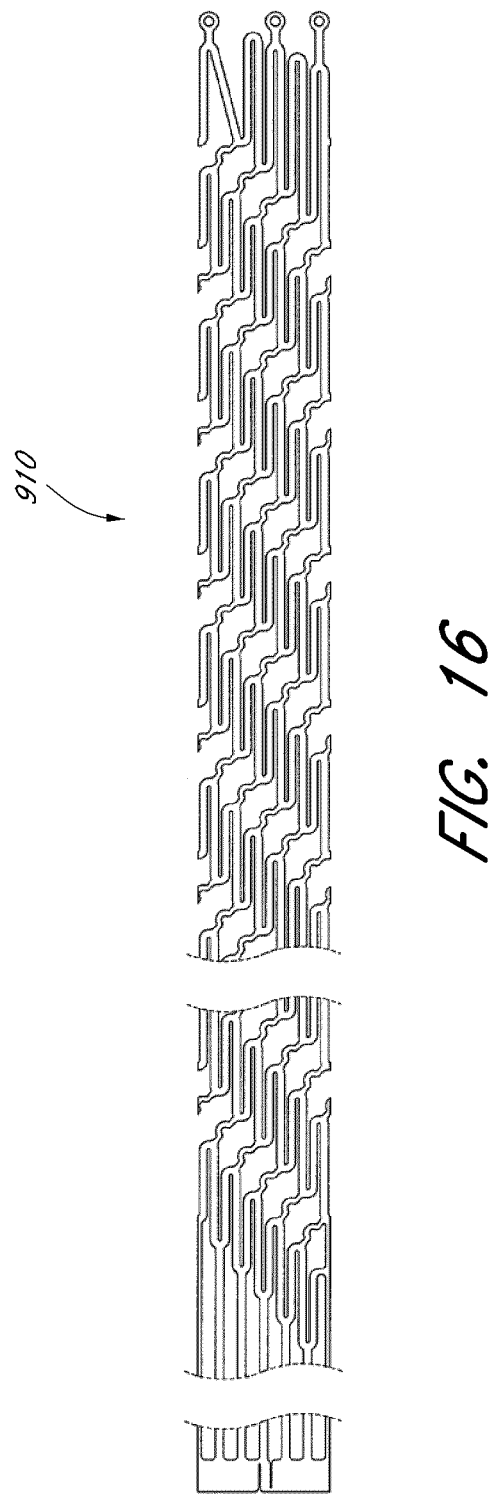
FIG. 16 illustrates a laser cut profile of the expandable scaffold of FIGS. 9A-9C.

FIG. 15A illustrates a laser cut profile of an embodiment of an expandable scaffold 1510 and FIGS. 15B and 15C illustrate a perspective view and a side view of the expandable scaffold 1510 formed from the cut profile of FIG. 15A in its expanded configuration. The expandable scaffold 1510 comprises an open-cell device that is substantially closed at its proximal end 1522 and its distal end 1524. The expandable scaffold 1510 includes a similar cell pattern as the expandable scaffold 1210 of FIGS. 12A-12D; however, the expandable scaffold 1510 includes fewer tether lines or tangs 1519.

Figure 17A:
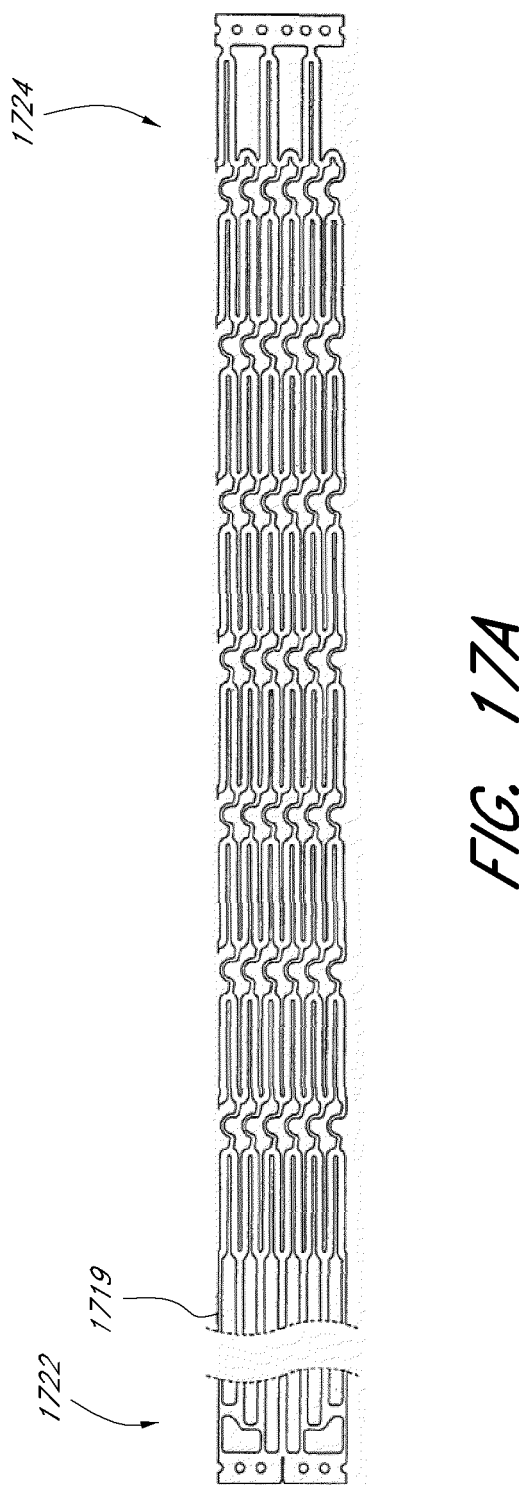

FIG. 17A illustrates a laser cut profile of an embodiment of an offset expandable scaffold 1710 and FIGS. 17B-17E illustrate a side view, a front view, a back view, and a section view of the offset expandable scaffold 1710 formed from the laser cut profile of FIG. 17A. The tether lines or tangs 1719 extend from a proximal collar 1709 that is offset, or eccentric, from a central longitudinal axis of the expandable scaffold 1710. The offset, or eccentric, deployment can facilitate increased blood flow through the expandable scaffold 1710 because the proximal end 1722 occupies less area of the vessel. In accordance with some embodiments, the offset expandable scaffold 1710 comprises an offset clot basket configured to provide effective clot removal. In some embodiments, the offset expandable scaffold 1710 includes struts or tangs at a proximal end 1722 that have a larger width or thickness than the struts along a main body portion of a distal end 1724 of the expandable scaffold 1710.

Figure 18A:
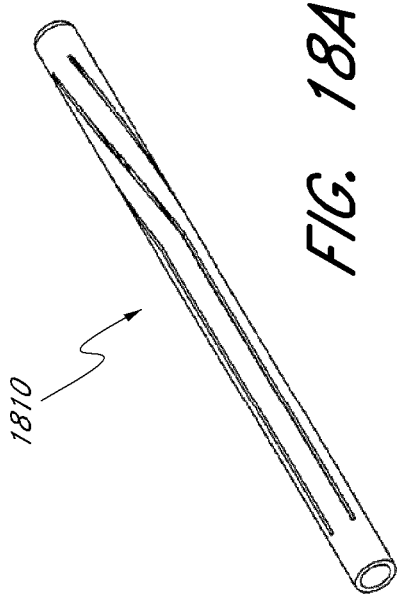
FIGS. 18A-18C illustrate a perspective view, a side view, and a front view of an embodiment of a spiral expandable scaffold in its compressed configuration
Figure 18B:
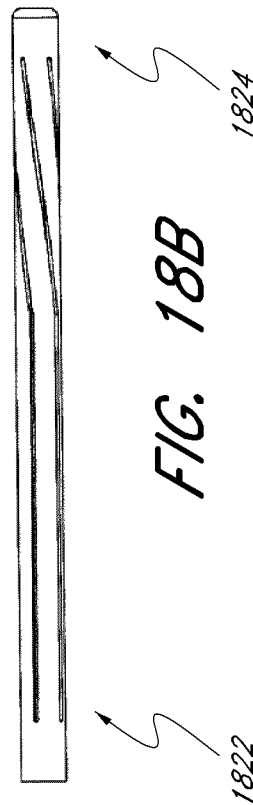
Figure 18C:
Figure 18D:
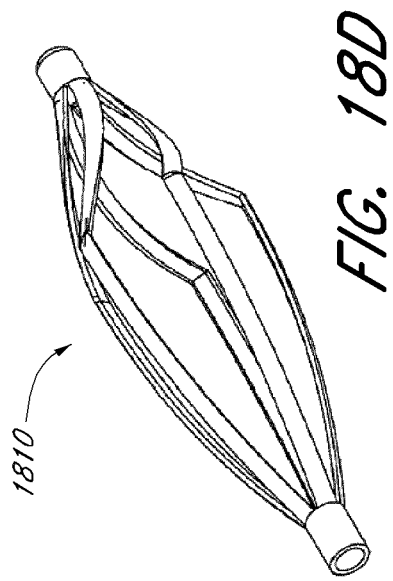
FIGS. 18D-18F illustrate a perspective view, a side view, and a front view of the spiral expandable scaffold in its expanded configuration.
Figure 18E:
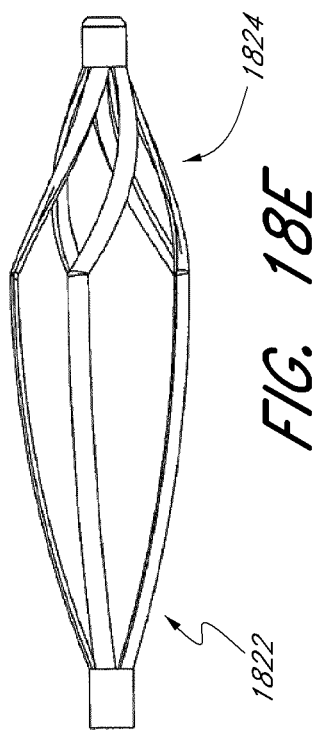
Figure 18F:
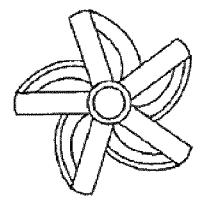

FIGS. 18A-18C illustrate a perspective view, a side view, and a front view of an embodiment of a spiral expandable scaffold 1810 in its compressed configuration and FIGS. 18D-18F illustrate a perspective view, a side view, and a front view of the spiral expandable scaffold 1810 in its expanded configuration. With reference to FIGS. 18A and 18B, the spiral expandable scaffold 1810 is formed of a laser cut tube wherein the laser cuts are straight or substantially straight from a proximal end 1822 of the expandable scaffold 1810 toward the distal end 1824 (e.g., more than half of the total length) and then veer off at an angle at the distal end 1824, thereby forming a spiral expandable scaffold when expanded. The spiral expandable scaffold 1810 advantageously can be used to facilitate effective clot removal.

Figure 19:
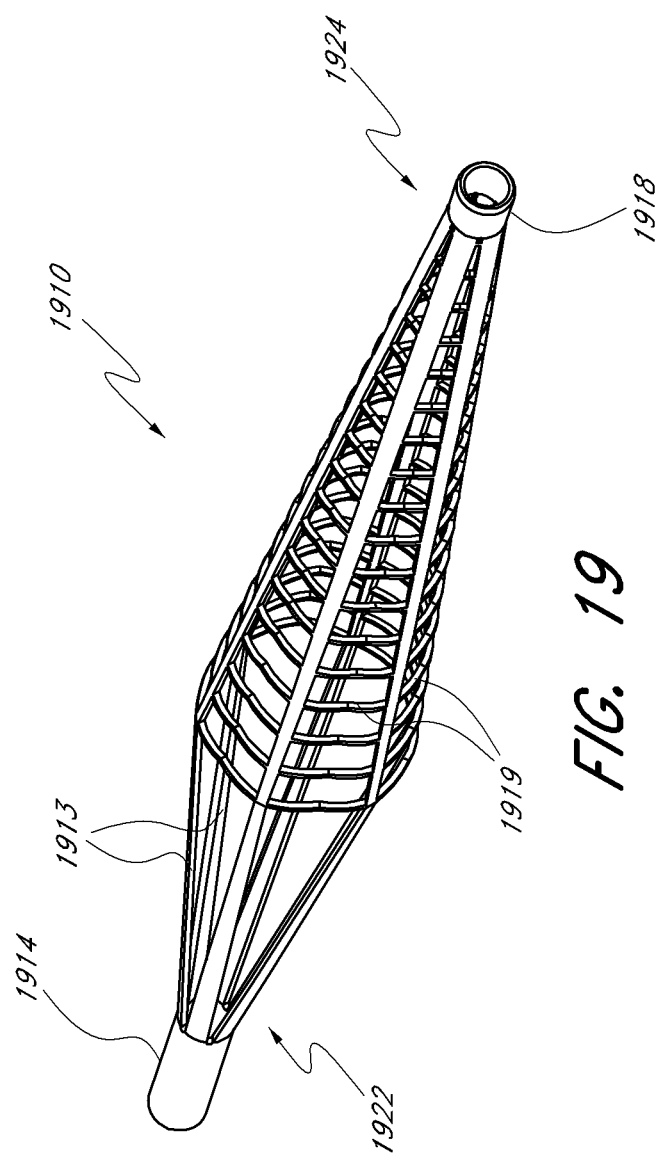
FIG. 19 illustrates a perspective view of an embodiment of an expandable scaffold.

FIG. 19 illustrates a perspective view of an embodiment of an expandable scaffold 1910. In some embodiments, the expandable scaffold 1910 comprises a woven basket. The expandable scaffold 1910 is substantially closed or closed at its proximal end 1822 and its distal end 1924. The expandable scaffold includes 1910 longitudinal or horizontal struts 1913 extending from a proximal collar 1914 to a distal collar 1918 that are equally angularly spaced and a plurality of vertical struts 1919 interconnecting the longitudinal or horizontal struts 1913. In some embodiments, the horizontal struts 1913 have greater thickness or width than the vertical struts 1919.

Figure 20:
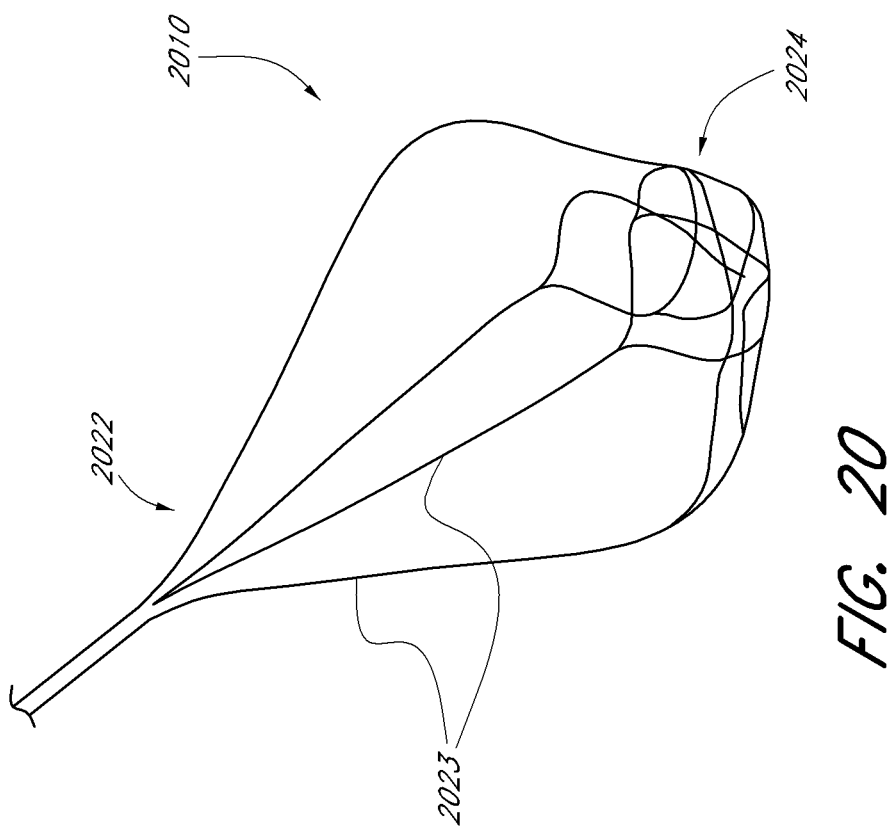
FIG. 20 illustrates a perspective view of an embodiment of a woven expandable scaffold configured for clot retrieval.

FIG. 20 illustrates a perspective view of an embodiment of a woven expandable scaffold 2010 configured for clot retrieval or extraction. In some embodiments, the woven expandable scaffold 2010 has wires of increased thickness adjacent to its proximal end 2022 to provide tensile strength for opening the expandable scaffold 2010. The expandable scaffold 2010 can comprise a mesh or woven basket having low porosity fine wires in the basket area 2021 to support a clot and thicker wires or tether lines 2023 at the proximal end 2022 that open the expandable scaffold 2010 and give strength to the woven expandable scaffold 2010.

The resheathing features of the expandable scaffolds described above (e.g., tapered proximal end, long tether lines, everted sections, eccentricity) advantageously can provide pain reduction and reduced loss of endothelial cells during treatment. The resheathing features can also facilitate clot capture and extraction. For example, expandable scaffolds having tapered proximal ends (e.g., expandable scaffold 610, expandable scaffold 910) taper away from a vessel wall as the expandable scaffold is withdrawn, thereby reducing vessel scraping and risk of vessel perforation or vasospasm. The reduced vessel scraping can reduce pain experienced by a patient and reduce loss of endothelial cells during treatment. The non-tapered distal end can remain fully deployed and in contact with a vessel wall during resheathing.

The expandable scaffolds (for example, but not limited to, expandable scaffold 610, expandable scaffold 810, expandable scaffold 910) may be coated with, covered by, or otherwise include substances imparting lubricous characteristics and/or therapeutic substances, as desired. According to several embodiments, coatings include vasodilators such as papaverine and nimodipine, rapamune (e.g., Sirolimus), paclitaxel, anti-coagulant materials, anti-platelet materials, or combinations thereof. Additionally, at least heparin and other coating materials of pharmaceutical nature may be used. In some embodiments, the expandable scaffolds can comprise a coating that increases or enhances clot adhesion to an expandable scaffold, such as a thrombogenic material that promotes the formation of fibrin bonds with the expandable scaffold or a material that enhances platelet activation or growth. In some embodiments, the expandable scaffolds are configured to be non-thrombogenic and, in some embodiments, can further be used without placing subjects on an anti-clotting drug (including but not limited to acetylsalicylic acid (e.g., aspirin) and clopidogrel (e.g., Plavix®)).

The length of the expandable scaffolds described herein can vary. In some embodiments, the length of the expandable scaffolds is between 10 mm and 50 mm, between 20 mm and 40 mm, between 25 mm and 35 mm (e.g., 30 mm), less than 10 min, greater than 50 mm, or overlapping ranges thereof. The diameter of the expandable scaffolds varies between the compressed and expanded configurations. The expanded diameter of the expandable scaffolds can be between 1 mm and 10 mm, between 1.5 mm and 6 mm, between 2 mm and 5 mm. In some embodiments, the expanded diameter is 1 mm, 2 mm, 3 mm, 4 mm, 5 mm, 6 mm, 7 mm, 8 mm, 9 mm, or 10 mm. In some embodiments, the expanded diameter can be greater than 10 mm.

The expandable scaffolds can be sized and configured to be deployed in particular blood vessels. For example, expandable scaffolds designed to be deployed within a middle cerebral artery can have an expanded diameter of between 1.5 mm and 3 mm and length between 10 mm and 30 mm. Expandable scaffolds designed to be deployed in an internal carotid artery can have an expanded diameter of between 3 mm and 6 mm and a length between 10 mm and 50 mm. In some embodiments, expandable scaffolds designed to be deployed in a posterior cerebral artery can have an expanded diameter of between about 2 mm and 3 mm and a length between 10 mm and 30 mm. Expandable scaffolds designed to be deployed in a basilar artery can have an expanded diameter between 3 mm and 4 mm and a length between 10 mm and 40 mm and expandable scaffolds designed to be deployed in a vertebral artery can have an expanded diameter between 3 mm and 4 mm and a length between 10 mm and 60 mm. Expandable scaffolds having an expanded diameter of 5 mm can be used as a default in any cerebral artery but may experience significant cell deformation in vessels having a diameter less than 5 mm.

1. Expandable Scaffold Parameters or Characteristics

Figure 21A:
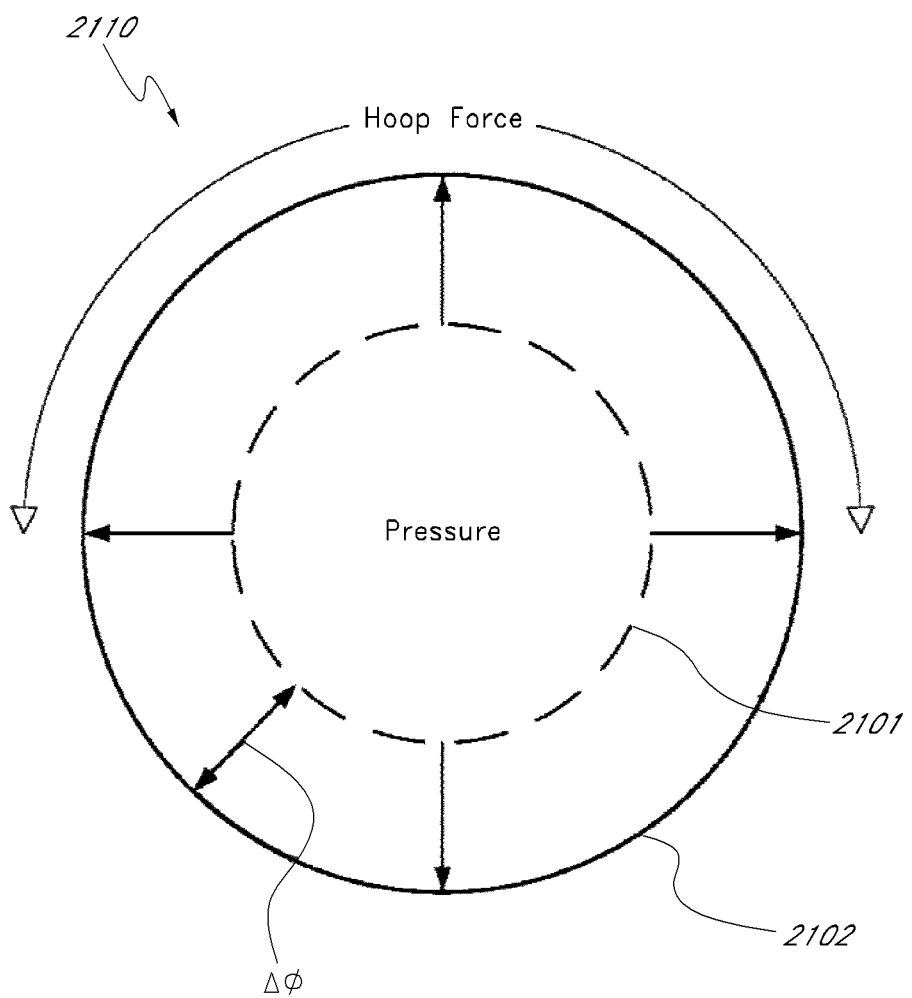
FIG. 21A shows an embodiment of an expandable scaffold in cross section having an unexpanded state and an expanded state.
Figure 21B:
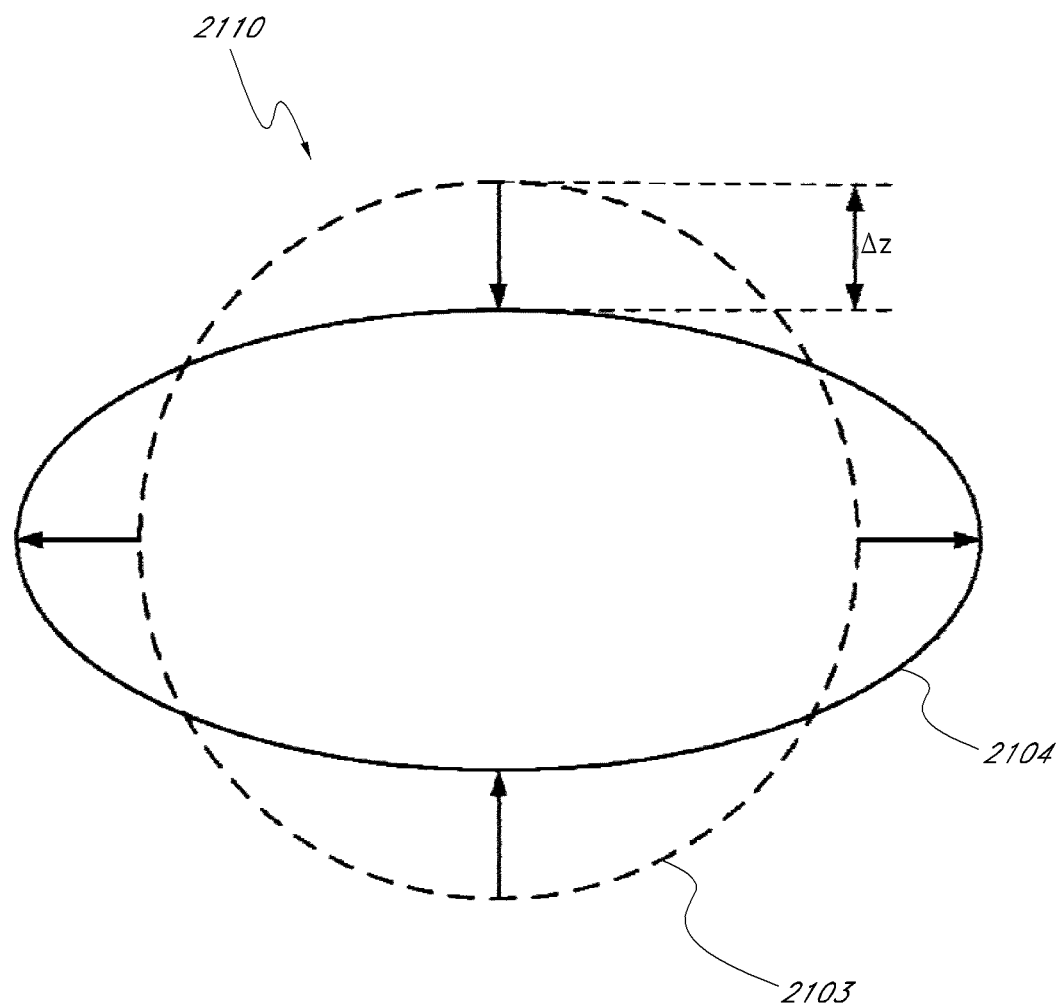
FIG. 21B shows an embodiment of an expandable scaffold in cross section having a first state and a second state under pinching load.

Turning to FIGS. 21A and 21B, according to several embodiments, characteristics of an expandable scaffold 2110 may be controlled to modify the effect of the expandable scaffold 2110 to achieve one or more of maceration, removal, and lysis of a clot. For example, hoop strength, stiffness, cell size, strut length, strut width, and strut thickness of the expandable scaffold 2110 may be varied to provide customizable therapies to a clot. In accordance with some embodiments, the expandable scaffold exhibits sufficient radial force to expand to a vessel wall but has a large enough cell size to increase the efficacy of removal (e.g., a cell size is configured to facilitate both reperfusion of the blood vessel and capture of the clot).

Blood vessels may experience loads from a variety of sources, such as the expansion of the expandable scaffold 2110. Pressures applied to any cylindrical structure, such as a blood vessel, result in hoop, or circumferential loading of the vessel (FIG. 21A). Both the applied pressure and the resulting hoop stress have units of force per unit area, but these may differ in direction. As used herein, "pressure" refers to the force normal to the vessel wall, divided by the surface area of the lumen. As used herein, "hoop stress" is the circumferential load in the vessel wall divided by the cross-sectional area of the vessel wall (length times wall thickness).

The relationship between the pressure (p) and the hoop stress (a) in a thin-walled cylindrical object, such as the expandable scaffold 2110, may be expressed as:

$$\sigma = \frac{\rho \phi}{2t}, \quad \text{(Eq. 1)}$$

where "φ" is the diameter of the expandable scaffold 2110 and "t" is the wall thickness of the expandable scaffold 2110. The hoop force ($F_\theta$) in a vessel wall may be expressed as:

$$F_\theta = \sigma t L = \frac{\rho \phi L}{2}, \quad \text{(Eq. 2)}$$

where "L" is the length of the expandable scaffold 2110 (or length "$L_s$" of a strut, depending on the scope of analysis). The hoop force per unit length ($f_\theta$) may be expressed as:

$$f_\theta = \frac{F_\theta}{L} = \sigma t = \frac{\rho \phi}{2}. \quad \text{(Eq. 3)}$$

a. Hoop Stiffness

"Stiffness," or the elastic response of a device to an applied load, reflects the effectiveness of the expandable scaffold 2110 in resisting deflection due to vessel recoil and other mechanical events. "Stiffness" is the inverse of "compliance," or diameter change (ΔΦ) at a specific applied pressure (p). As shown in FIG. 21A, the expandable scaffold 2110 shown in cross section may experience a change in diameter (ΔΦ) as it expands from a compressed state 2101 to an uncompressed state 2102. The hoop stiffness ($k_\theta$) of the expandable scaffold 2110 may be expressed as the hoop force per unit length ($f_\theta$) required to elastically change its diameter (ΔΦ), or:

$$k_\theta = \frac{f_\theta}{\Delta \phi}. \quad \text{(Eq. 4)}$$

Figure 22:
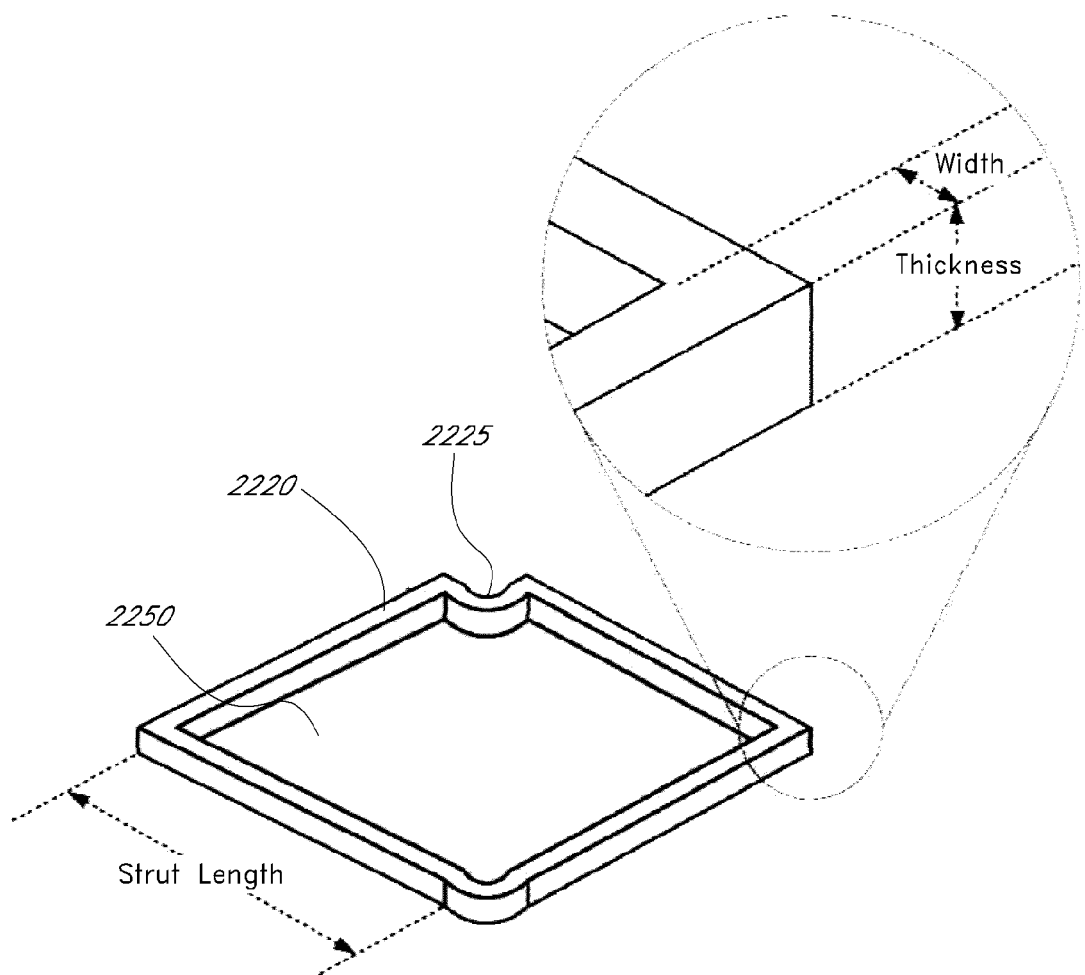
FIG. 22 shows a cell of one embodiment of an expandable scaffold with a portion in an expanded view.

A change in diameter (ΔΦ) of expandable scaffold 2110 due to an applied load is related to the geometry of expandable scaffold 2110 as expressed by:

$$\Delta \phi \propto \frac{f \phi n L_s^3}{E w^3 t}, \quad \text{(Eq. 5)}$$

where "$L_s$" is the length of a strut (as shown in FIG. 22), "w" is the strut width (as shown in FIG. 11), "t" is the thickness of expandable scaffold (as shown in FIG. 22), "n" is the number of struts around the circumference of expandable scaffold 2110, and "E" is the elastic modulus of the material. Combining Eq. 3 with Eq. 5, the change in diameter (ΔΦ) of expandable scaffold 2110 may be related to an applied pressure load (p) by:

$$\Delta\phi \propto \frac{p\phi n L_s^3}{E w^3 t}, \quad \text{(Eq. 6)}$$

Combining Eq. 4 and Eq. 6, the hoop stiffness ($k_\theta$) may be expressed as:

$$k_\theta \propto \frac{E w^3 t}{n L_s^3}. \quad \text{(Eq. 7)}$$

Thus, hoop stiffness ($k_\theta$) has a cubic relationship with strut width (w), a linear relationship with strut thickness (t), an inversely linear relationship with number of struts about the circumference (n), and an inversely cubic relationship with the strut length ($L_s$).

In contrast to symmetrical radial expansion and compression, an uneven load (i.e., pinching load) may be applied to an external surface of a portion of the expandable scaffold 2110, resulting in radially asymmetric deflection (Δz). For example, as shown in FIG. 21B, the expandable scaffold 2110 may be squeezed between two opposite loads, whereby the expandable scaffold 2110 is subjected to a pinching load. Under a pinching load, the expandable scaffold 2110 may deflect from an initial state 2103 to a deflected state 2104. A pinching load may cause struts 2220 (see FIG. 22) to be bent in a manner other than about the circumference. Pinching stiffness ($k_p$), or the force required to cause radially asymmetric deflection (Δz) may be generalized by the expression:

$$k_p \propto \frac{E t^3 w}{n L_s^3}. \quad \text{(Eq. 8)}$$

Under a pinching load, the pinching stiffness ($k_p$) of the expandable scaffold 2110 has a cubic relationship with strut thickness (t) and a linear relationship with strut width (w). This is relationship is the inverse of the strut's influence on hoop stiffness ($k_\theta$). Thus, strut thickness (t) has a dominant role in pinching stiffness ($k_p$) and strut width (w) has a dominant role in hoop stiffness ($k_\theta$).

According to several embodiments, a clot in an otherwise substantially radially symmetric vessel may tend to cause radially asymmetric deflection of the expandable scaffold 2110 as it is expanded against the clot. Both hoop stiffness ($k_\theta$) and pinching stiffness ($k_p$) of the expandable scaffold 2110 play a role in how the expandable scaffold 2110 interacts with the clot.

b. Lengths and Expansion Diameters

The sizes of the expandable scaffolds can vary depending on the size of the particular vessel in which they are configured to be inserted. For example, the lengths of the expandable scaffolds can vary from 1 cm to 5 cm (e.g., from 1 cm to 4 cm, from 2 cm to 5 cm, from 2 cm to 4 cm, overlapping ranges thereof, 1 cm, 1.5 cm, 2 cm. 2.5 cm, 3 cm, 3.5 cm, 4 cm, 4.5 cm, 5 cm) and the expansion diameter can vary from 1 mm to 6 mm (e.g., from 1 mm to 4 mm, from 2 mm to 6 mm, from 3 mm to 5 mm, overlapping ranges thereof, 1 mm, 2 mm, 3 mm, 4 mm, 5 mm, 6 mm) depending on the vessel to be addressed by the particular expandable tip assembly. In some embodiments, the expandable scaffolds can be configured to expand to diameters larger than 5 mm (e.g., 6 mm, 7 mm, 8 mm, 9 mm, 10 mm) or less than 2 mm (e.g., 1.8 mm, 1.6 mm, 1.4 mm, 1.2 mm, 1.0 mm).

In some embodiments, an expandable tip assembly can be selected based on expansion diameter of the expandable scaffold. An expandable tip assembly having an expandable scaffold that has a maximum expansion diameter roughly equivalent to the vessel diameter can be used to reduce cell deformation and minimize risk of vessel damage. If the expandable tip assembly is to be used for clot removal or extraction, selecting an expandable tip assembly having an expandable scaffold that has a maximum expansion diameter roughly equivalent to the vessel diameter can prevent the clot from sliding by the expandable scaffold, thereby increasing the efficacy of clot removal in several embodiments. For example, some expandable scaffolds can have an expansion diameter configured to be used in 3 mm vessels and other expandable scaffolds can have an expansion diameter configured to be used in 5 mm vessels. In some embodiments, an expandable tip assembly having an expandable scaffold that has a maximum expansion diameter greater than the vessel diameter or less than the vessel diameter is selected as desired and/or required by particular circumstances.

c. Radial Force (Chronic Outward Force and Radial Resistive Force)

According to several embodiments, the expandable scaffold 2110 may provide both a chronic outward force ("COF") and a radial resistive force ("RRF"). As used herein, chronic outward force ("COF") is the continuing radial opening force of a self-expanding scaffold acting on a vessel wall after having reached equilibrium with the vessel wall. As used herein, radial resistive force ("RRF") is the force generated by the self-expanding scaffold to resist compression, or the force required to compress the scaffold. Generally, RRF is expressed in relation to the amount of relative compression to be achieved. Generally, COF and RRF are expressed in terms of force per unit length (e.g., N/mm).

According to several embodiments, the expandable scaffold 2110 may have a range of COF per unit length across given diameters (e.g., 1 mm to 4.5 mm). In some embodiment, the COF per unit length of the expandable scaffold 2110 across given diameters is substantially uniform, or constant. In some embodiments, the COF per unit length of the expandable scaffold 2110 across given diameters (e.g., 1 mm to 4.5 mm) slightly decreases with increasing vessel diameter. For example, the COF may be from about 0.00590 N/mm to about 0.0090 N/mm at a diameter of about 2.0 mm and a COF from about 0.00165 N/mm to about 0.0038 N/mm at a diameter of about 4.5 mm. In some embodiments, the COF per unit length of the expandable scaffold 2110 decreases by less than 10% to 90% (e.g., less than 10%, less than 20%, less than 30%, less than 40%, less than 50%, less than 60%, less than 70%, less than 80%, less than 90%) over a range of expansion diameters from 1.5 mm to 4.5 mm. In one embodiment, the COF per unit length of the expandable scaffold 2110 decreases by between 50% to 75% over a range of expansion diameters from 1.5 mm to 4.5 mm. In some embodiments, the COF per unit length of the expandable scaffold 2110 across given diameters (e.g., 1 mm to 4.5 mm) is substantially non-zero across the entire range of diameters.

According to several embodiments, the expandable scaffold 2110 may have a range of RRF per unit length across given diameters (e.g., 1.5 mm to 4.5 mm). For example, RRF may be from about 0.011 N/mm to about 0.016 N/mm at a diameter of about 2.0 mm and from about 0.005 N/mm to about 0.007 N/mm at a diameter of about 4.5 mm.

According to several embodiments, the expandable scaffold 2110 may have an average COF per unit across a diameter of 2.0 mm to 4.5 mm length across a diameter of 2 mm to 4.5 mm of between about 0.0016 N/mm and at least about 0.0090 N/mm, (e.g., between about 0.0020 N/mm and about 0.0070 N/mm, between about 0.0025 N/mm and about 0.0065 N/mm, between about 0.00165 N/mm and about 0.0090 N/mm, between about 0.0023 N/mm and about 0.0073 N/mm, between about 0.0030 N/mm and about 0.0059 N/mm, or overlapping ranges thereof). According to several embodiments, the expandable scaffold 2110 may have an average RRF per unit length across a diameter of 2 mm to 4.5 mm of between about 0.0067 N/mm and about 0.0138 N/mm (e.g., between about 0.0065 N/mm and about 0.0140 N/mm, between about 0.0070 N/mm and about 0.0130 N/mm, between about 0.0083 N/mm and about 0.0127 N/mm, or overlapping ranges thereof). Therapy provided within these ranges may provide effective maceration toward the lower end of the range and effective removal toward the upper end of the range.

According to several embodiments, an expandable scaffold having relatively low COF and RRF is effective for facilitating maceration of a clot. For example, an expandable scaffold having an average COF of between about 0.015 N and about 0.0040 N (e.g., 0.12 N to 0.004 N) across a diameter of 1.5 mm to 4.5 mm and having an average RRF between about 0.0050 N and about 0.0220 N (e.g., 0.0080 N to 0.0200 N) across a diameter of 1.5 mm to 4.5 mm can provide effective therapy requiring maceration of a clot. According to several embodiments, an expandable scaffold having relatively high COF and RRF is effective for facilitating removal of a clot. For example, an expandable scaffold having an average COF of between about 0.0015 and about 0.0090 (e.g., between about 0.0040 N and about 0.0090 N, between about 0.0015 N and about 0.0060 N, between about 0.0020 N and about 0.0080 N, or overlapping ranges thereof) and having an average RRF between about 0.0060 N and about 0.0200 N (e.g., about 0.0060 N to about 0.0150 N, about 0.0070 N to about 0.0160 N, about 0.0100 to about 0.0200 N, or overlapping ranges thereof) can provide effective therapy requiring removal of a clot.

d. Cell Design

Figure 23:
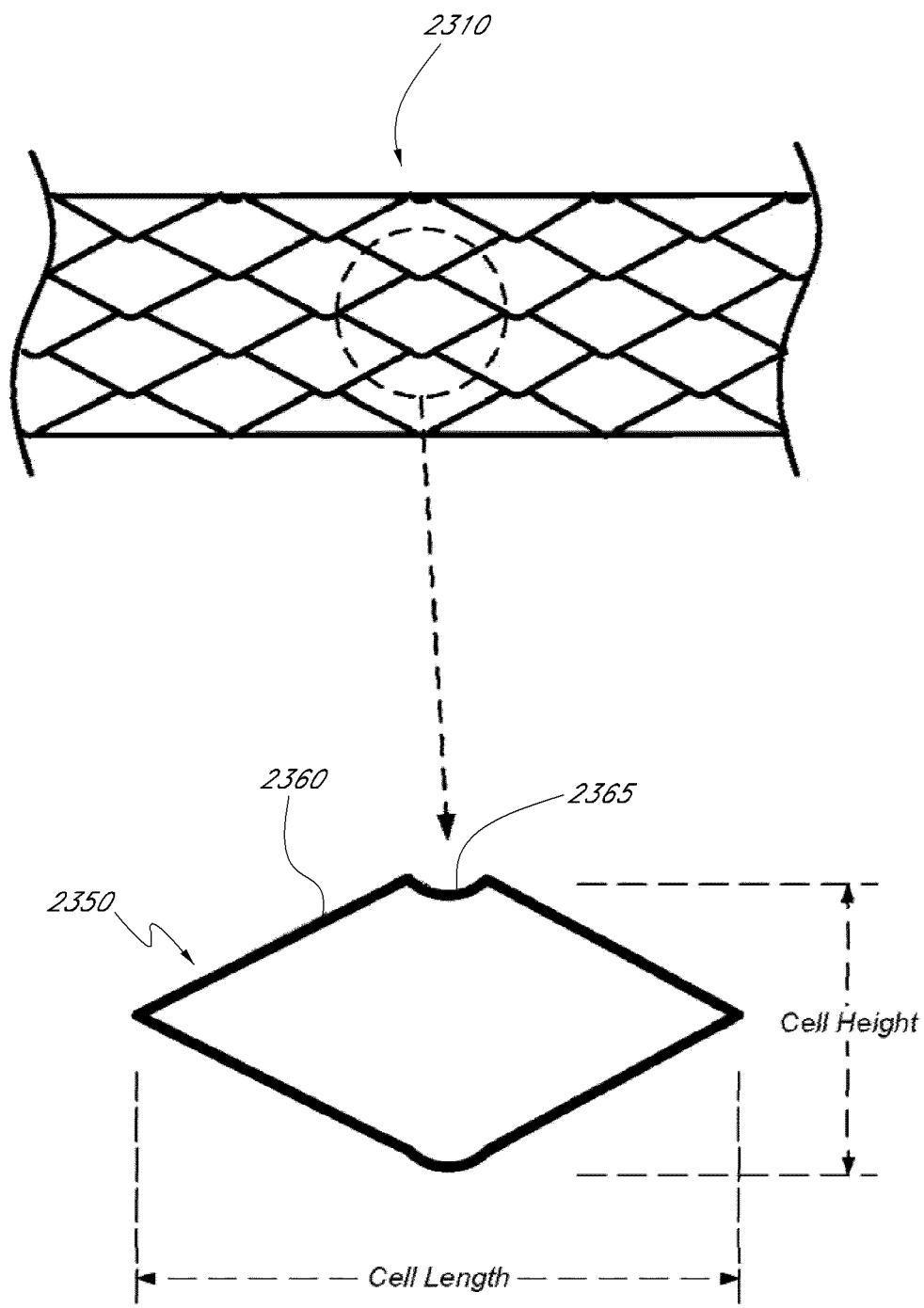
FIG. 23 shows a cell of one embodiment of an expandable scaffold with a cell thereof in an expanded view.

FIG. 23 illustrates a close-up schematic representation of a cell of an embodiment of an expandable scaffold 2310. According to several embodiments, cell size contributes to the effect that the expandable scaffold has on a clot. As shown in FIG. 23, each open cell 2350 of the expandable scaffold 2310 may have a cell height and cell length, providing exposure from an interior portion of the expandable scaffold 2310 to an exterior portion of the expandable scaffold 2310. The cells 2350 of the expandable scaffold 2310 may include struts 2360 and bridges 2365 connecting struts 2360. Bridges 2365 may be of a variety of shapes and sizes, including "C" shapes, "S" shapes, straight shapes, etc. Cells 2350 may form a variety of shapes, including diamonds, parallelograms, rectangles, and other polygonal shapes.

Figure 24B:
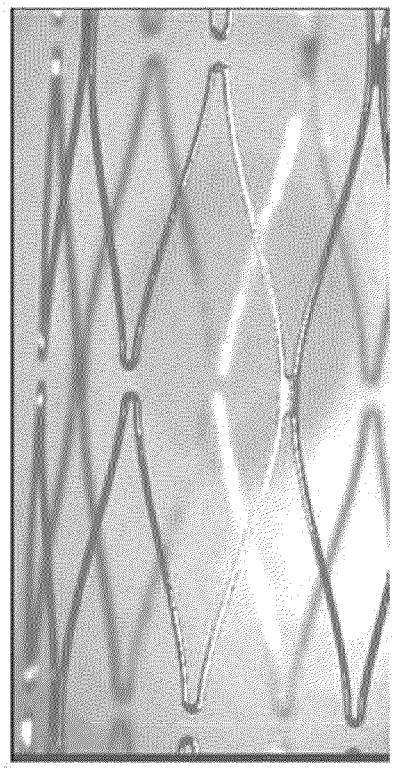
FIGS. 24A, 24B, 25A 25B, 26A, 26B, 27A, and 27B show a variety of cell sizes and geometries that may be provided to achieve desired outcomes during therapy.
Figure 24A:
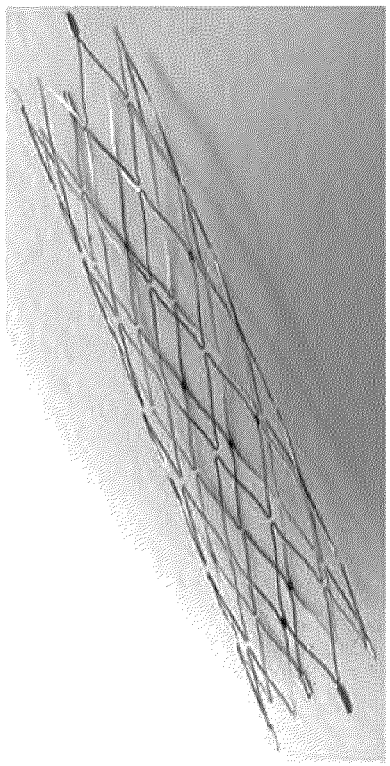
Figure 25B:
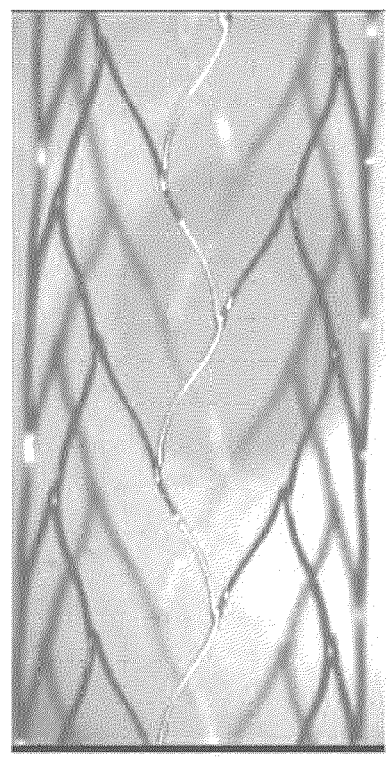
Figure 25A:
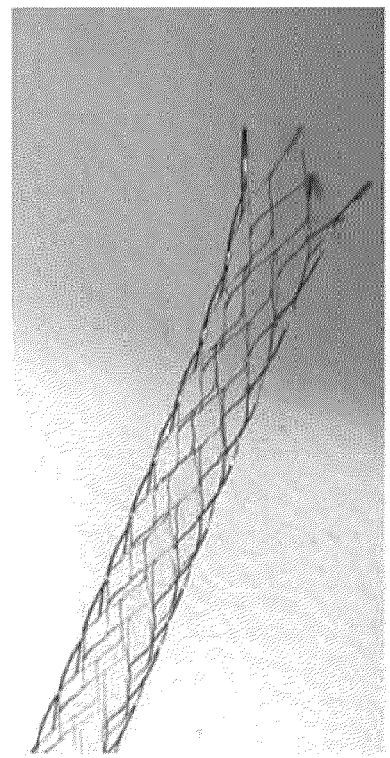
Figure 26B:
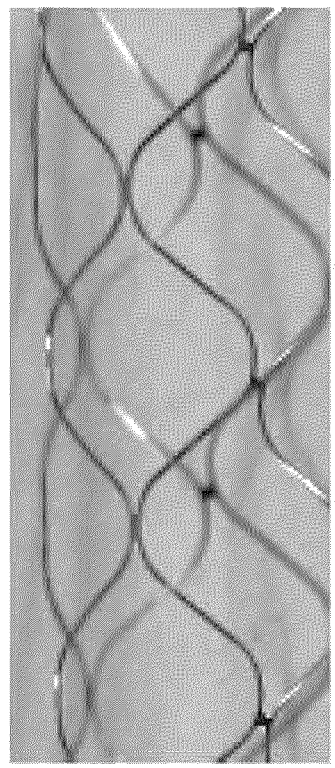
Figure 26A:
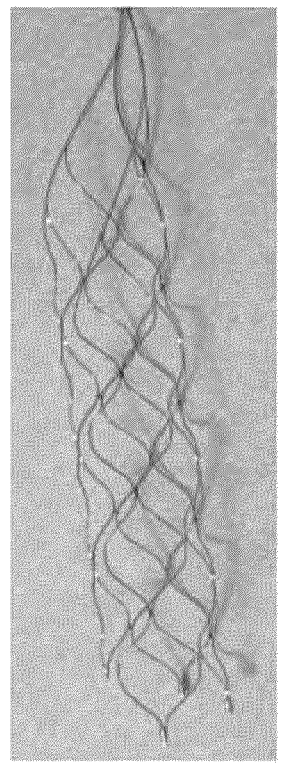
Figure 27B:
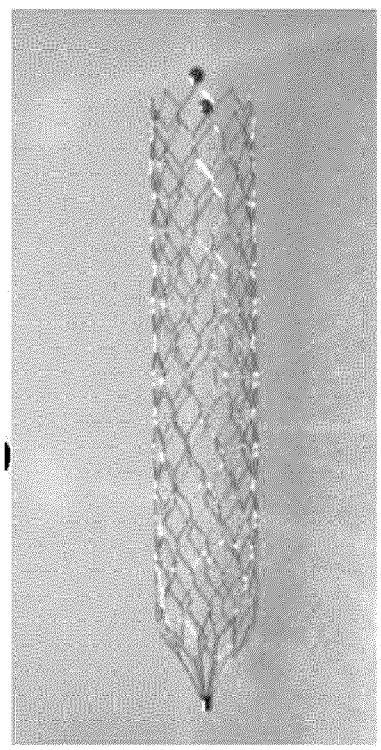
Figure 27A:
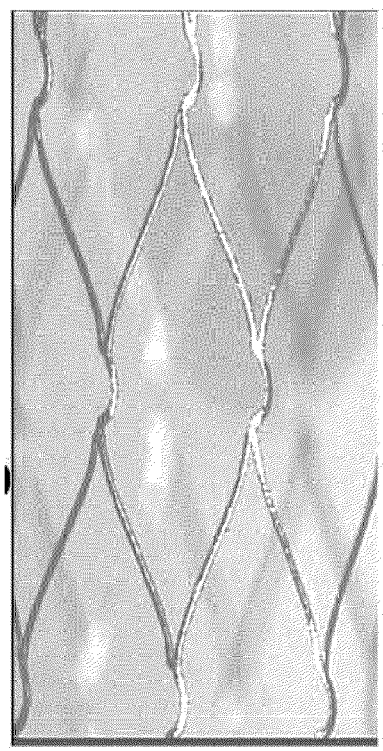

According to several embodiments, a variety of cell sizes and geometries may be provided to achieve desired outcomes during therapy. According to several embodiments, as shown in FIGS. 24A, 24B, 25A, 25B, 26A, 26B, 27A, and 27B, a variety of cell sizes and geometries may be provided to achieve desired outcomes during therapy. FIGS. 24A and 24B show a NeuroForm$^3$™ (by Boston Scientific® of Boston, Mass.) device. FIGS. 25A and 25B show an Enterprise™ device (by Cordis® of Bridgewater, N.J.). FIGS. 26A and 26B show a Solitaire™ AB device (by ev3® of Plymouth, Minn.). FIGS. 27A and 27B show an IRIIS™ device (by MindFrame® of Irvine, Calif.). The IRIIS™ device of FIGS. 27A and 27B is an embodiment of the expandable tip assemblies described herein.

Figure 28:
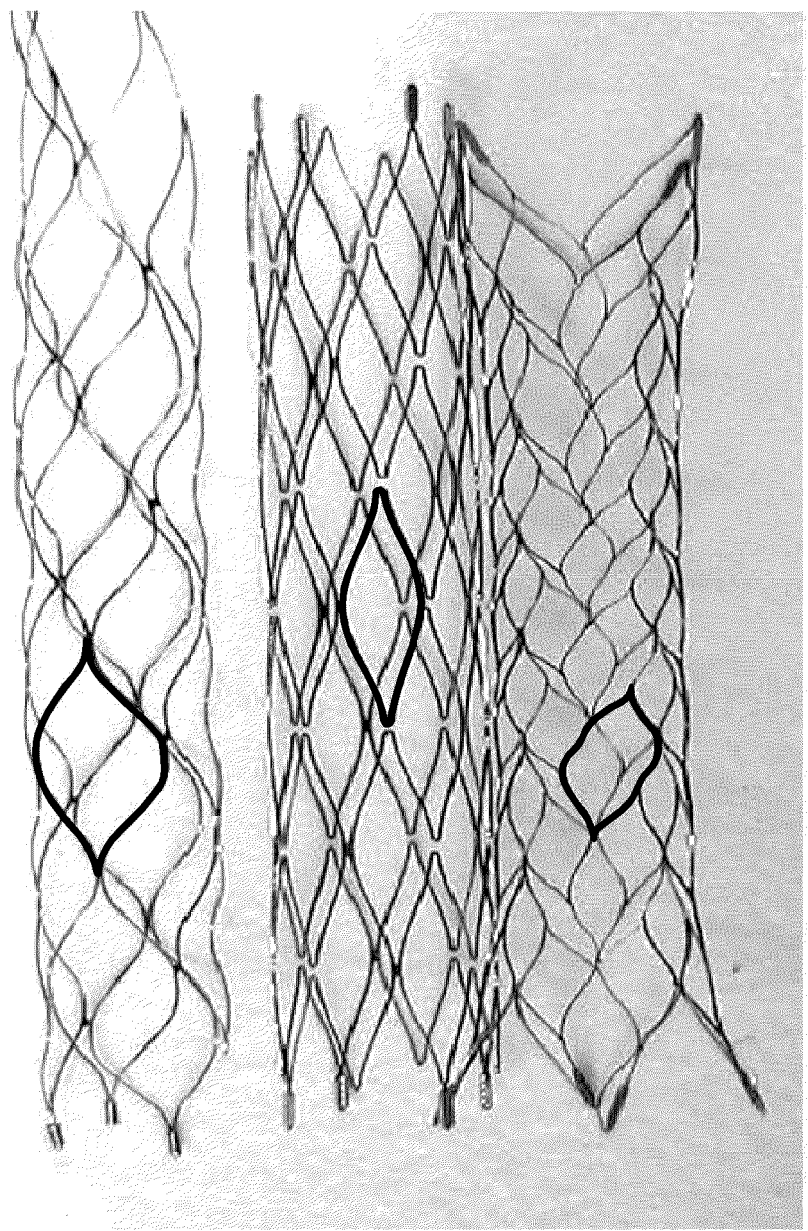
FIGS. 28, 29A, 29B and 29C show a variety of individual cell sizes, with emphasis.
Figure 29A:
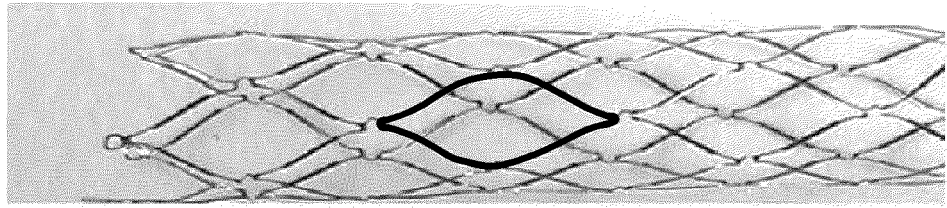
Figure 29B:
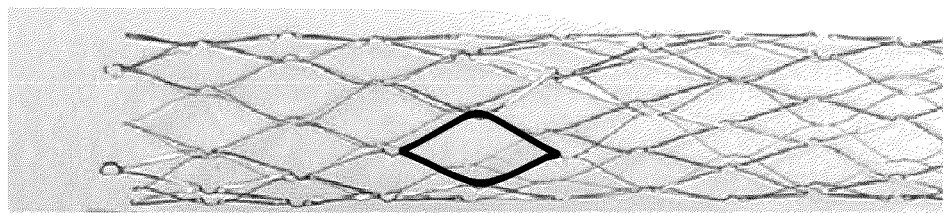
Figure 29C:
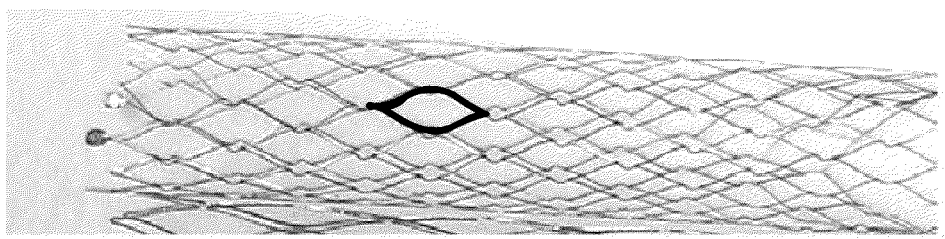

As shown in FIGS. 28, 29A, 29B, and 29C, individual cells 210 are shown with emphasis. FIG. 28 shows views of each of a Solitaire™ AB device, a NeuroForm$^3$™ device, and an Enterprise™ device. FIGS. 29A, 29B, and 29C each show an embodiment of an expandable scaffold (e.g., a MindFrame IRIIS™ device). The respective cell sizes of each are shown with emphasis. In particular, FIGS. 29A, 29B, and 29C show similar cell geometries with distinct cell sizes and the impact on the overall structure of the respective device. A relatively larger cell size is shown in FIG. 29A, with a relatively smaller cell size shown in FIG. 29C and an intermediate cell size shown in FIG. 29B.

According to several embodiments, an expandable scaffold (e.g., a removal scaffold or combination reperfusion and removal scaffold) of an expandable removal device) having a larger cell size facilitates removal of a clot by allowing larger portions of the clot to be isolated as the closed portions (e.g., struts) of the cells apply pressure and force to the clot. The larger cell sizes cause larger portions of the clot to remain within the scaffold, whereby the relatively larger portions may be more readily captured and removed with the expandable scaffold or other devices. The relatively large cells allow for more of the clot to enter, protrude or penetrate into the interior of the expandable scaffold (e.g., from the side exterior of the expandable scaffold), thereby enhancing clot adhesion and increasing the likelihood of clot capture. The relatively large cells can allow the expandable scaffold to more fully expand to the vessel diameter, thereby providing a shearing effect at the clot adhesion site to break sticky, firm bonds that may have formed between the clot and the vessel wall. The relatively large cells advantageously can allow for expansion to a greater diameter with a lower requisite radial force. Variation of radial strength can affect removal characteristic such as the ability to navigate through the intracranial vessel tortuosity.

According to several embodiments, the expandable scaffold having a small cell size facilitates lysis and maceration of a clot by breaking the clot into smaller portions. The smaller cell sizes cause smaller portions of the clot to remain, whereby more surface area of the clot is exposed to ambient materials for facilitating lysis. Variation of the cell size may affect clot lysis by varying the amount of surface area applying pressure from the structure to the clot. For example, smaller cell sizes will generally provide a greater amount of structure to transfer pressure and forces to a clot. Furthermore, a structure having smaller cells may provide a more consistently shaped channel (with fewer or less dramatic inflection points) for recanalization by more evenly distributing the outward forces and pressures. The improved recanalization in turn facilitates improved lysis by virtue of better exposure of the clot to vascular flow.

Referring back to FIGS. 27A and 27B, an embodiment of an expandable scaffold 2710 having a cell size and geometry that is configured for reperfusion and maceration is illustrated. According to several embodiments, the expandable scaffold 2710 may have cells 2750 of cell length from at least about 0.100 inches to at least about 0.250 inches (e.g., about 0.100 inches to about 0.175 inches, about 0.100 inches to about 0.150 inches, about 0.125 inches to about 0.185 inches, about 0.150 inches to about 0.200 inches, about 0.200 inches to about 0.250 inches, or overlapping ranges thereof). According to several embodiments, the expandable scaffold 2710 may have cells 2750 of cell height from about 0.035 inches to about 0.100 inches (e.g., about 0.035 inches to about 0.075 inches, about 0.040 inches to about 0.055 inches, about 0.050 inches to about 0.065 inches, about 0.085 inches to about 0.100 inches, or overlapping ranges thereof). For example, the expandable scaffold 2710 having cells 2750 of cell length of about 0.120 inches and cell height of about 0.050 inches may be effective for macerating a clot to which the expandable scaffold 2710 is applied. By further example, an expandable scaffold having cells of cell length of about 0.250 inches and cell height of about 0.100 inches may be effective for removing a clot to which the expandable scaffold is applied.

According to several embodiments, the cell height and cell length of each cell may yield an area defined by the boundaries of the cell. For example, the expandable scaffold 1110 may have cells each having an area of between about 0.006 square inches to about 0.025 square inches, between about 0.010 square inches to about 0.020 square inches, or overlapping ranges thereof. More specifically, each cell may yield an area defined by the boundaries of the cell. According to several embodiments, an expandable scaffold having small cells and high radial strength provides better channel development and maceration with relatively softer clots. According to several embodiments, an expandable scaffold having larger cells and high radial strength will provide better maceration and retrieval for firm, white clots.

In accordance with some embodiments, the cell size varies based on the size of the vessel into which the expandable tip assembly is configured to be inserted. In one embodiment, for an expandable tip assembly configured to be inserted into vessels having a diameter of between 1.5 mm and 4.5 mm and configured to facilitate reperfusion and maceration, the expandable scaffold can have a cell length of about 0.080 inches and a cell height of about 0.030 inches for a cell area of about 0.0012 square inches. As another example, for an expandable tip assembly configured to be inserted into 5 mm vessels and configured to facilitate reperfusion and maceration, the expandable scaffold can have a cell length of about 0.120 inches and a cell height of about 0.050 inches for a cell area of about 0.003 square inches.

As described above, the expandable scaffolds (for example, but not limited to, expandable scaffold 400, expandable scaffold 500) can have variable cell sizes along their lengths. In some embodiments, the cells at the proximal and/or distal end of the expandable scaffold have relatively small cell sizes and the cells of the central portion of the expandable scaffold have relatively large cell sizes (e.g., to facilitate progressive or multiple step therapy).

Figure 30A:
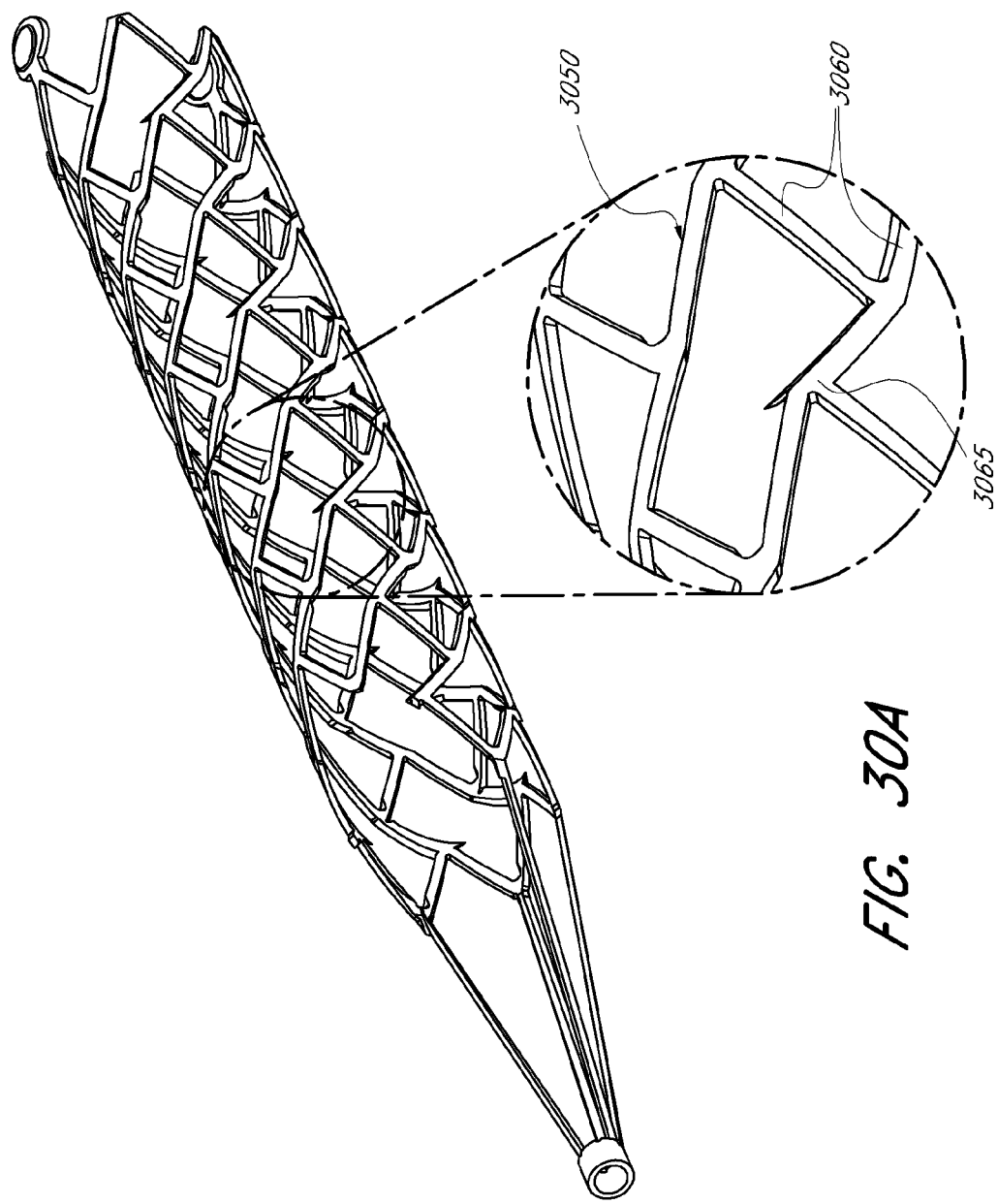
FIG. 30A shows a perspective view of an expandable scaffold and a close-up detailed view of a cell of one embodiment of an expandable scaffold.

According to several embodiments, the expandable scaffolds may have a radial geometry. As shown in FIG. 30A, cells 3050 may be defined by a plurality of struts 3060 connected by bridges 3065. As shown in FIG. 30A, each strut 3060 may connect at each of its ends at a bridge 3065. Each bridge 3065 may connect three struts. As further shown in FIG. 30A, each open cell 3050 may be defined by six struts 3060, wherein the open cell 3050 is substantially parallelogram-shaped. In some embodiments, each bridge 3065 may connect four struts (for example, as shown in FIGS. 27A and 27B).

The cell deformation properties or characteristics can be varied to achieve different therapeutic effects. For example, for flow restoration, cell deformation can be maximized or increased to minimize or decrease thrombus penetration into the expandable scaffold, thereby allowing maximum or increased blood flow through the blood vessel. For thrombus removal, cell deformation can be minimized or decreased to keep the largest cell shape and cell area open to maximize or increase thrombus penetration or protrusion into the scaffold, thereby enhancing the likelihood of clot capture and extraction in a single pass. Cell deformation can be affected by multiple factors such as, but not limited to, cell size, strut widths, strut thicknesses, strut lengths, cell connection types (e.g., bridges), and material properties.

e. Strut/Bridge Design

In some embodiments, the thickness, width, and/or shape of the struts can be varied depending on the purposes to be achieved by the expandable scaffolds (e.g., thrombus engagement, thrombus penetration).

According to several embodiments, for a given pressure provided by an expandable scaffold, a smaller strut width (w) increases the amount of pressure per unit area applied by the expandable scaffold. Thus, the struts of the expandable scaffold may more easily cut through a clot with a smaller strut width. According to several embodiments, a larger strut width (w) improves channel development through a clot. Where a strut provides a wider width, it displaces a greater amount of clot against the walls of the blood vessel. For example, strut width of an expandable scaffold may be from about 10 to about 100 microns (e.g., from about 10 microns to about 75 microns, from about 15 microns to about 65 microns, from about 25 microns to about 100 microns, from about 30 microns to about 75 microns, from about 40 microns to about 90 microns, from about 50 microns to about 100 microns, from about 10 microns to about 80 microns, from about 10 microns to about 50 microns, from about 50 microns to about 60 microns (e.g., about 54 microns), less than 10 microns, greater than 100 microns, or overlapping ranges thereof).

According to several embodiments, strut thickness of the expandable scaffolds may be from about 10 microns to about 100 microns (e.g., from about 10 microns to about 60 microns, from about 20 microns to about 80 microns, from about 25 microns to 75 microns, from about 30 microns to about 65 microns, from about 40 microns to about 60 microns, or overlapping ranges thereof).

Traditionally, in many stents and stent-like structures, one goal is to achieve a ratio of strut thickness to strut width of at least 1.4. Such high ratios have been traditionally preferred for sustaining long-term emplacement of the device. In one embodiment, a ratio of 1.4 or greater aides in the performance of the structure by guiding the manner in which the struts bend. By providing the struts with more thickness than width, the structure innately "knows" how to bend and load the struts. With such characteristics, the device is easier to manufacture because it improves shape setting, the device crimps better, and the device is better able to resist loading that is normal to diameter.

Because pinching stiffness ($k_p$) is predominantly determined by strut thickness and hoop stiffness ($k_\theta$) is predominantly determined by strut width, a structure with a relatively high ratio of strut thickness to strut width will provide relatively high pinching stiffness ($k_p$). In other words, given a thickness to width ratio of at least 1.4, the pinching stiffness of the device increases rapidly when greater hoop stiffness are desired. For example, to increase the hoop stiffness at a certain rate to achieve desired hoop stiffness characteristics would cause pinching stiffness to increase by at least about double the rate at which the hoop stiffness is increased for ratios exceeding 1.4. These increases in pinching stiffness may result in undesirable characteristics of the resulting structure. In contrast, a structure with a relatively low ratio of strut thickness to strut width will provide relatively high hoop stiffness ($k_\theta$) without yielding detrimentally rapid increases in pinching stiffness.

According to several embodiments, the expandable scaffolds of the present disclosure may have a strut thickness to strut width ratio of less than at least about 1.1, 1.2, 1.3, 1.4, or 1.5, etc. For example, the ratio of strut thickness to strut width may be between about 0.4 to about 1.2. The expandable scaffolds may achieve this strut thickness to strut width ratio of less than 1.4 due to dimensional constraints. For example, the expandable scaffolds may achieve lower ratios where it is applied for temporary or short-term therapy rather than permanent or long-term emplacement. In some embodiments, the strut thickness to strut width ratio can be greater than 1.4 (e.g., 1.5, 1.6, 1.7, 1.8, 1.9, 2.0, 2.1, 2.2, 2.3, 2.4, 2.5).

With reference to FIG. 30B, the expandable scaffolds can comprise cells having struts and/or bridges that vary in thickness. FIG. 30B illustrates a representative cell 3050' of an expandable scaffold having struts 3060' and bridges 3065' of varying thickness (e.g., dual thickness, step-wise thickness changes or gradually varying thickness). The struts 3060' vary in thickness along their length, with an increased thickness at a central portion 3070 of the struts 3060'. The bridges 3065' connecting the struts 3060' can form X-shaped connections of varying thickness (as shown). The varying thickness of the struts 3060' and/or the bridges 3060' advantageously can impart flexibility, kinkability, or bendability, which improves wall apposition on curves and bends, and can improve thrombus engagement. For example, the struts 3060' can flex at two or more points (e.g., two, three, four) rather than one. In some embodiments, each cell 3050' of the expandable scaffold flexes independently of each other. Referring back to FIGS. 23 and 27A and 27B, for example, the expandable scaffolds can comprise cells having uniform strut thickness. The expandable scaffolds of FIGS. 23 and 27A and 27B have relatively smaller nested cells having U-shaped connections between the cells. In some embodiments, the expandable scaffolds of FIGS. 23 and 27A and 27B allow for substantial cell deformation, which can improve flow restoration.

Turning to FIGS. 31A-31D, the shapes or profiles of the struts can be varied. For example, the contact surface of the struts can be rounded, squared off (FIG. 31A), pointed (FIG. 31B), or grooved (FIG. 31C) as desired and/or required for different purposes. The squared off profile or configuration can be used, for example, to enhance the contact surface area of the expandable scaffold, thereby enhancing compression of the clot and reperfusion of the vessel. The pointed profile or configuration (e.g., sharpened, tapered, wedge-like) can be used, for example, to enhance penetration of a clot, thereby facilitating engagement of the clot or maceration of the clot. The grooved profile or configuration can be used, for example, to enhance clot engagement and adhesion, thereby improving clot extraction.

Figure 31A:
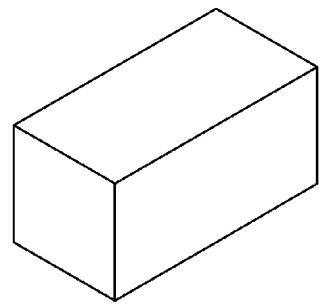
FIGS. 31A-31D illustrate various embodiments of strut profiles.
Figure 31B:
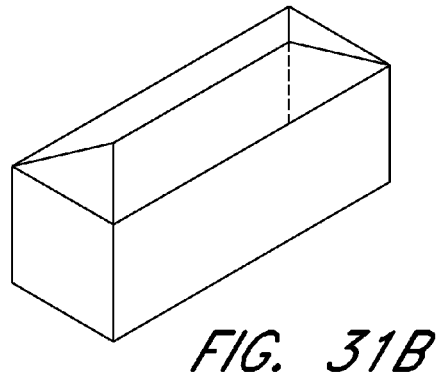
Figure 31C:
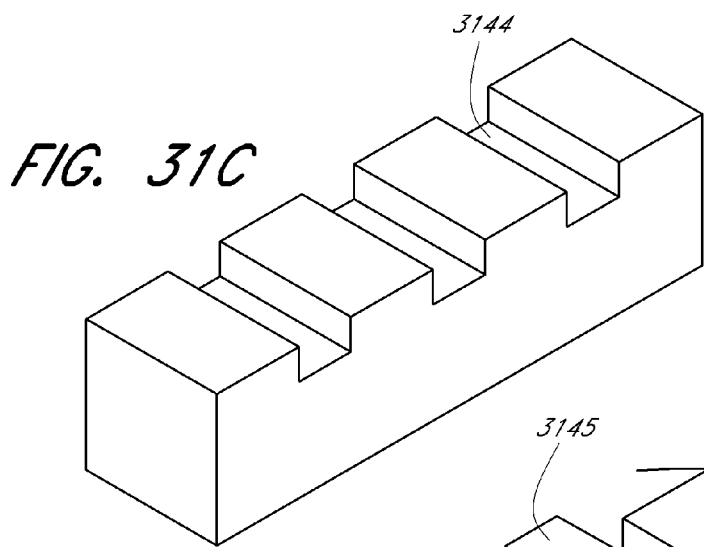
Figure 31D:
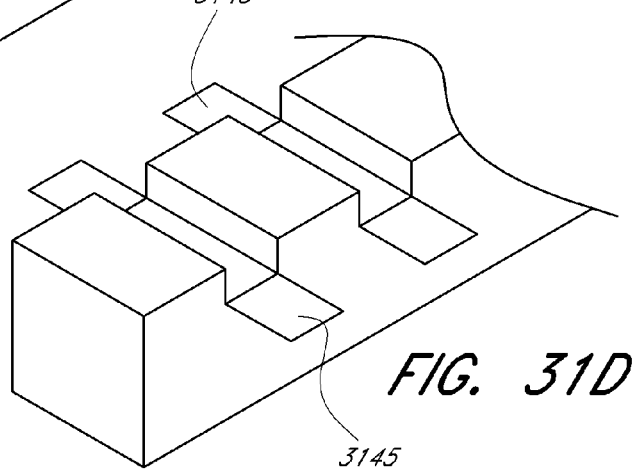
Figure 34A:
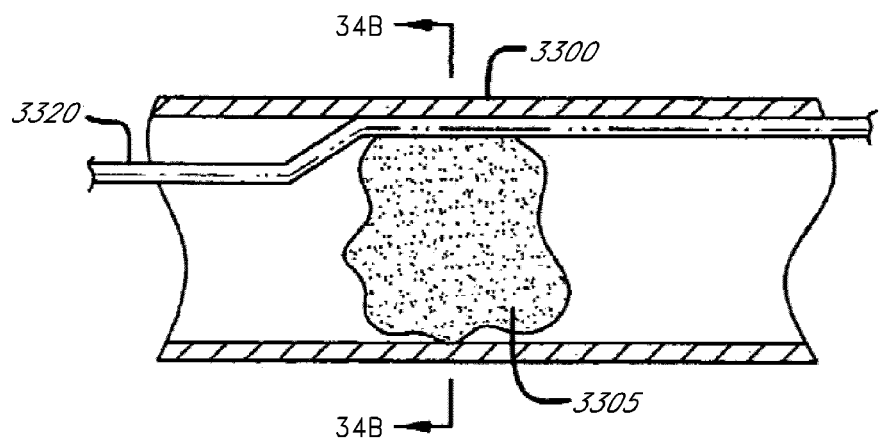
FIGS. 34A and 34B illustrate eccentric or offset deployment of a guidewire through an embolus, in accordance with an embodiment of the invention.
Figure 34B:
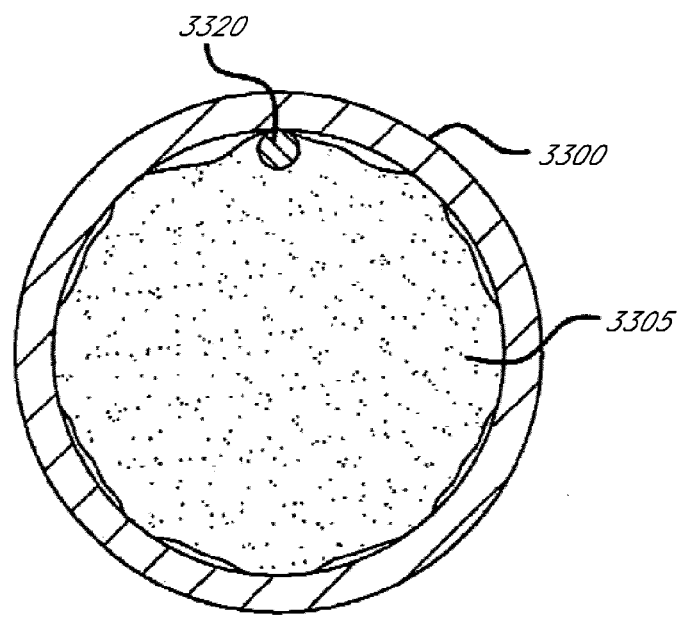

FIG. 31D illustrates a strut having a grooved profile that further includes projections or appendages 3145 extending from the grooves to enhance clot engagement and adhesion. The projections or appendages can be straight, angled, curved, or spiraled. The projections or appendages can include surface features or a surface finish to improve clot adhesion, such as roughened surfaces, bumps, rims, ridges, holes, cut-outs, recesses, serrations, and/or the like. In some embodiments, the grooved struts comprise ground grooves. The exterior surfaces of the grooved struts can be ground or roughened (e.g., via sandblasting, oxidation, and/or vapor deposition methods) to improve clot engagement and adhesion. The bridges can comprise flaring bridges. In some embodiments, the bridges include surface finishing such as described above (e.g., roughened surfaces formed by sandblasting, oxidation, and/or or vapor deposition methods).

In some embodiments, the exterior contact surfaces of the struts of the expandable scaffolds can be treated or altered to achieve desired effects. For example, the struts can be polished (e.g. using acid cleaning methods) to allow the expandable scaffold to slip across a clot, thereby minimizing or reducing clot adhesion and penetration. In some embodiments, polished scaffolds can be used for devices configured to provide effective reperfusion and in-situ clot management (e.g., lysis and maceration). In some embodiments, the exterior contact surfaces of the struts are roughened (e.g., using oxidation, vapor deposition, and/or sandblasting methods) to facilitate clot adhesion and clot capture.

f. Expandable Scaffold Profiles

With reference to FIGS. 32A-32F, the expandable scaffolds can comprise various profiles, shapes, geometries, or configurations. The profiles, shapes, geometries, or configurations can be selected based on a desired clinical effect. In some embodiments, the expandable scaffolds have a uniform diameter across their length. For example, FIG. 32A illustrates an expandable scaffold 3210A having a cylindrical shape having a constant diameter. In some embodiments, the expandable scaffolds have a varying diameter. For example, FIG. 32B illustrates an expandable scaffold 3210B having an undulating, or hourglass, shape. In various embodiments, the expandable scaffolds comprise triangular configurations (FIG. 32C), cross-shaped configurations (FIG. 32D), spiral configurations (FIG. 32E), and/or tapered (e.g., funnel-shaped, cone-shaped) configurations (FIG. 32F). The expandable scaffolds can have a shape or configuration that is generally planar.

V. Use

A. General Use/Indications

The present disclosure relates to revascularization systems and devices used to treat, among other things, ischemic stroke. Naturally, therefore, the revascularization devices of the present disclosure are designed to be used in neuro-type applications, wherein the specifications of the present catheters and revascularization devices may be deployed in the blood vessels of the cerebral vascular system. Similarly contemplated for the revascularization systems and catheters of the present disclosure is deployment in other parts of the body wherein the specifications of the present disclosure may be used in other vessels or lumens of the body in a minimally invasive or non-invasive manner.

The revascularization systems and devices of the present disclosure can be used for revascularization of blood vessels. When the catheter-based revascularization systems of the present disclosure are deployed into a blood vessel having an embolus, a revascularization device, such as an expandable tip assembly, is expanded, thereby opening the vessel so that the vessel can resume proper blood flow. In accordance with some embodiments, once the blood vessel is revascularized, a revascularization device (e.g., an expandable tip assembly) is modified to be in a removable state together with filtered detritus, and the catheter-based revascularization system is removed from the blood vessels of the patient.

Briefly stated, according to several embodiments a revascularization device (e.g., an expandable tip assembly) is deliverable through highly constricted and tortuous vessels, entering a zone associated with subject emboli, where deployment impacts an embolus, compacting the same into luminal walls which enables perfusion and lysis of the embolus, while the revascularization device itself remains continuous with the delivery system acting as a filter, basket or stand alone revascularization mechanism, depending on the status of the embolus and other therapeutic aspects of the treatment being offered for consideration.

According to several embodiments of the present disclosure, clot therapy may have one or more of at least three objectives or effects: maceration of a clot, removal of a clot, and lysis of a clot.

Maceration of a clot refers to the process or result of softening of the clot or breaking the same into pieces mechanically or by using vascular fluids. For example, pressing or compressing the clot with a mechanical member can cause the clot to soften, break up or fragment, whereby, exposure of more surface area of the clot (or portions thereof) to vascular flow may cause the clot (or portions thereof) to macerate, soften, or diffuse. In some embodiments, maceration can occur by natural lysis or by unsheathing and resheathing the expandable tip assembly from the microcatheter (which may be repeated multiple times if necessary). Maceration can comprise axial maceration, radial maceration or both. In some embodiments, maceration comprises only axial maceration.

In some embodiments, maceration comprises imploding a clot from within without regard or concern for distal embolization. The lack of concern for distal embolization can stem from the fact that blood flow has been reestablished and so any clot fragments that escape downstream will naturally be lysed without causing any further occlusion.

In accordance with several embodiments, maceration (alone or in combination with natural lysis) of the clot performed by the systems and devices described herein shaves down, or removes, from 10% to 30% of the clot; however, in some embodiments, more than 30% of the clot can be shaved down, or removed (e.g., 35%, 40%, 50%, 60%, 70%, 80%, 90% or 100%) depending on the nature of the clot. Although removal may still be required even after maceration, the maceration process (in combination with lysis) advantageously improves efficacy of clot removal by reducing the size (e.g., total volume, mass, cross-sectional dimension) of the clot or removing the rubbery soft portions of the clot.

In some embodiments, maceration improves clot extraction because the clot is better formed. For example, maceration can cause a rubbery soft portion of the clot comprising platelets and red blood cells to be lysed away so that only the hard fibrin core remains. In some embodiments, the clot can become easier for an expandable tip assembly to grab and therefore can make the clot more likely to be removed. Maceration can prevent distal embolization from occurring when removing the clot.

In some embodiments, multiple layer embolus removal is provided due to the combination of reperfusion, lysis and maceration. For example, reperfusion of the occluded vessel and maceration of the clot can facilitate an initial lysis or breakdown of the embolus. For example, as described above, the lysis and maceration can remove a soft rubbery outer portion of the embolus. After lysis and maceration, the remaining hard core portion of the embolus can be captured and extracted.

In some embodiments, clot removal can be enhanced or improved by deployment of adherents or compounds that enhance platelet activation. In some embodiments, the adherents or compounds can be delivered through a lumen of an expandable tip assembly. In other embodiments, the expandable tip assembly can comprise a coating comprising substances configured to enhance platelet activation or otherwise enhance clot adhesion.

Many of the embodiments described herein are especially advantageous because embolic protection devices (e.g., nets, braids, filters, baskets, placed distally or proximally) are not needed. Further, temporarily occluding blood flow (e.g., by a sealing balloon placed proximally or distally) to prevent the flow of emboli is not needed in some embodiments. In some embodiments, the present invention occludes blood flow during removal of the system (e.g., guide catheter, microcatheter), but does not occlude blood flow during treatment. Several embodiments of the invention are contrary to prior teachings that blood flow must be occluded while removing a thrombus. Instead, several embodiments enhance blood flow to facilitate the natural lysis of embolic particles. This natural lysis can optionally be supplemented with artificial thrombolytics and/or maceration. In accordance with some embodiments, besides providing essential blood flow to tissue (and reducing apoptosis), the lack of embolic protection devices or temporary occlusion devices during treatment aids in visualization of the vasculature, which may be impeded by the use of said devices. In some embodiments, the lack of embolic protection devices (such as filters, baskets, nets, etc.) is advantageous because of the associated risks of such devices. For example, embolic protection devices can be associated with deleterious slow flow or no flow due to clogging of the device.

According to several embodiments of the system and processes of the invention, in certain iterations, once deployed, the expandable tip assembly compacts the embolus against the luminal wall, creating a channel for blood flow which may act like a natural lytic agent to lyse or dissolve the embolus. It is noted that if blood flow does not lyse the blood embolus, natural lysis can be supplemented by the infusion of lytic agents in some embodiments. The lytic agents can be infused, for example, through a lumen (e.g., guidewire lumen) of the elongate member (e.g., pusher tube) of the expandable tip assembly or through a lumen of the microcatheter.

The use of artificial lytic agents or maceration has, in some cases, been discouraged prior to Applicant's discoveries, because it was thought that such agents or actions may facilitate the release of embolic particles, which would then cause distal occlusions. However, several embodiments of the present invention are particularly advantageous because artificial lytic agents or maceration is used in conjunction with the immediate restoration of blood flow. Thus, for example, the natural lytic process would lyse any embolic particles released (but not lysed) by the artificial lytic agent or maceration. In this manner, the natural lytic process and the artificial lytic agent (or maceration) act in concert or synergistically to treat embolic particles. In one embodiment, this is particularly beneficial because a lower dose of an artificial thrombolytic may be used (because of the synergistic or additive effects of the natural lytic process), thereby reducing the risks of the thrombolytic (including but not limited to hemorrhage).

Although embolic protection and temporary occlusion are not used in many embodiments, certain embodiments may be used in conjunction with embolic protection, temporary occlusion or both.

B. Example Clot Management Process

With reference to FIGS. 33A-33F, an example clot management process for treating an occluded vessel in the cerebral vasculature is illustrated. FIG. 33A illustrates an occluded vessel 3300 in the cerebral vasculature having a clot 3305. With reference to FIG. 33B, under standard interventional procedures, a guide catheter 3310 can be introduced into a patient's vasculature (e.g., via an incision in a femoral artery) and positioned in a desired vessel in sufficiently close proximity to the cerebral vasculature. In some embodiments, the location of the occluded vessel can be determined using angiography. In some embodiments, a guidewire 3320 is then advanced through the guide catheter 3310 and through the clot 3305. In some embodiments, the guidewire 3320 follows a path of least resistance through the clot 3305; however, the guidewire 3320 can be configured to traverse the clot 3305 along an edge of the vessel 3300 in an eccentric manner (e.g., to the side of the clot 3305) as shown, for example, in FIGS.

34A and 34B, or substantially through the middle of the clot 3305 in a concentric manner (as shown, for example, in FIG. 33B).

With reference to FIG. 33C, a microcatheter 3315 can then be inserted through the guide catheter 3310 and over the guidewire 3320 until the distal tip of the microcatheter 3315 is distal to the distal end of the clot 3305. In some embodiments, the distal tip of the microcatheter 3315 is positioned just distal (e.g., between 0.001 mm and 20 mm, between 0.5 mm and 15 mm, between 0.5 mm and 10 mm, between 0.5 mm and 20 mm) to the distal end of the clot 3305. Distal positioning of the microcatheter can be confirmed by infusing contrast through the microcatheter.

A particular expandable tip assembly 3325 can then be selected based on the determined location of the occluded vessel 3300 (e.g., based on size of the occluded vessel). With reference to FIG. 35, which illustrates a schematic representation of a portion of the cerebral vasculature 3500, a particular expandable tip assembly can be selected based on average diameters of the arteries of the cerebral vasculature. For example, the anterior cerebral artery 3575 can have a diameter of between 2.5 mm and 3.5 mm. The middle cerebral artery 3580 can have a diameter of between 1.5 mm and 3 mm, with the M1 segment having a diameter of between 2.0 mm and 3.0 mm and the M2 segment having a diameter of between 1.5 mm and 2.0 mm. The diameter of the internal carotid artery 3585 can be between 3 mm and 6 mm at various segments, with the carotid siphon 3590 having a diameter of about 4 mm. The vertebral artery (not shown) can have a diameter that ranges between 3 mm and 4 mm and the basilar artery (not shown) can have a diameter that ranges between 2.5 mm and 4 mm. FIG. 35 includes approximate example vessel diameters at various locations within the cerebral vasculature. As one example, an expandable tip assembly having a scaffold with an expansion diameter of 3 mm can be selected for use in the middle cerebral artery 3580 because the diameter of the middle cerebral artery 3580 is generally 3 mm or less. The use of an expandable tip assembly having a scaffold with an expansion diameter of 3 mm can decrease cell deformation of the scaffold, thereby increasing effectiveness.

Referring back to FIG. 33C, in some embodiments, the expandable tip assembly 3325 is inserted through the microcatheter 3315 and over the guidewire 3320 until the distal end of the expandable tip assembly 3325 is lined up with the distal end of the microcatheter 3315, which is positioned at or near the distal end of the clot 3305. In some embodiments, the microcatheter 3315 comprises a radiopaque marker at its distal tip to facilitate confirmation of proper positioning of the expandable tip assembly 3315 (which also may comprise radiopaque markers at its distal end) with respect to the microcatheter 3315. In some embodiments, the expandable tip assembly 3325 can be sheathed in an introducer tube (not shown) to preserve sterility during transit and during loading into the microcatheter 3315; however, the introducer tube can be removed during the advancement of the expandable tip assembly 3325. In some embodiments, the introducer tube comprises a high-density polyethylene (HDPE) sheath; however, the introducer tube can comprise one or more other polymeric materials.

With reference to FIGS. 33D and 33E, the microcatheter 3315 is then withdrawn or retracted while maintaining the position of the expandable tip assembly 3325, thereby unsheathing the expandable scaffold of the expandable tip assembly 3325 and deploying it within or against the clot 3305. FIG. 33D illustrates partial deployment of the expandable scaffold of the expandable tip assembly 3325 and FIG. 33E illustrates full deployment. The withdrawal or retraction of the microcatheter 3315 can be performed under fluoroscopic guidance.

Figure 36:
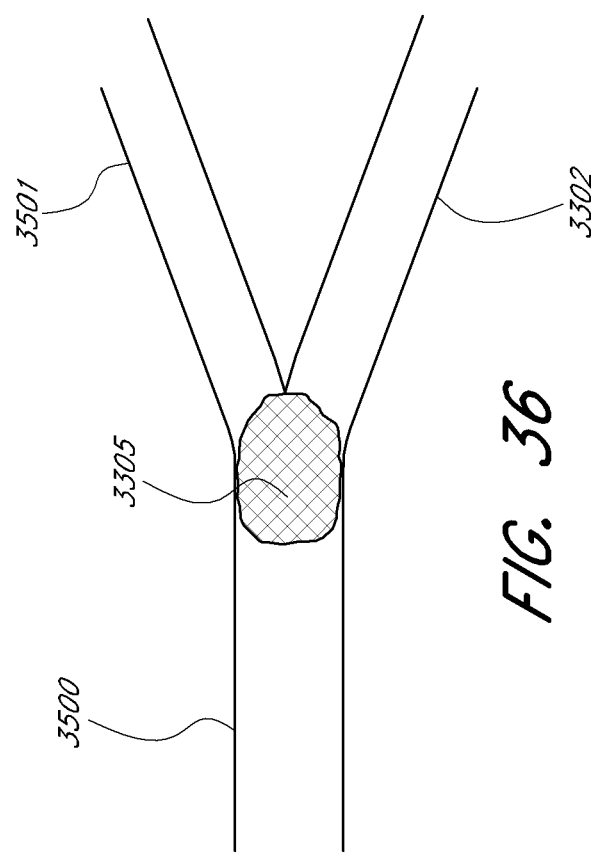
FIG. 36 illustrates an embolus positioned adjacent a junction of a portion of the cerebral vasculature.

In accordance with some embodiments, the expandable scaffold of the expandable tip assembly 3325 is deployed within or against the clot instead of distal to the clot to avoid damaging the vessel during lateral movement of the expandable tip assembly 3325. With reference to FIG. 36, deployment within the clot can prevent overexpansion of a smaller vessel or vessel region distal to the clot. For example, if the clot 3305 is positioned at or near a bifurcation (e.g., an MCA/ACA bifurcation) of an occluded vessel 3500 into two smaller-diameter branches or vessels 3501, 3502, deployment of the expandable tip assembly 3325 within the clot 3305 obviates the introduction of the expandable tip assembly 3325 within the smaller diameter vessels 3501, 3502, thereby reducing the likelihood of overexpansion of the smaller diameter vessels 3501, 3502.

Referring back to FIG. 33E, in accordance with some embodiments, the expandable tip assembly 3315 can be resheathed and repositioned as desired and/or required. Angiographic assessment can be performed to ensure blood flow has been restored after deployment of the expandable tip assembly 3315. Deployment can be maintained for several minutes (e.g., 1 to 3 minutes, 3 to 5 minutes, 5 to 10 minutes, greater than 10 minutes, or overlapping ranges thereof) depending on the circumstances. The expandable scaffold of the expandable tip assembly 3325 can be resheathed within the microcatheter 3315 and redeployed one or more times to provide further maceration of the clot 3305. In some embodiments, any remaining portions of the clot 3305 that have not been lysed are impacted, engaged and captured by the expandable scaffold of the expandable tip assembly 3325 and removed upon withdrawal of the expandable tip assembly 3325. For example, in some embodiments, a single expandable scaffold can be configured both to impact and compress the clot to immediately restore flow and allow natural lysis and to engage any remaining portions of the clot that are not lysed, as described above. In some embodiments, any remaining portions of the clot are at least partially captured, engaged, or grabbed by the expandable scaffold on the exterior surface of the expandable scaffold. The microcatheter 3315 can then be advanced over the expandable scaffold of the expandable tip assembly 3325 to reconstrain the expandable scaffold and the microcatheter 3315 together with the expandable tip assembly 3325 can be withdrawn into the guide catheter 3310 and removed from the body, as shown in FIG. 33F. As such, in some embodiments, the expandable tip assembly 3315 is never implanted, detached, or released into the blood vessel.

According to some embodiments, if the clot is not fully lysed and/or the clot has not been fully captured by the first expandable tip assembly 3325, a second expandable tip assembly configured to facilitate removal of clots can be inserted, deployed, and removed in a manner similar to that described above. In some embodiments, the guide catheter 3310 comprises a balloon that can be inflated during removal of the clot 3305. Angiographic assessment can be performed to confine that the clot 3305 has been completely lysed or otherwise removed.

In accordance with some embodiments (e.g., laser cut tube scaffolds), the design of the expandable tip assembly 3325 allows for insertion of the expandable tip assembly 3325 within the microcatheter 3315 and within the clot 3305 without concern for orientation.

C. Progressive, or Modular, Stroke Therapy Process

Figure 37:
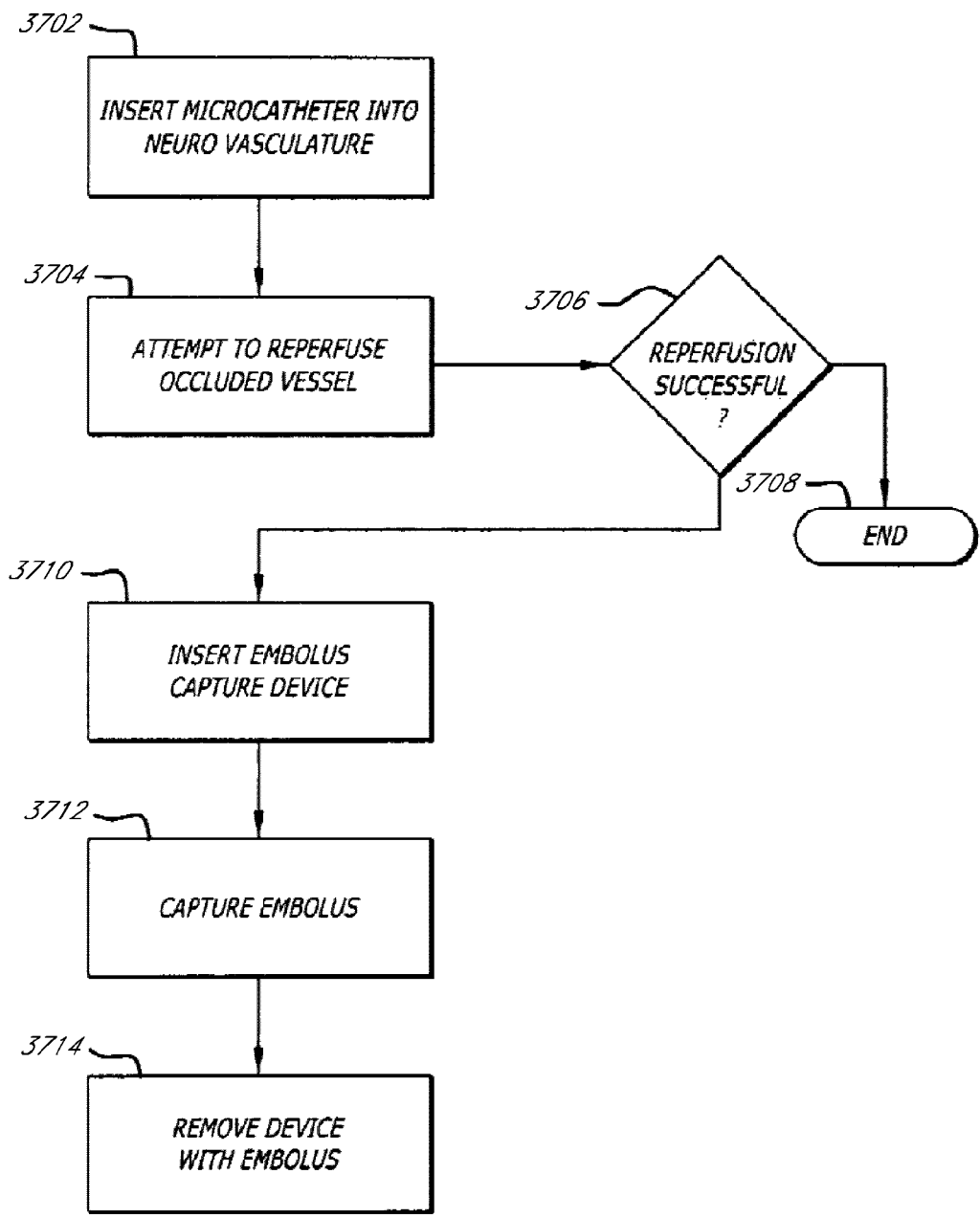
FIG. 37 is a flow diagram of an embodiment of a stroke treatment process for performing progressive, or modular, stroke therapy.

As described above, a kit of multiple expandable tip assemblies can be provided to achieve different effects or purposes in addressing a clot. FIG. 37 illustrates a flow diagram of an embodiment of a progressive stroke therapy process 3700. The progressive stroke therapy process 3700 starts at block 3702, wherein a microcatheter is inserted into the neurovasculature. The microcatheter can be inserted into the neurovasculature similar to the manner described above (e.g., via a guide catheter and/or over a guidewire to the site of the embolus).

Reperfusion can then be attempted, for example with a reperfusion device (e.g., an expandable tip assembly configured and designed to facilitate immediate reperfusion) at block 3704 of FIG. 37. In some embodiments, attempted reperfusion can comprise resheathing and unsheathing the reperfusion device one or more times using the microcatheter to attempt to macerate the thrombus, which can enhance lysis of the thrombus. After reperfusion is attempted, the success is determined at decision block 3706. For example, a contrast dye can be used to determine the level to which the occluded vessel is reperfused (e.g., an angiographic assessment). In some embodiments, determination of success can occur at least ten minutes after introduction of the reperfusion device.

If reperfusion is successful to a desired degree, the stroke therapy process 3700 ends at block 3708 and the reperfusion device is recaptured within the microcatheter and the reperfusion device and the microcatheter are removed from the body. If reperfusion is not successful to a desired degree, then an embolus capture device (e.g., an expandable tip assembly designed and configured to facilitate effective clot extraction) can be selected and inserted through the microcatheter as described herein and deployed distal to or within the embolus (block 3710). At block 3712, the embolus is captured by the embolus capture device. In some embodiments, the embolus capture device (e.g., an expandable tip assembly designed and configured to facilitate effective clot extraction) can be resheathed and unsheathed one or more times using the catheter to increase clot adhesion and the likelihood of clot capture. In some embodiments, one or more adherents, agents, or compounds can be delivered to promote clot adhesion or platelet activation, as described above. The stroke therapy process 3700 then proceeds to block 3714, wherein the embolus capture device, the embolus, and the microcatheter are removed from the body.

VI. Supplementary Modalities

In some embodiments, visualization is provided before, during, or after treatment. Visualization can be provided using angiography or fluoroscopy (in conjunction with radiopaque markers). In some embodiments, a visualization member (e.g., a visualization scope) can be inserted through a lumen of an expandable tip assembly, a microcatheter, and/or a guide catheter to provide visualization of a target site within a blood vessel. In some embodiments, the guidewire used for tracking and maintaining access can comprise a visualization member (e.g., at its distal tip). In some embodiments, images can be captured during treatment and output to a display for viewing. In some embodiments, the captured images can be stored in memory of a computing or storage device for documentation purposes. In some embodiments, the visualization member can transmit images to the display (e.g., via a wired or wireless connection). Visualization can facilitate positioning of the devices and systems described herein within a vessel, within a clot, and/or with respect to each other, can confirm blood flow restoration, and/or can confirm clot removal, for example.

In some embodiments, a suction or aspiration catheter, conduit, or line is inserted into a lumen of the expandable tip assembly, microcatheter, and/or guide catheter. The suction or aspiration means can be used to perform suctioning or aspiration during maceration and/or clot removal, thereby enhancing the removal of material. In some embodiments, the methods described herein can be performed without suction or aspiration.

In some embodiments, one or more fluids and/or other materials can be delivered to a target embolic region. In some embodiments, such fluids and/or other materials are configured to loosen, break up, penetrate, degrade, disperse, dissolve and/or otherwise undermine or affect an occlusion (e.g., clot) within a cerebral vessel. In some embodiments, such fluids and/or other materials can aid in removal of the clot and/or aid in clot adhesion (e.g., by deploying adherents or compounds configured to activate platelets or otherwise promote clot adhesion and penetration). The fluids or materials can be delivered to the target embolic region via a lumen of the microcatheter or a lumen of the expandable tip assembly or by a separate delivery catheter. In some embodiments, the elongate member of the expandable tip assembly can comprise one or more openings or apertures for delivery of fluids or materials to the target embolic region.

In some embodiments, fluids and/or other materials that are selectively delivered through a channel or lumen of the expandable tip assembly or microcatheter include, without limitation: medicaments, biologically active agents, platelet activation agents, thrombogenic agents, heparin, combinations of the same, and/or the like. Ultraviolet, germicidal and/or antimicrobial treatment may be incorporated in several embodiments. Therapeutic modalities are included in some embodiments, including but not limited to, radiofrequency, ultrasound, laser, microwave, heat, and cryotherapy, or combinations thereof. In one embodiment, the therapy is used to effect ablation or lysis. In some embodiments, various devices are used to provide sonication, vibration, radiation, and electrical stimulation, or combinations thereof.

VII. Over-the-Wire and Rapid Exchange Systems

According to some embodiments, the revascularization systems (e.g. clot management systems, stroke treatment systems) can provide maintained arterial access to the treatment site and provide greater support to the arterial tree by being either over-the-wire (OTW) or rapid exchange (RX) catheter-based systems. In some embodiments, the microcatheters described herein comprise rapid exchange microcatheters. The over-the-wire systems advantageously can facilitate maintained arterial access to treatment sites without compromise to reperfusion of blood flow. The over-the-wire systems advantageously can be used when multiple treatment devices are used during a treatment procedure to maintain arterial access as one device is removed and another is inserted. The rapid exchange systems advantageously can reduce the profile of the microcatheter or the expandable tip assembly, and provide enhanced vessel support.

In some embodiments, microcatheters having at least second lumens for vessel stability during removal of emboli and/or in adjunct therapy modes can be used, as described in U.S. application Ser. No. 12/422,105, the entire content of which has been expressly incorporated by reference above. The rapid exchange systems can allow and maintain arterial access to treatment sites, and provide enhanced support to the arterial tree, while working as a rapid exchange system. The rapid exchange feature can enable the embolus to be securely captured and removed by providing support within the vessel. The OTW or RX support provided can prevent the proximal vessel from buckling or kinking during tensioning upon embolus removal. Buckling or kinking of the vessel can cause the proximal vessel orifice to ovalize, thereby stripping the embolus from a capture device. Expressly incorporated by reference as if fully set forth herein are U.S. Pat. Nos. 7,018, 372; 6,893,417; and Publication Nos. US 2007/0293846; US 2007/0293821; US 2007/0282306; US 2007/0276325; US 2007/0149949; and US 2007/0197956.

According to some embodiments, an OTW system comprising an expandable stroke device (e.g., the expandable tip assemblies described herein such as but not limited to the expandable tip assembly 600) is combined with a rapid exchange system as discussed above. The OTW system may be configured to fit within a lumen of the RX system. A guidewire may be configured to fit within another lumen of the RX system. Examples of such a guidewire include Traxcess®, Agility®, Transend® or Synchro® brands. In some embodiments, the guidewire is a 0.010" or 0.014" exchange wire and has a length between 200 cm and 400 cm.

Figure 38:
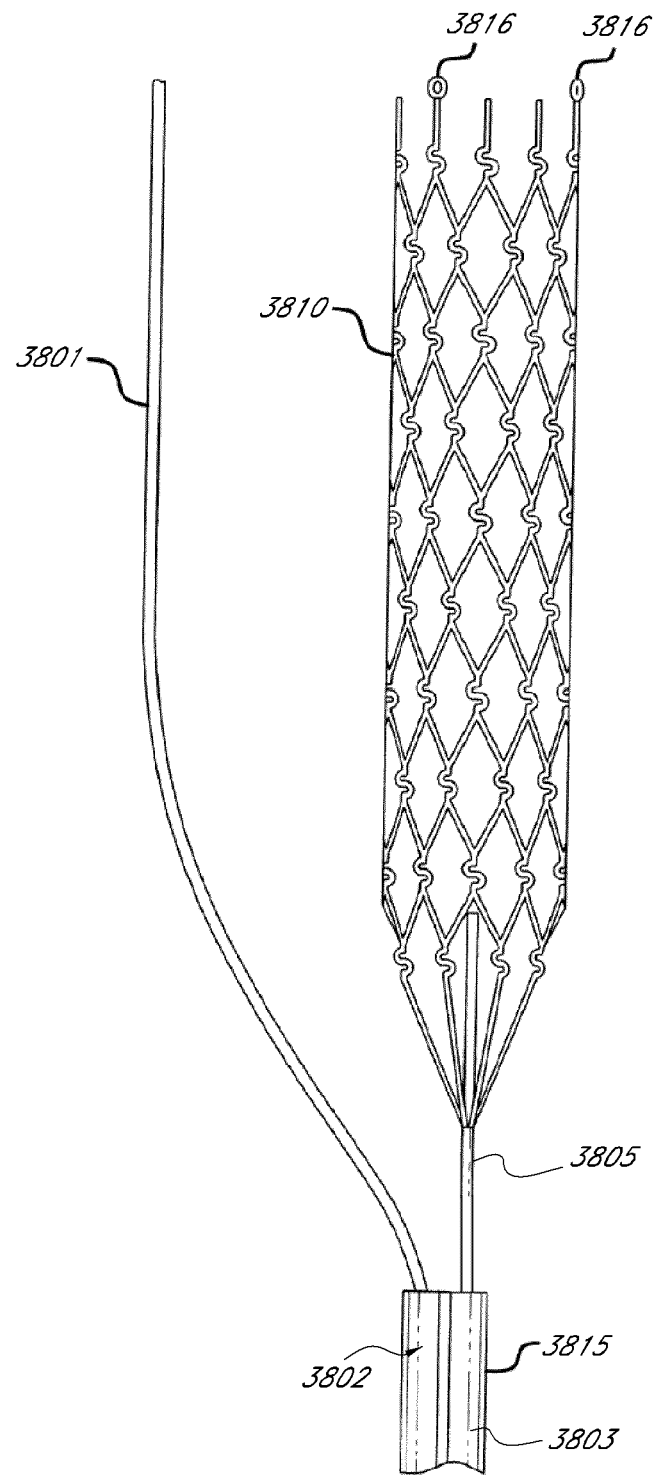
FIG. 38 illustrates deployment of an embodiment of an expandable tip assembly being delivered as a component of a rapid exchange catheter-based revascularization system.

Referring now to FIG. 38, according to several embodiments of the present disclosure, guidewire 3801 accesses and crosses a target lesion, providing a pathway for RX microcatheter 3815 having at least two lumens. In some embodiments, the guidewire 3801 may be at least partially disposed within a first lumen 3802 of the RX microcatheter 3815. As described above, the stroke device 3810 can include radiographic marking elements 3816 for visualization during placement.

According to several embodiments of the present disclosure, the stroke device 3810 (e.g., the expandable scaffolds described herein such as, but not limited to, expandable scaffold 810, expandable scaffold 910) is shown in a fully expanded position, whereby it functions consistently and safely such that arterial support is maintained by virtue of the guidewire 3801 keeping the arterial tree from mechanical stress, while rapid flow restoration, embolus removal, clot capture and/or other procedures are performed. The stroke device 3810 can be deployed in a manner similar to that described above in connection with the stroke treatment process 3300. In some embodiments, the stroke device 3810 is delivered over a second guidewire inserted within a second lumen 3803 that does not contain the guidewire 3801. Thus, reperfusion is established and therapy administered without risks to patients that may be present with other systems or devices. In some embodiments, the guidewire 3801 is a 0.010" or 0.014" guidewire and has a length between 100 cm and 300 cm.

According to several embodiments, as shown in FIG. 38, the stroke device 3810 may be tethered or otherwise coupled to an elongate delivery member 3805 such that, while emplaced at a treatment site within a blood vessel, it remains accessible via the RX microcatheter 3815 and readily retrievable therein while maintaining reperfusion of the blood vessel. In one embodiment, the stroke device 3810 may be emplaced on a long-term or permanent basis, or as needed based on the amount and type of recanalization prescribed.

According to some embodiments, the stroke device 3810 is self-expandable, such that is may expand substantially radially when removed from within the RX microcatheter 3815. In some embodiments, additional therapies may be provided while the stroke device 3810 is fully expanded, for example, through the first lumen 3802 of the RX microcatheter 3815. For example, therapeutic agents, lytic agents, adherents to promote clot adhesion, irrigation fluids, suction or aspiration catheters, and/or the like, or combinations thereof can be delivered through the first lumen 3802 of the RX microcatheter 3815 while the stroke device 3810 is deployed within the vessel.

According to several embodiments of the present disclosure, a process for making a neuro-monorail microcatheter (e.g., the RX microcatheter 3815) is disclosed. The process may include cutting a distal segment of a first tube having a first lumen. The distal segment may be cut at about 5 cm to 50 cm (e.g., 5 cm to 10 cm, 10 cm to 20 cm, 15 cm to 30 cm, 20 cm to 40 cm, 35 cm to 40 cm, or overlapping ranges thereof) from a distal end of the micro first microcatheter. The remaining distal segment of the first tube may be aligned adjacent to a distal section of a second tube having a second lumen. In some embodiments, the distal ends of the first and second tubes are aligned. Guidewires may be placed in each of the first and second tubes to maintain their respective alignments and keep their lumens open. A resin, such as PET or PTFE, or an adhesive, heat shrink, sealant, or other surface treatment may be applied in short segments along the lengths of the first and second tubes to secure and maintain alignment and adjacent status of the finished dual-lumen or neuro-monorail microcatheter. The distal segment of the first tube forms a rapid exchange lumen or port configured to receive the guidewire 3801.

In accordance with some embodiments of the present disclosure, a first and second tube, as described above, may be co-extruded together and then the first tube can be skived or cut to form the distal segment described above, in lieu of aligning and joining two separate tubes as described above.

VIII. Balloon Catheter Systems

Figure 39:
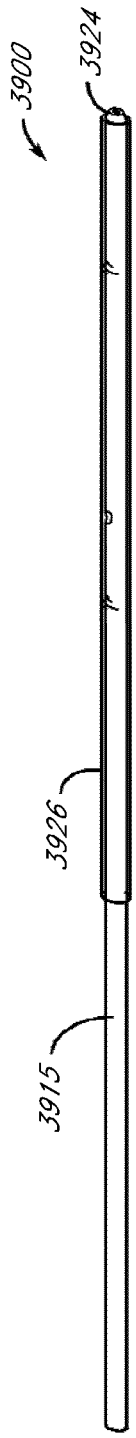
FIG. 39 is an illustration of a balloon catheter and delivery system, with a balloon in a deflated state, according to several embodiments of the present disclosure.
Figure 40:
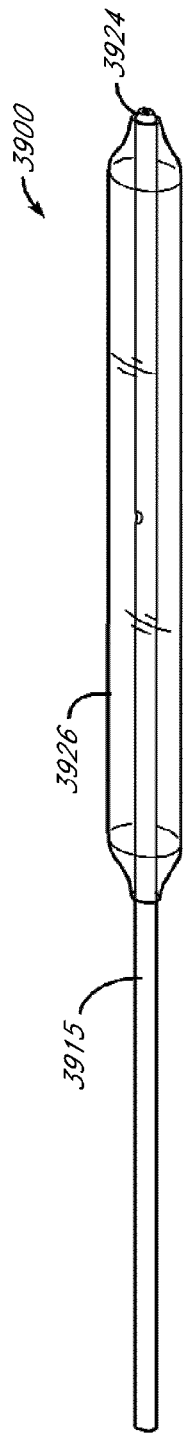
FIG. 40 is an illustration of a balloon catheter and delivery system, with a balloon in an inflated state, according to several embodiments of the present disclosure.
Figure 41:
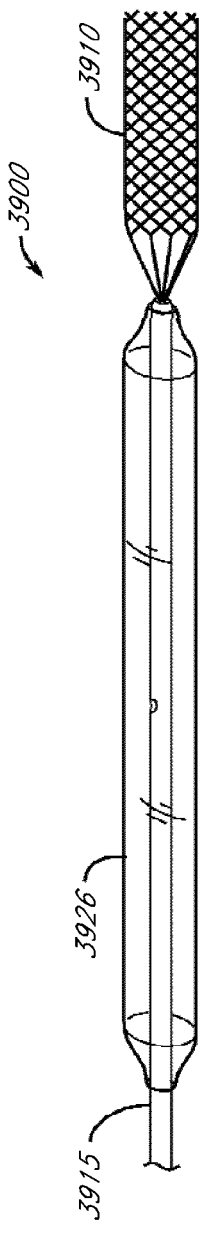
FIG. 41 is an illustration of a balloon catheter and delivery system, with a cage-like structure in a deployed state, according to several embodiments of the present disclosure.

In accordance with some embodiments, the revascularization systems (e.g., stroke treatment systems, clot management systems) comprise balloon catheter and delivery systems. Although described as a separate embodiment of a system, the devices and features described in connection with the balloon catheter systems can be used, combined with, or substituted for, devices and features of the other systems (e.g., revascularization system or clot management system 300) described herein. With reference to FIGS. 39-41, according to several embodiments of the present disclosure, a balloon catheter and delivery system 3900 includes a catheter 3915 and a balloon 3926. The system 3900 may have a distal end 3924 and a proximal end (not shown). FIGS. 39 and 40 illustrate the balloon 3926 in its non-inflated and inflated configurations, respectively. FIG. 41 illustrates deployment of an embodiment of an expandable scaffold (e.g., cage-like structure) 3910 from the catheter 3915.

Figure 42:
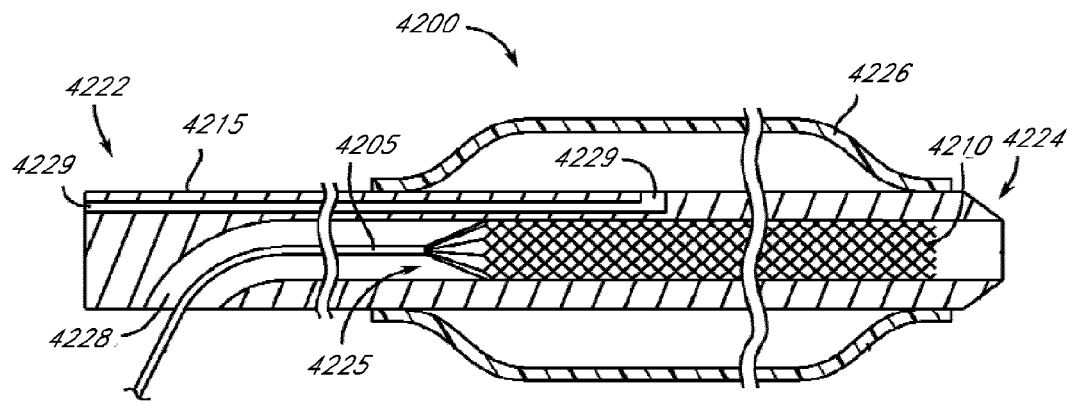
FIG. 42 is cross-sectional view of a balloon catheter and delivery system, with a cage-like structure in a retracted state, according to several embodiments of the present disclosure.

With reference to FIG. 42, according to several embodiments of the present disclosure, a balloon catheter and delivery system 4210 may comprise a proximal end 4222, a distal end 4224 and at least one lumen. A catheter 4215 may be of any length for performance of minimally invasive vascular treatments. For example, for treatment of stroke, aneurysm, or other treatments within the brain of a patient, a catheter 4215 may have a length of between about 135 cm and about 150 cm (e.g., between about 135 cm and 140 cm, between about 140 cm and 150 cm). However, in some embodiments, the catheter 4215 has a length less than 135 cm or greater than 150 cm.

The catheter 4215 may be of variable stiffness that is able to track to and through the tortuous anatomy or the cerebral vasculature (i.e., internal carotid artery, MCA, ACA, vertebral and basilar). The catheter 4215 may be one or two pieces and may have greater proximal pushability (stiffness) and greater distal flexibility (softness) to allow tracking to distal cerebral arteries.

According to several embodiments, there may be provided at least one balloon 4226 near a distal end 4224 of the catheter 4215 for lumen dilatation, treatment of ICAD, vasospasm, flow arrest and remodeling of aneurysm necks during coiling. According to several embodiments, the balloon 4226 is disposed outside the outer surface of the catheter 4215, such that the catheter 4215 is concentrically disposed within a portion of the balloon 4226, and such that the balloon 4226 expands radially away from the catheter 4215. The balloon 4226 may be a percutaneous transluminal angioplasty ("PTA") balloon. In one embodiment, a plurality of balloons 4226 may be provided on an outer surface of catheter 4215. In one embodiment, the balloon 4226 may have a diameter in an inflated state of between about 0.018" and about 0.035".

The balloon 4226 may be comprised of materials such as Pebax, nylon, PTFE, polyethylene terephthalate ("PET"), polyurethane, polyester, an elastomeric material, or other suitable materials or mixtures thereof. The balloon 4226 may be of any length that facilitates adequate crossing of an occlusion. For example, the balloon 4226 may be between about 1.5 cm and about 6.0 cm in length (e.g., 1.5 cm to 2 cm, 2 cm to 3 cm, 2.5 cm to 3.5 cm, 3 cm to 4 cm, 4 cm to 6 cm, or overlapping ranges thereof).

With continued reference to FIG. 42, at least one inflation lumen 4229 may provide fluid communication to the balloon 4226 from the proximal end 4222 of the catheter 4215. The inflation lumen 4229 may provide a fluid to the inner portion of the balloon 4226, such that the fluid fills and inflates the balloon 4226. The inflation lumen 4229 may be open at or near the proximal end 4222 of the catheter 3915, and may be configured to interface with a luer adaptor, fitting, handle, syringe, injector, plunger, or any other one or more selectable items for operation of the balloon catheter and delivery system by a user. Likewise, using ePTFE, PTFE, or other lubricious and/or drug eluting elements with the lumens 4228 and/or 4229 is contemplated.

According to several embodiments, an expandable device 4225 (e.g., any of the expandable tip assemblies described herein) is configured to be disposable within the delivery lumen 4228. The expandable device 4225 may include a tether 4205 (e.g., elongate member) and a cage-like structure 4210 (e.g., expandable scaffold). Tether 4205 may be attached to the cage-like structure 4210 and may be selectively detachable. Tether 4205 may extend to or beyond the proximal end 4222 of catheter 3915. The expandable device 4225 may be disposable and trackable within the delivery lumen 4228 of the catheter 4220.

According to some embodiments, at least a portion of the cage-like structure 4210 may be tapered at or near a point of attachment with the tether 4205. For example, a design may be provided tapering from the diameter of the tether 4205 to the largest diameter of the cage-like structure 4210. Likewise, alternate geometric configurations can be used (e.g., everted, scalloped, and other variant ends or edges).

According to several embodiments, the cage-like structure 4210 may be made of nitinol to allow it to be compressed and loaded into an introducer for packaging; however, "super-elastic" materials and other memory-based materials can be used. In one embodiment, the cage-like structure 4210 is compressible and expandable, such that it maintains a compressed state when within a lumen or sheath and may maintain an expanded state when outside the lumen. In one embodiment, the cage-like structure 4210 may be "self-expanding", such that it expands once unsheathed from the delivery lumen 4228 of the catheter 4215.

By attaching it to a delivery wire (e.g., tether 4205), in some embodiments, the cage-like structure 4210 can be placed, retracted, repositioned and recaptured into a catheter. These features allow for the following: 1) perfusion of blood through the artery during coiling; 2) perfusion from coiling herniation or prolapse; and 3) removal of the device, mitigating the use of Aspirin and Plavix.

According to several embodiments, the delivery lumen 4228 has an inner diameter sized to accommodate the cage-like structure 4210. According to several embodiments, at least one delivery lumen 4228 provides a pathway through the catheter 3915 from about the proximal end 4222 of the catheter 4215 to about the distal end 4224 of the catheter 4215. The delivery lumen 4228 may be open at or near proximal end 4222 of the catheter 4215, and may be configured to interface with a luer adaptor, fitting, handle, syringe, injector, plunger, or any other one or more selectable items for operation of the balloon catheter and delivery system by a user. As discussed, PTFE, ePTFE and other lubricious and/or eluting elements are incorporated within at least the lumen 28.

In some embodiments, delivery lumen 4228 may be lined with polytetrafluoroethylene ("PTFE") or a polymer thereof, alone or in combination with other materials, coatings, coverings, or delivery surfaces or substrates.

According to several embodiments, the catheter 4220 and the expandable device 4225 may be configured to travel together, such that the expandable device 4225 may selectively accompany the catheter 4215 as the catheter 3915 travels through or is placed within a vasculature. For example, the catheter 4215 and the expandable device 4225 may be jointly delivered to a location while the cage-like structure 4210 remains within delivery lumen 4228.

In several embodiments, the catheter 4215 and the expandable device 4225 may be configured to be separately disposable, such that they may be moved relative to each other. For example, the expandable device 4225 may be advanced or retracted relative to the catheter 3915 by advancement or retraction of only the tether 4205 at the proximal end 4222 of the catheter 4215. Likewise, the catheter 4215 may be advanced or retracted relative to the expandable device 4225 by advancement or retraction of only the catheter 4215.

According to some embodiments, the catheter 4215 is configured to provide tracking over a guidewire (not shown) as described in more detail herein. One or more lumens of the catheter 4215 may provide a pathway for a guidewire using an over-the-wire (OTW) system, as described in more detail herein.

Figure 43:
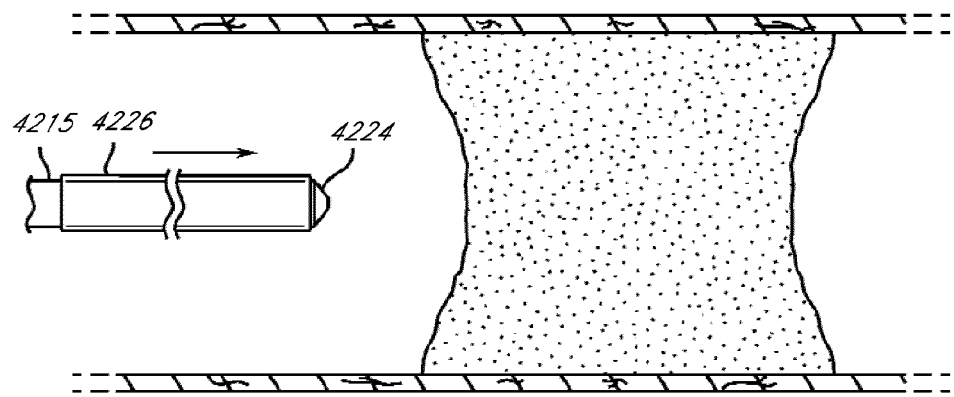
FIG. 43 is an illustration of a balloon catheter and delivery system shown approaching an occlusion, according to several embodiments of the present disclosure.

In some embodiments, a method is disclosed for treatment of a vascular occlusion, particularly a neurovascular occlusion. With reference to FIG. 43, according to several embodiments of the present disclosure, the balloon catheter and delivery system 4210 may be provided to an occlusion.

Figure 44:
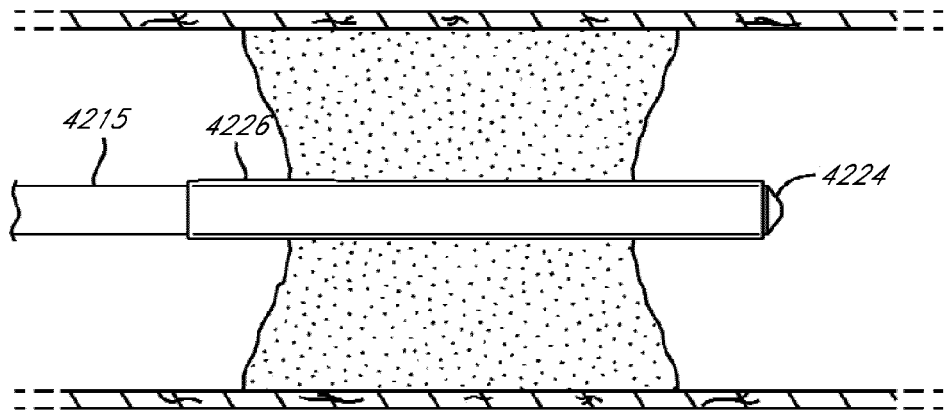
FIG. 44 is an illustration of a balloon catheter and delivery system shown crossing an occlusion, according to several embodiments of the present disclosure.

With reference to FIG. 44, according to several embodiments of the present disclosure, the balloon catheter and delivery system 4210 may cross the occlusion by leading with the distal end 4224 of catheter 3215. Crossing may be effectuated by pressure, force, ablation, or application of one of various types of energy at the distal end 4224 of the catheter 4215. Crossing may create an initial channel by displacement of the occlusion in the presence of the balloon catheter and delivery system 4210.

Figure 45:
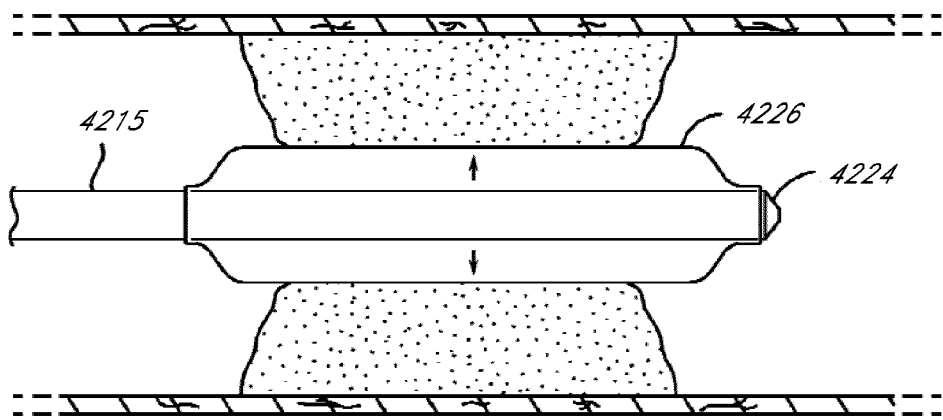
FIG. 45 is an illustration of a balloon catheter and delivery system, shown with a balloon in an inflated state, according to several embodiments of the present disclosure.

With reference to FIG. 45, according to several embodiments of the present disclosure, the balloon 4226 may be inflated or the catheter 4215 may otherwise be dilated. Inflation of the balloon 4226 may further displace or compress at least a portion of the occlusion away from the catheter 4215. Thereby, a broader channel may be created by the balloon 4226, wherein the diameter or cross sectional area of the channel exceeds the diameter or cross sectional area of the catheter 4215.

Figure 46:
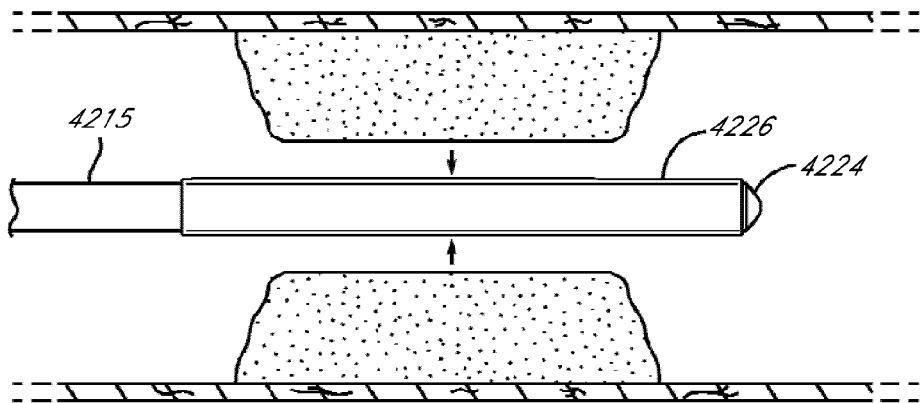
FIG. 46 is an illustration of a balloon catheter and delivery system, shown with a balloon in a deflated state after an inflated state, according to several embodiments of the present disclosure.

With reference to FIG. 46, according to some embodiments of the present disclosure, the balloon 4226 is deflated, whereby the broader channel exceeding the size of the catheter 4215 remains open at least temporarily.

Figure 47:
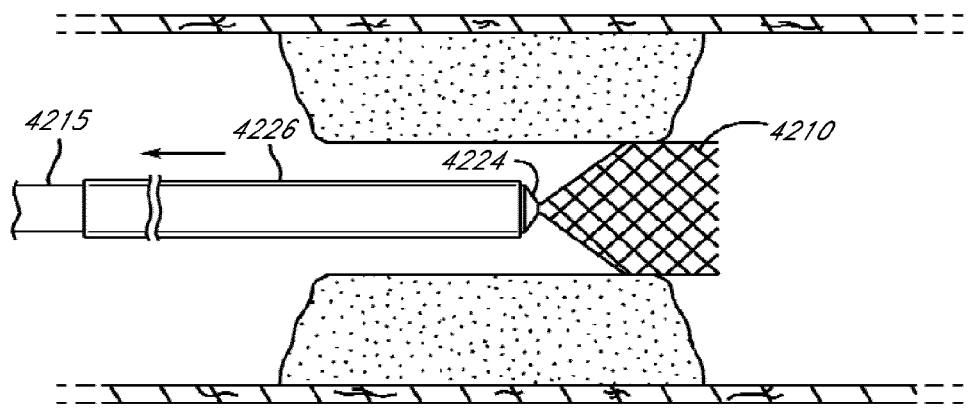
FIG. 47 is an illustration of a balloon catheter and delivery system shown withdrawing from an occlusion and with a cage-like structure in a partially deployed state, according to several embodiments of the present disclosure.

With reference to FIG. 47, according to several embodiments of the present disclosure, the catheter 4215 is withdrawn from an occlusion. The operation of withdrawing the catheter 4215 may simultaneously result in unsheathing and deployment of the cage-like structure 4210. Deployment of the cage-like structure 4210 may result in an expansion of any portion of the cage-like structure 4210 that is not within the lumen 4228 of the catheter 4215.

Figure 48:
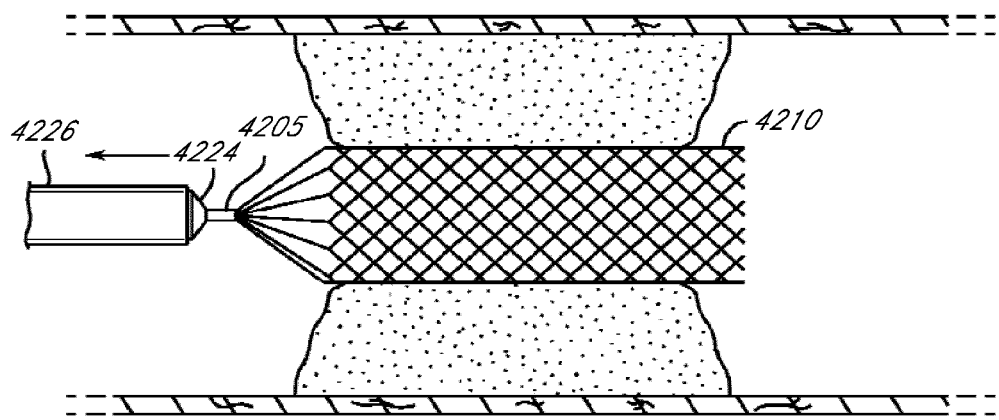
FIG. 48 is an illustration of a balloon catheter and delivery system shown withdrawing from an occlusion and with a cage-like structure in a fully deployed state, according to several embodiments of the present disclosure.

With reference to FIG. 48, according to some embodiments of the present disclosure, the catheter 4215 may be withdrawn such that the cage-like structure 4210 may achieve a fully deployed state. For example, a fully deployed state may be achieved when the entire length of the cage-like structure 4210 is outside the delivery lumen 4228 of the catheter 4215, or when at least a length of the cage-like structure 4210 corresponding to the length of the occlusion is outside the delivery lumen 4228 of the catheter 4215. Expansion of the cage-like structure 4210 may maintain the approximate size and dimensions of the broader channel created by previously inflating the balloon 3926.

Figure 49:
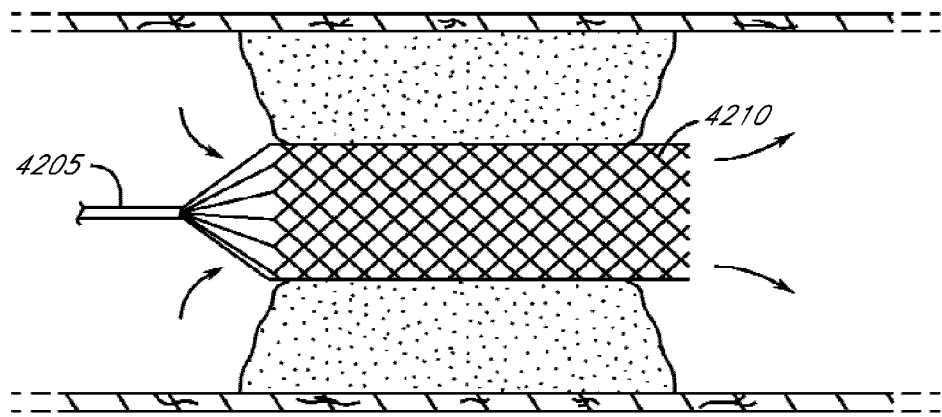
FIG. 49 is an illustration of a balloon catheter and delivery system shown fully withdrawn and with a cage-like structure in a temporary or long-term steady-state fully deployed state, according to several embodiments of the present disclosure.

With reference to FIG. 49, according to several embodiments of the present disclosure, the cage-like structure 4210 achieves a temporary or long-term steady-state fully deployed state, wherein improved flow may be achieved through the occlusion. The flow through the channel may facilitate lysis (e.g., natural lysis) of the occlusion and its constituent parts. The cage-like structure 4210 may maintain the channel created by the dilation or inflation of the balloon 4226, even as the channel deforms or is otherwise modified by the improved flow. According to several embodiments, the cage-like structure 4210 may be maintained within the channel of the occlusion.

In some embodiments, the cage-like structure 4210 may be retracted into the delivery lumen 4228 of the catheter 4215, and the catheter 4215 may be removed from the location of the occlusion.

IX. Expandable Tip Microcatheter

In accordance with some embodiments, a revascularization system (e.g., revascularization system 300) can include a microcatheter having an expandable tip at its distal end. Thus, in some embodiments, instead of a revascularization system comprising a microcatheter and a separate expandable tip assembly configured to be inserted through the microcatheter, the two components can be combined into a single expandable tip microcatheter.

In some embodiments, the expandable tip microcatheter operates as a microcatheter during introduction into a patient. An active segment of the expandable tip microcatheter may expand radially to reperfuse, lyse, or macerate emboli, thrombi, clots, occlusion, blockage, or other matter in a vessel (which terms may be used interchangeably according to embodiments of the present disclosure). After reperfusion is achieved, the active segment may be returned to its configuration maintained prior to expansion, and the expandable tip microcatheter may be removed.

According to several embodiments, and as illustrated by an embodiment in FIG. 50, there is shown a microcatheter 5000 with an active segment 5010 in an unexpanded state. The microcatheter 5000 comprises a proximal segment 5002 and a distal segment 5004. The proximal segment 5002 or portions thereof may remain accessible outside of the patient and may be used to insert and retract the microcatheter 5000, as well as to deploy the active segment 5010 during operation. As illustrated by an embodiment in FIG. 51, the active segment 5010 may be deployed to an expanded state, at least a portion thereof having a radius greater than in an unexpanded state.

According to several embodiments, the length and diameter of the microcatheter 5000 are suitable for inserting into a human patient and capable of reaching a target embolus, for example, in the region above the subclavian and common carotid arteries. For example, the microcatheter 5000 may be about 150 cm long; the proximal segment 102 may be about 115 cm with an outer diameter of about 4 F and the distal segment 104 is about 35 cm with an outer diameter of about 2.7 F. In one embodiment, the microcatheter 5000 is 135 cm long, proximal segment 1102 is 90 cm long, and distal segment 1104 is 45 cm long. In one embodiment, the microcatheter 5000 has an inner diameter of 0.012". In some embodiments, a gradual decrease (e.g., stepwise, tapered, etc.) in the outer diameter dimension may be provided as a function of the distance along proximal segment 5002. For example, the proximal segment 5002 may be 4 F at the most proximal end and the distal segment 5004 may be 2.7 F at the most distal end. Disposed between may be at least one segment having one or more intermediate outer diameters between 4 F and 2.7 F (e.g., 3.8 F, 3.6 F, 3.4 F, 3.2 F, 3.0 F, etc. (see FIGS. 50, 51, 54, and 55). Microcatheter 5000 may have at least one lumen having an inner diameter of about 0.007 to about 0.021 inches, which allows microcatheter to be inserted along a preinserted guidewire 5300 or used to infuse therapeutic agents. According to several embodiments, the performance of microcatheter 5000 is comparable to various microcatheters and is designed to track over the guidewire 5300 or other guidance structures through the neurovasculature. Other ranges of measurements, dimensions, or attributes that may be varied based on the needs and specification of the vasculature.

According to several embodiments, an activation member 5020 (see FIGS. 52B and 53B) may be provided to selectably radially expand and retract active segment 5010. The activation member 5020 may be a structure that connects the distal segment 5004 to the proximal segment 5002 or another component of the microcatheter 5000. According to several embodiments, the activation member 5020, components thereof, devices attached thereto, or devices capable of acting upon the activation member 5020 may be directly accessible by a user, for example, at a proximal end of the microcatheter 5000 (via a hub, luer, fitting, etc.). The activation member 5020 may allow a user of the microcatheter 5000 to deploy the active segment 5010.

According to several embodiments, the activation member 120 may comprise one or more materials, including stainless steel wire or braid, composites polymers and metal braids, ribbon or wire coils. As illustrated in FIGS. 52A, 52B, and 52C, the activation member 5020 may extend through a lumen of the microcatheter 5000. For example, as shown in FIG. 52B, the activation member 5020 may be a wire extending through at least a portion of the proximal segment 5002. Likewise, the guidewire 5300 may be provided in the same or another lumen of the microcatheter 5000. By further example, the activation member 5020 may attach to at least a portion of the distal segment 5004, such that distal or proximal travel of the activation member 5020 relative to the proximal segment 5002 causes corresponding distal or proximal travel of the distal segment 5004 relative to the proximal segment 5002.

As illustrated in FIGS. 53A, 53B, and 53C, the activation member 5020 may have a hollow lumen and extend through a lumen of microcatheter 5000. The guidewire 5300 may be disposed within the hollow lumen of the activation member 5020, as shown in FIG. 53B. The activation member 5020 may slidably move over guidewire 5300 to reach the distal segment 5004. Other devices operable during a procedure may be delivered via a hollow lumen of the activation member 5020.

According to several embodiments, the activation member 5020 may be a braid (stainless steel, nitinol, composite, polymer, metal, etc.) structure or a ribbon or wire coil. Accordingly, the activation member 5020 may be longitudinally or radially compressible, extendable, distensible, or otherwise responsive to forces applied thereto. For example, the activation member 5020 may cause the distal segment 5004 to move relative to the proximal segment 5002 by causing the activation member 5020 to compress or extend longitudinally. By further example, the longitudinal compression or extension of the activation member 5020 may result in adjustment of the relative position of the proximal segment 5002 and the distal segment 5004 where the activation member 5020 is attached to at least a portion of each of the proximal segment 5002 and the distal segment 5004. Another device (e.g., guidewire 5300, etc.) may be provided to the activation member 5020 to effect its compression, extension, etc. According to several embodiments, deployment of the active segment 5010 may be achieved by shortening of the activation member 5020, whereby the distance between the proximal segment 5002 and the distal segment 5004 is decreased.

According to several embodiments, when the active segment 5010 is expanded in a vessel, the radial expansion causes a channel to be formed in a thrombus for restored blood flow past the occlusion and thereby reperfuse the vessel. Activation of the active segment 5010 may be accomplished by mechanical methods, such as with the activation member 5020 or by using a liner of the microcatheter 5000. Use of the liner is accomplished by leaving the liner unfused with active segment 5010, such that the liner may be independently operable to deploy the active segment 5010.

According to several embodiments, the activation member 5020 may be fused to the distal-most portion of the active segment 5010 or the proximal-most portion of the distal segment 5004. The activation member 5020 may further be fused to the proximal-most portion of the active segment 5010 or the distal-most portion of the proximal segment 5002.

According to several embodiments, the active segment 5010 and the activation member 5020 may provide opposing forces. For example, the active segment 5010 may be heat set into a native configuration in an expanded state. When the activation member 5020 tensions the active segment 5010, its state changes from an expanded state into a deliverable state. Such tension may be provided by longitudinal extension of the activation member 5020 or travel thereof, thereby causing the proximal segment 5002 to distance itself from the distal segment 5004. Once delivered to the site of an embolus, the activation member 5020 is adjusted to allow the active segment 5010 to relax and thereby expand. Such adjustment may be achieved by shortening the longitudinal length of the activation member 5020 or travel thereof, thereby causing the proximal segment 5002 to approach the distal segment 5004.

By further example, the active segment 5010 may be heat set into a native configuration in an unexpanded state. The activation member 5020 may be used to tension active segment 5010 when delivered to the site of an embolus, thereby expanding it. Such tension may be provided by shortening the longitudinal length of the activation member 5020 or travel thereof, thereby causing the proximal segment 5002 to approach the distal segment 5004. Shortening of the activation member 5020 may be achieved in a variety of ways. For example, the activation member 5020 may be radially expanded, whereby its longitudinal length is decreased. By further example, the activation member 5020 may be transitioned from a substantially straight shape to serpentine shape, whereby its longitudinal length is decreased. The guidewire 5300 may act upon or within the activation member 5020 to effect such transitions.

Other activation methods include electrical, chemical, and thermal activators. Hydraulic activation may be accomplished with the activation member 5020 as a balloon in the interior of the catheter that is filled with a fluid, thereby expanding the balloon, which expands the active segment 5010. Fluids, devices, or other materials may be provided to activation member 5020 to effect a change in the shape, geometry, size, orientation, or position thereof, thereby deploying the active segment 5010.

According to several embodiments, the active segment 5010 comprises a radially expandable material. For example, as shown in FIGS. 50, 51, 54 and 55, the active segment 5010 may include a woven mesh. A mesh may be made from materials including polymers, PET, nylon, fluoropolymers, nitinol, stainless steel, vectran, kevlar, or combinations thereof. Other biocompatible materials that may be woven or coiled are similarly contemplated. The active segment 5010 is, according to several embodiments, about 5 mm to about 50 mm (e.g., from about 5 mm to about 10 mm, from about 10 mm to about 20 mm, from about 15 mm to about 30 mm, from about 20 mm to about 35 mm, from about 30 mm to about 45 mm, from about 35 mm to about 50 mm, or overlapping ranges thereof) in length when expanded and is designed to substantially return to its pre-expansion configuration for removal of the microcatheter 5000 after reperfusion. In some embodiments, active segment 5010 has an expanded diameter from 1.5 min to 3.5 mm and therapeutic lengths of 8 mm, 12 mm, or 16 mm. In one embodiment, active segment 5010 is 15 mm long. [0323] According to several embodiments, the active segment 5010 comprises a mesh. The mesh comprises a plurality of individual units, having a uniform size or spacing geometry or a variable size or spacing geometry. According to several embodiments where the size or spacing geometry is variable, smaller size or spacing geometry is used to provide a tight mesh for expanding a channel through the thrombus. Larger size or spacing geometry units allow for increased blood flow through the active segment 5010. In one embodiment, active segment 5010 comprises a woven polymer mesh that is heparin coated. In one embodiment, active segment 5010 has a suitable porosity to permit blood flow when expanded. In one embodiment, releasing expansion of active segment 5010 will trap thrombus in the mesh.

According to several embodiments, as shown in FIG. 55, the active segment 5010 may comprise both mesh 5010A (e.g., a mesh scaffold) and tethers 5010B. According to several embodiments, the mesh 5010A comprises an open braid, a covered braid, or other supporting structure which may provide at least some porosity. The covering may comprise a distal protection mechanism and may be a polymer, such as polyurethane, or other biocompatible cover materials such as ePTFE or related thin film. The tethers 5010E may serve to provide structure and support for the mesh 5010A, as well as attachment to at least one of the proximal segment 5002 and the distal segment 5004. Tethers 5010B may further provide openings whereby blood may freely flow from the proximal to distal end of the active segment 5010 through a lumen formed therein. The tethers 5010B may include braids, wires, coils, tangs, and/or other coupling structures. Materials for the tethers 5010B and mesh 5010A may be the same, different, or interchangeable, as needed.

According to several embodiments, as shown in FIGS. 56, 57, 58, and 59, the active segment 5010 comprises expandable coiled wires. The coiled wires may be made from stainless steel wire or braid, composite metal polymers, memory shape alloys (e.g., nitinol), wherein the coil is able to stably expand and return to an original state. As illustrated in FIG. 58, the diameter of the coil may be substantially the same as that of the microcatheter 5000 when in a non-expanded state. However, when expanded (as illustrated in FIG. 59) the coiled wires expand radially according to the reperfusion principles disclosed herein. Such radial expansion may be achieved by a variety of methods, including shortening of the longitudinal length of the active segment 5010, travel of the distal segment 5004 relative to the proximal segment 102, rotation of the distal segment 5004 relative to the proximal segment 5002. Other methods include mechanical methods, electrical methods, heat methods, chemical methods, etc., or combinations thereof.

According to several embodiments, as shown in FIGS. 54, 55, 58, and 59, revascularization ports 5012 may provide increased blood flow through the lumen of microcatheter 5000, as disclosed further herein. In some embodiments, one or more revascularization ports 5012 can be configured to delivery fluids or materials to a target treatment site (e.g., lytic agents to a target embolus, platelet activation compounds or clot-promoting adherents).

According to several embodiments, variable cell size or spacing geometry may be accomplished with points where the braid crosses over fixed filaments (PICS). Thus, the cell size or spacing geometry varies by varying the density of the braid. Where high radial force is needed to open a channel in an embolus, for example, the filaments of the mesh are denser and therefore cross each other more often, yielding small cell size or spacing geometry that leads to the application of greater radial force when the mesh expands. Where reperfusion is desired, the PICS may be less dense and the resulting cell size or spacing geometry is increased. Additionally, drug delivery through the microcatheter 5000 will be more effective in mesh configurations having a large size or spacing geometry.

The active segment 5010 may be coated or covered with substances, such as lubricious agents or pharmacologically active agents, according to several embodiments. For example, the active segment 5010 may be covered (e.g., coated) with heparin or other agents that are used in clot therapy, such as those that aid in dissolving clots, mitigating vasospasms, promoting activation of platelets, promoting cell adhesion or engagement.

According to several embodiments, the microcatheter 5000 is designed to follow a path of least resistance through a thrombus. The guidewire 5300 inserted through a thrombus tends to follow the path of least resistance through the softest parts of the thrombus. When the microcatheter 5000 crosses the thrombus, it likewise follows this path of least resistance. As blood flow is restored, a natural lytic action further helps to degrade (e.g., break up, lyse) the thrombus, as described in more detail herein.

According to similar embodiments, therapeutic agents are deployable through the lumen of microcatheter 5000, thereby allowing users of microcatheter 5000 to determine on a case-by-case basis whether to administer an agent. Active and passive perfusion can thus both be enabled. In some embodiments, the therapeutic agents can be delivered through the revascularization ports 5012. Accordingly, the braid/geometry of the active segment 5010 is porous to allow the agent to pass from the lumen of the microcatheter 5000 into the blood vessel at the site of an embolus, for example.

According to several embodiments, and as illustrated in FIG. 60A, the microcatheter 5000 is inserted into a vessel having an occlusion. As previously discussed, the microcatheter 5000 is insertable along the guidewire 5300 through a vessel lumen, according to several embodiments. The microcatheter 5000 penetrates embolus 5210 in the vessel. As shown in FIG. 60B, the active segment 5010 is positioned to coincide with the position of the embolus 5210. As shown in FIG. 60C, the active segment 5010 is expanded, thereby opening a channel in the embolus 5210 and restoring blood flow. According to several embodiments illustrated in FIGS. 61A, 61B, and 61C, similar principles may be applied where the active segment 5010 comprises coiled wires.

Once activated, the active segment 5010 allows blood to flow around or through the microcatheter 5000 and the active segment 5010 to create therapeutic benefits associated with reperfusion, as described in detail herein. For example and according to several embodiments, the portions of the proximal segment 5002 and the distal segment 5004 immediately proximal and distal to the active segment 5010 may have a diameter of about 2.0 French to about 3.0 French.

According to several embodiments, portions of the proximal segment 5002 and the distal segment 5004 may have installed therein revascularization ports 5012, as shown in FIGS. 60A, 60B, 60C, 61A, 61B, and 61C. The revascularization ports 5012 comprise openings in microcatheter 5000 that allow vascular fluids to flow through portions of the microcatheter 5000. For example, as shown in FIGS. 60C and 61C, fluid on a proximal side of the embolus 5210 may enter the microcatheter 5000 through at least one revascularization port 5012 of the proximal segment 5002. The vascular fluids may travel through portions of the microcatheter 5000, including the active segment 5010, and exit through at least one revascularization port 5012 of the distal segment 5004. In some embodiments, revascularization ports 5012 provide additional delivery points for therapeutic agents or other fluids or materials delivered through the microcatheter 5000.

According to several embodiments, a filter may be placed distal of the active segment 5010 to prevent embolus pieces detached in the reperfusion process from escaping and causing distal occlusions. Accordingly, the active segment 5010 may be designed to capture pieces of embolus during the reperfusion processes. These pieces are captured within the active segment 5010 when the active segment 5010 is returned to its initial confirmation after expansion. In other embodiments, a filter is not used.

Figure 61D:
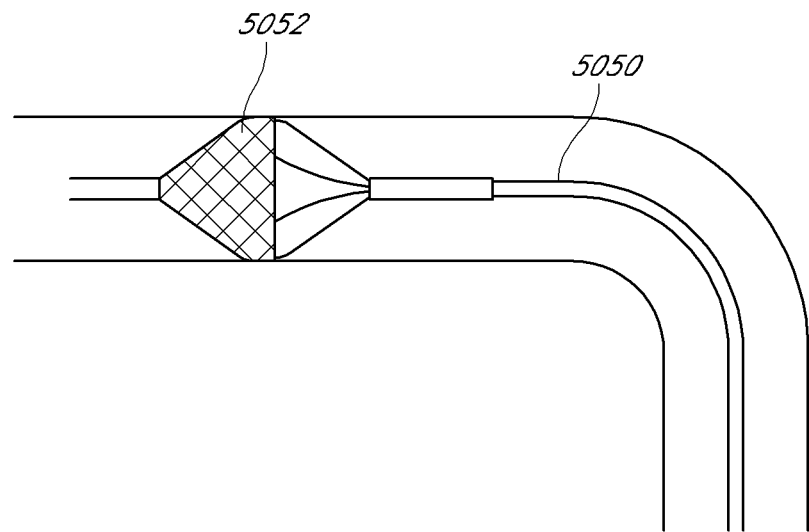
FIG. 61D is a side view of an embodiment of a rapid reperfusion device comprising an infusable microwire with an integrated filter.
Figure 61E:
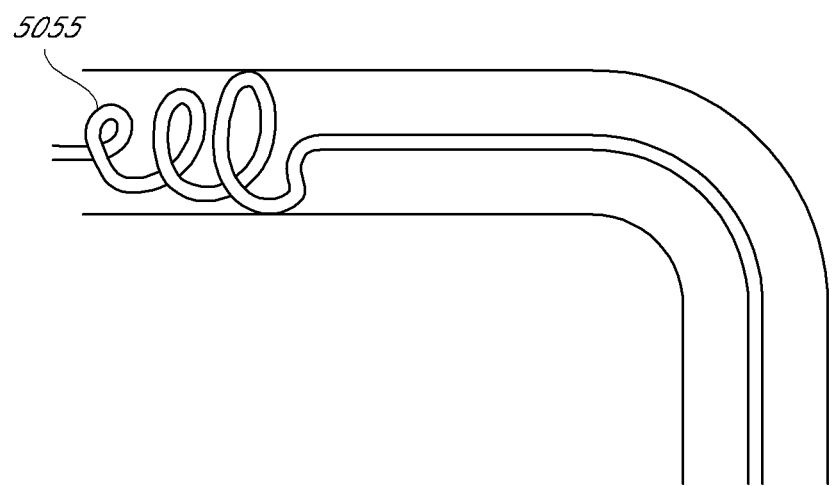
FIG. 61E is a side view of an embodiment of a rapid reperfusion device comprising an infusable coil.

In some embodiments, the rapid reperfusion device comprises an infusable microwire 5050 with an integrated filter 5052 as illustrated in FIG. 61D. According to embodiments and as illustrated in FIG. 61E, the rapid reperfusion device comprises an infusable coil 5055. In some embodiments, active segment 5010 is a coil that comprises a large portion of distal segment 5004, wherein microcatheter 5000 itself coils when activated to create a channel through an embolus whereby blood flow is restored.

Figure 61F:
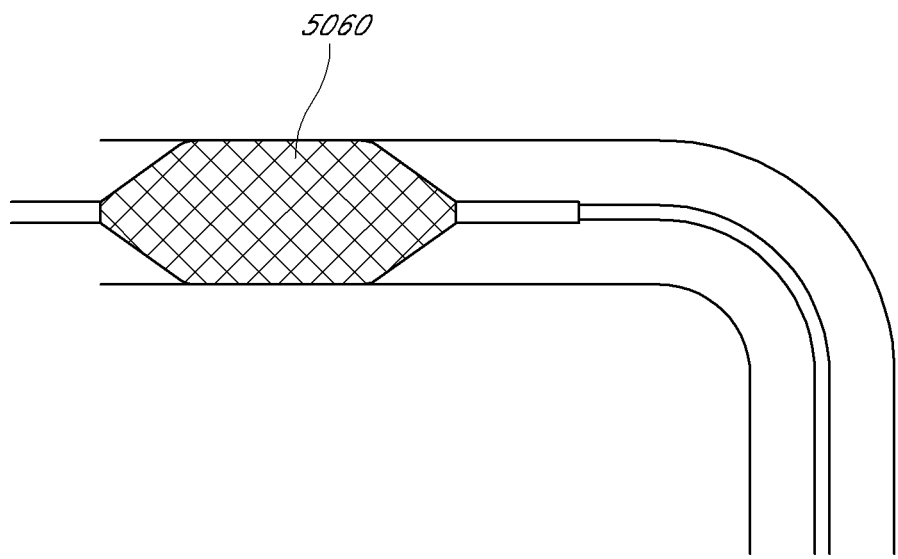
FIG. 61F is a side view of an embodiment of a rapid reperfusion device comprising an infusable temporary stent.
Figure 61G:
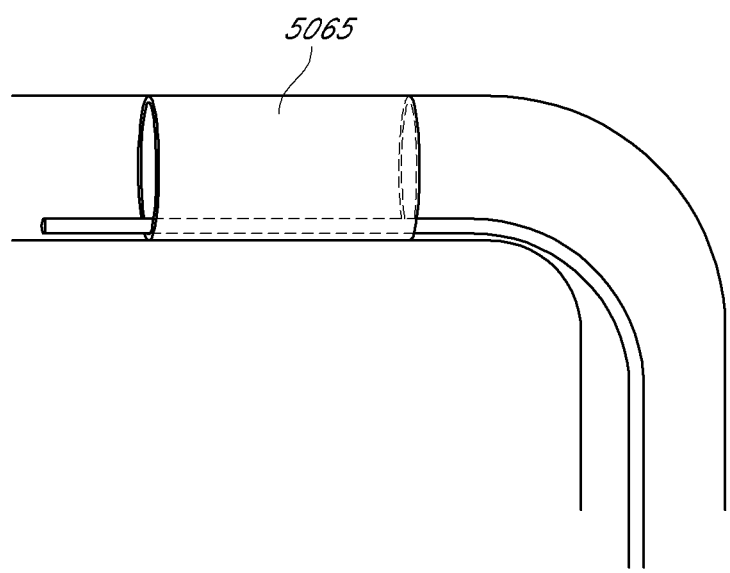
FIG. 61G is a side view of an embodiment of a rapid reperfusion device comprising an inflatable balloon.

In some embodiments, the rapid reperfusion device comprises an infusable temporary stent 5060 as illustrated in FIG. 61F. According to embodiments illustrated by FIG. 61G, an infusable balloon 5065 is connected to microcatheter 5000 and comprises active segment 5010. Inflation of the infusable balloon 5065 can open a channel through the embolus and begin a lytic process on the embolus (e.g., natural lytic action due to the restored blood flow or mechanical lytic action).

According to several embodiments, a kit of parts is disclosed. The kit may comprise components, devices, and systems disclosed herein, as well as any other compatible with the same, and instructions for use. Likewise, directions for use are included and the device may be part of a surgical tray or other packaged accessory set for surgeries. The kit may be a sub-component of a surgical tray.

X. Aneurysm Neck Bridging

In accordance with several embodiments, the systems, devices and methods described herein (e.g., expandable tip assemblies such as but not limited to expandable tip assembly 500, expandable tip assembly 600) can be used to improve or facilitate the treatment of aneurysms. The systems and devices described herein can be used in a support role with other therapies. The systems, devices and methods described herein provide ongoing revascularization or blood flow while aneurysms are being managed (e.g., by vaso-occlusive coils and/or drug use).

In several embodiments, a method of treating an aneurysm is provided. In one embodiment, the method comprises identifying a blood vessel having an aneurysm, inserting an expandable tip assembly into the blood vessel, wherein the expandable tip assembly has a scaffold. The scaffold, which has openings (such as pores or cells), is positioned to bridge the aneurysm while permitting blood flow. A microcatheter is inserted through at least one opening in the scaffold to deliver coils and/or other fillers into the aneurysm, which inhibits blood flow into the aneurysm, thereby preventing rupture of the aneurysm. The reduction in blood flow typically causes the formation of thrombus in the aneurysm. To the extent that the thrombus releases embolic particles (that may flow downstream and occlude other vessels), several embodiments are configured to facilitate lysis of those embolic particles—in many cases, without the need for a separate embolic protection device.

One type of aneurysm, commonly known as a "wide-neck aneurysm" is known to present particular difficulty in the placement and retention of vaso-occlusive coils. Wide-neck aneurysms are herein referred to as aneurysms of vessel walls having a neck or an "entrance zone" from the adjacent vessel, which entrance zone has a diameter of either (1) at least 80% of the largest diameter of the aneurysm; or (2) is clinically observed to be too wide to effectively retain vaso-occlusive coils. Wide neck aneurysms can refer to aneurysms having a dome to neck ratio less than 2:1 or a neck wider than 4 mm.

Vaso-occlusive coils lacking substantial secondary shape strength may also be difficult to maintain in position within an aneurysm no matter how skillfully they are placed. This may also be true of coils that have a secondary shape. For example, a 3D coil that takes a spherical shape may be herniated out of the parent vessel if the neck is too wide. Using the systems and devices disclosed herein (e.g., expandable tip assemblies such as but not limited to expandable tip assembly 500, expandable tip assembly 600) can permit the coils to be held in the aneurysm until a critical mass of coils is achieved within the aneurysm so that the coil mass will not move when the devices are withdrawn.

In some embodiments, the systems and devices described herein comprise a vessel reconstruction system. In some embodiments, the devices disclosed herein (expandable tip assemblies such as but not limited to expandable tip assembly 500, expandable tip assembly 600) are configured for maintaining the vaso-occlusive coils within an aneurysm. In one embodiment, the device comprises a retainer configured to retain coils within the aneurysm cavity. The retainer device (e.g., an expandable tip assembly) can be released into the vessel exterior to the aneurysm. The device can be held in place via the presence of radial pressure on the vessel wall. After the device is released and set in an appropriate place, a microcatheter can be inserted into the lumen so that the distal end of the microcatheter is inserted into the aneurysm cavity (for example, through open cells of a scaffold of the device, or expandable tip assembly). One or more vaso-occlusive devices can then be introduced into the aneurysm cavity. The retainer device can maintain or keep the vase-occlusive devices within the aneurysm whether it is a large-mouth (e.g., wide-neck) aneurysm or not.

Another approach to filling intracranial aneurysms includes the use of injectable fluids or suspensions, such as microfibrillar collagen, various polymeric beads, and/or polyvinyl alcohol foam. These polymeric agents may additionally be crosslinked, sometimes in vivo to extend the persistence of the agent at the vascular site. These agents may be introduced into the vasculature through any of a variety of known catheters. After introduction, the deployed materials form a solid space-filling mass. Other materials, including polymeric resins, typically cyanoacrylates, hydrogels and other gels, fibrin glues, and calcium binding seaweed extracts are also employed as injectable vaso-occlusive materials. These materials may be mixed with a radiopaque contrast material or made radiopaque by the addition of a tantalum powder. Several embodiments of the invention are used in conjunction with said injectable fluids or suspensions, and are particularly advantageous because the neck of the aneurysm is reconstructed by the aneurysm neck bridge (e.g., expandable tip assembly), thereby reducing hemodynamic stress to the aneurysm in the flow zone. In some embodiments, the neck of the aneurysm is the target of treatment and not the aneurysm sac. In accordance with several embodiments, treating the neck of the aneurysm is the solution and not filling the aneurysm with filler materials. In accordance with several embodiments, if the aneurysm neck bridge (e.g., the expandable tip assemblies described herein) is able to change or stop the existing flow pattern at the neck, then the aneurysm ceases to grow and the aneurysm is effectively treated.

The delivery of liquid filler agents into aneurysms in general can have numerous obstacles in some cases. The viscosity of the material can make delivery difficult, and can lead to run on even after the pressure head has been removed from the delivery catheter. Inadequate opacification of the material makes it difficult to see. As a result, the liquid filler agents can leak into the parent vessel, thereby resulting in vessel occlusion and distal embolization into the organ's vascular bed. Generally, these materials can be delivered using an inflated balloon adjacent to the abnormality to be treated. Inflation of the balloon during delivery leads to temporary vessel occlusion and can result in downstream organ ischemia and even infarction. Several embodiments of the invention are used in conjunction with said liquids are particularly advantageous because blood flow is not occluded or is occluded for less time than would otherwise have been done.

A second microcatheter may be introduced either alongside or through (or both) an internal lumen of a delivery wire or pushwire delivering a neck-bridge (e.g., expandable scaffold) so as to also permit the introduction of a filler (also called an embolic agent) into the aneurysm through, around or adjacent the mesh of the scaffold, which may have opened spaces or cells that permit the microcatheter and/or delivery wire to introduce the filler into the aneurysm. Such an agent may be comprised of metallic or plastic coils, a combination of plastic and metal braid or composite plastic and metal braid, liquid or polymerized polymeric agents, and/or biologic components of blood and plasma-like thrombin, fibrin or any biologic materials like DNA, RNA plasmids or the like, to fill the aneurysm.

However, after, or perhaps during, delivery of a coil (or other filler) into the aneurysm, there may be a risk that a portion of the coil might migrate out of the aneurysm entrance zone and into the feeding vessel. This can be especially true in aneurysms where the diameter of the aneurysm neck approaches the diameter of the aneurysm dome in a 1:1 ratio.

The presence of such a coil in that feeding vessel may cause the undesirable response of forming an occlusion there. Also, there is a quantifiable risk that the blood flow in the vessel and the aneurysm may induce movement of the coil farther out of the aneurysm, resulting in a more thoroughly developed embolus in the patent vessel. Being that coils are constructed from very low gauge wire, the coil mass can compact, resulting in aneurysm recanalization. Thus, in some embodiments, it can be advantageous to consider needs that can be addressed for aneurysms in light of the need for ongoing perfusion.

For example, when detachable coils are used to occlude an aneurysm which does not have a well-defined neck region, the detachable coils can migrate out of the sac of the aneurysm and into the parent artery. It can be difficult to gauge exactly how full the sac of the aneurysm is when detachable coils are being placed. Therefore, there is a risk of overfilling the aneurysm, in which case the detachable coils can also herniate or prolapse into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can reform over time.

Migration of the filler (sometimes called an embolic agent) may also be a problem. For instance, where a liquid polymer is placed into the sac of the aneurysm, it can migrate out of the sac of the aneurysm due to the hemodynamics of the system, which can lead to irreversible occlusion of the parent vessel. Several embodiments of the invention are used in conjunction with coils and other types of fillers, and are particularly advantageous because the cell size of the scaffold of the aneurysm neck bridge (e.g., the expandable tip assemblies described herein) can seal the neck to vessel interface, thereby preventing the fillers (e.g., liquid or solid fillers) from leaking or otherwise exiting from the aneurysm).

In some embodiments, a device is provided that can reconstruct the vessel wall at the aneurysm neck origin by tethering an expandable scaffold (e.g., a cage-like structure or stent-like structure) to the distal end of a trackable delivery system. For example, an expandable scaffold such as those described herein (e.g., expandable scaffold 810, expandable scaffold 910) can be placed across the neck of aneurysm without prophylactically administered aspirin and clopidogrel because the device is temporary, as well as without obstructing flow. The tethered expandable scaffold allows perfusion through the body of the scaffold and provides support to the neck of the aneurysm, thereby allowing a coil procedure. After the coil procedure, the tethered expandable scaffold can be withdrawn proximally into a standard delivery microcatheter (e.g., microcatheter 315, microcatheter 3315).

The vessel wall reconstruction device (e.g., expandable tip assembly such as, but not limited to, expandable tip assembly 600) can be delivered through standard microcatheters currently available to the interventionalist. A microcatheter can either be placed into the aneurysm prior to placement of the tethered expandable scaffold or after placement of the tethered expandable scaffold. If the latter is preferred, then the coil microcatheter can be placed through the openings between struts of the tethered expandable scaffold to access the body of the aneurysm to commence coiling.

Figure 62:
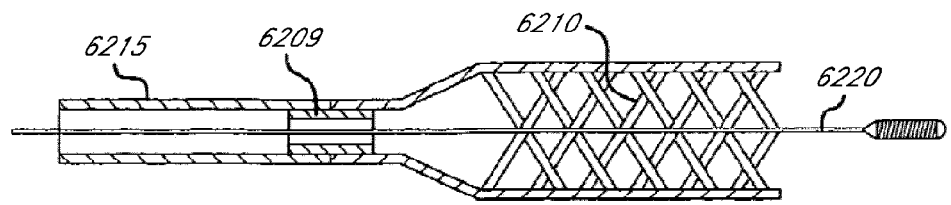
FIG. 62 shows a schematic of a delivery system and an embodiment of a temporary aneurysmal treatment device mechanism.

Referring now to FIG. 62, a delivery tube 6215 deploys a tethered expandable scaffold 6210 (e.g., cage-like device, stent-like device such as, but not limited to, expandable scaffold 610, expandable scaffold 810, expandable scaffold 910) prior to insertion of the coil(s) (or other filler), using a standard over-the-wire (OTW) system including guide-wire 6220. The tethered expandable scaffold 6210 can include the structure or features of any of the expandable scaffolds described herein. The delivery tube 6215 and the tethered expandable scaffold 6210 can together form an expandable tip assembly (such as but not limited to expandable tip assembly 510, expandable tip assembly 610). The delivery tube 6215 and the tethered expandable scaffold 6210 can comprise a vessel reconstruction system that is able to be deployed prior to filling, be used to reconstruct the arterial wall at the aneurysm neck, hold filler in place, and then is able to be removed after filling of the aneurysm sac is complete.

The vessel reconstruction system (e.g., clot management system, revascularization system) can provide a method to assist in aneurysm filling that does not restrict blood flow and can be used without placing patients on an anti-clotting drug (including but not limited to acetylsalicylic acid (e.g., aspirin), clopidogrel (e.g., Plavix®) during filling of the aneurysm.

According to several embodiments of the invention, the vessel reconstruction system uses both passive and active reperfusion to address aneurysms without the detriments of balloon re-modeling. A temporary tethered expandable scaffold 6210 (e.g., cage-like structure) is non-detachable in some embodiments but attached either to a hypotube or guide-wire allowing it to be navigated into tortuous vasculature in the brain. The device and system are deployed prior to filling, as discussed above. The expandable scaffold 6210 may be attached to guidewire 6220 or tube 6215.

Figure 63:
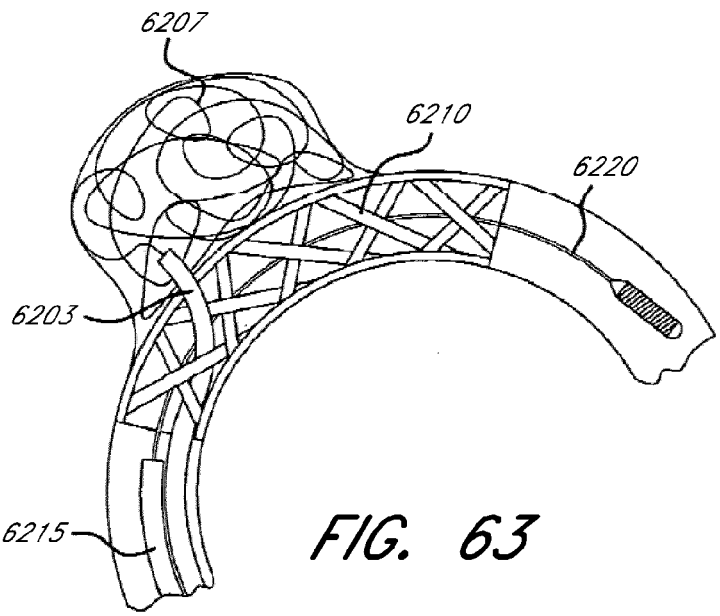
FIG. 63 shows a temporary aneurysmal treatment device and mechanism bridging the neck of an aneurysm, according to an embodiment of the invention.
Figure 64:
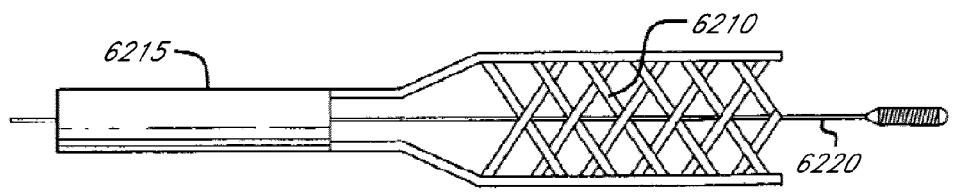
FIG. 64 schematically depicts a delivery system with several embodiments of an aneurysmal treatment device.
Figure 65:
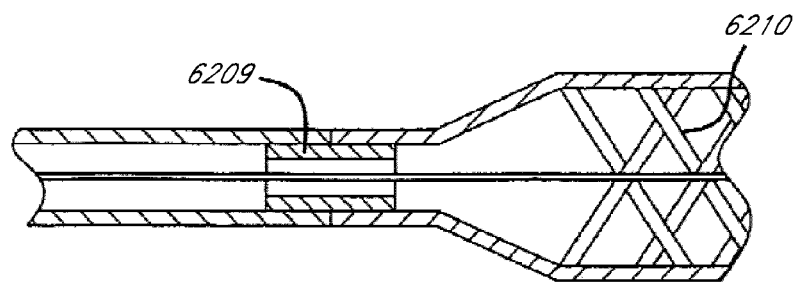
FIGS. 65 and 66 illustrate detachability of the aneurysmal treatment device in accordance with an embodiment of the invention.

Referring also to FIG. 63 through FIG. 65, the microcatheter or delivery tube 6215 emplaces the expandable scaffold 6210 at an aneurysm neck, while a coiling microcatheter 6203 accesses the aneurysm, and allows one or more coils 6207 to be placed therein. The delivery tube 6215 and the scaffold 6210 may include nitinol or the like "super-elastic" materials.

FIG. 64 likewise provides further details of the vessel reconstruction system, with the expandable scaffold 6210 being released from the delivery tube 6215 using known OTW techniques. In some embodiments, a detachable aneurysm neck bridging system includes a detachable coupling member 6209 that enables detachment of the expandable scaffold 6210 from the delivery tube 6215 for permanent or long-term implantation of the expandable scaffold 6210.

Figure 66:
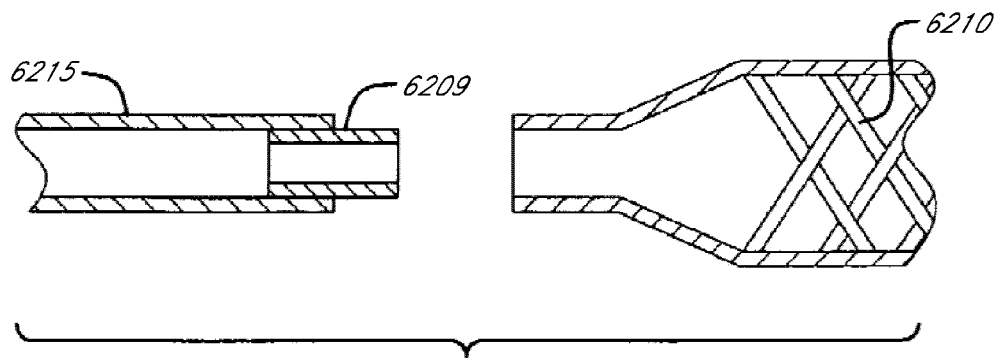

FIG. 65 and FIG. 66 likewise show intermediate steps, whereby placement of the vessel reconstruction system allows an aneurysm to be isolated, at the neck, whereby the coils 6207 may be used. According to several embodiments illustrated by FIG. 66, if one of the coils 6207 somehow gets caught in the expandable scaffold 6210, it may be impossible to remove the device without causing damage to or rupturing the vessels. Therefore, according to several embodiments, the expandable scaffold 6210 may be detachable, enabling it to be left in the vessel in the event of a complication where it cannot be safely removed, or as needed otherwise.

The delivery tube 6215 should also have a lumen that enables tracking over a guidewire (e.g., the guidewire 6220). This feature provides a few benefits; ability to track and be delivered; ability to maintain access in the event different size devices need to be exchanged; provide support to arterial tree during device deployment and recovery. A flexible device may tend to herniate or prolapse into openings. The guidewire provides a pathway (concentric) to the artery and supports the device preventing such technical complications. The delivery tube 6215 can comprise any of the elongate members, microcatheters, or catheters and the associated features as described herein.

The delivery tube 6215 can be mechanically attached to the expandable scaffold 6210 (e.g., cage-like structure) by soldering, welding or press fitting or other suitable attachment methods. In some embodiments, the delivery tube 6215 is attached to the expandable scaffold 6210 via the detachable coupling member 6209. By attaching the expandable scaffold 6210 to the delivery tube 6215, the expandable scaffold 6210 can be placed, retracted, repositioned and recaptured into a microcatheter. In some embodiments, the vessel reconstruction system formed by the delivery tube 6215 and the expandable scaffold 6210 can be delivered through a separate microcatheter. In other embodiments, the expandable scaffold 6210 is attached to a delivery wire to form an expandable tip assembly and the expandable tip assembly can be inserted within the delivery tube 6215.

The expandable scaffold 6210, being temporary, allows for the following: 1) perfusion of blood through artery during coiling; 2) perfusion from coiling herniation or prolapse; and 3) removal of the device, mitigating the use of Aspirin and Plavix.

The expandable scaffold 6210 (e.g., cage-like structure) can be made of nitinol or other memory-based or shape memory materials to allow it to be compressed and loaded into an introducer for packaging. The introducer enables the device to be transferred into a microcatheter and deployed to a trusted (e.g., target) location such as an aneurysm neck.

In some embodiments, the expandable scaffold 6210 can comprise alloys containing at least 1.5% (wt) and up to about 85% (wt) or more, of one or more alloying members selected from the group consisting of one or more of: vanadium, chromium, manganese, iron, and cobalt. U.S. Pat. Nos. 3,351,463 and 3,753,700 are incorporated by reference herein.

EXAMPLES

The following Examples illustrate some embodiments of the invention and are not intended in any way to limit the scope of the disclosure. Moreover, the methods and procedures described in the following examples, and in the above disclosure, need not be performed in the sequence presented.

Example 1

Stress Test Evaluation for Vessel Tolerance of Revascularization System with Multiple Device Use A study was performed to demonstrate that embodiments of multiple revascularization system devices (e.g., expandable tip assemblies) can be challenged and delivered to the target vessel, deployed and then withdrawn from the target vessel in serial fashion without inducing vessel trauma or injury. Angiographic assessment of the target vessels was performed after each device deployment and retrieval to assess performance and outcomes.

Testing was performed on swine animal models. The swine models were selected because the vascular anatomy and pathological response is comparable to that of the human. Specifically, the internal maxillary and renal arteries are of similar diameter to the human middle cerebral and basilar arteries with diameters of 2.5-3.0 mm respectively. Swine models have been used by neurovascular companies in support of U.S. FDA IDE studies and/or for 510(k) clearance. Two swine were used in the study. The animals were quarantined and examined by qualified veterinary staff to ensure that they were in good clinical condition. The devices were deployed within the inferior and superior renal arteries and the internal maxillary arteries In accordance with one embodiment, the testing procedure was performed as follows:

1. As this was an acute study the animals were sedated, anesthetized, prepped and draped for a clean but not necessarily aseptic procedure. Animals were weighed prior to leaving the prep area. The animal was placed in dorsal recumbency and the hair removed from the access area (inguinal area).
2. Blood was drawn for a baseline activated clotting time (ACT). Heparin 100-200 IU/kg, IV, was administered to achieve a target ACT of ≥250 seconds. ACTs were periodically measured in order to maintain a target ACT of ≥250 seconds. Heparin boluses were administered as needed in order to achieve this target.
3. The femoral artery was accessed via surgical cutdown. A 6Fr Cook® introducer sheath was placed in the vessel followed by placement of a 6Fr Envoy® guide catheter.
4. A Renegade® Hi-Flow™ Microcatheter was inserted into the guide catheter and the target vessel cannulated.
5. Baseline angiographic assessment of the targeted vessel was performed and vessel diameter measurements obtained and recorded.
6. The rotating hemostasis valve (RHV) on the microcatheter was loosened and the test device was inserted and advanced to the target vessel as indicated below.
7. Angiography was performed to verify the position of the device within the target vessel. The device was deployed and then the Microcatheter and deployed device were retracted back into the guide catheter (simulated thrombectomy) while applying syringe aspiration to the guide catheter.
8. Post procedure angiography was performed with each device deployment to assess the target vessel for visible evidence of trauma, injury or dissection. If evidence of severe vasospasm was noted 5 mg of Verapamil was administered to relieve the spasm.
9. The next device in the test sequence was then introduced within the target vessel and steps 6-8 repeated.
10. Upon completion of the test sequence the device, microcatheter and guide catheter were removed from the animal.

The following attributes were assessed: movement of the devices through the microcatheter, tracking through the vessel, guidewire movement through the system, device deployment, radiopacity, recapture (e.g., resheathing), withdrawal, thrombectomy, vessel dissection or perforation, and embolization post-treatment. The tested devices received performed as intended ratings for all the above-listed attributes. Vessel response, as evidenced by intra-procedural angiographic assessment, was similar for all devices evaluated with no angiographic evidence of vessel trauma or injury. Thus according to several embodiments of the invention, devices disclosed herein are a safe means of restoring flow in blocked arteries without causing major lesions or defects such as intramural dissection or perforation of target vessels.

Example 2

Usability, Safety and Effectiveness of Expandable Tip Assemblies

A study was performed to determine the usability, safety and effectiveness of embodiments of neurothrombectomy devices comprising expandable tip assemblies designed and configured to facilitate clot removal. Testing was performed on swine animal models. The swine models were selected because the vascular anatomy and pathological response is comparable to that of the human. Swine models have been used by neurovascular companies in support of U.S. FDA IDE studies and/or for 510(k) clearance. A total of two subject animals and six blood vessels were treated. The blood vessels treated were the left and right ascending pharyngeal, lingual and internal maxillary arteries.

Embodiments of the expandable tip assemblies or devices were introduced into the target vessels, deployed, pulled through the vessels and retracted into the guide catheter in a manner similar to that described above. This process was repeated up to six times or until the vessel was no longer accessible.

The following attributes were assessed: movement of the devices through the microcatheter, tracking through the vessel, guidewire movement through the system, device deployment, radiopacity, recapture (e.g., resheathing), withdrawal, thrombectomy, vessel dissection or perforation, and embolization post-treatment. The tested devices received "performed as intended" ratings for all of the above-listed attributes. Thus, several embodiments of the expandable tip assemblies caused minimal disruption or activation of the endothelium (e.g., less than 1% endothelial loss, less than 5% endothelial loss, less than 10% endothelial loss).

Example 3

Radial Force and Cell Characteristics Measurements

Testing was performed to compare radial force and cell characteristics of various vascular therapy devices, including embodiments of the expandable tip assemblies described herein. The vascular therapy devices tested and/or measured included a NeuroForm³™ device provided by Boston Scientific, an IRIIS™ Plus device provided by MindFrame, an IRIIS™ device provided by MindFrame, a Solitaire™ AB device provided by ev3, and an Enterprise™ device provided by Cordis. The IRIIS™ Plus and the IRIIS™ devices are embodiments of the expandable tip assemblies described herein.

The following tables illustrate the data collected from the testing. Graphical results of the data from Tables 1 and 2 can be found in FIGS. 6 and 7, respectively, of U.S. Patent Application Publication No. 2010/0174309, the entire contents of which has been incorporated by reference herein.

Table 1 below lists the data obtained from testing performed to determine the chronic outward force (COF) of the devices at selected expansion diameters ranging from 2 mm to 4.5 mm (which diameters correspond to the vessel diameters of the cerebral vasculature). The units for the COF data reproduced below are force per unit length (N/mm).

TABLE 1

| Diameter | NeuroForm³ ™ | IRIIS ™ Plus | IRIIS ™ | Solitaire ™ AB | Enterprise ™ |
|---|---|---|---|---|---|
| 2.0 mm | 0.01130 | 0.0090 | 0.00590 | 0.00700 | 0.00517 |
| 2.5 mm | 0.00950 | 0.0066 | 0.00340 | 0.00410 | 0.00320 |
| 3.0 mm | 0.00870 | 0.0061 | 0.00255 | 0.00210 | 0.00068 |
| 3.5 mm | 0.00710 | 0.0056 | 0.00255 | 0.00090 | 0.00000 |
| 4.0 mm | 0.00460 | 0.0045 | 0.00185 | 0.00000 | 0.00000 |
| 4.5 mm | 0.00230 | 0.0038 | 0.00165 | 0.00000 | 0.00000 |

Table 2 below lists the data obtained from testing performed to determine the radial resistive force (RRF) of the devices at selected expansion diameters ranging from 2 mm to 4.5 mm. The units for the RRF data reproduced below are force per unit length (N/mm).

TABLE 2

| Diameter | NeuroForm³ ™ | IRIIS ™ Plus | IRIIS ™ | Solitaire ™ AB | Enterprise ™ |
|---|---|---|---|---|---|
| 1.5 mm | 0.022 | 0.016 | 0.014 | 0.018 | 0.005 |
| 2.0 mm | 0.019 | 0.016 | 0.011 | 0.014 | 0.005 |
| 2.5 mm | 0.018 | 0.014 | 0.009 | 0.011 | 0.005 |
| 3.0 mm | 0.016 | 0.014 | 0.009 | 0.008 | 0.005 |
| 3.5 mm | 0.014 | 0.014 | 0.009 | 0.005 | 0.004 |
| 4.0 mm | 0.010 | 0.012 | 0.008 | 0.002 | 0.003 |
| 4.5 mm | 0.006 | 0.007 | 0.005 | 0.000 | 0.001 |

Table 3 below lists the average COF and RRF of each of the devices as determined from the testing results.

TABLE 3

| | NeuroForm³ ™ | IRIIS ™ Plus | IRIIS ™ | Solitaire ™ AB | Enterprise ™ |
|---|---|---|---|---|---|
| Average COF per unit length (N/mm) (across 2.0 mm to 4.5 mm diameter) | 0.0073 | 0.0059 | 0.0030 | 0.0023 | 0.0015 |
| Average RRF per unit length (N/mm) (across 2.0 mm to 4.5 mm diameter) | 0.0138 | 0.0127 | 0.0083 | 0.0067 | 0.037 |

Table 4 below provides a comparison of the strut thickness, cell size, and cell area of various vascular devices. The vascular devices include the five devices included in the testing described above with respect to Tables 1-3, as well as a MindFrame IRIIS™ Large Cell device.

TABLE 4

| | NeuroForm³ ™ | IRIIS ™ Plus | IRIIS ™ | Solitaire ™ AB | Enterprise ™ | IRIIS ™ Large Cell |
|---|---|---|---|---|---|---|
| Strut Thickness (inches) | 0.0065" | 0.0024" | 0.0027" | 0.0035" | 0.0027" | 0.0024" |
| Cell Size (inches) | 0.200" × 0.070" | 0.120" × 0.050" | 0.120" × 0.050" | 0.230" × 0.200" | 0.100" × 0.050" | 0.250" × 0.100" |
| Cell Area (sq. inches) | 0.007 | 0.003 | 0.003 | 0.023 | 0.0025 | 0.0250 |

Example 4

Performance Measurements

Table 5 below summarizes the average performance measurements obtained from published studies of various ischemic stroke treatment devices. Embodiments of the systems, methods and devices described herein were used in the EU-PRIISM-01 study and the Karolinska University Hospital (PRIISM Subgroup) studies. As shown in Table 5 below, the embodiments of the systems, methods and devices described herein resulted in much faster "time to flow" results and overall flow results than the systems, methods and devices used in the other studies.

TABLE 5

| Study Baseline Info/ Endpoints | EU-PRIISM-01 | Karolinska (PRIISM Subgroup) | ev3 Solitaire FR (Barcelona) | Concentric Merci US Registry | Penumbra Aspiration International 'POST' |
|---|---|---|---|---|---|
| Number of Patients | 35 | 23 | 20 | 164 | 157 |
| Baseline NIHSSS | 16.4 | 16.7 | 19 | 16 | 19 |
| Groin to Initial Flow (min) | 26.5 | 20.5 | NR | 96 | 41 |
| Groin to final flow (min) | 34.6 | 33.4 | 80.9 | 96 | 41 |
| TIMI II/III on 1$^{st}$ deployment (%) | 96.8 | 90 | 80 | 0 | 0 |
| TIMI II/III at procedure end (%) | 96.8 | 95 | 90 | 68.3 | 87 |
| mRs ≤2 at 90 Days (%) | 51.6 | 60 | 45 | 36 | 41 |
| Device related SAE's (%) | 0 | 0 | 0 | 2.4 | 3.9 |
| SICH (%) | 2.9 | 0 | 10 | 9.8 | 6.4 |
| Mortality at 90 days (%) | 17.1 | 10 | 20 | 34.0 | 20.0 |

Conditional language, for example, among others, "can," "could," "might," or "may," unless specifically stated otherwise, or otherwise understood within the context as used, is generally intended to convey that certain embodiments include, while other embodiments do not include, certain features, elements and/or steps.

Although certain embodiments and examples have been described herein, aspects of the methods and devices shown and described in the present disclosure may be differently combined and/or modified to form still further embodiments. Additionally, it will be recognized that the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein.

For purposes of this disclosure, certain aspects, advantages, and novel features of the inventions are described herein. Embodiments embodied or carried out in a manner may achieve one advantage or group of advantages as taught herein without necessarily achieving other advantages. The headings used herein are merely provided to enhance readability and are not intended to limit the scope of the embodiments disclosed in a particular section to the features or elements disclosed in that section. The features or elements from one embodiment of the disclosure can be employed by other embodiments of the disclosure. For example, features described in one figure may be used in conjunction with embodiments illustrated in other figures.

What is claimed is:

1. An expandable tip assembly adapted to address an occlusive thrombus within a blood vessel, comprising:
   an elongate member;
   a tubular scaffold coupled to a distal end of the elongate member, the scaffold comprising a plurality of cells and configured to radially self-expand from a non-expanded configuration within a catheter to an expanded configuration upon unsheathing of the scaffold from the catheter;
   wherein the scaffold has a chronic outward force (COF) per unit length that does not decrease by more than 75% from a scaffold diameter of 1.5 mm to a scaffold diameter of 4.5 mm; and
   wherein the open cells are sized to promote at least one of vessel reperfusion or thrombus removal.

2. The expandable tip assembly of claim 1, wherein the plurality of cells is defined by struts and bridges.

3. The expandable tip assembly of claim 1, wherein the scaffold is coupled to the distal end of the elongate member by a plurality of tethers that extend eccentrically from the distal end of the elongate member.

4. The expandable tip assembly of claim 1, wherein the scaffold has a chronic outward force (COF) per unit length that does not decrease by more than 50% from a diameter of 1.5 mm to a diameter of 4.5 mm.

5. The expandable tip assembly of claim 1, wherein the cells of the scaffold have a uniform cell size.

6. The expandable tip assembly of claim 1, wherein the cells of the scaffold have a variable cell size.

7. The expandable tip assembly of claim 1, wherein the cells of the scaffold have a cell size adapted to inhibit protrusion of portions of the thrombus within an interior of the scaffold.

8. The expandable tip assembly of claim 1, wherein the cells of the scaffold have a cell size adapted to promote protrusion of portions of the thrombus within an interior of the scaffold.

9. The expandable tip assembly of claim 1, wherein the cells of the scaffold have a cell length of between 4 mm and 6 mm and a cell height between 2 mm and 4 mm in the expanded configuration.

10. The expandable tip assembly of claim 1, wherein the scaffold has an average chronic outward force across a diameter of 1.5 mm to 4.5 mm of between 0.0020 N and 0.0090 N.

11. The expandable tip assembly of claim 1, wherein the scaffold is permanently, non-removably coupled to the elongate member.

12. The expandable tip assembly of claim 1, wherein the scaffold is detachably coupled to the elongate member.

13. The expandable tip assembly of claim 1, wherein a proximal end of the scaffold is open.

14. The expandable tip assembly of claim 1, wherein the scaffold has a maximum expansion diameter of about 1 mm to about 5 mm.

15. The expandable tip assembly of claim 1, wherein the scaffold has a length of about from about 5 mm to about 50 mm.

16. The expandable tip assembly of claim 1, wherein the scaffold comprises one or more of the following features:
- a tapered body;
- a coating configured to increase platelet activation or adhesion of the thrombus to the scaffold;
- a length configured to at least partially span the thrombus;
- sufficient radial force to provide continuous radial expansion as the thrombus is lysed;
- does not comprise a backbone; and
- is not a rolled mesh scaffold that is configured to overlap on itself.

17. The expandable tip assembly of claim 1, wherein the scaffold comprises one or more of the following features:
- a body having a triangular, elliptical, spiral or undulating configuration;
- a non-thrombogenic coating or a coating with an anti-clotting drug;
- a ratio of strut thickness to strut width is less than at least about 1.4;
- parallelogram-shaped cells; and
- U-shaped bridges between cells of the scaffold.

18. The expandable tip assembly of claim 1, wherein the scaffold comprises an open distal end without a distal embolic protection member or device.

19. The expandable tip assembly of claim 1, wherein a proximal end of the scaffold is tapered to facilitate re-sheathing of the scaffold.

20. The expandable tip assembly of claim 1, wherein the scaffold comprises a laser-cut tube.

* * * * *